US005760032A

United States Patent [19]

Kitajima et al.

[11] Patent Number: 5,760,032

[45] Date of Patent: Jun. 2, 1998

[54] THIENYLAZOLE COMPOUND AND THIENOTRIAZOLODIAZEPINE COMPOUND

[75] Inventors: Hiroshi Kitajima; Syuji Ehara; Hideaki Sato, all of Fukuoka; Minoru Moriwaki, Osaka; Kenichi Onishi, Fukuoka, all of Japan

[73] Assignee: Yoshitomi Pharmaceutical Industries, Ltd., Osaka, Japan

[21] Appl. No.: 750,025

[22] PCT Filed: Jun. 1, 1995

[86] PCT No.: PCT/JP95/01071

§ 371 Date: Nov. 22, 1996

§ 102(e) Date: Nov. 22, 1996

[87] PCT Pub. No.: WO95/32964

PCT Pub. Date: Dec. 7, 1995

[30] Foreign Application Priority Data

Jun. 1, 1994 [JP] Japan .................................... 6-00889

[51] Int. Cl.$^6$ ...................... A61K 31/55; C07D 491/00; C07D 513/00; C07D 515/00

[52] U.S. Cl. ........................................ 514/220; 540/560

[58] Field of Search ........................... 540/560; 514/220

[56] References Cited

U.S. PATENT DOCUMENTS

| | | | |
|---|---|---|---|
| 4,094,984 | 6/1978 | Weber et al. | 424/269 |
| 4,199,588 | 4/1980 | Weber et al. | 424/267 |
| 5,190,939 | 3/1993 | Rault et al. | 514/220 |
| 5,532,233 | 7/1996 | Weber et al. | 514/219 |

FOREIGN PATENT DOCUMENTS

| | | |
|---|---|---|
| 0 254 245 | 1/1988 | European Pat. Off. . |
| 0 446 133 A1 | 9/1991 | European Pat. Off. . |
| 0 559 891 A1 | 9/1993 | European Pat. Off. . |
| 0 661 284 A1 | 7/1995 | European Pat. Off. . |
| 2 361 398 | 3/1978 | France . |
| 2405682 | 8/1974 | Germany . |
| 49-42669 | 4/1974 | Japan . |
| 49-61197 | 6/1974 | Japan . |
| 49-69667 | 7/1974 | Japan . |
| 49-102698 | 9/1974 | Japan . |
| 50-58098 | 5/1975 | Japan . |
| 50-89369 | 7/1975 | Japan . |
| 50-148385 | 11/1975 | Japan . |
| 55-105681 | 8/1980 | Japan . |
| 55-105682 | 8/1980 | Japan . |
| 57-45754 | 9/1982 | Japan . |
| 55-12434 | 4/1989 | Japan . |
| 1-294676 | 11/1989 | Japan . |
| 2-28181 | 1/1990 | Japan . |
| 3-223290 | 10/1991 | Japan . |
| 5-155871 | 6/1993 | Japan . |
| 599 960 | 6/1978 | Switzerland . |
| 602741 | 7/1978 | Switzerland . |
| 603660 | 8/1978 | Switzerland . |

OTHER PUBLICATIONS

T. Tahara et al. "Syntheses and Structure-Activity Relationships of 6-Aryl-4H-s-triazolo[3,4-c]thieno[2,3-e][1,4]diazepines" Arzneimittel Forschung Drug Research, vol. 28, 1978.

Walser, et al. J. Med. Chem. (1991), 34(3), 1209-21.

G.N. Woodruff et al., "Cholecyst Antagonists", Annu. Rev. Pharmacol. Toxicol., vol. 31, pp. 469-501, 1991.

J. Martinez et al., "Synthesis and Biological Activity of New Peptide Segments of Gastrin Exhibiting Gastrin Antagonist Property", J. Med. Chem. vol. 27, pp. 1597-1601, 1984.

B.E. Evans, "Methods for Drug Discovery: Development of Potent, Selective, Orally Effective Cholecystokinin Antagonists", J. Med. Chem., vol. 31, pp. 2235-2246, 1988.

*Primary Examiner*—Mukund J. Shah
*Assistant Examiner*—Bruck Kifle
*Attorney, Agent, or Firm*—Wenderoth, Lind & Ponack

[57] ABSTRACT

Thienylazole compounds (I) and thienotriazolodiazepine compounds (II) of the formulas

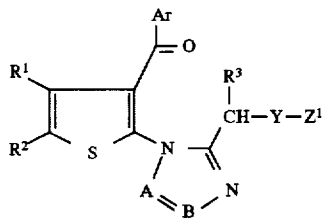

(I)

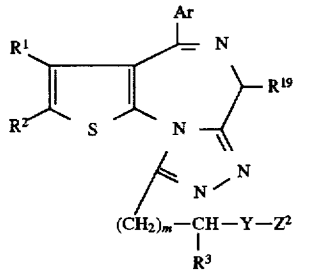

(II)

wherein $R^1$ and $R^2$ are hydrogen, halogen, $C_1$-$C_5$ alkyl and the like; —A=B— is —N=N— and the like; $R^3$ and $R^{19}$ are hydrogen, $C_1$-$C_5$ alkyl and the like; Y is —NHCO—, —NHCONH—, —NHCOO— and the like; $Z^1$ and $Z^2$ are aryl, heteroaryl and the like; Ar is halogen-substituted phenyl and the like; and m is 0 or an integer of 1-5.

The compounds of the present invention have CCK antagonistic action and gastrin antagonistic action, particularly potent antagonistic action against CCK-A receptor, and are useful as agents for the prophylaxis and treatment of central and peripheral nervous system diseases (e.g., anxiety, schizophrenia, and the like) and digestive diseases (e.g., pancreatitis, gastric ulcer, enterelcosis, irritable bowel syndrome, constipation, and the like).

5 Claims, No Drawings

THIENYLAZOLE COMPOUND AND THIENOTRIAZOLODIAZEPINE COMPOUND

TECHNICAL FIELD

The present invention relates to novel thienylazole compounds and thienotriazolodiazepine compounds having cholecystokinin (hereinafter abbreviated as CCK) and gastrin antagonistic activities, which are utilized in the medical field.

BACKGROUND ART

There have been heretofore reported a 2-thienyltriazole compound (Japanese Patent Examined Publication No. 12434/1980) showing action on the central nervous system, such as anti-convulsion activity and sedative activity; a thienotriazolodiazepine compound (Japanese Patent Unexamined Publication No. 61197/1974) used as an antianxiety drug; a 2-thienyltriazole compound (Japanese Patent Unexamined Publication No. 69667/1974) used as an antianxiety drug or an intermediate for pharmaceutical products; a 2-thienyltriazole compound (Japanese Patent Unexamined Publication No. 58098/1975) which is an intermediate for a thienotriazolopyridine compound used as an antiinflammatory drug, an antipyretic analgesic and the like; a 2-thienylimidazole compound (Japanese Patent Unexamined Publication No. 89369/1975) which has central muscle relaxing activity, antianxiety activity and the like; a 2-thienyltriazole compound (Japanese Patent Examined Publication No. 45754/1982) used as a starting compound of a pharmaceutical product such as an antianxiety drug; a 2-thienyltriazole compound (Japanese Patent Unexamined Publication No. 10568 1/1980) which is used as an antianxiety drug; a 2-thienylimidazole compound (Japanese Patent Unexamined Publication No. 105682/1980) which is used as an antianxiety drug; a 2-thienylazole compound (Japanese Patent Unexamined Publication No. 294676/1989) having calmodulin antagonistic activity, coronary and cerebral vasodilating activities and PAF antagonistic activity; and the like.

In addition, Japanese Patent Unexamined Publication No. 102698/1974 discloses that a thienotriazolodiazepine compound which may be substituted by alkoxycarbonylaminoalkyl, alkylcarbonyloxyalkyl and the like at the 9-position thereof can be used as a tranquilizer or an antianxiety drug. Japanese Patent Unexamined Publication Nos. 28181/1990 and 223290/1991 disclose thienotriazolodiazepine compounds having cholecystokinin antagonistic activity, which have, at the 6-position thereof, an amide substituent (e.g., indole-2-carboxamide) or ureido substituent [e.g., (3-(3methylphenyl)ureido], which substituent being considered to be essential for the expression of cholecystokinin antagonistic activity.

The cholecystokinin (also referred to as CCK) is a neuropeptide consisting of 33 amino acids, and CCK-8 which consists of 8 amino acids at the C terminus also shows activity. The gastrin consists of 34 amino acids, and pentagastrin which consists of 5 amino acids at the C terminus also shows activity. The amino acid sequence of the pentagastrin is identical to that at the C terminus of CCK. There have been reported different subtypes of CCK receptors which are generally classified into CCK-A receptor distributed in peripheral tissues such as pancreas and gallbladder, and CCK-B receptor distributed in the central nervous system. It is considered that CCK-B receptor and gastrin receptor are the same. The physiological activity of CCK via CCK-A receptor reportedly includes secretion of pancreatic juice, promotion of insulin release, control of pepsinogen secretion, gastric delay of emptying, stimulation of ileum movement, contraction of gallbladder, and the like. The physiological activity of CCK via CCK-B receptor reportedly includes suppression of feeling of hunger, control of dopaminergic nerves, control of pain and pain relief with morphine, acceleration of memory, and the like, and CCK-B receptor antagonist is useful for the treatment and prophylaxis of gastric ulcer and enterelcosis, emesis, control of appetite, pain, anxiety, dementia, schizophrenia, and the like.

Mainly in experimental studies of pancreatitis in recent years, the involvement of CCK in the onset, evolution and aggravation of pancreatitis has been reported. Pancreatitis is a symptom wherein pancreatic tissues are digested by the enzyme secreted by the pancreas itself (autodigestion), and is mostly treated by pancreatic enzyme inhibitors such as a trypsin inhibitor. However, the therapeutic effects afforded by them are not entirely satisfactory and a pharmaceutical agent exhibiting greater treatment effects has been desired. Unlike other enzyme inhibitors, the CCK-A receptor antagonist suppresses secretion of pancreatic enzyme itself and is useful as a new agent for the treatment and prophylaxis of pancreatitis. It is also effective for the treatment and prophylaxis of gallbladder disorders, irritable bowel syndrome, gastric ulcer, enterelcosis, emesis, pancreatic malignant tumor, constipation and the like.

As a review on physiological activity of CCK and therapeutic usefulness of CCK antagonists, there is known, for example, Annu. Rev. Pharmacol. Toxicol., Vol. 31, p. 469 (1991). A compound having a CCK-A antagonistic activity, such as proglumide, is reported in J. Med. Chem., Vol. 27, p. 1597 (1984); a benzodiazepine compound, which is typically devazepide [3(S)-1,3-dihydro-3-(2-indolecarbonylamino)-1-methyl-5-phenyl-2H-1,4-benzodiazepin-2-one], is reported in J. Med. Chem., Vol. 31, p. 2235 (1988); and a 2-acylamino-5-thiazole derivative is reported in Japanese Patent Unexamined Publication No. 155871/1993. However, these compounds are not satisfactory from the aspects of the level of activity in vitro or in vivo, selectivity for CCK-A receptor, physicochemical properties (e.g., solubility in water), bioavailability, safety and the like.

DISCLOSURE OF THE INVENTION

The present inventors conducted intensive studies with the aim of providing a useful compound which serves well for the treatment and prophylaxis of various diseases caused by peripheral CCK, by the action of selectively blocking the binding to CCK-A receptor, and found that certain thienylazole compounds and thienotriazolodiazepine compounds can achieve the object, which resulted in the completion of the present invention. Accordingly, the present invention provides the following.

(1) Thienylazole compounds of the formula

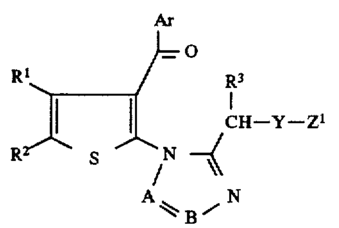

(I)

wherein $R^1$ is a hydrogen, a halogen or an alkyl having 1 to 5 carbon atoms(s);

$R^2$ is a hydrogen, a halogen, a cyano, an alkyl having 1 to 5 carbon atom(s), a cycloalkyl having 3 to 7 carbon atoms, an alkyl having 1 to 5 carbon atom(s) which is substituted by 1 to 3 hydroxyl group(s), an alkyl having 1 to 5 carbon atom(s) which is substituted by 1 to 3 amino group(s), an alkanoyl having 2 to 5 carbon atoms, a phenylalkyl wherein phenyl ring is substituted by alkyl having 1 to 5 carbon atom(s), a group of the formula:

$$-(CH_2)nCOOR^4$$

wherein n is 0 or an integer of 1–5 and $R^4$ is hydrogen, alkyl having 1 to 5 carbon atom(s) or aralkyl, a group of the formula:

$$-(CH_2)nCON(R^5)(R^6)$$

wherein n is 0 or an integer of 1–5, and $R^5$ and $R^6$ are the same or different and each is hydrogen or alkyl having 1 to 5 carbon atom(s), or $R^5$ and $R^6$ in combination optionally form, together with the adjacent nitrogen atom, a hetero ring, a group of the formula:

$$-C{\equiv}C-(CH_2)p-R^{21}$$

wherein p is 0, 1 or 2 and $R^{21}$ is aryl or a heterocyclic group, a group of the formula:

$$-C{\equiv}C-(CH_2)q-O-R^{22}$$

wherein q is 1 or 2 and $R^{22}$ is aryl or a heterocyclic group, or a group of the formula:

$$-(CH_2)nR^{24}$$

wherein n is 0 or an integer of 1–5, and $R^{24}$ is 5-tetrazolyl; or $R^1$ and $R^2$ combinedly form a ring optionally having a group of the formula:

$$-(CH_2)nCON(R^{5a})(R^{6a})$$

wherein n is 0 or an integer of 1–5, and $R^{5a}$ and $R^{6a}$ are the same or different and each is hydrogen or alkyl having 1 to 5 carbon atom(s), or $R^{5a}$ and $R^{6a}$ in combination optionally form, together with the adjacent nitrogen atom, a hetero ring; or $R^1$ and $R^2$ combinedly form a group of the formula

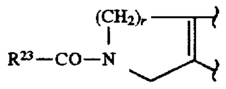

wherein r is 1 or 2, and $R^{23}$ is cycloalkyl having 3 to 7 carbon atoms;

$R^3$ is a hydrogen, an alkyl having 1 to 5 carbon atom(s), an alkyl having 1 to 5 carbon atom(s) which is substituted by 1 to 3 hydroxyl group(s), an aralkyl optionally substituted by 1 to 3 hydroxyl group(s) on an aromatic ring, a heteroarylalkyl, a group of the formula:

$$-(CH_2)nCOOR^{14}$$

wherein n is 0 or an integer of 1–5, and $R^{14}$ is hydrogen, alkyl having 1 to 5 carbon atom(s), cycloalkyl having 3 to 7 carbon atoms or aralkyl, a group of the formula:

$$-(CH_2)nN(R^{17})(R^{18})$$

wherein n is 0 or an integer of 1–5, and $R^{17}$ and $R^{18}$ are the same or different and each is hydrogen or alkyl having 1 to 5 carbon atom(s), or $R^{17}$ and $R^{18}$ in combination optionally form, together with the adjacent nitrogen atom, a hetero ring, a group of the formula:

$$-(CH_2)nCON(R^{25})(R^{26})$$

wherein n is 0 or an integer of 1–5, and $R^{25}$ and $R^{26}$ are the same or different and each is hydrogen or alkyl having 1 to 5 carbon atom(s), or $R^{25}$ and $R^{26}$ in combination optionally form, together with the adjacent nitrogen atom, a hetero ring, or a group of the formula:

$$-(CH_2)nR^{27}$$

wherein n is 0 or an integer of 1–5, and $R^{27}$ is 5-tetrazolyl;

$-A{=}B-$ is $-N{=}N-$, $-C(R^7){=}N-$ or $-C(R^7){=}CH-$ wherein $R^7$ is hydrogen, halogen, alkyl having 1 to 5 carbon atom(s), alkoxy having 1 to 5 carbon atom(s), alkyl having 1 to 5 carbon atom(s) which is substituted by 1 to 3 hydroxyl group(s), alkanoyl having 2 to 5 carbon atoms, cycloalkyl having 3 to 7 carbon atoms, haloalkyl having 1 or 2 carbon atom(s), alkenyl, alkynyl, cycloalkylalkyl, aryl, heteroaryl, aralkyl, heteroarylalkyl, aryloxyalkyl, adamantyl, adamantylmethyl, bicyclo group, a group of the formula:

$$-(CH_2)nCOOR^8$$

wherein n is 0 or an integer of 1–5, and $R^8$ is hydrogen, alkyl having 1 to 5 carbon atom(s) or aralkyl, a group of the formula:

$$-(CH_2)nCON(R^9)(R^{10})$$

wherein n is 0 or an integer of 1–5, and $R^9$ and $R^{10}$ are the same or different and each is hydrogen or alkyl having 1 to 5 carbon atom(s), or $R^9$ and $R^{10}$ in combination optionally form, together with the adjacent nitrogen atom, a hetero ring, or a group of the formula:

$$-(CH_2)nN(R^{11})(R^{12})$$

wherein n is 0 or an integer of 1–5, and $R^{11}$ and $R^{12}$ are the same or different and each is hydrogen or alkyl having 1 to 5 carbon atom(s), or $R^{11}$ and $R^{12}$ in combination optionally form, together with the adjacent nitrogen atom, a hetero ring;

Y is $-NHCO-$, $-NHCONH-$, $-NHCSNH-$, $-NHSO_2-$, $-NHCOO-$, $-OCONH-$, $-OCO-$, $-NHCONHCO-$, $-NHCSNHCO-$, $-NHCONHSO_2-$, $-NHCSNHSO_2-$ or $-NHCOCONH-$;

$Z^1$ is an alkyl having 1 to 5 carbon atom(s), an alkenyl, an alkynyl, a cycloalkyl having 3 to 7 carbon atoms, a cycloalkylalkyl, an aralkyl, an aryl, a heteroaryl, a heteroarylalkyl, or a group of the formula:

$—CH=CH—R^{13}$ wherein $R^{13}$ is cycloalkyl having 3 to 7 carbon atoms, aryl or heteroaryl, wherein these rings are optionally substituted by an optional number of substituent(s) selected from the group consisting of halogen, hydroxyl group, amino, nitro, alkyl having 1 to 5 carbon atom(s), alkyl having 1 to 5 carbon atom(s) which is substituted by 1 to 3 hydroxyl group(s), alkanoyl having 2 to 5 carbon atoms, haloalkyl having 1 or 2 carbon atom(s), alkoxy having 1 to 5 carbon atom(s), alkylthio having 1 to 5 carbon atom(s), aryloxy, a group of the formula:

$—(CH_2)nCOOR^{14a}$ wherein n is 0 or an integer of 1–5, and $R^{14a}$ is hydrogen, alkyl having 1 to 5 carbon atom(s) or aralkyl, a group of the formula:

$—(CH_2)nCON(R^{15})(R^{16})$ wherein n is 0 or an integer of 1–5, and $R^{15}$ and $R^{16}$ are the same or different and each is hydrogen or alkyl having 1 to 5 carbon atom(s), or $R^{15}$ and $R^{16}$ in combination optionally form, together with the adjacent nitrogen atom, a hetero ring, a group of the formula:

$—(CH_2)nN(R^{17a})(R^{18a})$ wherein n is 0 or an integer of 1–5, and $R^{17a}$ and $R^{18a}$ are the same or different and each is hydrogen or alkyl having 1 to 5 carbon atom(s), or $R^{17a}$ and $R^{18a}$ in combination optionally form, together with the adjacent nitrogen atom, a hetero ring, and a group of the formula:

$—(CH_2)nR^{28}$ wherein n is 0 or an integer of 1–5, and $R^{28}$ is 5-tetrazolyl; and Ar is a phenyl, a pyridyl, a thienyl, or a phenyl, pyridyl or thienyl, having at least one substituent selected from the group consisting of halogen, alkyl having 1 to 5 carbon atom(s), alkoxy having 1 to 5 carbon atom(s), haloalkyl having 1 or 2 carbon atom(s), alkylthio having 1 to 5 carbon atom(s), carboxyl, carboxyalkyl, nitro, amino and hydroxyl group, and pharmaceutically acceptable salts thereof.

(2) Pharmaceutical compositions comprising the compound of the above formula (I) or a pharmaceutically acceptable salt thereof in an amount effective for treatment, and a pharmaceutically acceptable additive.

(3) Agents for the treatment and prophylaxis of central nervous system diseases, which comprise the compound of the above formula (I) or a pharmaceutically acceptable salt thereof.

(4) Agents for the treatment and prophylaxis of peripheral nervous system diseases, which comprise the compound of the above formula (I) or a pharmaceutically acceptable salt thereof.

(5) Agents for the treatment and prophylaxis of digestive diseases, which comprise the compound of the above formula (I) or a pharmaceutically acceptable salt thereof.

(6) Thienotriazolodiazepine compounds of the formula

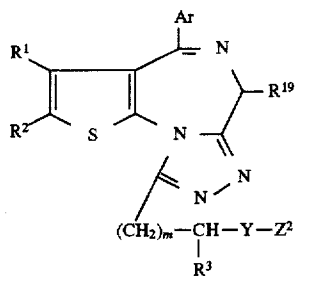

(II)

wherein $R^1$ is a hydrogen, a halogen or an alkyl having 1 to 5 carbon atom(s);

$R^2$ is a hydrogen, a halogen, a cyano, an alkyl having 1 to 5 carbon atom(s), a cycloalkyl having 3 to 7 carbon atoms, an alkyl having 1 to 5 carbon atom(s) which is substituted by 1 to 3 hydroxyl group(s), an alkyl having 1 to 5 carbon atom(s) which is substituted by 1 to 3 amino group(s), an alkanoyl having 2 to 5 carbon atoms, a phenylalkyl wherein phenyl ring is substituted by alkyl having 1 to 5 carbon atom(s), a group of the formula:

$—(CH_2)nCOOR^4$ wherein n is 0 or an integer of 1–5 and $R^4$ is hydrogen, alkyl having 1 to 5 carbon atom(s) or aralkyl, a group of the formula:

$—(CH_2)nCON(R^5)(R^6)$ wherein n is 0 or an integer of 1–5, and $R^5$ and $R^6$ are the same or different and each is hydrogen or alkyl having 1 to 5 carbon atom(s), or $R^5$ and $R^6$ in combination optionally form, together with the adjacent nitrogen atom, a hetero ring, a group of the formula:

$—C≡C—(CH_2)p-R^{21}$ wherein p is 0, 1 or 2 and $R^{21}$ is aryl or a heterocyclic group, a group of the formula:

$—C≡C—(CH_2)q-O—R^{22}$ wherein q is 1 or 2 and $R^{22}$ is aryl or heterocyclic group, or a group of the formula:

$—(CH_2)nR^{24}$ wherein n is 0 or an integer of 1–5, and $R^{24}$ is 5-tetrazolyl; or $R^1$ and $R^2$ combinedly form a ring optionally having a group of the formula:

$—(CH_2)nCON(R^{5a})(R^{6a})$ wherein n is 0 or an integer of 1–5, and $R^{5a}$ and $R^{6a}$ are the same or different and each is hydrogen or alkyl having 1 to 5 carbon atom(s), or $R^{5a}$ and $R^{6a}$ in combination optionally form, together with the adjacent nitrogen atom, a hetero ring; or $R^1$ and $R^2$ combinedly form a group of the formula

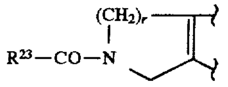

wherein r is 1 or 2, and $R^{23}$ is cycloalkyl having 3 to 7 carbon atoms;

$R^3$ is a hydrogen, an alkyl having 1 to 5 carbon atom(s), an alkyl having 1 to 5 carbon atom(s) which is substituted by 1 to 3 hydroxyl group(s), an aralkyl optionally substituted by 1 to 3 hydroxyl group(s) on an aromatic ring, a heteroarylalkyl, a group of the formula:

$-(CH_2)nCOOR^{14}$ wherein n is 0 or an integer of 1–5, and $R^{14}$ is hydrogen, alkyl having 1 to 5 carbon atom(s), cycloalkyl having 3 to 7 carbon atoms or aralkyl, a group of the formula:

$-(CH_2)nN(R^{17})(R^{18})$ wherein n is 0 or an integer of 1–5, and $R^{17}$ and $R^{18}$ are the same or different and each is hydrogen or alkyl having 1 to 5 carbon atom(s), or $R^{17}$ and $R^{18}$ in combination optionally form, together with the adjacent nitrogen atom, a hetero ring, a group of the formula:

$-(CH_2)nCON(R^{25})(R^{26})$ wherein n is 0 or an integer of 1–5, and $R^{25}$ and $R^{26}$ are the same or different and each is hydrogen or alkyl having 1 to 5 carbon atom(s), or $R^{25}$ and $R^{26}$ in combination optionally form, together with the adjacent nitrogen atom, a hetero ring, or a group of the formula:

$-(CH_2)nR^{27}$ wherein n is 0 or an integer of 1–5, and $R^{27}$ is 5-tetrazolyl;

$R^{19}$ is a hydrogen, an alkyl having 1 to 5 carbon atom(s), a group of the formula:

$-(CH_2)nCOOR^{14b}$ wherein n is 0 or an integer of 1–5, and $R^{14b}$ is hydrogen, alkyl having 1 to 5 carbon atom(s) or aralkyl, or a group of the formula:

$-(CH_2)nN(R^{17b})(R^{18b})$ wherein n is 0 or an integer of 1–5, and $R^{17b}$ and $R^{18b}$ are the same or different and each is hydrogen or alkyl having 1 to 5 carbon atom(s), or $R^{17b}$ and $R^{18b}$ in combination optionally form, together with the adjacent nitrogen atom, a hetero ring;

m is 0 or an integer of 1–5;

Y is —NHCO—, —NHCONH—, —NHCSNH—, $-NHSO_2-$, —NHCOO—, —OCONH—, —OCO—, —NHCONHCO—, —NHCSNHCO—, $-NHCONHSO_2-$, $-NHCSNHSO_2-$ or —NHCOCONH—;

$Z^2$ is an alkenyl, an alkynyl, a cycloalkyl having 3 to 7 carbon atoms, a cycloalkylalkyl, an aralkyl, an aryl, a heteroaryl, a heteroarylalkyl or a group of the formula:

$-CH{=}CH-R^{13}$ wherein $R^{13}$ is cycloalkyl having 3 to 7 carbon atoms, aryl or heteroaryl, wherein these rings are optionally substituted by an optional number of substituent(s) selected from the group consisting of halogen, hydroxyl group, amino, nitro, alkyl having 1 to 5 carbon atom(s), alkyl having 1 to 5 carbon atom(s) which is substituted by 1 to 3 hydroxyl group(s), alkanoyl having 2 to 5 carbon atoms, haloalkyl having 1 or 2 carbon atom(s), alkoxy having 1 to 5 carbon atom(s), alkylthio having 1 to 5 carbon atom(s), aryloxy, a group of the formula:

$-(CH_2)nCOOR^{14c}$ wherein n is 0 or an integer of 1–5, and $R^{14c}$ is hydrogen, alkyl having 1 to 5 carbon atom(s) or aralkyl, a group of the formula:

$-(CH_2)nCON(R^{15})(R^{16})$ wherein n is 0 or an integer of 1–5, and $R^{15}$ and $R^{16}$ are the same or different and each is hydrogen or alkyl having 1 to 5 carbon atom(s), or $R^{15}$ and $R^{16}$ in combination optionally form, together with the adjacent nitrogen atom, a hetero ring, a group of the formula:

$-(CH_2)nN(R^{17c})(R^{18c})$ wherein n is 0 or an integer of 1–5, and $R^{17c}$ and $R^{18c}$ are the same or different and each is hydrogen or alkyl having 1 to 5 carbon atom(s), or $R^{17c}$ and $R^{18c}$ in combination optionally form, together with the adjacent nitrogen atom, a hetero ring, and a group of the formula:

$-(CH_2)nR^{28}$ wherein n is 0 or an integer of 1–5, and $R^{28}$ is 5-tetrazolyl; and Ar is a phenyl, a pyridyl, a thienyl, or a phenyl, pyridyl or thienyl, having at least one substituent selected from the group consisting of halogen, alkyl having 1 to 5 carbon atom(s), alkoxy having 1 to 5 carbon atom(s), haloalkyl having 1 or 2 carbon atom(s), alkylthio having 1 to 5 carbon atom(s), carboxyl, carboxyalkyl, nitro, amino and hydroxyl group, and pharmaceutically acceptable salts thereof.

(7) Pharmaceutical compositions comprising the compound of the above formula (II) or a pharmaceutically acceptable salt thereof in an amount effective for treatment, and a pharmaceutically acceptable additive.

(8) Agents for the treatment and prophylaxis of central nervous system diseases, which comprise the compound of the above formula (II) or a pharmaceutically acceptable salt thereof.

(9) Agents for the treatment and prophylaxis of peripheral nervous system diseases, which comprise the compound of the above formula (II) or a pharmaceutically acceptable salt thereof.

(10) Agents for the treatment and prophylaxis of digestive diseases, which comprise the compound of the above formula (II) or a pharmaceutically acceptable salt thereof.

In the above definition and the present specification, halogen means chlorine, bromine, fluorine and iodine.

Alkyl having 1 to 5 carbon atoms is straight or branched chain alkyl, and exemplified by methyl, ethyl, propyl, isopropyl, butyl, isobutyl, tert-butyl, pentyl, isopentyl and the like, with preference given to methyl, ethyl and isopropyl. Alkoxy having 1 to 5 carbon atoms is straight or branched chain alkoxy, and exemplified by methoxy, ethoxy, propoxy, isopropoxy, butoxy, isobutoxy, tert-butoxy, pentyloxy, isopentyloxy and the like, with preference given to methoxy and ethoxy. Particularly preferred is methoxy. Haloalkyl having 1 or 2 carbon atoms is exemplified by chloromethyl, fluoromethyl, difluoromethyl, trifluoromethyl, 2,2,2-trichloroethyl, 2,2,2-trifluoroethyl and the like, with preference given to trifluoromethyl. Alkylthio having 1 to 5 carbon atoms is straight or branched chain alkylthio, and exemplified by methylthio, ethylthio, propylthio, isopropylthio, butylthio, isobutylthio, tert-butylthio, pentylthio, isopentylthio and the like, with preference given to methylthio. Carboxyalkyl is exemplified by carboxymethyl, 2-carboxyethyl and the like, with preference given to carboxymethyl.

Aralkyl is exemplified by benzyl, 2-phenylethyl, 1-phenylethyl, 3-phenylpropyl and the like. Preferred is benzyl. Cycloalkyl having 3 to 7 carbon atoms is exemplified by cyclopropyl, cyclobutyl, cyclopentyl, cyclohexyl, cycloheptyl and the like, with preference given to that having 3 to 6 carbon atoms. Particularly preferred are cyclopropyl and cyclohexyl. Aryl is exemplified by phenyl, naphthyl and the like, with preference given to phenyl. Aryloxy is exemplified by phenoxy, 1-naphthyloxy, 2-naphthyloxy and the like, with preference given to phenoxy. Alkyl having 1 to 5 carbon atoms which is substituted by 1 to 3 hydroxyl groups is exemplified by hydroxymethyl, 1-hydroxyethyl, 2-hydroxyethyl, 3-hydroxypropyl, 4-hydroxybutyl and the like, with preference given to hydroxymethyl. Alkanoyl having 2 to 5 carbon atoms is exemplified by acetyl, propionyl, butyryl, valeryl, pivaloyl and the like, with preference given to acetyl. Phenylalkyl wherein phenyl ring is substituted by alkyl having 1 to 5 carbon atoms is exemplified by 2-(4-isobutylphenyl)ethyl, 2-(4-butylphenyl)ethyl and the like, with preference given to 2-(4-isobutylphenyl)ethyl. Hetero ring which is formed together with the adjacent nitrogen atom is exemplified by 1-aziridinyl, 1-azetidinyl, 1-pyrrolidinyl, piperidino, 1-piperazinyl, 4-methyl-1-piperazinyl, 1-azepinyl, morpholino, thiomorpholino, 4-methylpipreidino, phthalimide, succinimide and the like. Heteroaryl is exemplified by pyridyl, thienyl, furyl, pyrrolyl, imidazolyl, oxazolyl, isoxazolyl, thiazolyl, pyridazinyl, pyrimidinyl, pyrazinyl, indolyl, indolinyl, benzofuranyl, 2,3-dihydrobenzofuranyl, benzothienyl, benzoxazolyl, benzimidazolyl, benzothiazolyl, quinolyl, isoquinolyl, quinoxalinyl, quinazolinyl and the like. Preferred are 3-quinolyl, 2-benzofuranyl, 2,3-dihydro-7-benzofuranyl, 2-benzothienyl, 2-indolyl, 2-indolinyl and the like, and particularly preferred is 2-indolyl. The ring which is combinedly formed by $R^1$ and $R^2$ means cyclopentene ring, cyclopentadiene ring, cyclohexene ring, cyclohexadiene ring, benzene ring, cycloheptene ring, cycloheptadiene ring, cycloheptatriene ring and the like, with preference given to cyclohexene ring.

The heterocyclic group is exemplified by pyridyl, imidazolyl, thienyl, furyl, pyrimidinyl, oxazolyl and the like. Alkenyl is that having 2 to 6 carbon atoms, which is exemplified by vinyl, propenyl, 2-methyl-1-propenyl, 1-butenyl, 3-butenyl, 3-hexenyl and the like. Alkynyl is exemplified by ethynyl, 1-propynyl, propargyl, 3-hexynyl and the like. Cycloalkylalkyl is exemplified by cyclopropylmethyl, cyclobutylmethyl, cyclopentylmethyl, cyclohexylmethyl and the like. Heteroarylalkyl is exemplified by indolylmethyl, pyridylmethyl, quinolylmethyl, thienylmethyl, furylmethyl and the like. Aryloxyalkyl is exemplified by phenoxymethyl, 2-phenoxyethyl, 3-phenoxypropyl, 4-phenoxybutyl and the like.

Each group of the formula (I) is preferably as follows: $R^1$ is hydrogen, halogen or alkyl having 1 to 5 carbon atoms; $R^2$ is hydrogen, halogen, alkyl having 1 to 5 carbon atoms, alkyl having 1 to 5 carbon atoms which is substituted by 1 to 3 hydroxyl groups, alkanoyl having 2 to 5 carbon atoms, phenylalkyl wherein phenyl ring is substituted by alkyl having 1 to 5 carbon atoms, a group of the formula:

$$—(CH_2)nCOOR^4$$

wherein n is 0 or an integer of 1–5 and $R^4$ is hydrogen, alkyl having 1 to 5 carbon atoms or aralkyl, a group of the formula:

$$—(CH_2)nCON(R^5)(R^6)$$

wherein n is 0 or an integer of 1–5, and $R^5$ and $R^6$ are the same or different and each is hydrogen or alkyl having 1 to 5 carbon atoms, or $R^5$ and $R^6$ in combination optionally form, together with the adjacent nitrogen atom, a hetero ring, a group of the formula $$—C{\equiv}C—(CH_2)p\text{-}R^{21}$$

wherein p is 0, 1 or 2 and $R^{21}$ is aryl or heterocyclic group, or a group of the formula $$—C{\equiv}C—(CH_2)q\text{-}O—R^{22}$$

wherein q is 1 or 2 and $R^{22}$ is aryl or heterocyclic group; or $R^1$ and $R^2$ combinedly form a ring, which optionally has a group of the formula:

$$—(CH_2)nCON(R^{5a})(R^{6a})$$

wherein n is 0 or an integer of 1–5, and $R^{5a}$ and $R^{6a}$ are the same or different and each is hydrogen or alkyl having 1 to 5 carbon atoms, or $R^{5a}$ and $R^{6a}$ in combination optionally form, together with the adjacent nitrogen atom, hetero ring, or $R^1$ and $R^2$ combinedly form a group of the formula

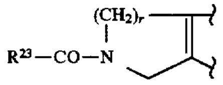

wherein r is 1 or 2, and $R^{23}$ is cycloalkyl having 3 to 7 carbon atoms; $R^3$ is hydrogen, alkyl having 1 to 5 carbon atoms, a group of the formula:

$$—(CH_2)nCOOR^{14}$$

wherein n is 0 or an integer of 1–5, and $R^{14}$ is hydrogen, alkyl having 1 to 5 carbon atoms or aralkyl, or a group of the formula:

$$—(CH_2)nN(R^{17})(R^{18})$$

wherein n is 0 or an integer of 1–5, and $R^{17}$ and $R^{18}$ are the same or different and each is hydrogen or alkyl having 1 to 5 carbon atoms, or $R^{17}$ and $R^{18}$ in combination optionally form, together with the adjacent nitrogen atom, hetero ring;

$$—A{=}B— \text{ is } —N{=}N—, —C(R^7){=}N— \text{ or } —C(R^7){=}CH—$$

wherein $R^7$ is hydrogen, halogen, alkyl having 1 to 5 carbon atoms, alkyl having 1 to 5 carbon atoms which is substituted by 1 to 3 hydroxyl groups, alkanoyl having 2 to 5 carbon atoms, cycloalkyl having 3 to 7 carbon atoms, haloalkyl having 1 or 2 carbon atoms, alkenyl, alkynyl, cycloalkylalkyl, aryl, heteroaryl, aralkyl, heteroarylalkyl, aryloxyalkyl, adamantyl, adamantylmethyl, bicyclo group, a group of the formula:

$—(CH_2)nCOOR^8$ wherein n is 0 or an integer of 1–5, and $R^8$ is hydrogen, alkyl having 1 to 5 carbon atoms or aralkyl, a group of the formula:

$—(CH_2)nCON(R^9)(R^{10})$ wherein n is 0 or an integer of 1–5, and $R^9$ and $R^{10}$ are the same or different and each is hydrogen or alkyl having 1 to 5 carbon atoms, or $R^9$ and $R^{10}$ in combination optionally form, together with the adjacent nitrogen atom, hetero ring, or a group of the formula:

$—(CH_2)nN(R^{11})(R^{12})$ wherein n is 0 or an integer of 1–5, and $R^{11}$ and $R^{12}$ are the same or different and each is hydrogen or alkyl having 1 to 5 carbon atoms, or $R^{11}$ and $R^{12}$ in combination optionally form, together with the adjacent nitrogen atom, hetero ring;

Y is —NHCO—, —NHCONH—, —NHCSNH—, $—NHSO_2—$, —NHCOO—, —OCONH—, —OCO—, —NHCONHCO—, —NHCSNHCO—, $—NHCONHSO_2—$, $—NHCSNHSO_2—$ or —NHCOCONH—;

$Z^1$ is alkyl having 1 to 5 carbon atoms, alkenyl, alkynyl, cycloalkyl having 3 to 7 carbon atoms, cycloalkylalkyl, aralkyl, aryl, heteroaryl, heteroarylalkyl, or a group of the formula:

$—CH=CH—R^{13}$ wherein $R^{13}$ is cycloalkyl having 3 to 7 carbon atoms, aryl or heteroaryl, wherein these rings in the definition of $Z^1$ are optionally substituted by an optional number of substituent (s) selected from the group consisting of halogen, hydroxyl group, amino, nitro, alkyl having 1 to 5 carbon atoms, alkyl having 1 to 5 carbon atoms which is substituted by 1 to 3 hydroxyl groups, alkanoyl having 2 to 5 carbon atoms, haloalkyl having 1 or 2 carbon atoms, alkoxy having 1 to 5 carbon atoms, alkylthio having 1 to 5 carbon atoms, aryloxy, a group of the formula:

$—(CH_2)nCOOR^{14a}$ wherein n is 0 or an integer of 1–5, and $R^{14a}$ is hydrogen, alkyl having 1 to 5 carbon atoms or aralkyl, a group of the formula:

$—(CH_2)nCON(R^{15})(R^{16})$ wherein n is 0 or an integer of 1–5, and $R^{15}$ and $R^{16}$ are the same or different and each is hydrogen or alkyl having 1 to 5 carbon atoms, or $R^{15}$ and $R^{16}$ in combination optionally form, together with the adjacent nitrogen atom, hetero ring, and a group of the formula:

$—(CH_2)nN(R^{17a})(R^{18a})$ wherein n is 0 or an integer of 1–5, and $R^{17a}$ and $R^{18a}$ are the same or different and each is hydrogen or alkyl having 1 to 5 carbon atoms, or $R^{17a}$ and $R^{18a}$ in combination optionally form, together with the adjacent nitrogen atom, hetero ring; and Ar is phenyl, pyridyl, thienyl, or phenyl, pyridyl or thienyl, having at least one substituent selected from the group consisting of halogen, alkyl having 1 to 5 carbon atoms, alkoxy having 1 to 5 carbon atoms, haloalkyl having 1 or 2 carbon atoms, alkylthio having 1 to 5 carbon atoms, carboxyl, carboxyalkyl, nitro, amino and hydroxyl group.

Each group of the formula (I) is more preferably as follows:

$R^1$ is hydrogen or alkyl having 1 or 2 carbon atoms;

$R^2$ is alkyl having 1 to 3 carbon atoms, cycloalkyl having 3 to 7 carbon atoms, $—(CH_2)nCOOR^4$ wherein n is 0 or 1 and $R^4$ is hydrogen or alkyl having 1 to 4 carbon atoms, or 5-tetrazolyl;

$R^3$ is hydrogen or $—(CH_2)nCOOR^{14}$ wherein n is an integer of 1–4, and $R^{14}$ is hydrogen, cyclohexyl or benzyl;

—A=B— is —N=N—, —CH=CH— or $—C(R^7)=N—$ wherein $R^7$ is hydrogen, halogen, alkyl having 1 to 4 carbon atoms, alkyl having 1 or 2 carbon atoms which is substituted by one hydroxyl group, cyclohexyl, trifluoromethyl, $—(CH_2)nCOOR^8$ wherein n is 0, 1 or 2, and $R^8$ is hydrogen or alkyl having 1 or 2 carbon atoms, or $—(CH_2)nN(R^{11})(R^{12})$ wherein n is 1, and $R^{11}$ and $R^{12}$ are the same or different and each is alkyl having 1 or 2 carbon atoms;

Y is —NHCO—, —NHCONH—, —NHCSNH—, $—NHSO_2—$, —OCONH— or —OCO—;

$Z^1$ is aryl, heteroaryl or $—CH=CH—R^{13}$ wherein $R^{13}$ is phenyl, wherein these rings may have 1 or 2 substituents selected from the group consisting of halogen, amino, nitro, methyl, methoxy, $—(CH_2)nCOOR^{14a}$ wherein n is 0 or an integer of 1–4, and $R^{14a}$ is hydrogen or alkyl having 1 to 4 carbon atoms, and 1H-tetrazol-5-ylmethyl; and Ar is phenyl or phenyl having halogen on the ring.

Each group of the formula (I) is still more preferably as follows:

$R^1$ is hydrogen; $R^2$ is alkyl having 1 to 3 carbon atoms, cycloalkyl having 3 to 6 carbon atoms or $—(CH_2)nCOOH$ wherein n is 0 or 1; $R^3$ is hydrogen; —A=B— is $—C(R^7)=N—$ wherein $R^7$ is halogen, trifluoromethyl, 1-adamantyl, alkyl having 1 to 4 carbon atoms or cyclohexyl; Y is —NHCO— or —NHCONH—; $Z^1$ is phenyl or heteroaryl, wherein these rings may have 1 or 2 substituents selected from the group consisting of halogen, amino, methyl, methoxy, 1H-tetrazol-5-ylmethyl and $—(CH_2)nCOOH$ wherein n is an integer of 1 to 3; and Ar is phenyl having halogen on the ring.

Heteroaryl at $Z^1$ is exemplified by the following.

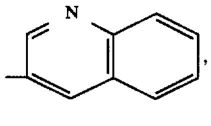,
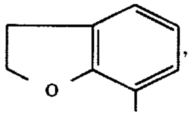,
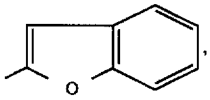,
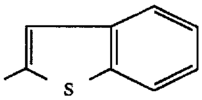

-continued

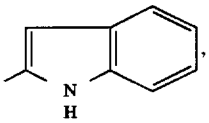, 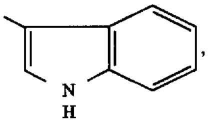,

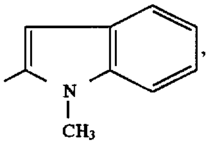, 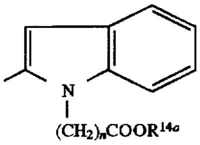

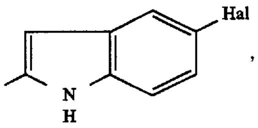,

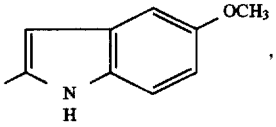, 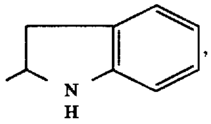,

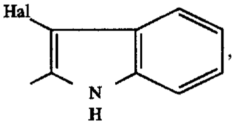,

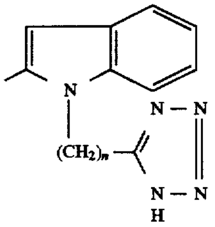

Each group of the formula (I) is most preferably as follows:

$R^1$ is hydrogen; $R^2$ is methyl, ethyl, propyl, isopropyl, cyclopropyl or —COOH; $R^3$ is hydrogen; —A=B— is —C($R^7$)=N— wherein $R^7$ is methyl, chlorine or bromine; Y is —NHCO— or —NHCONH—; $Z^1$ is 2-indolyl, 1-methyl-2-indolyl, 1-(1H-5-tetrazolylmethyl)-2-indolyl, 2-indolyl-1-acetic acid, 2-indolyl-1-propionic acid, 2-indolyl-1-butanoic acid, 2-amino-4-chlorophenyl, 3,4-dichlorophenyl, 3-chlorophenyl, 3-methylphenyl or 3-methoxyphenyl; and Ar is 2-chlorophenyl or 2-fluorophenyl.

Examples of the compounds of the formula (I) are as follows, wherein the numbers in the parentheses correspond to Example numbers:

(11) N-(4-(3-(2-chlorobenzoyl)-5-ethylthiophen-2-yl)-5-methyl[1,2,4]triazol-3-ylmethyl)-3,4-dichlorobenzamide,

(14) N-(4-(3-(2-chlorobenzoyl)-5-ethylthiophen-2-yl)-5-methyl[1,2,4]triazol-3-ylmethyl)indole-2-carboxamide,

(16) N-(4-(3-(2-chlorobenzoyl)-5-ethylthiophen-2-yl)-5-methyl[1,2,4]triazol-3-ylmethyl)-1-methylindole-2-carboxamide,

(19) 2-(4-(3-(2-chlorobenzoyl)-5-ethylthiophen-2-yl)-5-methyl[1,2,4]triazol-3-ylmethylcarbamoyl)indole-1-acetic acid,

(26) N-(4-(3-(2-chlorobenzoyl)-5-ethylthiophen-2-yl)-5-methyl[1,2,4]triazol-3-ylmethyl)-N'-(3-methylphenyl) urea,

(27) N-(4-(3-(2-chlorobenzoyl)-5-ethylthiophen-2-yl)-5-methyl[1,2,4]triazol-3-ylmethyl)-N'-(3-methoxyphenyl) urea,

(35) 2-(4-(3-(2-chlorobenzoyl)-5-ethylthiophen-2-yl)-5-ethyl[1,2,4]triazol-3-ylmethylcarbamoyl)indole-1-acetic acid,

(39) 2-(4-(3-(2-chlorobenzoyl)-5-ethylthiophen-2-yl)-5-cyclohexyl[1,2,4]triazol-3-ylmethylcarbamoyl)indole-1-acetic acid,

(40) N-(4-(3-(2-chlorobenzoyl)-5-ethylthiophen-2-yl)-5-trifluoromethyl[1,2,4]triazol-3-ylmethyl)-3,4-dichlorobenzamide,

(72) N-(3-bromo-4-(3-(2-chlorobenzoyl)-5-ethylthiophen-2-yl) [1,2,4]triazol-5-ylmethyl)indole-2-carboxamide, (182) 3-(2-(4-(3-(2-chlorobenzoyl)-5-ethylthiophen-2-yl)-5-methyl[1,2,4]triazol-3-ylmethylcarbamoyl)indol-1-yl) propionic acid, (198) N-(4-(3-(2-chlorobenzoyl)-5-methylthiophen-2-yl)-5-methyl[1,2,4]triazol-3-ylmethyl)indole-2-carboxamide, (226) N-(4-(5-ethyl-3-(2-fluorobenzoyl)thiophen-2-yl)-5-isopropyl[1,2,4]triazol-3-ylmethyl)indole-2-carboxamide, (240) N-(4-(3-(2-chlorobenzoyl)-5-ethylthiophen-2-yl)-5-isopropyl[1,2,4]triazol-3-ylmethyl)indole-2-carboxamide, (252) (3-(2-chlorobenzoyl)-2-(3-(2-indolecarbonylaminomethyl)-5-methyl[1,2,4]triazol-4-yl)thiophen-5-yl)carboxylic acid, (255) (3-(2-chlorobenzoyl)-2-(3-(3-(3-methoxyphenyl) ureidomethyl)-5-methyl[1,2,4]triazol-4-yl)thiophen-5-yl) carboxylic acid, (290) N-(4-(3-(2-chlorobenzoyl)-5-ethylthiophen-2-yl)-5-methyl-1,2,4-triazolo-3-ylmethyl)-1-(1H-tetrazol-5-yl) methylindole-2-carboxamide, (302) 4-((2-(4-(3-(2-chlorobenzoyl)-5-ethylthiophen-2-yl)-5-methyl[1,2,4]triazol-3-yl)methylcarbamoyl)indol-1-yl) butanoic acid, (316) ethyl 2-(5-chloro-4-(3-(2-chlorobenzoyl)-5-ethylthiophen-2-yl) [1,2,4]triazol-3-ylmethylcarbamoyl) indole-1-acetate, (338) 2-amino-4-chloro-N-(4-(3-(2-chlorobenzoyl)-5-ethylthiophen-2-yl)-5-methyl[1,2,4]triazol-3-ylmethyl) benzamide, (345) N-(4-(3-(2-chlorobenzoyl)-5-ethylthiophen-2-yl)-5-(1-adamantyl) [1,2,4]triazol-3-ylmethyl)indole-2-carboxamide, (368) N-(4-(3-(2-chlorobenzoyl)-5-propylthiophen-2-yl)-5-methyl[1,2,4]triazol-3-ylmethyl)indole-2-carboxamide, (369) N-(4-(3-(2-chlorobenzoyl)-5-isopropylthiophen-2-yl)-5-methyl[1,2,4]triazol-3-ylmethyl)indole-2-carboxamide, (370) N-(4-(3-(2-chlorobenzoyl)-5-cyclopropylthiophen-2-yl)-5-methyl[1,2,4]triazol-3-ylmethyl)indole-2-carboxamide, (371) N-(4-(3-(2-chlorobenzoyl)-5-propylthiophen-2-yl)-5-methyl[1,2,4]triazol-3-ylmethyl)-N'-(3-methoxyphenyl) urea, (372) N-(4-(3-(2-chlorobenzoyl)-5-isopropylthiophen-2-yl)-5-methyl[1,2,4]triazol-3-ylmethyl)-N'-(3-methoxyphenyl)urea, (373) N-(4-(3-(2-chlorobenzoyl)-5-cyclopropylthiophen-2-yl)-5-methyl[1,2,4]triazol-3-ylmethyl)-N'-(3-methoxyphenyl)urea,

(24) N-(4-(3-(2-chlorobenzoyl)-5-ethylthiophen-2-yl)-5-methyl[1,2,4]triazol-3-ylmethyl)-N'-(3-chlorophenyl) urea, (254) (3-(2-chlorobenzoyl)-2-(3-(3-(3-methylphenyl) ureidomethyl)-5-methyl[1,2,4]triazol-4-yl)thiophen-5-yl) carboxylic acid, (374) (3-(2-chlorobenzoyl)-2-(3-(3-(3-chlorophenyl)ureidomethyl)-5-methyl[1,2,4]triazol-4-yl)thiophen-5-yl)carboxylic acid, (253) (3-(2-chlorobenzoyl)-2-(3-(3-(2-chlorophenyl)ureidomethyl)-5-methyl[1,2,4]triazol-4-yl)thiophen-5-yl)carboxylic acid, (251) (3-(2-chlorobenzoyl)-2-(3-(3,4-dichlorobenzoylaminomethyl)-5-methyl[1,2,4]triazol-4-yl)thiophen-5-yl)carboxylic acid.

Each group of the formula (II) is preferably as follows:

$R^1$ is hydrogen, halogen or alkyl having 1 to 5 carbon atoms;

$R^2$ is hydrogen, halogen, alkyl having 1 to 5 carbon atoms, alkyl having 1 to 5 carbon atoms which substituted by 1 to 3 hydroxyl groups, alkanoyl having 2 to 5 carbon atoms, phenylalkyl wherein phenyl ring is substituted by alkyl having 1 to 5 carbon atoms, a group of the formula $-(CH_2)nCOOR^4$ wherein n is 0 or an integer of 1–5 and $R^4$ is hydrogen, alkyl having 1 to 5 carbon atoms or aralkyl, a group of the formula $-(CH_2)nCON(R^5)(R^6)$ wherein n is 0 or an integer of 1–5 and $R^5$ and $R^6$ are the same or different and each is hydrogen or alkyl having 1 to 5 carbon atoms, or $R^5$ and $R^6$ in combination optionally form, together with the adjacent nitrogen atom, hetero ring, a group of the formula $-C \equiv C-(CH_2)p-R^{21}$ wherein p is 0, 1 or 2 and $R^{21}$ is aryl or heterocyclic group, or a group of the formula $-C \equiv C-(CH_2)q-O-R^{22}$ wherein q is 1 or 2 and $R^{22}$ is aryl or heterocyclic group; or $R^1$ and $R^2$ combinedly form a ring, which optionally have a group of the formula $-(CH_2)nCON(R^{5a})(R^{6a})$ wherein n is 0 or an integer of 1–5, and $R^{5a}$ and $R^{6a}$ are the same or different and each is hydrogen or alkyl having 1 to 5 carbon atoms, or $R^{5a}$ and $R^{6a}$ in combination optionally form, together with the adjacent nitrogen atom, hetero ring, or $R^1$ and $R^2$ combinedly form a group of the formula

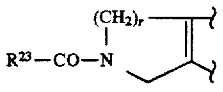

wherein r is 1 or 2, and $R^{23}$ is cycloalkyl having 3 to 7 carbon atoms;

$R^3$ is hydrogen, alkyl having 1 to 5 carbon atoms, a group of the formula $-(CH_2)nCOOR^{14}$ wherein n is 0 or an integer of 1–5, and $R^{14}$ is hydrogen, alkyl having 1 to 5 carbon atoms or aralkyl, or a group of the formula $-(CH_2)nN(R^{17})(R^{18})$ wherein n is 0 or an integer of 1–5, and $R^{17}$ and $R^{18}$ are the same or different and each is hydrogen or alkyl having 1 to 5 carbon atoms, or $R^{17}$ and $R^{18}$ in combination optionally form, together with the adjacent nitrogen atom, hetero ring;

$R^{19}$ is hydrogen, alkyl having 1 to 5 carbon atoms, a group of the formula $-(CH_2)nCOOR^{14b}$ wherein n is 0 or an integer of 1–5, and $R^{14b}$ is hydrogen, alkyl having 1 to 5 carbon atoms or aralkyl, or a group of the formula $-(CH_2)nN(R^{17b})(R^{18b})$ wherein n is 0 or an integer of 1–5, and $R^{17b}$ and $R^{18b}$ are the same or different and each is hydrogen or alkyl having 1 to 5 carbon atoms, or $R^{17b}$ and $R^{18b}$ in combination optionally form, together with the adjacent nitrogen atom, hetero ring;

m is 0 or an integer of 1–5;

Y is —NHCO—, —NHCONH—, —NHCSNH—, —$NHSO_2$—, —NHCOO—, —OCONH—, —OCO—, —NHCONHCO—, —NHCSNHCO—, —$NHCONHSO_2$—, —$NHCSNHSO_2$— or —NHCOCONH—;

$Z^2$ is alkenyl, alkynyl, cycloalkyl having 3 to 7 carbon atoms, cycloalkylalkyl, aralkyl, aryl, heteroaryl, heteroarylalkyl or a group of the formula $-CH=CH-R^{13}$ wherein $R^{13}$ is cycloalkyl having 3 to 7 carbon atoms, aryl or heteroaryl, wherein these rings in the definition of $Z^2$ are optionally substituted by an optional number of substituent (s) selected from the group consisting of halogen, hydroxyl group, amino, nitro, alkyl having 1 to 5 carbon atoms, alkyl having 1 to 5 carbon atoms which substituted by 1 to 3 hydroxyl groups, alkanoyl having 2 to 5 carbon atoms, haloalkyl having 1 or 2 carbon atoms, alkoxy having 1 to 5 carbon atoms, alkylthio having 1 to 5 carbon atoms, aryloxy, a group of the formula $-(CH_2)nCOOR^{14c}$ wherein n is 0 or an integer of 1–5, and $R^{14c}$ is hydrogen, alkyl having 1 to 5 carbon atoms or aralkyl, a group of the formula $-(CH_2)nCON(R^{15})(R^{16})$ wherein n is 0 or an integer of 1–5, and $R^{15}$ and $R^{16}$ are the same or different and each is hydrogen or alkyl having 1 to 5 carbon atoms, or $R^{15}$ and $R^{16}$ in combination optionally form, together with the adjacent nitrogen atom, hetero ring, and a group of the formula $-(CH_2)nN(R^{17c})(R^{18c})$ wherein n is 0 or an integer of 1–5, and $R^{17c}$ and $R^{18c}$ are the same or different and each is hydrogen or alkyl having 1 to 5 carbon atoms, or $R^{17c}$ and $R^{18c}$ in combination optionally form, together with the adjacent nitrogen atom, hetero ring; and Ar is phenyl, pyridyl, thienyl, or phenyl, pyridyl or thienyl, which have at least one substituent selected from the group consisting of halogen, alkyl having 1 to 5 carbon atoms, alkoxy having 1 to 5 carbon atoms, haloalkyl having 1 or 2 carbon atoms, alkylthio having 1 to 5 carbon atoms, carboxyl, carboxyalkyl, nitro, amino and hydroxyl group.

Each group of the formula (II) is more preferably as follows:

$R^1$ is hydrogen or alkyl having 1 or 2 carbon atoms;

$R^2$ is hydrogen, alkyl having 1 to 3 carbon atoms, cycloalkyl having 3 to 7 carbon atoms, $-(CH_2)nCOOR^4$ wherein n is 0 or 1 and $R^4$ is hydrogen or alkyl having 1 to 4 carbon atoms, or 5-tetrazolyl;

$R^3$ is hydrogen, alkyl having 1 to 3 carbon atoms, $-(CH_2)nCOOR^{14}$ wherein n is an integer of 1–3 and $R^{14}$ is hydrogen, cyclohexyl or benzyl, or $-(CH_2)nN(R^{17})(R^{18})$ wherein n is 0 or an integer of 1–5 and $R^{17}$ and $R^{18}$ are the same or different and each is hydrogen or alkyl having 1 to 5 carbon atoms;

$R^{19}$ is hydrogen or alkyl having 1 to 3 carbon atoms;

m is 0;

Y is —NHCO—, —NHCONH—, —NHCSNH— or $-NHSO_2-$;

$Z^2$ is aryl, heteroaryl or a group of the formula $$-CH=CH-R^{13}$$

wherein $R^{13}$ is phenyl, wherein these rings may have 1 or 2 substituents selected from the group consisting of halogen, amino, nitro, methyl, methoxy, $-(CH_2)nCOOR^{14c}$ wherein n is 1 or 2 and $R^{14c}$ is hydrogen or alkyl having 1 to 4 carbon atoms, and 1H-tetrazol-5-ylmethyl; and Ar is phenyl or phenyl having halogen on the ring.

Each group of the formula (II) is still more preferably as follows:

$R^1$ is hydrogen; $R^2$ is alkyl having 1 to 3 carbon atoms or cycloalkyl having 3 to 6 carbon atoms; $R^3$ is hydrogen or $-(CH_2)nCOOR^{14}$ wherein n is an integer of 1–3 and $R^{14}$ is hydrogen or cyclohexyl; $R^{19}$ is hydrogen; m is 0; Y is —NHCO— or —NHCONH—; $Z^2$ is phenyl or heteroaryl, wherein these rings may have 1 or 2 substituents selected from the group consisting of halogen, amino and methyl; and Ar is phenyl having halogen on the ring.

Heteroaryl at $Z^2$ is exemplified by the following.

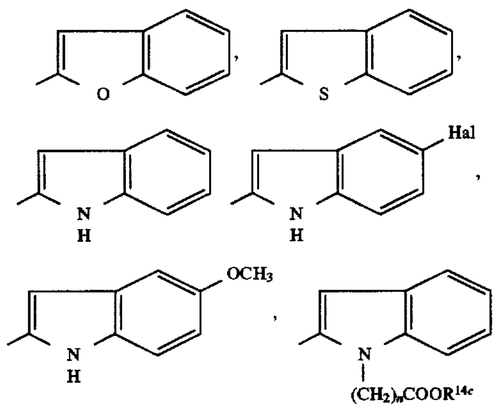

Each group of the formula (II) is most preferably as follows:

$R^1$ is hydrogen; $R^2$ is ethyl, propyl, isopropyl or cyclopropyl; $R^3$ is hydrogen or $-CH_2CH_2COOH$; $R^{19}$ is hydrogen; m is 0; Y is —NHCO— or —NHCONH—; $Z^2$ is 2-indolyl, 3,4-dichlorophenyl, 2-amino-4-chlorophenyl, 2-naphthyl, 3-quinolyl, 2-chlorophenyl or 3-methylphenyl; and Ar is 2-chlorophenyl or 2-fluorophenyl.

Examples of the compounds of the formula (II) are as follows, wherein the numbers in the parentheses correspond to Example numbers:

(59) N-(4-(2-chlorophenyl)-2-ethyl-6H-thieno[3,2-f] [1,2,4] triazolo[4,3-a] [1,4]diazepin-9-ylmethyl)-3,4-dichlorobenzamide,

(60) N-(4-(2-chlorophenyl)-2-ethyl-6H-thieno[3,2-f] [1,2,4] triazolo[4,3-a] [1,4]diazepin-9-ylmethyl)indole-2-carboxamide,

(65) N-(2-chlorophenyl)-N'-(4-(2-chlorophenyl)-2-ethyl-6H-thieno[3,2-f] [1,2,4]triazolo[4,3-a] [1,4]diazepin-9-ylmethyl)urea, (277) (R)-(−)-4-(3,4-dichlorobenzoylamino)-4-(4-(2-chlorophenyl)-2-ethyl-6H-thieno[3,2-f] [1,2,4]triazolo[4,3-a] [1,4]diazepin-9-yl)butanoic acid, (279) cyclohexyl (R)-(−)-4-(4-(2-chlorophenyl)-2-ethyl-6H-thieno[3,2-f] [1,2,4]triazolo[4,3-a] [1,4]diazepin-9-yl)-4-(1H-indole-2-carboxamide)butanoate, (280) (R)-(−)-4-(4-(2-chlorophenyl)-2-ethyl-6H-thieno[3,2-f] [1,2,4]triazolo[4,3-a] [1,4]diazepin-9-yl)-4-(1H-indole-2-carboxamide)butanoic acid, (353) N-(4-(2-chlorophenyl)-2-propyl-6H-thieno[3,2-f] [1,2,4]triazolo[4,3-a] [1,4]diazepin-9-ylmethyl)-3,4-dichlorobenzamide, (361) (R)-(−)-4-(4-(2-chlorophenyl)-2-ethyl-6H-thieno[3,2-f] [1,2,4]triazolo[4,3-a] [1,4]diazepin-9-yl)-4-(3-(2-chlorophenyl)ureido)butanoic acid, (365) (R)-(−)-5-(3,4-dichlorobenzoylamino)-5-(4-(2-chlorophenyl)-2-ethyl-6H-thieno[3,2-f] [1,2,4]triazolo[4,3-a] [1,4]diazepin-9-yl)pentanoic acid, (375) N-(4-(2-chlorophenyl)-2-propyl-6H-thieno[3,2-f] [1,2,4]triazolo[4,3-a] [1,4]diazepin-9-ylmethyl)indole-2-carboxamide, (376) N-(4-(2-chlorophenyl)-2-isopropyl-6H-thieno[3,2-f] [1,2,4]triazolo[4,3-a] [1,4]diazepin-9-ylmethyl)indole-2-carboxamide, (377) N-(4-(2-chlorophenyl)-2-cyclopropyl-6H-thieno[3,2-f] [1,2,4]triazolo[4,3-a] [1,4]diazepin-9-ylmethyl)indole-2-carboxamide, (378) N-(2-chlorophenyl)-N'-(4-(2-chlorophenyl)-2-propyl-6H-thieno[3,2-f] [1,2,4]triazolo[4,3-a] [1,4]diazepin-9-ylmethyl)urea, (379) N-(2-chlorophenyl)-N'-(4-(2-chlorophenyl)-2-isopropyl-6H-thieno[3,2-f] [1,2,4]triazolo[4,3-a] [1,4] diazepin-9-ylmethyl)urea, (380) N-(2-chlorophenyl)-N'-(4-(2-chlorophenyl)-2-cyclopropyl-6H-thieno[3,2-f] [1,2,4]triazolo[4,3-a] [1,4] diazepin-9-ylmethyl)urea, (382) (R)-4-(4-(2-chlorophenyl)-2-propyl-6H-thieno[3,2-f] [1,2,4]triazolo[4,3-a] [1,4]diazepin-9-yl)-4-(indole-2-carboxamide)butanoic acid, (384) (R)-4-(4-(2-chlorophenyl)-2-isopropyl-6H-thieno[3,2-f] [1,2,4]triazolo[4,3-a] [1,4]diazepin-9-yl)-4-(indole-2-carboxamide)butanoic acid, (386) (R)-4-(4-(2-chlorophenyl)-2-cyclopropyl-6H-thieno [3,2-f] [1,2,4]triazolo[4,3-a] [1,4]diazepin-9-yl)-4-(indole-2-carboxamide)butanoic acid, (388) (R)-4-(4-(2-chlorophenyl)-2-propyl-6H-thieno[3,2-f] [1,2,4]triazolo[4,3-a] [1,4]diazepin-9-yl)-4-(3-(2-chlorophenyl)ureido)butanoic acid, (390) (R)-4-(4-(2-chlorophenyl)-2-isopropyl-6H-thieno[3,2-f] [1,2,4]triazolo[4,3-a] [1,4]diazepin-9-yl)-4-(3-(2-chlorophenyl)ureido)butanoic acid, (392) (R)-4-(4-(2-chlorophenyl)-2-cyclopropyl-6H-thieno [3,2-f] [1,2,4]triazolo[4,3-a] [1,4]diazepin-9-yl)-4-(3-(2-chlorophenyl)ureido)butanoic acid.

Examples of pharmaceutically acceptable salts of the compound of formulas (I) and (II) include all salts.

However, preferred are salts with an inorganic acid such as hydrochloric acid, sulfuric acid, nitric acid, phosphoric acid and hydrobromic acid, salts with an organic acid such as acetic acid, propionic acid, succinic acid, glycolic acid, lactic acid, malic acid, tartaric acid, citric acid, ascorbic acid, maleic acid, fumaric acid, methanesulfonic acid, benzenesulfonic acid, p-toluenesulfonic acid and pamoic acid, salts with an alkali metal such as lithium, sodium, potassium, calcium, magnesium and aluminium, salts with an organic base such as piperidine, pyrrolidine, piperazine, morpholine, guanidine, dicyclohexylamine and N-methylglucamine, and salts with an amino acid such as aspartic acid, glutamic acid, lysine and arginine.

When the compound of the present invention has an asymmetric center in a molecule, the present invention encompasses optically pure enantiomorph, diastereomer and mixtures thereof.

The production methods of the compounds of the present invention of the formula (I) are shown in the following Method I-1 to Method I-15, to which the production methods are not limited.

Method I-1

A compound of the formula (I) wherein Y is —NHCO— is synthesized by condensing an amino compound of the formula

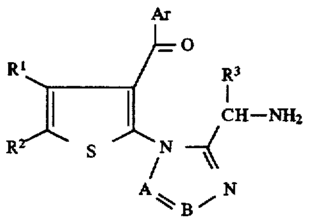

(I)

wherein each symbol is as defined above, or an acid addition salt thereof and a carboxylic acid of the formula $$HOOC—Z^1 \qquad (2)$$

wherein each symbol is as defined above, or a reactive derivative thereof.

The above condensation can be carried out by a known method such as amidation, peptide synthesis and the like. When the reactive derivative of carboxylic acid is an acid halide (e.g., acid chloride and acid bromide) or acid anhydride (e.g., symmetric acid anhydride, mixed anhydride with lower alkyl carbonate, and mixed anhydride with alkylphosphoric acid), the reaction is generally carried out in an inert solvent or without solvent, preferably in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) at a temperature of from −20° C. to 80° C. When the reactive derivative is a lower alkyl ester (e.g., methyl ester and ethyl ester) or a so-called active ester (e.g., 4-nitrophenyl ester, 4-chlorobenzyl ester, 4-chlorophenyl ester, succinimide ester, benzotriazole ester and 4-dimethylsulfoniumphenyl ester), the reaction is generally carried out in an inert solvent or without solvent at a temperature of from −20° C. to the refluxing temperature of the solvent. Amidation of free carboxylic acid is carried out in the presence of a condensing agent such as carbodiimide [e.g., N,N-dicyclohexylcarbodiimide and 1-ethyl-3-(3-dimethylaminopropyl)-carbodiimide], diphenylphosphorylazide, carbonyldiimidazole, 1-benzotriazolyloxytris(dimethylamino)phosphonium hexafluorophosphate (Bop reagent) and 2-chloro-N-methylpyridinium iodide-tributylamine (Mukaiyama method) in an inert solvent or without solvent, preferably at a temperature of from −20° C. to 80° C. These reactions generally end in 24 hours. The inert solvent to be used in the above-mentioned amidation is exemplified by hydrocarbons such as hexane, benzene, toluene and the like, halogenated hydrocarbons such as chloroform, dichloromethane, dichloroethane and the like, ethers such as tetrahydrofuran, dioxane and the like, esters such as acetate and the like, ketones such as acetone, methyl ethyl ketone and the like, amides such as dimethylformamide, dimethylacetamide and the like, acetonitrile, dimethyl sulfoxide and water, and a mixed solvent thereof, which can be selected as appropriate according to the reaction.

Method I-2

A compound of the formula (I) wherein Y is —NHCONH— is synthesized by reacting the amino compound of the formula (1) or an acid addition salt thereof with an isocyanate of the formula $$O{=}C{=}N—Z^1 \qquad (3)$$

wherein $Z^1$ is as defined above, or by reacting an amino compound of the formula $$H_2N—Z^1 \qquad (4)$$

wherein $Z^1$ is as defined above, with phosgene [e.g., trichloromethyl chloroformate and bis(trichloromethyl)carbonate] or carbonyldiimidazole, and then reacting the obtained reaction mixture with the amino compound of the formula (1) or an acid addition salt thereof.

These reactions are carried out in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) as necessary without solvent or in an inert solvent, preferably at a temperature of from −20° C. to 80° C. The reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method I-3

A compound of the formula (I) wherein Y is —NHCSNH— is synthesized by reacting the amino compound of the formula (1) or an acid addition salt thereof and an isothiocyanate of the formula $$S{=}C{=}N—Z^1 \qquad (5)$$

wherein $Z^1$ is as defined above. The reaction proceeds under the same conditions as in Method I-2.

Method I-4

A compound of the formula (I) wherein Y is $—NHSO_2—$ is synthesized by reacting the amino compound of the formula (1) or an acid addition salt thereof with a sulfonyl halide of the formula $$Z^1—SO_2—X^1 \qquad (6)$$

wherein $X^1$ is a halogen such as chlorine, bromine and the like, and $Z^1$ is as defined above, or with a sulfonic acid anhydride of the formula $(Z^1—SO_2)_2O$ (7)

wherein $Z^1$ is as defined above.

This amidation is carried out preferably in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) without solvent or in an inert solvent, preferably at a temperature of from −20° C. to 80° C. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method I-5

A compound of the formula (I) wherein Y is —NHCOO— is synthesized by reacting the amino compound of the formula (1) or an acid addition salt with a compound of the formula $Z^1—OCO—X^2$ (8)

wherein $X^2$ is a halogen such as chlorine, bromine and the like, and $Z^1$ is as defined above, or with a compound of the formula $(Z^1—OCO)_2O$ (9)

wherein $Z^1$ is as defined above.

This amidation is carried out preferably in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) without solvent or in an inert solvent, preferably at a temperature of from −20° C. to 80° C. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method I-6

The amino compound of the formula (1) is easily synthesized, for example, according to the method described in Japanese Patent Unexamined Publication No. 36677/1974 by hydrolyzing, with an acidic aqueous solution, a thienodiazepine compound of the formula

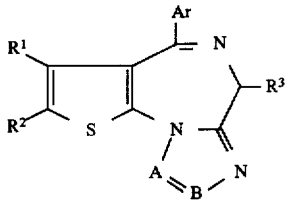

(10)

wherein each symbol is as defined above.

The reaction generally proceeds with ease in the presence of hydrochloric acid, sulfuric acid, phosphoric acid, p-toluenesulfonic acid, methanesulfonic acid, camphorsulfonic acid and the like, in an aqueous solution or an organic solvent containing water. The solvent to be used is exemplified by alcohols such as methanol, ethanol, isopropyl alcohol and the like, ethers such as tetrahydrofuran, dioxane and the like, amides such as dimethylformamide, dimethylacetamide and the like, and dimethyl sulfoxide. While the concentration of the acid and the reaction temperature depend on stability of diazepine ring of the compound of the formula (10) to be used, the reaction is generally carried out for 30 minutes to several hours at a pH of not more than 5 at a temperature of from room temperature to the refluxing temperature of the solvent. The obtained amino compound is separated as a suitable acid addition salt and can be used as a starting compound, or can be subjected to the next preparation step without separation.

Method I-7

A compound of the formula (I) wherein Y is —OCONH— is synthesized by reacting a hydroxy compound of the formula

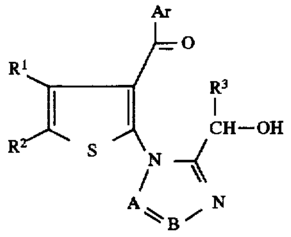

(11)

wherein each symbol is as defined above, with the isocyanate of the formula (3), or by reacting the amino compound of the formula (4) with phosgene [e.g., trichloromethyl chloroformate and bis(trichloromethyl)carbonate] or carbonyldiimidazole, and reacting the obtained reaction mixture with the hydroxy compound of the formula (11) or an acid addition salt thereof.

These reactions are carried out in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) as necessary without solvent or in an inert solvent, preferably at a temperature of from −20° C. to 80° C. The reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method I-8

A compound of the formula (I) wherein Y is —OCO— can be easily synthesized by a known esterification reaction of the carboxylic acid of the formula (2) or an acid halide thereof and the hydroxy compound of the formula (11).

When an acid halide of the compound of the formula (2), such as acid chloride, acid bromide and the like, is used, the esterification is carried out in an inert solvent or without solvent, preferably at a temperature of from −20° C. to the boiling point of the solvent to be used. When a free carboxylic acid of the formula (2) is used, the esterification is carried out in the presence of a condensing agent such as carbodiimide [e.g., N,N-dicyclohexylcarbodiimide and 1-ethyl-3-(3-dimethylaminopropyl)-carbodiimide] and carbonyldiimidazole, preferably at a temperature of from −20° C. to 80° C. The esterification can be carried out in an inert solvent, preferably in the presence of an acid catalyst (e.g., hydrogen chloride, sulfuric acid and p-toluenesulfonic acid). The reaction may rapidly proceed by raising the reaction temperature to the boiling point of the solvent to evaporate the water produced. The inert solvent for the above-mentioned esterification is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone and the like, dimethylformamide, dimethylacetamide, and dimethyl sulfoxide, and a mixed solvent thereof, which can be selected as appropriate according to the reaction.

Method I-9

The hydroxy compound of the formula (11) can be obtained by hydrolyzing the thienodiazepine compound of the formula (10) and then reacting the obtained compound with an alkali metal nitrite.

The hydrolysis of the compound of the formula (10) generally proceeds with ease in an aqueous solution in the presence of hydrochloric acid, sulfuric acid, phosphoric acid, p-toluenesulfonic acid, methanesulfonic acid and the like. While the concentration of the acid and the reaction temperature depend on stability of diazepine ring of the compound of the formula (10) to be used, the reaction is generally carried out for 30 minutes to several hours at a pH of not more than 5 at a temperature of from room temperature to the refluxing temperature of the solvent. Then, an alkali metal nitrite (e.g., sodium nitrite and potassium nitrite) is added to the reaction mixture, and the mixture is reacted at a temperature of from room temperature to under heating for several minutes to give the compound of the formula (11).

Method I-10

A compound of the formula (I) wherein —A=B— is —C($R^7$)=N— wherein $R^7$ is 1-hydroxyalkyl can be also synthesized from the compound of the formula (II) of the present invention. For example, a compound of the formula

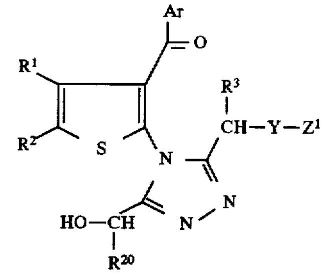

(I-a)

wherein $R^{20}$ is lower alkyl and other symbols are as defined above, can be also obtained by hydrolysis of a compound of the formula

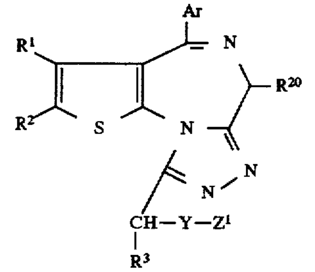

(12)

wherein each symbol is as defined above, and then reacting the obtained compound with an alkali metal nitrite.

The hydrolysis of the compound of the formula (12) generally proceeds easily in an aqueous solution in the presence of hydrochloric acid, sulfuric acid, phosphoric acid, p-toluenesulfonic acid, methanesulfonic acid and the like. While the concentration of the acid and the reaction temperature depend on stability of diazepine ring of the compound of the formula (12) to be used, the reaction is generally carried out for 30 minutes to several hours at a pH of not more than 5 at a temperature of from room temperature to the refluxing temperature of the solvent. Then, an alkali metal nitrite (e.g., sodium nitrite and potassium nitrite) is added to the reaction mixture, and the mixture is reacted at room temperature to under heating for several minutes to give the compound of the formula (I-a).

Method I-11

A compound of the formula (I) wherein —A=B— is —C($R^7$)=N— wherein $R^7$ is dimethylaminomethyl, can be also synthesized from the compound of the formula (II) of the present invention. For example, a compound of the formula

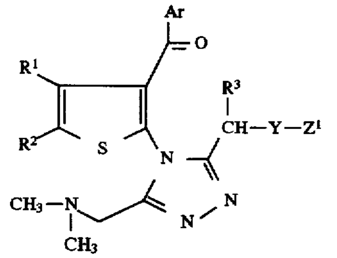

(I-b)

wherein each symbol is as defined above, can be also synthesized by reacting a compound of the following formula, which is a compound of the formula (II) wherein m is 0 and $R^{19}$ is hydrogen,

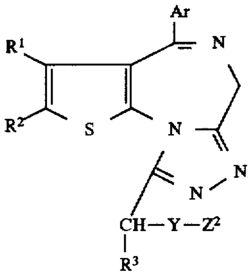

(13)

wherein each symbol is as defined above, with formic acid and formaldehyde.

The formic acid to be used may be one having a concentration of 60–90%, which is industrially available. Those having higher or lower concentrations may be also used. Formaldehyde may be an aqueous solution or a solid such as paraformaldehyde. The starting compound (13) is once hydrolyzed with formic acid to give a compound wherein $R^7$ is aminomethyl, and the obtained compound is reacted with formic acid and formaldehyde to give a compound wherein $R^7$ is dimethylaminomethyl. The reaction is preferably carried out in a solution of formic acid and formaldehyde as a solvent, but can be carried out in various inert solvents such as methanol, ethanol, tetrahydrofuran, dioxane, benzene, dimethylformamide and the like. Generally, it is most advantageous that the reaction be carried out for 1–24 hours while refluxing under heating. The reaction can be also carried out at a lower temperature.

Method I-12

A compound of the formula (I) wherein Y is —NHCONHCO— is synthesized by reacting the amino compound of the formula (1) or an acid addition salt thereof, with an isocyanate of the formula $$O{=}C{=}N{-}CO{-}Z^1 \qquad (14)$$

wherein $Z^1$ is as defined above.

The reaction proceeds under the same conditions as in Method I-2.

Method I-13

A compound of the formula (I) wherein Y is —NHCSNHCO— is synthesized by reacting the amino compound of the formula (I) or an acid addition salt thereof, with an isothiocyanate of the formula $$S{=}C{=}N{-}CO{-}Z^1 \qquad (15)$$

wherein $Z^1$ is as defined above.

The reaction proceeds under the same conditions as in Method I-2.

Method I-14

A compound of the formula (I) wherein Y is —$NHCONHSO_2$— is synthesized by reacting the amino compound of the formula (1) or an acid addition salt thereof, with an isocyanate of the formula $$O{=}C{=}N{-}SO_2{-}Z^1 \qquad (16)$$

wherein $Z^1$ is as defined above.

The reaction proceeds under the same conditions as in Method I-2.

Method I-15

A compound of the formula (I) wherein Y is —$NHCSNHSO_2$— is synthesized by reacting the amino compound of the formula (1) or an acid addition salt thereof, with an isothiocyanate of the formula $$S{=}C{=}N{-}SO_2{-}Z^1 \qquad (17)$$

wherein $Z^1$ is as defined above.

The reaction proceeds under the same conditions as in Method I-2.

Method I-16

A compound of the formula (I) wherein Y is —NHCOCONH— is synthesized by reacting the amino compound of the formula (4) or an acid addition salt thereof, with oxalyl chloride in an inert solvent in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) at room temperature or under ice-cooling, and then reacting the resulting reaction mixture with the amino compound of the formula (1) preferably at a temperature of from −20° C. to room temperature. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

The preparation methods of the compounds of the formula (II) are shown in the following Method II-1 to Method II-17, to which the preparation methods are not limited.

Method II-1

A compound of the formula (II) can be synthesized by reacting a thieno[2,3-e]-1,4-diazepine-2-thione compound of the formula

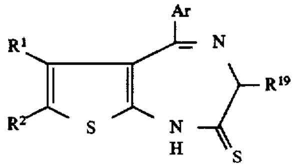

(21)

wherein each symbol is as defined above, which is synthesized by the method described in Arzneim.-Forsch./Drug Res., vol. 28, p. 1153, with an acid hydrazide compound of the formula $$H_2NNHCO{-}(CH_2)m{-}CH(R^3){-}Y{-}Z^2 \qquad (22)$$

wherein each symbol is as defined above.

The reaction generally proceeds in an inert solvent such as benzene, toluene, xylene, dioxane, tetrahydrofuran, methanol, ethanol, isopropyl alcohol and the like, in the presence of an organic acid (e.g., acetic acid, propionic acid and trifluoroacetic acid), an inorganic acid (e.g., hydrochloric acid and sulfuric acid) or silica gel, at a temperature of from room temperature to the refluxing temperature of the solvent used.

Method II-2

A compound of the formula (II) can be synthesized by reacting a compound of the formula

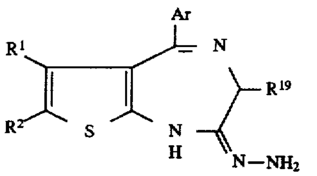

(23)

wherein each symbol is as defined above, which is obtained by reacting the compound of the formula (21) with hydrazine or a hydrate thereof, with a carboxylic acid of the formula $$HOOC-(CH_2)m-CH(R^3)-Y-Z^2 \quad (24)$$

wherein each symbol is as defined above, or a reactive derivative thereof, and then subjecting the obtained compound of the formula

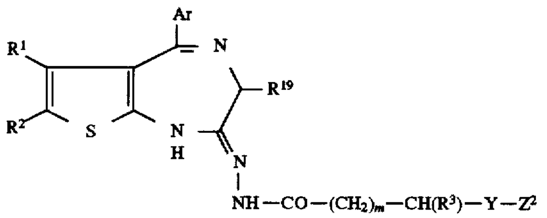

(25)

wherein each symbol is as defined above, to ring closure reaction to form a triazole ring.

The reaction of the compound of the formula (21) and hydrazine or a hydrate thereof generally proceeds in an inert solvent such as dioxane, tetrahydrofuran, methanol, ethanol, isopropyl alcohol, butanol and the like at a temperature of from −20° C. to 50° C.

In the reaction of the compound of the formula (23) and the compound of the formula (24), when the carboxylic acid derivative of the formula (24) is an acid halide (e.g., acid chloride and acid bromide) or an acid anhydride (e.g., symmetric acid anhydride, mixed anhydride with lower alkyl carbonate, and mixed anhydride with alkylphosphoric acid), the reaction is carried out in an inert solvent or without solvent in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) as necessary, at a temperature of from under ice-cooling to under heating. When the reactive derivative of the formula (24) is a lower alkyl ester (e.g., methyl ester and ethyl ester) or a so-called active ester (e.g., 4-nitrophenyl ester, 4-chlorobenzyl ester, 4-chlorophenyl ester, succinimide ester, benzotriazole ester and 4-dimethylsulfoniumphenyl ester), the reaction is carried out in an inert solvent or without solvent at a temperature of from room temperature to under heating. When the formula (24) is a free carboxylic acid, the amidation is carried out in the presence of a condensing agent such as carbodiimide [e.g., N,N-dicyclohexyl- carbodiimide and 1-ethyl-3-(3-dimethylaminopropyl)-carbodiimide], diphenylphosphoryl azide, carbonyldiimidazole, 1-benzotriazoryloxytris (dimethylamino)phosphonium hexafluorophosphate (Bop reagent), 2-chloro-N-methylpyridinium iodide-tributylamine (Mukaiyama method) in an inert solvent or without solvent preferably at a temperature of from −20° C. to 80° C. These reactions generally end in 24 hours. The inert solvent to be used is exemplified by hydrocarbons such as hexane, benzene, toluene and the like, alcohols such as methanol, ethanol, propanol, isopropyl alcohol, butanol and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof.

The compound of the formula (25) can be obtained by the above reactions, and can be converted to the compound of the formula (II) without separation. In this case, the reaction proceeds in the above-mentioned inert solvent, in the presence of an organic acid (e.g., acetic acid, propionic acid and trifluoroacetic acid), an inorganic acid (e.g., hydrochloric acid and sulfuric acid) or silica gel at a temperature of from room temperature to the refluxing temperature of the solvent used.

Method II-3

The compound of the formula (II) can be synthesized by reacting the compound of the formula (23) and an ortho ester derivative of the formula $$(R^{29}O)_3C-(CH_2)m-CH(R^3)-Y-Z^2 \quad (26)$$

wherein $R^{29}$ is alkyl having 1 to 5 carbon atoms and other symbols are as defined above.

The reaction generally proceeds in an inert solvent (e.g., benzene, toluene, xylene, dioxane, tetrahydrofuran, methanol, ethanol and isopropyl alcohol) in the presence of an organic acid (e.g., acetic acid, propionic acid and trifluoroacetic acid), an inorganic acid (e.g., hydrochloric acid and sulfuric acid) or silica gel at a temperature of from room temperature to the refluxing temperature of the solvent used.

Method II-4

A compound of the formula (II) wherein Y is —NHCO— is synthesized by condensing an amino compound of the formula

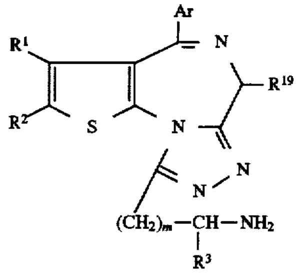

(27)

wherein each symbol is as defined above, or an acid addition salt thereof and a carboxylic acid of the formula $$HOOC-Z^2 \quad (28)$$

wherein $Z^2$ is as defined above, or a reactive derivative thereof.

The above-mentioned condensation can be carried out according to a known method such as amidation, peptide synthesis and the like. When the reactive derivative of carboxylic acid is an acid halide (e.g., acid chloride and acid bromide) or an acid anhydride (e.g., symmetric acid anhydride, mixed anhydride with lower alkyl carbonate, and mixed anhydride with alkylphosphoric acid), the reaction is generally carried out in an inert solvent or without solvent, preferably in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) at a temperature of from −20° C. to 80° C. When the reactive derivative is a lower alkyl ester (e.g., methyl ester and ethyl ester) or a so-called active ester (e.g., 4-nitrophenyl ester, 4-chlorobenzyl ester, 4-chlorophenyl ester, succinimide ester, benzotriazole ester and 4-dimethylsulfoniumphenyl ester), the reaction is generally carried out in an inert solvent or without solvent at a temperature of from −20° C. to the refluxing temperature of the solvent. Amidation of free carboxylic acid is carried out in the presence of a condensing agent such as carbodiimide [e.g., N,N-dicyclohexylcarbodiimide and 1-ethyl-3-(3-dimethylaminopropyl)-carbodiimide], diphenylphosphorylazide, carbonyldiimidazole, 1-benzotriazolyloxytris(dimethylamino)phosphonium hexafluorophosphate (Bop reagent), 2-chloro-N-methylpyridinium iodide-tributylamine (Mukaiyama method) in an inert solvent or without solvent preferably at a temperature of from −20° C. to 80° C. These reactions generally end in 24 hours. The inert solvent to be used in the above-mentioned amidation is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile, dimethyl sulfoxide and water, and a mixed solvent thereof, which can be selected as appropriate according to the reaction.

Method II-5

A compound of the formula (II) wherein Y is —NHCONH— is synthesized by reacting the amino compound of the formula (27) or an acid addition salt thereof with an isocyanate of the formula $$O{=}C{=}N{-}Z^2 \quad (29)$$

wherein $Z^2$ is as defined above, or by reacting an amino compound of the formula $$H_2N{-}Z^2 \quad (30)$$

wherein $Z^2$ is as defined above, with phosgene [e.g., trichloromethyl chloroformate and bis(trichloromethyl)carbonate] or carbonyldiimidazole, and then reacting the resulting reaction mixture with the amino compound of the formula (27) or an acid addition salt thereof.

The reaction is carried out in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) as necessary, without solvent or in an inert solvent, preferably at a temperature of from −20° C. to 80° C. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method II-6

A compound of the formula (II) wherein Y is —NHCSNH— is synthesized by reacting the amino compound of the formula (27) or an acid addition salt thereof with an isothiocyanate of the formula $$S{=}C{=}N{-}Z^2 \quad (31)$$

wherein $Z^2$ is as defined above.

The reaction proceeds under the same conditions as in Method II-5.

Method II-7

A compound of the formula (II) wherein Y is —$NHSO_2$— is synthesized by reacting the amino compound of the formula (27) or an acid addition salt thereof with a sulfonyl halide of the formula $$Z^2{-}SO_2{-}X^3 \quad (32)$$

wherein $X^3$ is halogen such as chlorine, bromine and the like and $Z^2$ is as defined above, or a sulfonic acid anhydride of the formula $$(Z^2{-}SO_2)_2O \quad (33)$$

wherein $Z^2$ is as defined above.

The amidation is carried out preferably in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide), without solvent or in an inert solvent, preferably at a temperature of from −20° C. to 80° C. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method II-8

A compound of the formula (II) wherein Y is —NHCOO— is synthesized by reacting the amino compound of the formula (27) or an acid addition salt thereof with a compound of the formula $$Z^2{-}OCO{-}X^4 \quad (34)$$

wherein $X^4$ is a halogen such as chlorine, bromine and the like and $Z^2$ is as defined above, or a compound of the formula $$(Z^2{-}OCO)_2O \quad (35)$$

wherein $Z^2$ is as defined above.

The amidation is carried out preferably in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide), without solvent or in an inert solvent, preferably at a temperature of from −20° C. to 80° C. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method II-9

The amino compound of the formula (27) is easily synthesized, for example, according to the method described in Japanese Patent Unexamined Publication No. 102698/1974, by deprotecting an amino group of the compound of the formula

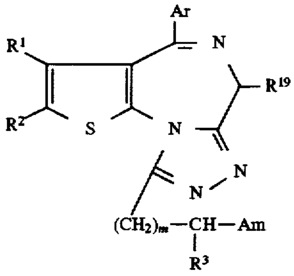
(36)

wherein Am is a protected amino group and other symbols are as defined above.

The amino-protecting group is that which is commonly used in organic chemistry, such as tert-butyloxycarbonyl, phthaloyl, (substituted) benzoyl, acetyl, trifluoroacetyl, benzyloxycarbonyl and the like. These protecting groups are easily eliminated by a method using an acid (e.g., hydrofluoric acid, methanesulfonic acid, trifluoromethanesulfonic acid, hydrochloric acid, hydrobromic acid, trifluoroacetic acid and formic acid), or a method using a base such as an alkali metal hydroxide (e.g., sodium hydroxide, potassium hydroxide and barium hydroxide), hydrazine and a hydrate thereof, or hydrogenolysis using a metal catalyst (e.g., palladium and Raney nickel).

Method II-10

A compound of the formula (II) wherein Y is —OCONH— is synthesized by reacting a hydroxy compound of the formula

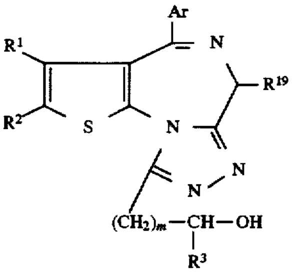
(37)

wherein each symbol is as defined above, with the isocyanate of the formula (29), or by reacting the amino compound of the formula (30) with phosgene [e.g., trichloromethyl chloroformate and bis(trichloromethyl)carbonate] or carbonyldiimidazole, and then reacting the resulting reaction mixture with the hydroxy compound of the formula (37) or an acid addition salt thereof.

The reaction is carried out in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) as necessary, without solvent or in an inert solvent, preferably at a temperature of from −20° C. to 80° C. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Method II-11

A compound of the formula (II) wherein Y is —OCO— can be easily synthesized by a known esterification reaction of the carboxylic acid of the formula (28) or an acid halide thereof and the hydroxy compound of the formula (37).

When an acid halide of the compound of the formula (28) such as acid chloride, acid bromide and the like is used, the esterification is carried out in an inert solvent or without solvent, preferably at a temperature of from −20° C. to the boiling point of the solvent to be used. When a free carboxylic acid of the formula (28) is used, the esterification is carried out in the presence of a condensing agent such as carbodiimide [e.g., N,N-dicyclohexylcarbodiimide and 1-ethyl-3-(3-dimethylaminopropyl)-carbodiimide] and carbonyldiimidazole, preferably at a temperature of from −20° C. to 80° C. The esterification can be carried out in an inert solvent, preferably in the presence of an acid catalyst (e.g., hydrogen chloride, sulfuric acid and p-toluenesulfonic acid). The reaction may rapidly proceed by raising the reaction temperature to the boiling point of the solvent to evaporate the water produced. The inert solvent of the above-mentioned esterification is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone and the like, dimethylformamide, dimethylacetamide and dimethyl sulfoxide, and a mixed solvent thereof, which can be selected as appropriate according to the reaction.

Method II-12

The hydroxy compound of the formula (37) is easily synthesized according to a known method such as the method described in Japanese Patent Unexamined Publication No. 102698/1974.

Method II-13

A compound of the formula (II) wherein Y is —NHCONHCO— is synthesized by reacting the amino compound of the formula (27) or an acid addition salt thereof with an isocyanate of the formula $$O{=}C{=}N{-}CO{-}Z^2 \quad (38)$$

wherein $Z^2$ is as defined above.

The reaction proceeds under the same conditions as in Method II-5.

Method II-14

A compound of the formula (II) wherein Y is —NHCSNHCO— is synthesized by reacting the amino compound of the formula (27) or an acid addition salt thereof with an isothiocyanate of the formula $$S{=}C{=}N{-}CO{-}Z^2 \quad (39)$$

wherein $Z^2$ is as defined above.

The reaction proceeds under the same conditions as in Method II-5.

Method II-15

A compound of the formula (II) wherein Y is —$NHCONHSO_2$— is synthesized by reacting the amino compound of the formula (27) or an acid addition salt thereof with an isocyanate of the formula $O{=}C{=}N{-}SO_2{-}Z^2$ (40)

wherein $Z^2$ is as defined above.

The reaction proceeds under the same conditions as in Method II-5.

Method II-16

A compound of the formula (II) wherein Y is $-NHCSNHSO_2-$ is synthesized by reacting the amino compound of the formula (27) or an acid addition salt thereof with an isothiocyanate of the formula $S{=}C{=}N{-}SO_2{-}Z^2$ (41)

wherein $Z^2$ is as defined above.

The reaction proceeds under the same conditions as in Method II-5.

Method II-17

A compound of the formula (II) wherein Y is —NHCOCONH— is synthesized by reacting the amino compound of the formula (30) or an acid addition salt thereof with oxalyl chloride in an inert solvent in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) at room temperature or under ice-cooling, and then reacting the obtained compound with the amino compound of the formula (27), preferably at a temperature of from −20° C. to room temperature. These reactions generally end in 24 hours. The inert solvent to be used is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile and dimethyl sulfoxide, and a mixed solvent thereof, which can be selected as appropriate according to the reaction.

Of the compounds of the formula (I) and formula (II) of the present invention, a compound having an acid amide structure of $-(CH_2)nCON(R^5)(R^6)$, $-(CH_2)nCON(R^9)(R^{10})$ or $-(CH_2)nCON(R^{15})(R^{16})$ is also synthesized by condensing the corresponding carboxylic acid or a reactive derivative thereof and an amino compound of the formula $HN(R^a)(R^b)$ (42)

wherein $R^a$ and $R^b$ are $R^5$ and $R^6$, $R^9$ and $R^{10}$, or $R^{15}$ and $R^{16}$, respectively, and each symbol is as defined above.

The above-mentioned amidation can be carried out according to a known method such as amidation, peptide synthesis and the like. When the reactive derivative of carboxylic acid is an acid halide (e.g., acid chloride and acid bromide) or an acid anhydride (e.g., symmetric acid anhydride, mixed anhydride with lower alkyl carbonate, and mixed anhydride with alkylphosphoric acid), the reaction is generally carried out in an inert solvent or without solvent, preferably in the presence of an acid scavenger such as an organic base (e.g., triethylamine, N-methylmorpholine, pyridine and dimethylaniline) or an inorganic base (e.g., alkali hydrogencarbonate, alkali carbonate and alkali hydroxide) at a temperature of from −20° C. to 80° C. When the reactive derivative is a lower alkyl ester (e.g., methyl ester and ethyl ester) or a so-called active ester (e.g., 4-nitrophenyl ester, 4-chlorobenzyl ester, 4-chlorophenyl ester, succinimide ester, benzotriazole ester and 4-dimethylsulfoniumphenyl ester), the reaction is generally carried out in an inert solvent or without solvent at a temperature of from −20° C. to the refluxing temperature of the solvent. Amidation of free carboxylic acid is carried out in the presence of a condensing agent such as carbodiimide [e.g., N,N-dicyclohexylcarbodiimide and 1-ethyl-3-(3-dimethylaminopropyl)carbodiimide], diphenylphosphorylazide, carbonyldiimidazole, 1-benzotriazolyloxytris(dimethylamino)phosphonium hexafluorophosphate (Bop reagent) and 2-chloro-N-methylpyridinium iodide-tributylamine (Mukaiyama method) in an inert solvent or without solvent, preferably at a temperature of from −20° C. to 80° C. These reactions generally end in 24 hours. The inert solvent to be used in the above-mentioned amidation is exemplified by hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, amides such as dimethylformamide, dimethylacetamide and the like, acetonitrile, dimethyl sulfoxide and water, and a mixed solvent thereof, which can be selected as appropriate according to the reaction.

Of the compounds of the formulas (I) and (II), a compound having a free carboxyl group can be also synthesized by a synthesis with protection of carboxyl as an ester and deprotection at the final step. The deprotection in this case includes those known in organic chemistry (e.g., hydrolysis using acid or base and catalytic reduction using metallic catalyst). A compound having hydroxy can be also synthesized in the same manner as above by a synthesis with protection of hydroxy and deprotection at the final step. The protecting group includes, for example, (substituted) acetyl, (substituted) benzoyl, (substituted) benzyl, (substituted) tert-butyl, tetrahydropyranyl, trimethylsilyl and tert-dibutyldimethylsilyl, which may be eliminated with ease by a known method.

Of the compounds of the formulas (I) and (II), a compound having a free 5-tetrazolyl can be synthesized with protection of tetrazole ring with trityl, (substituted) benzyl and the like, and deprotection at the final step, or by conversion of cyano or cyanoalkyl represented by $-(CH_2)nCN$ which has been obtained by conversion of a compound having an amide structure represented by $-(CH_2)nCONH_2$ by dehydration, and conversion of such cyano to 5-tetrazolyl. This tetrazolylation can be carried out by reacting a cyano compound with sodium azide or trimethylsilyl azide in an inert solvent such as benzene, toluene, xylene, dimethylformamide, pyridine, chloroform, dichloromethane, 1,2-dichloroethane, methanol and ethanol at a temperature of from 0° C. to 250° C.

Of the compounds of the formulas (I) and (II), a compound wherein $Z^1$ and $Z^2$ are 2-indole and the 3-position of the indole ring is substituted by halogen can be also synthesized by directly subjecting a compound wherein the 3-position of indole ring is hydrogen to halogenation. For example, fluorine gas, transition metal fluoride (e.g., cobalt fluoride, silver fluoride and cesium fluoride) or a fluoridated reagent (e.g., 1-fluoro-2,6-dichloropyridine, 1-fluoro-3,5-dichloropyridine and 1-fluoropyridine) is used for fluoridation; chlorine, sulfuryl chloride, phosphorus pentachloride, copper(II) chloride and the like are used for chlorination; and bromine is used for bromination. These halogenation reactions are carried out in an inert solvent or without solvent, preferably at −20° C.–80° C. In general, these reactions end in 24 hours. Examples of the inert solvent to be used for the above halogenation include hydrocarbons such as hexane, benzene, toluene and the like, halogenated hydrocarbons such as chloroform, dichloromethane, dichloroethane and the like, ethers such as tetrahydrofuran, dioxane, diethyl ether, diisopropyl ether and the like, esters such as acetate and the like, ketones such as acetone, methyl ethyl ketone and the like, alcohols such as methanol, ethanol, isopropyl alcohol and the like, and amides such as dimethylformamide, dimethylacetamide and the like, acetonitrile, dimethyl sulfoxide and water, and a mixed solvent thereof, which can be selected as appropriate according to the reaction.

The compounds of the formulas (I) and (II) thus obtained can be converted to their salts by, for example, treating the compounds with an inorganic acid such as hydrochloric acid, sulfuric acid, nitric acid, phosphoric acid and hydrobromic acid; an organic acid such as acetic acid, propionic acid, succinic acid, glycolic acid, lactic acid, malic acid, tartaric acid, citric acid, ascorbic acid, maleic acid, fumaric acid, methanesulfonic acid, benzenesulfonic acid, p-toluenesulfonic acid and pamoic acid; an alkali metal such as lithium, sodium, potassium, calcium, magnesium and aluminum; an organic base such as piperidine, pyrrolidine, piperazine, morpholine, guanidine and dicyclohexylamine; or an amino acid such as aspartic acid, glutamic acid, lysine and arginine by a conventional method.

When the compound of the present invention has an asymmetric center in a molecule, the compound is generally obtained as a racemate. The racemate can be resolved into optical isomers by a conventional method such as chromatography using a column containing an optically active carrier. Such optical isomer can be also produced by the use of an optically active starting compound. Respective diastereomers can be purified by fractional crystallization using an optically active acid or base, or chromatography.

The compounds of the formulas (I) and (II) of the present invention show superior CCK and gastrin antagonistic activities, particularly a strong selective antagonistic action on CCK-A receptor, as well as strong and long-lasting suppression of the secretion of pancreatic enzyme and gastric acid. Thus, the compounds of the present invention are useful as agents for prophylaxis and treatment of diseases of central and peripheral nervous systems, such as anxiety, schizophrenia, dementia, pain, sitophobia, emesis and the like, and digestive diseases such as pancreatitis, gallbladder disorders, gastric ulcer and enterelcosis, irritable bowel syndrome, constipation, pancreatic malignant tumor and the like. Inasmuch as the compounds of the present invention are superior in solubility in water and have extremely weak affinity for benzodiazepine receptor, they can make pharmaceutical agents superior in properties such as bioavailability and safety. Moreover, the compound of the formula (II) can be used as a synthesis starting material of the compound of the formula (I).

The pharmacological activity of the compounds of the present invention is shown in the following.

Experimental Example 1

Binding to CCK receptor

Whole pancreas was removed from male Wister rats. Fat tissue was removed and the pancreas was homogenized (Blinkman Polytron PT20) in 10 mM MES buffer (0.02% Bacitracin, 0.02% soy bean-derived trypsin inhibitor, 0.0001% phenylmethanesulfonyl fluoride, pH 6.5). The homogenate was passed through a nylon cloth (120 mesh) and the filtrate was centrifuged at 40,000×g for 15 minutes. The obtained sediment was homogenized in Tris buffer and centrifuged in the same manner as above. The sediment was suspended in a buffer for binding assay (50 mM MES containing 130 mM sodium chloride, 4.7 mM potassium chloride, 5 mM magnesium chloride, 0.02% Bacitracin, 0.0001% phenylmethanesulfonyl fluoride, pH 6.5) and used as a peripheral receptor source. In the case of central tissue, rat cerebral cortex was used for the preparation by suspending same in a buffer (pH 6.5) containing 5 mM magnesium chloride, 1 mM EGTA [ethylene glycol bis(2-aminoethylether)tetraacetic acid], 360 mM sodium chloride, 15 mM potassium chloride, 20 mM HEPES (N-2-hydroxyethylpiperazine-N'-2-ethanesulfonic acid) and 0.25 mg/ml Bacitracin. For binding assay, 50 μl buffer (for total binding use) and unlabelled CCK-8 sulfate (for non-specific binding) having a final concentration of 1 μM or a test compound ($^{125}$I-CCK-8, 63–67 TBq/mmol, 40,000–50,000 cpm, 50 μl) were added to a membrane suspension (450 μl, containing 100 μg as protein). The reaction mixture was incubated at 20° C. for 30 minutes and filtered through a glass fiber filter (Whatman G/FB) by suction. Immediately thereafter, the filter was washed three times with ice-cold Tris buffer (2.5 ml) and the radioactivity on the filter was determined.

The effects of the test compound on the CCK receptor binding were evaluated by the concentration ($IC_{50}$, nM) necessary for inhibiting the specific binding by 50%, which was obtained by calculating the inhibition ratio by the following formula:

$$\%\ \text{Inhibition} = 100 - \frac{\text{Binding when compound was added} - \text{non-specific binding}}{\text{Total binding} - \text{non-specific binding}} \times 100$$

The results of the effects of the test compounds on the CCK receptor binding are shown in the following

| Test compound (Example No.) | Pancreas (CCK-A) $IC_{50}$ (nM) | Brain (CCK-B) $IC_{50}$ (nM) |
|---|---|---|
| 11 | 7.5 | >1000 |
| 14 | 3.7 | >1000 |
| 19 | 10.6 | >1000 |
| 26 | 5.6 | >1000 |
| 27 | 4.8 | >1000 |
| 59 | 13.0 | >1000 |
| 72 | 3.2 | >1000 |
| 226 | 11.0 | >1000 |
| 252 | 6.6 | >1000 |
| 277 | 9.6 | >1000 |
| 280 | 2.7 | >1000 |
| 316 | 2.5 | >1000 |
| 338 | 7.6 | >1000 |

In the following, the test method with respect to CCK-A antagonistic action is shown.

Experimental Example 2

Effects on CCK-induced secretion of pancreatic juice in guinea pig under anesthesia Male guinea pigs weighing about 650 g were anesthetized by subcutaneous administration of urethane (1.6 g/kg), and a cannula for injection of perfusing solution was inserted into the pyloric part of stomach and a discharge cannula was inserted at a position 2 cm distal from Treitz ligament. Duodenum was perfused with physiological saline at a rate of 8 ml/15 min, and trypsin secretion in the perfusate was determined. For the determination, Na-benzoyl-arginine p-nitroanilide (BAPNA) was used as a synthetic substrate and spectrophotometer was used for the determination. Secretion of pancreatic juice was induced by an intravenous administration of CCK-8 (0.1 μg/kg), and 60 minutes later, CCK-8 was administered again. The inhibition ratio of the test compound which was intravenously administered at 5 minutes before the second administration of CCK-8 was calculated by the following formula:

% Inhibition = {1 − (amount of tryspin secreted in 60 minutes as a result of induction by second *CCK* administration/amount of secretion induced by first *CCK* administration)} × 100

The effects of the test compounds on inhibition of secretion of pancreatic juice induced by CCK receptor in guinea pig under anesthesia are shown in the following

| Test compound (Example No.) | Dose (μg/kg) | Inhibition (%) |
|---|---|---|
| 19 | 300 | 81.9 ± 5.9 (n = 4) |
| 252 | 300 | 82.6 ± 2.6 (n = 4) |
| 277 | 300 | 85.1 ± 12.1 (n = 2) |
| 280 | 300 | 78.1 ± 7.6 (n = 4) |

Experimental Example 3

Effects on caerulein-induced pancreatitis in rat models

The method described in Pancreas, Vol. 5, p. 284 (1990) is modified and used. Caerulein (20 μg/kg) is subcutaneously administered 4 times at one hour intervals to male rats weighing about 200 g. Blood is taken and pancreas is removed at 4 hours after the last administration. The amylase activity in blood is determined by the method using maltopentaose as a synthetic substrate. After weighing and fixing with a 10% aqueous formalin solution, the pancreas is subjected to hematoxylin-eosin staining and microscopy with an optical microscope. The test compound is administered orally or intravenously at 30 minutes before the first caerulein administration. Amylase activity and inhibition of pancreatic weight gaining are calculated by the following formulas. The tissue is rated 0 when changes are not found, and rated from 1 to 4 depending on the degree of changes found in the tissue, which rating being used to indicate improvement in pancreatic tissue disorders.

Amylase activity inhibition (%) = {1 − (Average amylase activity of group administered with test compound/Average amylase activity of control group)} × 100

Inhibition (%) of pancreas weight = {1 − (Average pancreas weight of group administered with test compound/Average pancreas weight of control group)} × 100

Experimental Example 4

Effects on CCK-induced delay in gastric emptying in mice

The test compound is orally or intravenously administered to male mice weighing about 20 g and at 25 minutes thereafter, CCK-8 (30 μg/kg) is subcutaneously administered. Five minutes later, 1.5% aqueous methyl cellulose solution (0.1 ml) containing 0.05% phenol red is orally administered. Fifteen minutes later, the content of the stomach is recovered and mixed with 10% aqueous trichloroacetic acid solution for deproteinization. After centrifugation, 1N NaOH is added to the supernatant and recentrifuged. Absorbance (590 nm) of the supernatant is determined by spectrophotometer. The ratio of improvement is calculated by the following formula.

Improvement (%) = {1 − (Average absorbance of group administered with test compound/Average absorbance of control group)} × 100

By admixing the compound of the formula (I) or (II) of the present invention and a pharmaceutically acceptable additive, a pharmaceutical composition is provided. The above-mentioned additive includes, for example, pharmaceutically acceptable carriers, excipients, diluents, solubilizers, disintegrants, binders and the like. The pharmaceutical composition is prepared by mixing the compound of the formula (I) or (II) and the above-mentioned additive to give tablets, powders, capsules, injections, suppositories, infusions and the like, which can be safely administered to patients by an oral or parenteral route. The dose is generally about 0.5–1,000 mg by oral administration and about 0.1–500 mg by intravenous administration to an adult per day.

BEST MODE FOR CARRYING OUT THE INVENTION

The present invention is described in more detail in the following by illustrative Starting Material Preparation Examples (Production Examples) and Examples, to which the present invention is not limited.

Production Example 1

4-(2-Chlorophenyl)-2-ethyl-6H-thieno[3,2-f] [1,2,4]triazolo[4,3-a] [1,4]diazepine (50 g) was stirred at 60° C. for 7 hours with 2.5% hydrochloric acid (1 l). Then, sodium hydrogencarbonate was added to the reaction mixture to make the solution alkaline. The mixture was extracted with ethyl acetate and the extract was dried over sodium sulfate. A solution of p-toluenesulfonic acid (58 g) in methanol was added thereto, and the mixture was allowed to stand overnight. The reaction mixture was filtered to give crystals and the crystals were washed with ethyl acetate and dried to give 50 g of 3-aminomethyl-4-(3-(2-chlorobenzoyl)-5-ethylthiophen-2-yl) [1,2,4]triazole di-p-toluenesulfonate.

Production Example 2

4-(2-Chlorophenyl)-2-ethyl-9-methyl-6H-thieno[3,2-f] [1,2,4]triazolo[4,3-a] [1,4]diazepine (702 g) was suspended in a mixed solvent (4.9 l) of ethanol and water (9:1), and p-toluenesulfonic acid monohydrate (1165 g) was added. The mixture was stirred at 80° C. for 1.5 hours. The mixture was concentrated to about 2.5 l by evaporating the solvent under reduced pressure, and ethyl acetate (4 l) was added. The reaction mixture was filtered to give crystals, and the crystals were washed with ethyl acetate and ethanol and dried to give 1214 g of 3-aminomethyl-4-(3-(2-chlorobenzoyl)-5-ethylthiophen-2-yl)-5-methyl[1,2,4] triazole di-p-toluenesulfonate.

m.p. 179°–180° C. (dec.)

EXAMPLE 1

3-Aminomethyl-4-(3-(2-chlorobenzoyl)-5-ethylthiophen-2-yl) [1,2,4]triazole di-p-toluenesulfonate (2.0 g) was dissolved in dimethylformamide (20 ml), and benzoyl chloride (0.42 ml) and triethylamine (1.5 ml) were added under ice-cooling. The mixture was stirred at room temperature for 8 hours. A saturated aqueous sodium hydrogencarbonate solution was added to the reaction mixture, and the mixture was extracted with ethyl acetate. The organic layer was washed with an aqueous citric acid solution and saturated brine, and dried over magnesium sulfate. After the solvent was evaporated, the residue was recrystallized from ethyl acetate to give 0.3 g of N-(4-(3-(2-chlorobenzoyl)-5-ethylthiophen-2-yl) [1,2,4]triazol-3-ylmethyl)benzamide.

m.p. 140°–142° C.

EXAMPLE 2

3,4-Dichlorobenzoic acid (1.52 g) and thionyl chloride (6.0 ml) were added to dichloroethane (15 ml), and the mixture was refluxed with stirring for 1 hour. The solvent was evaporated, and the residue was dissolved in dimethylformamide (20 ml). 3-Aminomethyl-4-(3-(2-chlorobenzoyl)-5-ethylthiophen-2-yl) [1,2,4]triazole di-p-toluenesulfonate (5.0 g) and triethylamine (5.0 ml) were added under ice-cooling. The mixture was stirred at room temperature for 1 hour. A saturated aqueous sodium hydrogencarbonate solution was added to the reaction mixture, and the mixture was extracted with ethyl acetate. The organic layer was washed with an aqueous citric acid solution and saturated brine, and dried over magnesium sulfate. The solvent was evaporated, and the residue was recrystallized from ethyl acetate to give 1.62 g of N-(4-(3-(2-chlorobenzoyl)-5-ethylthiophen-2-yl) [1,2,4]triazol-3-ylmethyl)-3,4-dichlorobenzamide.

m.p. 158°–160° C.

EXAMPLE 3

N-(4-(3-(2-Chlorobenzoyl)-5-ethylthiophen-2-yl) [1,2,4] triazol-3-ylmethyl)naphthalene-2-carboxamide (0.98 g) was obtained in the same manner as in Example 2 using naphthalene-2-carboxylic acid (1.49 g) and 3-aminomethyl-4-(3-(2-chlorobenzoyl)-5-ethylthiophen-2-yl) [1,2,4] triazole di-p-toluenesulfonate (5.0 g).

m.p. 128°–130° C.

EXAMPLE 4

N-(4-(3-(2-Chlorobenzoyl)-5-ethylthiophen-2-yl) [1,2,4] triazol-3-ylmethyl)quinoline-3-carboxamide (1.17 g) was obtained in the same manner as in Example 2 using quinoline-3-carboxylic acid (1.54 g) and 3-aminomethyl-4-(3-(2-chlorobenzoyl)-5-ethylthiophen-2-yl) [1,2,4]triazole di-p-toluenesulfonate (5.0 g).

m.p. 160°–162° C.

EXAMPLE 5

N-(4-(3-(2-Chlorobenzoyl)-5-ethylthiophen-2-yl) [1,2,4] triazol-3-ylmethyl)indole-2-carboxamide (0.67 g) was obtained in the same manner as in Example 2 using indole-2-carboxylic acid (1.40 g) and 3-aminomethyl-4-(3-(2-chlorobenzoyl)-5-ethylthiophen-2-yl) [1,2,4]-triazole di-p-toluenesulfonate (5.0 g).

m.p. 234°–235° C.

EXAMPLE 6

N-(4-(3-(2-Chlorobenzoyl)-5-ethylthiophen-2-yl) [1,2,4] triazol-3-ylmethyl)-1-methylindole-2-carboxamide (0.58 g) was obtained in the same manner as in Example 2 using 1-methylindole-2-carboxylic acid (1.52 g) and 3-aminomethyl-4-(3-(2-chlorobenzoyl)-5-ethylthiophen-2-yl) [1,2,4]triazole di-p-toluenesulfonate (5.0 g).

m.p. 200°–202° C.

EXAMPLE 7

Benzyl 2-(4-(3-(2-chlorobenzoyl)-5-ethylthiophen-2-yl) [1,2,4]triazol-3-ylmethylcarbamoyl)-2,3-dihydroindole-1-carboxylate (2.57 g) was obtained in the same manner as in Example 2 using 1-benzyloxycarbonyl-2,3-dihydroindole-2-carboxylic acid (2.60 g) and 3-aminomethyl4-(3-(2-chlorobenzoyl)-5-ethylthiophen-2-yl) [1,2,4]triazole di-p-toluenesulfonate (5.0 g).

m.p. 161°–165° C.

EXAMPLE 8

1-Ethoxycarbonylmethylindole-2-carboxylic acid (2.15 g) synthesized by a known method such as the method disclosed in Japanese Patent Unexamined Publication No. 279374/1991 and thionyl chloride (6.3 ml) were added to dichloroethane (20 ml), and the mixture was refluxed with stirring for 1.5 hours. The solvent was evaporated, and the residue was dissolved in dimethylformamide (20 ml). 3-Aminomethyl-4-(3-(2-chlorobenzoyl)-5-ethylthiophen-2-yl) [1,2,4]triazole di-p-toluenesulfonate (5.0 g) and triethylamine (5.0 ml) were added to the mixture under ice-cooling, and the mixture was stirred at room temperature for 1 hour. Then, a saturated aqueous sodium hydrogen-carbonate solution was added to the reaction mixture, and the mixture was extracted with ethyl acetate. The organic layer was washed with an aqueous citric acid solution and saturated brine, and dried over magnesium sulfate. The solvent was evaporated, and the residue was recrystallized from ethyl acetate-hexane to give 2.36 g of ethyl 2-(4-(3-(2-chlorobenzoyl)-5-ethylthiophen-2-yl) [1,2,4]triazol-3-ylmethylcarbamoyl) indole-1-acetate.

m.p. 158°–160° C.

EXAMPLE 9

Ethyl 2-(4-(3-(2-chlorobenzoyl)-5-ethylthiophen-2-yl) [1,2,4]triazol-3-ylmethylcarbamoyl)indole-1-acetate (2.0 g) and a solution of sodium hydroxide (0.39 g) in ethanol were added to ethanol (20 ml), and the mixture was stirred at 50° C. for 20 minutes. The solvent was evaporated, and the residue was dissolved in water. Toluene was added to the solution for washing. The aqueous layer was taken out, and 2M hydrochloric acid was added to adjust the solution to pH 2. The solution was extracted with chloroform. The extract was dried over magnesium sulfate, and the solvent was evaporated. The residue was recrystallized from ethyl acetate to give 0.45 g of 2-(4-(3-(2-chlorobenzoyl)-5-ethylthiophen-2-yl) [1,2,4]triazol-3-ylmethylcarbamoyl) indole-1-acetic acid.

m.p. 218°–220° C.

EXAMPLE 10

3-Aminomethyl-4-(3-(2-chlorobenzoyl)-5-ethylthiophen-2-yl)-5-methyl[1,2,4]triazole di-p-toluenesulfonate (3.70 g) was dissolved in dichloroethane (20 ml). Benzoyl chloride (0.64 ml) and triethylamine (2.8 ml) were added to the solution under ice-cooling, and the mixture was stirred at room temperature overnight. A saturated aqueous sodium hydrogencarbonate solution was added to the reaction mixture, and the mixture was extracted with chloroform. The organic layer was washed with saturated brine and dried over magnesium sulfate. The solvent was evaporated. The residue was purified by silica gel column chromatography (developing solvent:chloroform-methanol), and recrystallized from ethyl acetate to give 1.50 g of N-(4-(3-(2-chlorobenzoyl)-5-ethylthiophen-2-yl)-5-methyl[1,2,4] triazol-3-ylmethyl)benzamide.

m.p. 160°–161° C.

EXAMPLE 11

3,4-Dichlorobenzoic acid (1.05 g) and thionyl chloride (0.72 ml) were added to dichloroethane (10 ml), and the mixture was refluxed for 3 hours. The solvent was evaporated, and the residue was dissolved in dichloroethane (20 ml). 3-Aminomethyl-4-(3-(2-chlorobenzoyl)-5-ethylthiophen-2-yl)-5-methyl[1,2,4]triazole di-p-toluenesulfonate (3.70 g) and triethylamine (2.8 ml) were added under ice-cooling, and the mixture was stirred at room temperature for 1 hour. A saturated aqueous sodium hydrogencarbonate solution was added to the reaction mixture, and the mixture was extracted with chloroform. The organic layer was washed with an aqueous citric acid solution and saturated brine, and dried over magnesium sulfate. The solvent was evaporated, and the residue was recrystallized from ethyl acetate to give 0.90 g of N-(4-(3-(2-chlorobenzoyl)-5-ethylthiophen-2-yl)-5-methyl[1,2,4]triazol-3-ylmethyl)-3,4-dichlorobenzamide.

m.p. 151°–152° C.

EXAMPLE 12

3-Aminomethyl-4-(3-(2-chlorobenzoyl)-5-ethylthiophen-2-yl)-5-methyl[1,2,4]triazole di-p-toluenesulfonate (3.70 g) was dissolved in dimethylformamide (20 ml). Naphthalene-2-carboxylic acid (0.95 g) and diphenylphosphoryl azide (1.29 ml) were added under ice-cooling and dissolved in the solution. A solution of triethylamine (2.24 ml) in dimethylformamide was dropwise added, and the mixture was allowed to stand overnight at room temperature. Then, a 10% aqueous citric acid solution was added to the reaction mixture, and the mixture was extracted with ethyl acetate. The organic layer was washed with a saturated aqueous sodium hydrogencarbonate solution and saturated brine, and dried over magnesium sulfate. The solvent was evaporated, and the residue was recrystallized from ethyl acetate to give 0.53 g of N-(4-(3-(2-chlorobenzoyl)-5-ethylthiophen-2-yl)-5-methyl[1,2,4]triazol-3-ylmethyl)naphthalene-2-caboxamide.

m.p. 164°–165° C.

EXAMPLE 13

N-(4-(3-(2-Chlorobenzoyl)-5-ethylthiophen-2-yl)-5-methyl[1,2,4]triazol-3-ylmethyl)quinoline-3-carboxamide (0.63 g) was obtained in the same manner as in Example 12 using 3-aminomethyl-4-(3-(2-chlorobenzoyl)-5-ethylthiophen-2-yl)-5-methyl[1,2,4]triazole di-p-toluenesulfonate (3.70 g) and quinoline-3-carboxylic acid (0.95 g).

m.p. 213°–214° C.

EXAMPLE 14

N-(4-(3-(2-Chlorobenzoyl)-5-ethylthiophen-2-yl)-5-methyl[1,2,4]triazol-3-ylmethyl)indole-2-carboxamide (3.60 g) was obtained in the same manner as in Example 11 using 3-aminomethyl-4-(3-(2-chlorobenzoyl)-5-ethylthiophen-2-yl)-5-methyl[1,2,4]triazole di-p-toluenesulfonate (7.40 g) and indole-2-carboxylic acid (1.77 g).

m.p. 252°–254° C.

EXAMPLE 15

Indole-3-carboxylic acid (0.885 g) and thionyl chloride (4.0 ml) were added to dichloroethane (10 ml), and the mixture was refluxed with stirring for 5 hours. The solvent was evaporated, and the residue was dissolved in dichloroethane (20 ml). 3-Aminomethyl-4-(3-(2-chlorobenzoyl)-5-ethylthiophen-2-yl)-5-methyl[1,2,4]triazole di-p-toluenesulfonate (3.70 g) and triethylamine (3.5 ml) were added under ice-cooling, and the mixture was allowed to stand overnight at room temperature. A saturated aqueous sodium hydrogencarbonate solution was added to the reaction mixture, and the mixture was extracted with chloroform. The organic layer was washed with saturated brine, and dried over magnesium sulfate. The solvent was evaporated, and the residue was purified by silica gel column chromatography (developing solvent:chloroform-methanol), and recrystallized from ethyl acetate to give 0.94 g of N-(4-(3-(2-chlorobenzoyl)-5-ethylthiophen-2-yl)-5-methyl[1,2,4]triazol-3-ylmethyl)indole-3-carboxamide.

m.p. 140°–145° C.

EXAMPLE 16

N-(4-(3-(2-Chlorobenzoyl)-5-ethylthiophen-2-yl)-5-methyl[1,2,4]triazol-3-ylmethyl)-1-methylindole-2-carboxamide (0.20 g) was obtained in the same manner as in Example 15 using 1-methylindole-2-carboxylic acid (0.963 g) and 3-aminomethyl-4-(3-(2-chlorobenzoyl)-5-ethylthiophen-2-yl)-5-methyl[1,2,4]triazole di-p-toluenesulfonate (3.70 g).

m.p. 178°–180° C.

EXAMPLE 17 tert-Butyl 2-(4-(3-(2-chlorobenzoyl)-5-ethylthiophen-2-yl)-5-methyl[1,2,4]triazol-3-ylmethylcarbamoyl)indole-1-acetate (0.53 g) was obtained in the same manner as in Example 15 using 1-tert-butoxycarbonylmethylindole-2-carboxylic acid (0.790 g) synthesized by a known method such as the method disclosed in Japanese Patent Unexamined Publication No. 1558771/1993 and 3-aminomethyl-4-(3-(2-chlorobenzoyl)-5-ethylthiophen-2-yl)-5-methyl[1,2,4]triazole di-p-toluenesulfonate (2.07 g).

m.p. 164°–165° C.

EXAMPLE 18

3-Aminomethyl-4-(3-(2-chlorobenzoyl)-5-ethylthiophen-2-yl)-5-methyl[1,2,4]triazole di-p-toluenesulfonate (7.4 g) was dissolved in dimethylformamide (70 ml). 1-Ethoxycarbonylmethylindole-2-carbonyl chloride (3.03 g) and triethylamine (7.0 ml) were added under ice-cooling, and the mixture was stirred at room temperature for 8 hours. A saturated aqueous sodium hydrogencarbonate solution was added to the reaction mixture, and the mixture was extracted with ethyl acetate. The organic layer was washed with an aqueous citric acid solution and saturated brine, and dried over magnesium sulfate. The solvent was evaporated, and the residue was crystallized from ethanol to give 4.33 g of ethyl 2-(4-(3-(2-chlorobenzoyl)-5-ethylthiophen-2-yl)-5-methyl[1,2,4]triazol-3-ylmethylcarbamoyl)indole-1-acetate.

m.p. 138°–140° C.

EXAMPLE 19

Methanol (60 ml) and a 2M aqueous sodium hydroxide solution (7.0 ml) were added to ethyl 2-(4-(3-(2-chlorobenzoyl)-5-ethylthiophen-2-yl)-5-methyl[1,2,4]triazol-3-ylmethylcarbamoyl)indole-1-acetate (4.0 g), and the mixture was stirred at 50° C. for 30 minutes and at room temperature for 4 hours. Methanol was evaporated, and water and ethyl acetate were added. The aqueous layer was taken out, and citric acid was added to adjust the solution to pH 3. The solution was extracted with ethyl acetate. The organic layer was washed with saturated brine and dried over magnesium sulfate. The solvent was evaporated, and the residue was recrystallized from ethyl acetate to give 2.6 g of 2-(4-(3-(2-chlorobenzoyl)-5-ethylthiophen-2-yl)-5-methyl[1,2,4]triazol-3-ylmethylcarbamoyl)indole-1-acetic acid.

m.p. 208°–210° C.

EXAMPLE 20

N-(4-(3-(2-Chlorobenzoyl)-5-ethylthiophen-2-yl)-5-methyl[1,2,4]triazol-3-ylmethyl)-2,3-dihydrobenzofuran-7- carboxamide (1.42 g) was obtained in the same manner as in Example 11 using 2,3-dihydrobenzofuran-7-carboxylic acid (0.902 g) and 3-aminomethyl-4-(3-(2-chlorobenzoyl)-5-ethylthiophen-2-yl)-5-methyl[1,2,4]triazole di-p-toluenesulfonate (3.70 g).

m.p. 127°–129° C.

EXAMPLE 21

3-Aminomethyl-4-(3-(2-chlorobenzoyl)-5-ethylthiophen-2-yl)-5-methyl[1,2,4]triazole di-p-toluenesulfonate (4.0 g) was dissolved in dimethylformamide (20 ml). Phenylacetyl chloride (0.9 ml) and triethylamine (3.2 ml) were added under ice-cooling, and the mixture was stirred at room temperature for 1.5 hours. A saturated aqueous sodium hydrogencarbonate solution was added to the reaction mixture, and the mixture was extracted with ethyl acetate. The organic layer was washed with an aqueous citric acid solution and saturated brine, and dried over magnesium sulfate. The solvent was evaporated, and the residue was recrystallized from ethyl acetate to give 1.56 g of N-(4-(3-(2-chlorobenzoyl)-5-ethylthiophen-2-yl)-5-methyl[1,2,4]triazol-3-ylmethyl)-2-phenylacetamide.

m.p. 153°–155° C.

EXAMPLE 22

3-Aminomethyl-4-(3-(2-chlorobenzoyl)-5-ethylthiophen-2-yl)-5-methyl[1,2,4]triazole di-p-toluenesulfonate (5.0 g) was dissolved in dichloroethane (80 ml). Phenyl isocyanate (0.807 ml) and triethylamine (2.8 ml) were added at room temperature, and the mixture was stirred for 4 hours. Then, the reaction mixture was washed with water and dried over magnesium sulfate. The solvent was evaporated, and the residue was recrystallized from ethyl acetate to give 2.1 g of N-(4-(3-(2-chlorobenzoyl)-5-ethylthiophen-2-yl)-5-methyl[1,2,4]triazol-3-ylmethyl)-N'-phenylurea.

m.p. 141°–143° C.

EXAMPLE 23

3-Aminomethyl-4-(3-(2-chlorobenzoyl)-5-ethylthiophen-2-yl)-5-methyl[1,2,4]triazole di-p-toluenesulfonate (7.40 g) was dissolved in dichloroethane (100 ml). 2-Chlorophenyl isocyanate (1.2 ml) and triethylamine (4.2 ml) were added under ice-cooling, and the mixture was stirred for 4 hours. Then, the reaction mixture was washed with water and dried over magnesium sulfate. The solvent was evaporated, and the residue was purified by silica gel column chromatography (developing solvent:chloroform-methanol) to give 4.50 g of N-(4-(3-(2-chlorobenzoyl)-5-ethylthiophen-2-yl)-5-methyl[1,2,4]triazol-3-ylmethyl)-N'-(2-chlorophenyl)urea as an oil.

NMR (270 MHz, $CDCl_3$): 1.26(3H,t,J=7.9 Hz), 2.32(3H,s), 2.82(2H,q,J=7.9 Hz), 4.51(1H,dd,J=3.96 Hz,6.50 Hz), 4.65(1H,dd,J=4.94 Hz, 6.50 Hz), 6.80(1H,s), 6.90(1H,m), 7.16(1H,m), 7.23–7.40(6H), 7.55(1H,m), 8.00–8.15(2H)

EXAMPLE 24

4-(2-Chlorophenyl)-2-ethyl-9-methyl-6H-thieno[3,2-f][1,2,4]triazolo[4,3-a] [1,4]diazepine (2.25 g) was added to 6M hydrochloric acid (22.5 ml), and the mixture was stirred at 80° C. overnight. Then, 3M sodium hydroxide was added to the reaction mixture to make the mixture alkaline. The mixture was extracted with chloroform and the extract was dried over magnesium sulfate. 3-Chlorophenyl isocyanate (0.4 ml) was added thereto, and the mixture was stirred at room temperature for 30 minutes. The solvent was evaporated, and the residue was purified by silica gel column chromatography (developing solvent:chloroform-methanol) and recrystallized from ethanol to give 0.90 g of N-(4-(3-(2-chlorobenzoyl)-5-ethylthiophen-2-yl)-5-methyl[1,2,4]triazol-3-ylmethyl)-N'-(3-chlorophenyl)urea.

m.p. 163°–164° C.

EXAMPLE 25

N-(4-(3-(2-Chlorobenzoyl)-5-ethylthiophen-2-yl)-5-methyl[1,2,4]triazol-3-ylmethyl)-N'-(4-chlorophenyl)urea (0.75 g) was obtained in the same manner as in Example 24 using 4-(2-chlorophenyl)-2-ethyl-9-methyl-6H-thieno[3,2-f] [1,2,4]triazolo[4,3-a] [1,4]diazepine (3.0 g) and 4-chlorophenyl isocyanate (0.56 ml).

m.p. 155°–158° C.

EXAMPLE 26

N-(4-(3-(2-Chlorobenzoyl)-5-ethylthiophen-2-yl)-5-methyl[1,2,4]triazol-3-ylmethyl)-N'-(3-methylphenyl)urea (0.90 g) was obtained in the same manner as in Example 24 using 4-(2-chlorophenyl)-2-ethyl-9-methyl-6H-thieno[3,2-f] [1,2,4]triazolo[4,3-a] [1,4]diazepine (2.25 g) and 3-methylphenyl isocyanate (0.40 ml).

m.p. 148°–150° C.

EXAMPLE 27

N-(4-(3-(2-Chlorobenzoyl)-5-ethylthiophen-2-yl)-5-methyl[1,2,4]triazol-3-ylmethyl)-N'-(3-methoxyphenyl)urea (1.65 g) was obtained in the same manner as in Example 24 using 4-(2-chlorophenyl)-2-ethyl-9-methyl-6H-thieno[3,2-f] [1,2,4]triazolo[4,3-a] [1,4]diazepine (4.0 g) and 3-methoxyphenyl isocyanate (0.76 ml).

m.p. 139°–142° C.

EXAMPLE 28

N-(4-(3-(2-Chlorobenzoyl)-4,5-dimethylthiophen-2-yl)-5-methyl[1,2,4]triazol-3-ylmethyl)-N'-(3-methylphenyl)urea (2.2 g) was obtained in the same manner as in Example 24 using 4-(2-chlorophenyl)-2,3,9-trimethyl-6H-thieno[3,2-f] [1,2,4]triazolo[4,3-a] [1,4]diazepine (3.0 g) and 3-methylphenyl isocyanate (0.6 ml).

m.p. 186°–188° C.

EXAMPLE 29

N-(4-(3-(2-Chlorobenzoyl)-4,5,6,7-tetrahydrobenzothiophen-2-yl)-5-methyl[1,2,4]triazol-3-ylmethyl)-N'-(3-methylphenyl)urea (1.3 g) was obtained in the same manner as in Example 24 using 6-(2-chlorophenyl)-11-methyl-2,3,4,5-tetrahydro-8H-benzo(b)thieno[3,2-f] [1,2,4]triazolo[4,3-a] [1,4]diazepine (2.0 g) and 3-methylphenyl isocyanate (0.4 ml).

m.p. 191°–194° C.

EXAMPLE 30

3-Aminomethyl-4-(3-(2-chlorobenzoyl)-5-ethylthiophen-2-yl) [1,2,4]triazole di-p-toluenesulfonate (5.0 g) was dissolved in dimethylformamide (20 ml). Phenyl isocyanate (0.87 ml) and triethylamine (3.0 ml) were added under ice-cooling, and the mixture was stirred at room temperature for 1 hour. A saturated aqueous sodium hydrogencarbonate solution was added to the reaction mixture, and the mixture was extracted with ethyl acetate. The organic layer was washed with an aqueous citric acid solution and saturated brine, and dried over magnesium sulfate. The solvent was evaporated, and the residue was recrystallized from ethyl acetate-hexane to give 2.47 g of N-(4-(3-(2-chlorobenzoyl)-5-ethylthiophen-2-yl) [1,2,4]triazol-3-ylmethyl)-N'-phenylurea.

m.p. 194°–197° C.

Production Example 3

5-(2-Chlorophenyl)-7-ethyl-2-hydrazino-3H-thieno[2,3-e] [1,4]diazepine (80 g) was suspended in chloroform (2 l) under ice-cooling. Ethyl oxalyl chloride (30.7 ml) was added, and the mixture was stirred for 1 hour. The reaction mixture was washed with a saturated aqueous sodium hydrogencarbonate solution, and dried over magnesium sulfate. The solvent was evaporated, and isopropyl ether was added to give a red solid (92.2 g). The solid (78.8 g) was dissolved in a mixed solvent of toluene (1.5 l) and acetic acid (13 ml), and the solution was refluxed for 3 hours. The reaction mixture was concentrated, and the residue was purified by silica gel column chromatography (eluted with chloroform:methanol=50:1). 4-(2-Chlorophenyl)-9-ethoxycarbonyl-2-ethyl-6H-thieno[3,2-f] [1,2,4]triazolo[4,3-a] [1,4]diazepine (23.3 g) was obtained from a fraction containing the objective compound.

m.p. 138°–140° C.

EXAMPLE 31

4-(2-Chlorophenyl)-9-ethoxycarbonyl-2-ethyl-6H-thieno [3,2-f] [1,2,4]triazolo[4,3-a] [1,4]diazepine (2.1 g) was added to 5% hydrochloric acid (21 ml), and the mixture was stirred at 50° C. for 3 hours. Then, potassium carbonate was added to the reaction mixture to make the mixture alkaline. The mixture was extracted with ethyl acetate and the extract was dried over sodium sulfate. p-Toluenesulfonic acid (2.0 g) was added thereto to give 5-aminomethyl-4-(3-(2-chlorobenzoyl)-5-ethylthiophen-2-yl)-3-ethoxycarbonyl[1,2,4]triazole di-p-toluenesulfonate. Ethyl acetate (50 ml), phenyl isocyanate (0.54 ml) and triethylamine (2.1 ml) were added thereto at room temperature, and the mixture was stirred for 30 minutes. Then, a saturated aqueous sodium hydrogencarbonate solution was added to the reaction mixture, and the mixture was extracted with ethyl acetate. The organic layer was washed with an aqueous citric acid solution and saturated brine, and dried over magnesium sulfate. The solvent was evaporated, and the residue was recrystallized from diisopropyl ether to give 0.67 g of ethyl (4-(3-(2-chlorobenzoyl)-5-ethylthiophen-2-yl)-5-(3-phenylureidomethyl[1,2,4]triazol-3-yl))carboxylate.

m.p. 123°–125° C.

EXAMPLE 32

4-(2-Chlorophenyl)-2,9-diethyl-6H-thieno[3,2-f] [1,2,4] triazolo[4,3-a] [1,4]diazepine (1.8 g) was added to 2.5% hydrochloric acid (35 ml), and the mixture was stirred at 60° C. overnight. Then, sodium hydrogencarbonate was added to the reaction mixture to make the mixture alkaline. Chloroform (40 ml) and 3,4-dichlorobenzoyl chloride (1.15 g) were added, and the mixture was stirred at room temperature for 2 hours. Then, the organic layer was washed with an aqueous citric acid solution and saturated brine, and dried over magnesium sulfate. After the solvent was evaporated, the residue was purified by silica gel column chromatography (developing solvent:ethyl acetate) and recrystallized from ethyl acetate to give 0.73 g of N-(4-(3-(2-chlorobenzoyl)-5-ethylthiophen-2-yl)-5-ethyl[1,2,4]triazol-3-ylmethyl)-3,4-dichlorobenzamide.

m.p. 136°–138° C.

EXAMPLE 33

N-(4-(3-(2-Chlorobenzoyl)-5-ethylthiophen-2-yl)-5-ethyl [1,2,4]triazol-3-ylmethyl)indole-2-carboxamide (0.79 g) was obtained in the same manner as in Example 32 using 4-(2-chlorophenyl)-2,9-diethyl-6H-thieno[3,2-f] [1,2,4] triazolo[4,3-a] [1,4]diazepine (1.8 g) and indole-2-carbonyl chloride (1.35 g).

m.p. 242°–243° C.

EXAMPLE 34

Ethyl 2-(4-(3-(2-chlorobenzoyl)-5-ethylthiophen-2-yl)-5-ethyl[1,2,4]triazol-3-ylmethylcarbamoyl)indole-1-acetate (1.4 g) was obtained in the same manner as in Example 32 using 4-(2-chlorophenyl)-2,9-diethyl-6H-thieno[3,2-f] [1,2,4]triazolo[4,3-a] [1,4]diazepine (2.1 g) and 1-(ethoxycarbonylmethyl)indole-2-carbonyl chloride (1.8 g).

m.p. 132°–134° C.

EXAMPLE 35

Ethyl 2-(4-(3-(2-chlorobenzoyl)-5-ethylthiophen-2-yl)-5-ethyl[1,2,4]triazol-3-ylmethylcarbamoyl)indole-1-acetate (1.0 g) and a solution of sodium hydroxide (0.13 g) in ethanol were added to ethanol (20 ml), and the mixture was stirred at 50° C. for 1 hour. The solvent was evaporated, and the residue was dissolved in water. Toluene was added to the solution for washing. The aqueous layer was taken out, and 2M hydrochloric acid was added to adjust the solution to pH 2. The solution was extracted with chloroform, and the extract was dried over magnesium sulfate. The solvent was evaporated, and the residue was recrystallized from ethyl acetate to give 0.34 g of 2-(4-(3-(2-chlorobenzoyl)-5-ethylthiophen-2-yl)-5-ethyl[1,2,4]triazol-3-ylmethylcarbamoyl)indole-1-acetic acid.

m.p. 201°–203° C.

Production Example 4

5-(2-Chlorophenyl)-7-ethyl-2-hydrazino-3H-thieno[2,3-e] [1,4]diazepine (20 g) was suspended in chloroform (200 ml) at room temperature. Cyclohexanecarboxylic acid chloride (10.1 g) was added, and the mixture was stirred for 3 hours. The reaction mixture was washed with a saturated aqueous sodium hydrogencarbonate solution and saturated brine, and dried over magnesium sulfate. The solvent was evaporated to give an oil. The oil was dissolved in a mixed solvent of toluene (200 ml) and acetic acid (5.4 ml), and the mixture was refluxed for 3 hours. The reaction mixture was washed with a saturated aqueous sodium hydrogencarbonate solution and saturated brine and dried over magnesium sulfate. The solvent was evaporated. The residue was purified by silica gel column chromatography (eluted with ethyl acetate), and isopropyl ether was added to give 15 g of 4-(2-chlorophenyl)-9-cyclohexyl-2-ethyl-6H-thieno[3,2-f] [1,2,4]triazolo[4,3-a] [1,4]diazepine.

EXAMPLE 36

4-(2-Chlorophenyl)-9-cyclohexyl-2-ethyl-6H-thieno[3,2-f] [1,2,4]triazolo[4,3-a] [1,4]diazepine (1.85 g) was added to 2.5% hydrochloric acid (40 ml), and the mixture was stirred at 60° C. overnight. Then, sodium hydrogencarbonate was added to the reaction mixture to make the mixture alkaline. The mixture was extracted with ethyl acetate, and the extract was dried over sodium sulfate. p-Toluenesulfonic acid (2.0 g) was added thereto to give 3-aminomethyl-4-(3-(2-chlorobenzoyl)-5-ethylthiophen-2-yl)-5-cyclohexyl[1,2,4]triazole di-p-toluenesulfonate. Dimethylformamide (10 ml), 3,4-dichlorobenzoyl chloride (1.16 g) and triethylamine (5 ml) were added thereto under ice-cooling, and the mixture was stirred for 2 hours. Then, a saturated aqueous sodium hydrogencarbonate solution was added to the reaction mixture, and the mixture was extracted with ethyl acetate. The organic layer was washed with an aqueous citric acid solution and saturated brine, and dried over magnesium sulfate. The solvent was evaporated, and the residue was purified by silica gel column chromatography (developing solvent:ethyl acetate) and recrystallized from ethyl acetate to give 0.17 g of N-(4-(3-(2-chlorobenzoyl)-5-ethylthiophen-2-yl)-5-cyclohexyl[1,2,4]triazol-3-ylmethyl)-3,4-dichlorobenzamide.

m.p. 206°–208° C.

EXAMPLE 37

N-(4-(3-(2-Chlorobenzoyl)-5-ethylthiophen-2-yl)-5-cyclohexyl[1,2,4]triazol-3-ylmethyl)indole-2-carboxamide (1.26 g) was obtained in the same manner as in Example 36 using 4-(2-chlorophenyl)-9-cyclohexyl-2-ethyl-6H-thieno[3,2-f] [1,2,4]triazolo[4,3-a] [1,4]diazepine (2.0 g) and indole-2-carbonyl chloride (1.1 g).

m.p. 196° C. (dec.)

EXAMPLE 38

Ethyl 2-(4-(3-(2-chlorobenzoyl)-5-ethylthiophen-2-yl)-5-cyclohexyl[1,2,4]triazol-3-ylmethylcarbamoyl)indole-1-acetate (1.46 g) was obtained in the same manner as in Example 32 using 4-(2-chlorophenyl)-9-cyclohexyl-2-ethyl-6H-thieno[3,2-f] [1,2,4]triazolo[4,3-a] [1,4]diazepine (2.0 g) and 1-(ethoxycarbonylmethyl)indole-2-carbonyl chloride (1.6 g).

NMR (270 MHz, DMSO-$d_6$): 0.96(3H,t,J=7.3 Hz), 1.17 (3H,t,J=7.3 Hz), 1.10–1.90(11H,m), 2.66(2H,q,J=7.3 Hz), 4.19(2H,q,J=7.3 Hz), 4.55(1H,dd,J=15.5 Hz,4.6 Hz), 4.61 (1H,dd,J=15.5 Hz,6.6 Hz), 5.23(2H,s), 6.71(1H,s), 7.12–7.30(5H,m), 7.52–7.65(4H,m), 8.92(1H,dd,J=4.6 Hz,6.6 Hz)

EXAMPLE 39

Ethyl 2-(4-(3-(2-chlorobenzoyl)-5-ethylthiophen-2-yl)-5-cyclohexyl[1,2,4]triazol-3-ylmethylcarbamoyl)indole-1-acetate (0.8 g) and a solution of sodium hydroxide (0.08 g) in ethanol was added to ethanol (10 ml), and the mixture was stirred at 50° C. for 30 minutes. The solvent was evaporated, and the residue was dissolved in water. Toluene was added to the solution for washing. The aqueous layer was taken out, and 2M hydrochloric acid was added to adjust the solution to pH 2. The solution was extracted with chloroform and the extract was dried over magnesium sulfate. The solvent was evaporated, and the residue was recrystallized from ethyl acetate-hexane to give 0.36 g of 2-(4-(3-(2-chlorobenzoyl)-5-ethylthiophen-2-yl)-5-cyclohexyl[1,2,4] triazol-3-ylmethylcarbamoyl)indole-1-acetic acid.

m.p. 159°–162° C.

Production Example 5

5-(2-Chlorophenyl)-7-ethyl-2-hydrazino-3H-thieno[2,3-e] [1,4]diazepine (100 g) was suspended in chloroform (2 l) at room temperature, and triethylamine (193 ml) was added. Trifluoroacetic anhydride (70 ml) was dropwise added, and the mixture was stirred for 3 hours. The reaction mixture was washed with a saturated aqueous sodium hydrogencarbonate solution, an aqueous citric acid solution and saturated brine, and dried over magnesium sulfate. The solvent was evaporated to give an oil. The oil was dissolved in a mixed solvent of toluene (2 l) and acetic acid (18.5 ml), and the mixture was refluxed for 3 hours. The reaction mixture was washed with a saturated aqueous sodium hydrogencarbonate solution and saturated brine, and dried over magnesium sulfate. The solvent was evaporated. The residue was purified by silica gel column chromatography (eluted with a mixed solvent of ethyl acetate and hexane) and crystallized from a mixed solvent of ethyl acetate and hexane to give 9.4 g of 4-(2-chlorophenyl)-2-ethyl-9-trifluoromethyl-6H-thieno[3,2-f] [1,2,4]triazolo[4,3-a] [1,4] diazepine.

EXAMPLE 40

4-(2-Chlorophenyl)-2-ethyl-9-trifluoromethyl-6H-thieno [3,2-f] [1,2,4]triazolo[4,3-a] [1,4]diazepine (1.0 g) was added to 10% hydrochloric acid (20 ml), and the mixture was stirred at 70° C. overnight. Then, sodium hydrogencarbonate was added to the reaction mixture to make the mixture alkaline. Chloroform (20 ml) and 3,4-dichlorobenzoyl chloride (0.58 g) were added, and the mixture was stirred under ice-cooling for 1 hour. Then, the organic layer was washed with an aqueous citric acid solution, a saturated aqueous sodium hydrogencarbonate solution and saturated brine, and dried over magnesium sulfate. The solvent was evaporated, and the residue was recrystallized from ethyl acetate-hexane to give 0.60 g of N-(4-(3-(2-chlorobenzoyl)-5-ethylthiophen-2-yl)-5-trifluoromethyl[1,2,4]triazol-3-ylmethyl)-3,4-dichlorobenzamide.

m.p. 75°–80° C.

EXAMPLE 41

N-(4-(3-(2-Chlorobenzoyl)-5-ethylthiophen-2-yl)-5-trifluoromethyl[1,2,4]triazol-3-ylmethyl)indole-2-carboxamide (0.35 g) was obtained in the same manner as in Example 40 using 4-(2-chlorophenyl)-2-ethyl-9-trifluoromethyl-6H-thieno[3,2-f] [1,2,4]triazolo[4,3-a] [1,4] diazepine (1.0 g) and indole-2-carbonyl chloride (0.62 g).

m.p. 115°–120° C.

EXAMPLE 42

Ethyl 2-(4-(3-(2-chlorobenzoyl)-5-ethylthiophen-2-yl)-5-trifluoromethyl[1,2,4]triazol-3-ylmethylcarbamoyl)indole-1-acetate (2.0 g) was obtained in the same manner as in Example 40 using 4-(2-chlorophenyl)-2-ethyl-9-trifluoromethyl-6H-thieno[3,2-f] [1,2,4]triazolo[4,3-a] [1,4]-diazepine (2.4 g) and 1-ethoxycarbonylmethylindole-2-carbonyl chloride (2.1 g).

m.p. 193°–196° C.

EXAMPLE 43

Ethyl 2-(4-(3-(2-chlorobenzoyl)-5-ethylthiophen-2-yl)-5-trifluoromethyl[1,2,4]triazol-3-ylmethylcarbamoyl)indole-1-acetate (1.5 g) and a 2M aqueous sodium hydroxide solution (1.25 ml) were added to methanol (20 ml), and the mixture was stirred at room temperature for 30 minutes. Then, the solvent was evaporated and the residue was dissolved in water. Ethyl acetate was added to the solution for washing. The aqueous layer was taken out, and citric acid was added to adjust the solution to pH 3. The solution was extracted with ethyl acetate and the extract was dried over magnesium sulfate. The solvent was evaporated, and the residue was crystallized from ethyl acetate to give 2-(4-(3-(2-chlorobenzoyl)-5-ethylthiophen-2-yl)-5-trifluoromethyl [1,2,4]triazol-3-ylmethylcarbamoyl)indole-1-acetic acid.

m.p. 200°–203° C.

EXAMPLE 44

4-(2-Chlorophenyl)-9-ethoxycarbonyl-2-ethyl-6H-thieno [3,2-f] [1,2,4]triazolo[4,3-a] [1,4]diazepine (2.8 g) was added to 5% hydrochloric acid (28 ml), and the mixture was stirred at 50° C. for 3 hours. Then, potassium carbonate was added to the reaction mixture to make the mixture alkaline. The mixture was extracted with ethyl acetate and the extract was dried over magnesium sulfate. p-Toluenesulfonic acid (2.65 g) was added thereto to give 5-aminomethyl-4-(3-(2-chlorobenzoyl)-5-ethylthiophen-2-yl)-3-ethoxycarbonyl[1,2,4]triazole di-p-toluenesulfonate. The solvent was evaporated without isolation and dichloroethane (50 ml), indole-2-carbonyl chloride (1.26 g) and triethylamine (7 ml) were added at room temperature. The mixture was allowed to stand overnight. Then, a saturated aqueous sodium hydrogencarbonate solution was added, and the mixture was extracted with dichloroethane. The organic layer was washed with an aqueous citric acid solution and then saturated brine, and dried over magnesium sulfate. The solvent was evaporated, and the residue was purified by silica gel column chromatography (developing solvent:ethyl acetate-hexane) and recrystallized from ethanol to give 0.82 g of ethyl (4-(3-(2-chlorobenzoyl)-5-ethylthiophen-2-yl)-5-(indole-2-carbonylaminomethyl) [1,2,4]triazol-3-yl) carboxylate.

m.p. 233°–235° C.

Production Example 6

5-(2-Chlorophenyl)-7-ethyl-2-hydrazino-3H-thieno[2,3-e] [1,4]diazepine (40 g) was suspended in chloroform (500 ml) under ice-cooling. Ethyl succinyl chloride (19.3 ml) was added, and the mixture was stirred for 3 hours. The reaction mixture was washed with a saturated aqueous sodium hydrogencarbonate solution and dried over magnesium sulfate, and the solvent was evaporated to give an oil. The oil was dissolved in a mixed solvent of toluene (1 l) and acetic acid (9 ml), and the solution was refluxed for 3 hours. The reaction mixture was concentrated, and the residue was purified by silica gel column chromatography (eluted with a mixed solvent of ethyl acetate and methanol). 4-(2-Chlorophenyl)-9-(2-ethoxycarbonylethyl)-2-ethyl-6H-thieno[3,2-f] [1,2,4]triazolo[4,3-a] [1,4]diazepine (30.0 g) was obtained as an oil from a fraction containing the objective compound.

EXAMPLE 45

4-(2-Chlorophenyl)-9-(2-ethoxycarbonylethyl)-2-ethyl-6H-thieno[3,2-f] [1,2,4]triazolo[4,3-a] [1,4]diazepine (3.3 g) was added to 5% hydrochloric acid (35 ml), and the mixture was stirred at 40° C. for 4 hours. Then, sodium hydrogencarbonate was added to the reaction mixture to make the mixture alkaline. Chloroform (50 ml) and 3,4-dichlorobenzoyl chloride (1.61 g) were added under ice-cooling, and the mixture was allowed to stand overnight. Then, the organic layer was taken out, washed with an aqueous citric acid solution and saturated brine, and dried over magnesium sulfate. The solvent was evaporated, and the residue was purified by silica gel column chromatography (developing solvent:ethyl acetate-methanol) and recrystallized from ethyl acetate-hexane to give 1.08 g of ethyl 3-(4-(3-(2-chlorobenzoyl)-5-ethylthiophen-2-yl)-3-(3,4-dichlorobenzoylaminomethyl) [1,2,4]triazol-5-yl) propionate.

m.p. 153°–155° C.

EXAMPLE 46

Ethyl 3-(4-(3-(2-chlorobenzoyl)-5-ethylthiophen-2-yl)-3-(3,4-dichlorobenzoylaminomethyl) [1,2,4]triazol-5-yl) propionate (0.7 g) and a 2M aqueous sodium hydroxide solution (1.13 ml) were added to methanol (10 ml), and the mixture was stirred at 50° C. for 3 hours. The solvent was evaporated, and the residue was dissolved in water. Ethyl acetate was added to the solution for washing. The aqueous layer was taken out, and citric acid was added to adjust the solution to pH 3. The solution was extracted with ethyl acetate. The extract was washed with saturated brine and dried over magnesium sulfate. The solvent was evaporated, and the residue was recrystallized from diisopropyl ether to give 0.56 g of 3-(4-(3-(2-chlorobenzoyl)-5-ethylthiophen-2-yl)-3-(3,4-dichlorobenzoylaminomethyl) [1,2,4]triazol-5-yl) propionic acid.

m.p. 197°–199° C.

EXAMPLE 47

4-(2-Chlorophenyl)-9-(2-ethoxycarbonylethyl)-2-ethyl-6H-thieno[3,2-f] [1,2,4]triazolo[4,3-a] [1,4]diazepine (5.78 g) was heated with 5% hydrochloric acid for 3 hours, and the mixture was cooled to room temperature. Sodium hydrogencarbonate (25.2 g) and chloroform were added. Indole-2-carbonyl chloride (2.67 g) was added with vigorous stirring, and the mixture was stirred for 4 hours. The organic layer was concentrated, and the residue was dissolved in methanol (39 ml). The solution was hydrolyzed with 2M sodium hydroxide (3.9 ml) and the reaction mixture was made acidic. The mixture was extracted with ethyl acetate and the extract was dried over magnesium sulfate. The solvent was evaporated and the obtained residue was recrystallized from ethanol to give 0.26 g of 3-(4-(3-(2-chlorobenzoyl)-5-ethylthiophen-2-yl)-3-(indole-2-carbonylaminomethyl) [1,2,4]triazol-5-yl)propionic acid.

m.p. 155°–165° C. (dec.)

EXAMPLE 48

3-Aminomethyl-4-(3-(2-chlorobenzoyl)-5-ethylthiophen-2-yl) [1,2,4]triazole di-p-toluenesulfonate (5.0 g) was dissolved in dimethylformamide (20 ml). 2-Naphthalenesulfonyl chloride (1.8 g) and triethylamine (5.0 ml) were added under ice-cooling, and the mixture was stirred at room temperature for 5 hours. A saturated aqueous sodium hydrogencarbonate solution was added to the reaction mixture, and the mixture was extracted with ethyl acetate. The organic layer was washed with an aqueous citric acid solution and then saturated brine, and dried over magnesium sulfate. The solvent was evaporated, and the residue was recrystallized from ethyl acetate to give 2.73 g of N-(4-(3-(2-chlorobenzoyl)-5-ethylthiophen-2-yl) [1,2,4] triazol-3-ylmethyl)naphthalene-2-sulfonamide.

m.p. 165°–167° C.

EXAMPLE 49

3-Aminomethyl-4-(3-(2-chlorobenzoyl)-5-ethylthiophen-2-yl)-5-methyl[1,2,4]triazole di-p-toluenesulfonate (1.85 g)

was dissolved in dimethylformamide (20 ml). 2-Naphthalenesulfonyl chloride (0.62 g) and triethylamine (1.75 ml) were added under ice-cooling, and the mixture was allowed to stand overnight. A saturated aqueous sodium hydrogencarbonate solution was added to the reaction mixture, and the mixture was extracted with ethyl acetate. The organic layer was washed with saturated brine, and dried over magnesium sulfate. The solvent was evaporated, and the residue was recrystallized from ethyl acetate to give 0.32 g of N-(4-(3-(2-chlorobenzoyl)-5-ethylthiophen-2-yl)-5-methyl[1,2,4]triazol-3-ylmethyl)naphthalene-2-sulfonamide.

m.p. 184°–186° C.

Production Example 7

4-(2-Chlorophenyl)-2-ethyl-9-methyl-6H-thieno[3,2-f][1,2,4]triazolo[4,3-a] [1,4]diazepine (34.3 g) was added to water (500 ml), and conc. sulfuric acid (74 ml) was dropwise added with vigorous stirring. The mixture was further stirred at 90° C. for 1 hour, and sodium nitrite (74 g) was added. Then, potassium carbonate was added to the reaction mixture to make the mixture alkaline. The mixture was extracted with ethyl acetate and washed with water. The mixture was dried over magnesium sulfate. The solvent was evaporated, and the residue was recrystallized from ethyl acetate-diisopropyl ether to give 26.06 g of 4-(3-(2-chlorobenzoyl)-5-ethylthiophen-2-yl)-3-hydroxymethyl-5-methyl[1,2,4]triazole.

m.p. 145°–148° C.

EXAMPLE 50

4-(3-(2-Chlorobenzoyl)-5-ethylthiophen-2-yl)-3-hydroxymethyl-5-methyl[1,2,4]triazole (1.8 g) was dissolved in tetrahydrofuran (20 ml). 2-Chlorophenyl isocyanate (0.84 g) was added, and the mixture was stirred at room temperature for 4 hours. The solvent was evaporated, and the residue was purified by silica gel column chromatography (developing solvent:ethyl acetate-methanol) and recrystallized from ethyl acetate-diisopropyl ether to give 1.85 g of (4-(3-(2-chlorobenzoyl)-5-ethylthiophen-2-yl)-5-methyl[1,2,4]triazol-3-ylmethyl)-2-chlorophenyl carbamate.

m.p. 134°–136° C.

EXAMPLE 51

(4-(3-(2-Chlorobenzoyl)-5-ethylthiophen-2-yl)-5-methyl[1,2,4]-triazol-3-ylmethyl)-3-chlorophenyl carbamate (1.80 g) was obtained in the same manner as in Example 50 using 4-(3-(2-chlorobenzoyl)-5-ethylthiophen-2-yl)-3-hydroxymethyl-5-methyl[1,2,4]triazole (1.8 g) and 3-chlorophenyl isocyanate (0.84 g).

m.p. 141°–143° C.

EXAMPLE 52

(4-(3-(2-Chlorobenzoyl)-5-ethylthiophen-2-yl)-5-methyl[1,2,4]triazol-3-ylmethyl)-4-chlorophenyl carbamate (1.80 g) was obtained in the same manner as in Example 50 using 4-(3-(2-chlorobenzoyl)-5-ethylthiophen-2-yl)-3-hydroxymethyl-5-methyl[1,2,4]triazole (1.8 g) and 4-chlorophenyl isocyanate (0.84 g).

m.p. 169°–171° C.

EXAMPLE 53

(4-(3-(2-Chlorobenzoyl)-5-ethylthiophen-2-yl)-5-methyl[1,2,4]triazol-3-ylmethyl)-2-methylphenyl carbamate (1.66 g) was obtained in the same manner as in Example 50 using 4-(3-(2-chlorobenzoyl)-5-ethylthiophen-2-yl)-3-hydroxymethyl-5-methyl[1,2,4]triazole (1.8 g) and 2-methylphenyl isocyanate (0.77 g).

m.p. 158°–160° C.

EXAMPLE 54

(4-(3-(2-Chlorobenzoyl)-5-ethylthiophen-2-yl)-5-methyl[1,2,4]triazol-3-ylmethyl)-3-methylphenyl carbamate (1.28 g) was obtained in the same manner as in Example 50 using 4-(3-(2-chlorobenzoyl)-5-ethylthiophen-2-yl)-3-hydroxymethyl-5-methyl[1,2,4]triazole (1.8 g) and 3-methylphenyl isocyanate (0.73 g).

m.p. 174°–177° C.

EXAMPLE 55

(4-(3-(2-Chlorobenzoyl)-5-ethylthiophen-2-yl)-5-methyl[1,2,4]triazol-3-ylmethyl)phenyl carbamate (1.89 g) was obtained in the same manner as in Example 50 using 4-(3-(2-chlorobenzoyl)-5-ethylthiophen-2-yl)-3-hydroxymethyl-5-methyl[1,2,4]triazole (1.8 g) and phenyl isocyanate (0.65 g).

m.p. 184°–186° C.

EXAMPLE 56

(4-(3-(2-Chlorobenzoyl)-5-ethylthiophen-2-yl)-5-methyl[1,2,4]triazol-3-ylmethyl)-3-methoxyphenyl carbamate (1.62 g) was obtained in the same manner as in Example 50 using 4-(3-(2-chlorobenzoyl)-5-ethylthiophen-2-yl)-3-hydroxymethyl-5-methyl[1,2,4]triazole (1.8 g) and 3-methoxyphenyl isocyanate (0.82 g).

m.p. 136°–139° C.

EXAMPLE 57

4-(3-(2-Chlorobenzoyl)-5-ethylthiophen-2-yl)-3-hydroxymethyl-5-methyl[1,2,4]triazole (1.08 g) was dissolved in chloroform (50 ml). Triethylamine (0.34 g) and 3,4-dichlorobenzoyl chloride (0.69 g) were added, and the mixture was stirred at room temperature for 2 hours. Then, water was added to the solution for washing, and the mixture was dried over magnesium sulfate. The solvent was evaporated, and the residue was purified by silica gel column chromatography (developing solvent:ethyl acetate-methanol) and recrystallized from ethyl acetate-diisopropyl ether to give 1.10 g of (4-(3-(2-chlorobenzoyl)-5-ethylthiophen-2-yl)-5-methyl[1,2,4]triazol-3-ylmethyl)-3,4-dichlorobenzoate.

m.p. 117°–119° C.

EXAMPLE 58

(4-(3-(2-Chlorobenzoyl)-5-ethylthiophen-2-yl)-5-methyl[1,2,4]triazol-3-ylmethyl)indole-2-carboxylate (0.35 g) was obtained in the same manner as in Example 57 using 4-(3-(2-chlorobenzoyl)-5-ethylthiophen-2-yl)-3-hydroxymethyl-5-methyl[1,2,4]triazole (1.8 g) and indole-2-carbonyl chloride (0.66 g).

m.p. 80°–85° C.

Production Example 8

5-(2-Chlorophenyl)-7-ethyl-2-hydrazino-3H-thieno[2,3-e] [1,4]diazepine (200 g) synthesized by the method described in Artneim.-Forsch./Drug Res. 28 (II), Heft 7, 1153–1158 (1978) was dissolved in chloroform (2.95 l).

Acid chloride (154.7 g) of N-phthaloylglycine was added at room temperature, and the mixture was stirred for 2 hours. The reaction mixture was washed with a saturated aqueous sodium hydrogencarbonate solution, and dried over magnesium sulfate. The solvent was evaporated. The obtained oil was dissolved in a mixed solvent of toluene (4 l) and acetic acid (68.8 ml), and the solution was refluxed for 3 hours. The reaction mixture was concentrated, and extracted with chloroform. The organic layer was washed with a saturated aqueous sodium hydrogencarbonate solution and saturated brine, and dried over magnesium sulfate. The solvent was evaporated under reduced pressure. The obtained residue was crystallized from ethyl acetate to give 185 g of 4-(2-chlorophenyl)-2-ethyl-9-(N-phthalimidemethyl)-6H-thieno [3,2-f] [1,2,4]triazolo[4,3-a] [1,4]diazepine. Thus obtained 4-(2-chlorophenyl)-2-ethyl-9-(N-phthalimidemethyl)-6H-thieno[3,2-f] [1,2,4]triazolo[4,3-a] [1,4]diazepine was dissolved in ethanol (3.7 l), and hydrazine monohydrate (18.4 ml) was added, and the mixture was refluxed for 6 hours. The reaction mixture was concentrated and the residue was dissolved in chloroform. The insoluble matter was filtered off, and the filtrate was concentrated. The residue was purified by silica gel column chromatography, and crystallized from ethanol to give 76.7 g of 9-aminomethyl-4-(2-chlorophenyl)-2-ethyl-6H-thieno[3,2-f] [1,2,4]triazolo[4,3-a] [1,4]diazepine.

EXAMPLE 59

9-Aminomethyl-4-(2-chlorophenyl)-2-ethyl-6H-thieno[3,2-f] [1,2,4]triazolo[4,3-a] [1,4]diazepine (0.28 g) and triethylamine (0.115 ml) were dissolved in dichloroethane (15 ml). 3,4-Dichlorobenzoyl chloride (0.17 g) was added at room temperature, and the mixture was stirred for 1 hour. The reaction mixture was concentrated, and the residue was purified by silica gel column chromatography using a mixed solvent of ethyl acetate and methanol as a developing solvent. The obtained solid was recrystallized from a mixed solvent of ethyl acetate and hexane to give 0.27 g of N-(4-(2-chlorophenyl)-2-ethyl-6H-thieno[3,2-f] [1,2,4] triazolo[4,3-a] [1,4]diazepin-9-ylmethyl)-3,4-dichlorobenzamide.

m.p. 141°–145° C.

EXAMPLE 60

N-(4-(2-Chlorophenyl)-2-ethyl-6H-thieno[3,2-f] [1,2,4] triazolo[4,3-a] [1,4]diazepin-9-ylmethyl)indole-2-carboxamide (0.75 g) was obtained in the same manner as in Example 59 using 9-aminomethyl-4-(2-chlorophenyl)-2-ethyl-6H-thieno[3,2-f] [1,2,4]triazolo[4,3-a] [1,4]diazepine (1.79 g), indole-2-carbonyl chloride (1.07 g) and triethylamine (0.84 ml).

m.p. 290°–291° C.

EXAMPLE 61

1-Ethoxycarbonylmethylindole-2-carboxylic acid (1.36 g) synthesized by a known method such as the method described in Japanese Patent Unexamined Publication No. 279374/1991, 9-aminomethyl-4-(2-chlorophenyl)-2-ethyl-6H-thieno[3,2-f] [1,2,4]triazolo[4,3-a] [1,4]diazepine (1.79 g) and triethylamine (1.4 ml) were dissolved in dimethylformamide (15 ml). 1-Benzotriazolyloxytris (dimethylamino)phosphonium hexafluorophosphate (Bop reagent, 2.43 g) was added at room temperature, and the mixture was stirred for one day. The reaction mixture was partitioned between ethyl acetate and water. The organic layer was washed with a saturated aqueous sodium hydrogencarbonate solution and saturated brine, and dried over magnesium sulfate. The solvent was evaporated, and the residue was crystallized from ethanol and isopropyl ether to give 2.78 g of crude crystals. The crystals were recrystallized from ethanol to give 1.77 g of ethyl 2-(4-(2-chlorophenyl)-2-ethyl-6H-thieno[3,2-f] [1,2,4]triazolo[4,3-a] [1,4]diazepin-9-ylmethylcarbamoyl)indole-1-acetate.

m.p. 215°–217° C.

EXAMPLE 62

Crude crystals (1.41 g) of the objective compound were obtained in the same manner as in Example 61 using cinnamic acid (0.81 g), 9-aminomethyl-4-(2-chlorophenyl) -2-ethyl-6H-thieno[3,2-f] [1,2,4]triazolo[4,3-a] [1,4] diazepine (1.36 g), triethylamine (1.4 ml) and 1-benzotriazolyloxytris(dimethylamino)phosphonium hexafluorophosphate (Bop reagent, 2.43 g). The crystals were recrystallized from ethanol to give 0.90 g of trans-N-(4-(2-chlorophenyl)-2-ethyl-6H-thieno[3,2-f] [1,2,4]triazolo [4,3-a] [1,4]diazepin-9-ylmethyl)-3-phenylacrylamide.

m.p. 143°–145° C.

EXAMPLE 63

Ethyl 2-(4-(2-chlorophenyl)-2-ethyl-6H-thieno[3,2-f] [1,2,4]triazolo[4,3-a] [1,4]diazepin-9-ylmethylcarbamoyl) indole-1-acetate (0.83 g) obtained in Example 61 was dissolved in methanol (20 ml). A 2M aqueous sodium hydroxide solution (1.5 ml) was added, and the mixture was allowed to stand at room temperature for 4 hours. The reaction mixture was concentrated, and the residue was extracted with water. The aqueous layer was washed with ethyl acetate. Citric acid was added to adjust the aqueous layer to about pH 3.0, and the layer was extracted with ethyl acetate. The organic layer was washed with saturated brine and dried over magnesium sulfate. The solvent was evaporated, and the residue was crystallized from isopropyl ether to give 0.71 g of crude crystals. The crystals were recrystallized from ethyl acetate to give 0.63 g of 2-(4-(2-chlorophenyl)-2-ethyl-6H-thieno[3,2-f] [1,2,4]triazolo[4,3-a] [1,4]diazepin-9-ylmethylcarbamoyl)indole-1-acetic acid.

m.p. 222°–223° C.

EXAMPLE 64

9-Aminomethyl-4-(2-chlorophenyl)-2-ethyl-6H-thieno[3,2-f] [1,2,4]triazolo[4,3-a] [1,4]diazepine (1.07 g) was dissolved in chloroform (50 ml). 3-Methylphenyl isocyanate (0.44 g) was added at room temperature, and the mixture was stirred for 3 hours. The reaction mixture was concentrated, and crystallized from ethyl acetate. The crude crystals were recrystallized from methanol to give 1.47 g of N-(4-(2-chlorophenyl)-2-ethyl-6H-thieno[3,2-f] [1,2,4] triazolo[4,3-a] [1,4]diazepin-9-ylmethyl)-N'-(3-methylphenyl)urea.

m.p. 260°–262° C.

EXAMPLE 65

N-(2-Chlorophenyl)-N'-(4-(2-chlorophenyl)-2-ethyl-6H-thieno[3,2-f] [1,2,4]triazolo[4,3-a] [1,4]diazepin-9-ylmethyl)urea (1.53 g) was obtained in the same manner as in Example 64 using 9-aminomethyl-4-(2-chlorophenyl)-2-ethyl-6H-thieno[3,2-f] [1,2,4]triazolo[4,3-a] [1,4]diazepine (1.07 g) and 2-chlorophenyl isocyanate (0.51 g).

m.p. 210°–212° C.

EXAMPLE 66

N-(4-(2-Chlorophenyl)-2-ethyl-6H-thieno[3,2-f] [1,2,4] triazolo[4,3-a] [1,4]diazepin-9-ylmethyl)-N'-(3- methoxyphenyl)urea (1.52 g) was obtained in the same manner as in Example 64 using 9-aminomethyl-4-(2-chlorophenyl)-2-ethyl-6H-thieno[3,2-f] [1,2,4]triazolo[4,3-a] [1,4]diazepine (1.07 g) and 3-methoxyphenyl isocyanate (0.49 g).

m.p. 197°–199° C.

EXAMPLE 67

N-(4-(2-Chlorophenyl)-2-ethyl-6H-thieno[3,2-f] [1,2,4] triazolo[4,3-a] [1,4]diazepin-9-ylmethyl)-N'-phenylurea (1.43 g) was obtained in the same manner as in Example 64 using 9-aminomethyl-4-(2-chlorophenyl)-2-ethyl-6H-thieno [3,2-f] [1,2,4]triazolo[4,3-a] [1,4]diazepine (1.07 g) and phenyl isocyanate (0.39 g).

m.p. 230°–232° C.

EXAMPLE 68

N-(3-Chlorophenyl)-N'-(4-(2-chlorophenyl)-2-ethyl-6H-thieno[3,2-f] [1,2,4]triazolo[4,3-a] [1,4]diazepin-9-ylmethyl)urea (1.53 g) was obtained in the same manner as in Example 64 using 9-aminomethyl-4-(2-chlorophenyl)-2-ethyl-6H-thieno[3,2-f] [1,2,4]triazolo[4,3-a] [1,4]diazepine (1.07 g) and 3-chlorophenyl isocyanate (0.51 g).

m.p. 224°–226° C.

EXAMPLE 69

N-(4-Chlorophenyl)-N'-(4-(2-chlorophenyl)-2-ethyl-6H-thieno[3,2-f] [1,2,4]triazolo[4,3-a] [1,4]diazepin-9-ylmethyl)urea (1.31 g) was obtained in the same manner as in Example 64 using 9-aminomethyl-4-(2-chlorophenyl)-2-ethyl-6H-thieno[3,2-f] [1,2,4]triazolo[4,3-a] [1,4]diazepine (1.07 g) and 4-chlorophenyl isocyanate (0.51 g).

m.p. 235°–237° C.

EXAMPLE 70

N-(4-(2-Chlorophenyl)-2-ethyl-6H-thieno[3,2-f] [1,2,4] triazolo[4,3-a] [1,4]diazepin-9-ylmethyl)-N'-(2-methylphenyl)urea (1.09 g) was obtained in the same manner as in Example 64 using 9-aminomethyl-4-(2-chlorophenyl)-2-ethyl-6H-thieno[3,2-f] [1,2,4]triazolo[4,3-a] [1,4]diazepine (1.07 g) and 2-methylphenyl isocyanate (0.44 g).

m.p. 185°–187° C.

Production Example 9

4-(2-Chlorophenyl)-2-ethyl-6H-thieno[3,2-f] [1,2,4] triazolo[4,3-a] [1,4]diazepine (10 g) was dissolved in dichloroethane (100 ml), and bromine (1.7 ml) was added under ice-cooling. The mixture was heated to room temperature, and allowed to stand overnight. The solvent was evaporated, and chloroform was added. The mixture was washed with an aqueous sodium thiosulfate solution, a saturated aqueous sodium hydrogencarbonate solution and brine, and dried over magnesium sulfate. The solvent was evaporated, and the residue was purified by silica gel column chromatography (developing solvent:ethyl acetate-hexane) and crystallized from ethyl acetate to give 3.4 g of 9-bromo-4-(2-chlorophenyl)-2-ethyl-6H-thieno[3,2-f] [1,2,4]triazolo[4,3-a] [1,4]diazepine.

m.p. 162°–164° C.

EXAMPLE 71

9-Bromo-4-(2-chlorophenyl)-2-ethyl-6H-thieno[3,2-f] [1,2,4]triazolo[4,3-a] [1,4]diazepine is added to 2M sulfuric acid, and the mixture is stirred at 80° C. overnight. Sodium hydrogencarbonate is added to the reaction mixture to make the mixture alkaline. Chloroform and 3,4-dichlorobenzoyl chloride are added, and the mixture is stirred at room temperature for 2 hours to give N-(3-bromo-4-(3-(2-chlorobenzoyl)-5-ethylthiophen-2-yl) [1,2,4]triazol-5-ylmethyl)-3,4-dichlorobenzamide.

EXAMPLE 72

9-Bromo-4-(2-chlorophenyl)-2-ethyl-6H-thieno[3,2-f] [1,2,4]triazolo[4,3-a] [1,4]diazepine (1.0 g) was added to 2M sulfuric acid (26.5 ml), and the mixture was stirred at 80° C. overnight. Sodium hydrogencarbonate was added to the reaction mixture to make the mixture alkaline. Chloroform and indole-2-carbonyl chloride were added, and the mixture was stirred at room temperature for 1.5 hours. The obtained crystals were filtered and washed with ethyl acetate to give 0.196 g of N-(3-bromo-4-(3-(2-chlorobenzoyl)-5-ethylthiophen-2-yl) [1,2,4]triazol-5-ylmethyl)indole-2-carboxamide.

m.p. 241°–243° C.

EXAMPLE 73

9-Bromo-4-(2-chlorophenyl)-2-ethyl-6H-thieno[3,2-f] [1,2,4]triazolo[4,3-a] [1,4]diazepine is added to 2M sulfuric acid, and the mixture is stirred at 80° C. overnight. Sodium hydrogencarbonate is added to the reaction mixture to make the mixture alkaline. Chloroform and 1-ethoxycarbonylmethylindole-2-carbonyl chloride are added, and the mixture is stirred at room temperature for 2 hours to give ethyl 2-(3-bromo-4-(3-(2-chlorobenzoyl)-5-ethylthiophen-2-yl) [1,2,4]triazol-5-ylmethylcarbamoyl) indole-1-acetate.

EXAMPLE 74

Ethyl 2-(3-bromo-4-(3-(2-chlorobenzoyl)-5-ethylthiophen-2-yl) [1,2,4]triazol-5-ylmethylcarbamoyl) indole-1-acetate and a 2M aqueous sodium hydroxide solution are added to ethanol, and the mixture is refluxed with stirring for 1 hour. An aqueous citric acid solution is added to adjust the reaction mixture to pH 3 to give 2-(3-bromo-4-(3-(2-chlorobenzoyl)-5-ethylthiophen-2-yl) [1,2,4]triazol-5-ylmethylcarbamoyl)indole-1-acetic acid.

EXAMPLE 75

9-Bromo-4-(2-chlorophenyl)-2-ethyl-6H-thieno[3,2-f] [1,2,4]triazolo[4,3-a] [1,4]diazepine is added to 2M sulfuric acid, and the mixture is stirred at 80° C. overnight. Sodium hydrogencarbonate is added to the reaction mixture to make the mixture alkaline. The mixture is extracted with chloroform and the extract is dried over magnesium sulfate. 3-Methoxyphenyl isocyanate is added thereto, and the mixture is stirred at room temperature for 2 hours to give N-(3-bromo-4-(3-(2-chlorobenzoyl)-5-ethylthiophen-2-yl) [1,2,4]triazol-5-ylmethyl)-N'-(3-methoxyphenyl)urea.

EXAMPLE 76

Water (20 ml) and dioxane (20 ml) were added to N-(4-(2-chlorophenyl)-2-ethyl-6H-thieno[3,2-f] [1,2,4]triazolo[4,3-a] [1,4]diazepin-9-ylmethyl)-3,4-dichlorobenzamide (3.0 g), and conc. sulfuric acid (1.2 ml) was dropwise added with vigorous stirring. Then, the mixture was stirred at 80° C. for 1.5 hours. Sodium nitrite (3.9 g) was added, and the mixture was further stirred for 1 hour. A saturated aqueous sodium hydrogencarbonate solution was added to the reaction mixture, and the mixture was extracted with ethyl acetate. The organic layer was dried over magnesium sulfate, and the solvent was evaporated. The residue was purified by silica gel column chromatography (developing solvent:ethyl acetate) and recrystallized from a mixed solvent of ethyl acetate-hexane to give 0.9 g of N-(4-(3-(2-chlorobenzoyl)-5-ethylthiophen-2-yl)-3-hydroxymethyl[1,2,4]triazol-5-ylmethyl)-3,4-dichlorobenzamide.

m.p. 125°–128° C.

EXAMPLE 77

9-Hydroxymethyl-4-(2-chlorophenyl)-2-ethyl-6H-thieno[3,2-f] [1,2,4]triazolo[4,3-a] [1,4]diazepine (0.5 g) which can be synthesized by a known method (Japanese Patent Unexamined Publication No. 102698/1974) was stirred with 5% hydrochloric acid (10 ml) at 60° C. overnight. Then, sodium hydrogencarbonate was added to the reaction mixture to make the mixture alkaline. Chloroform and indole-2-carbonyl chloride (0.35 g) were added, and the mixture was stirred under ice-cooling for 3 hours. The organic layer was washed with saturated brine and dried over magnesium sulfate. The solvent was evaporated, and the residue was purified by silica gel thin-layer chromatography (developing solvent:ethyl acetate) and recrystallized from ethyl acetate-hexane to give 0.015 g of N-(4-(3-(2-chlorobenzoyl)-5-ethylthiophen-2-yl)-3-hydroxymethyl[1,2,4]triazol-5-ylmethyl)indole-2-carboxamide.

m.p. 174°–176° C.

EXAMPLE 78

Ethyl 2-(4-(3-(2-chlorobenzoyl)-5-ethylthiophen-2-yl)-3-hydroxymethyl[1,2,4]triazol-5-ylmethylcarbamoyl)indole-1-acetate (0.32 g) was obtained in the same manner as in Example 77 using 9-hydroxymethyl-4-(2-chlorophenyl)-2-ethyl-6H-thieno[3,2-f] [1,2,4]triazolo[4,3-a] [1,4]diazepine and 1-ethoxycarbonylmethylindole-2-carbonyl chloride.

m.p. 92°–96° C.

EXAMPLE 79

Ethyl 2-(4-(3-(2-chlorobenzoyl)-5-ethylthiophen-2-yl)-3-hydroxymethyl[1,2,4]triazol-5-ylmethylcarbamoyl)indole-1-acetate is subjected to alkali hydrolysis using a 2M aqueous sodium hydroxide solution to give 2-(4-(3-(2-chlorobenzoyl)-5-ethylthiophen-2-yl)-3-hydroxymethyl[1,2,4]triazol-5-ylmethylcarbamoyl)indole-1-acetic acid.

EXAMPLE 80

N-(4-(3-(2-Chlorobenzoyl)-5-ethylthiophen-2-yl)-3-hydroxymethyl[1,2,4]triazol-5-ylmethyl)-N'-(3-methoxyphenyl)urea is obtained in the same manner as in Example 294 using 9-hydroxymethyl-4-(2-chlorophenyl)-2-ethyl-6H-thieno[3,2-f] [1,2,4]triazolo[4,3-a] [1,4]diazepine, camphor-10-sulfonic acid and 3-methoxyphenyl isocyanate.

EXAMPLE 81

N-(1-(3-(2-Chlorobenzoyl)-5-ethylthiophen-2-yl) [1,3]imidazol-2-ylmethyl)-3,4-dichlorobenzamide is obtained in the same manner as in Example 1 using 2-aminomethyl-3-(3-(2-chlorobenzoyl)-5-ethylthiophen-2-yl) [1,3]imidazole and 3,4-dichlorobenzoyl chloride.

EXAMPLE 82

N-(1-(3-(2-Chlorobenzoyl)-5-ethylthiophen-2-yl) [1,3]imidazol-2-ylmethyl)indole-2-carboxamide is obtained in the same manner as in Example 1 using 2-aminomethyl-3-(3-(2-chlorobenzoyl)-5-ethylthiophen-2-yl) [1,3]imidazole and indole-2-carbonyl chloride.

EXAMPLE 83

Ethyl 2-(1-(3-(2-chlorobenzoyl)-5-ethylthiophen-2-yl) [1,3]imidazol- 2-ylmethylcarbamoyl)indole-1-acetate is obtained in the same manner as in Example 1 using 2-aminomethyl-3-(3-(2-chlorobenzoyl)-5-ethylthiophen-2-yl) [1,3]imidazole and 1-ethoxycarbonylmethylindole-2-carbonyl chloride.

EXAMPLE 84

Ethyl 2-(1-(3-(2-chlorobenzoyl)-5-ethylthiophen-2-yl) [1,3]imidazol-2-ylmethylcarbamoyl)indole-1-acetate is subjected to alkali hydrolysis using a 2M aqueous sodium hydroxide solution to give 2-(1-(3-(2-chlorobenzoyl)-5-ethylthiophen-2-yl) [1,3]imidazol-2-ylmethylcarbamoyl) indole-1-acetic acid.

EXAMPLE 85

N-(1-(3-(2-Chlorobenzoyl)-5-ethylthiophen-2-yl) [1,3] imidazol-2-ylmethyl)-N'-(3-methoxyphenyl)urea is obtained in the same manner as in Example 23 using 2-aminomethyl-3-(3-(2-chlorobenzoyl)-5-ethylthiophen-2-yl) [1,3]imidazole and 3-methoxyphenyl isocyanate.

EXAMPLE 86

N-(1-(3-(2-Chlorobenzoyl)-5-ethylthiophen-2-yl) [1,3] imidazol-2-ylmethyl)-N'-(2-chlorophenyl)urea is obtained in the same manner as in Example 23 using 2-aminomethyl-3-(3-(2-chlorobenzoyl)-5-ethylthiophen-2-yl) [1,3] imidazole and 2-chlorophenyl isocyanate.

EXAMPLE 87

N-(1-(3-(2-Chlorobenzoyl)-5-ethylthiophen-2-yl) [1,3] imidazol-2-ylmethyl)-N'-(3-methylphenyl)urea is obtained in the same manner as in Example 23 using 2-aminomethyl-3-(3-(2-chlorobenzoyl)-5-ethylthiophen-2-yl) [1,3] imidazole and 3-methylphenyl isocyanate.

EXAMPLE 88

4-(2-Chlorophenyl)-2-ethyl-6H-thieno[3,2-f]-1,2,3,4-tetrazolo[4,5-a] [1,4]diazepine synthesized by a known method (see Japanese Patent Unexamined Publication No. 26297/1974) is hydrolyzed in the same manner as in Example 89, and reacted with 3,4-dichlorobenzoyl chloride to give N-(1-(3-(2-chlorobenzoyl)-5-ethylthiophen-2-yl)-1,2,3,4-tetrazol-5-ylmethyl)-3,4-dichlorobenzamide.

EXAMPLE 89

4-(2-Chlorophenyl)-2-ethyl-6H-thieno[3,2-f]-1,2,3,4-tetrazolo[4,5-a] [1,4]diazepine (2.0 g) and p-toluenesulfonic acid monohydrate (3.5 g) were added to a mixed solvent (20 ml) of ethanol-water (9:1), and the mixture was refluxed under heating for 2 hours. The solvent was evaporated. Dimethylformamide (20 ml), indole-2-carbonyl chloride (1.4 g) and triethylamine (5.0 ml) were added under ice-cooling, and the mixture was stirred for 1 hour. The reaction mixture was partitioned between ethyl acetate and a saturated aqueous sodium hydrogencarbonate solution. The organic layer was washed with brine, an aqueous citric acid solution and brine. The solvent was concentrated under reduced pressure. The obtained residue was purified by silica gel column chromatography (developing solvent:ethyl acetate-diisopropyl ether) and crystallized from a mixed solvent of ethyl acetate-hexane to give 0.64 g of N-(1-(3-(2-chlorobenzoyl)-5-ethylthiophen-2-yl)-1,2,3,4-tetrazol-5-ylmethyl)indole-2-carboxamide.

m.p. 146°–149° C.

EXAMPLE 90

4-(2-Chlorophenyl)-2-ethyl-6H-thieno[3,2-f]-1,2,3,4-tetrazolo[4,5-a] [1,4]diazepine is hydrolyzed in the same manner as in Example 89, and reacted with 1-ethoxycarbonylmethylindole-2-carbonyl chloride to give ethyl 2-(1-(3-(2-chlorobenzoyl)-5-ethylthiophen-2-yl)-1,2,3,4-tetrazol-5-ylmethylcarbamoyl)indole-1-acetate.

EXAMPLE 91

Ethyl 2-(1-(3-(2-chlorobenzoyl)-5-ethylthiophen-2-yl)-1,2,3,4-tetrazol-5-ylmethylcarbamoyl)indole-1-acetate is hydrolyzed using a 2M aqueous sodium hydroxide solution to give 2-(1-(3-(2-chlorobenzoyl)-5-ethylthiophen-2-yl)-1,2,3,4-tetrazol-5-ylmethylcarbamoyl)indole-1-acetic acid.

EXAMPLE 92

4-(2-Chlorophenyl)-2-ethyl-6H-thieno[3,2-f]-1,2,3,4-tetrazolo[4,5-a] [1,4]diazepine is hydrolyzed in the same manner as in Example 89, and reacted with 3-methoxyphenyl isocyanate to give N-(1-(3-(2-chlorobenzoyl)-5-ethylthiophen-2-yl)-1,2,3,4-tetrazol-5-ylmethyl)-N'-(3-methoxyphenyl)urea.

EXAMPLE 93

4-(2-Chlorophenyl)-2-ethyl-6H-thieno[3,2-f]-1,2,3,4-tetrazolo[4,5-a] [1,4]diazepine is hydrolyzed in the same manner as in Example 89, and reacted with 2-chlorophenyl isocyanate to give N-(1-(3-(2-chlorobenzoyl)-5-ethylthiophen-2-yl)-1,2,3,4-tetrazol-5-ylmethyl)-N'-(2-chlorophenyl)urea.

EXAMPLE 94

4-(2-Chlorophenyl)-2-ethyl-6H-thieno[3,2-f]-1,2,3,4-tetrazolo[4,5-a] [1,4]diazepine is hydrolyzed in the same manner as in Example 89, and reacted with 3-methylphenyl isocyanate to give N-(1-(3-(2-chlorobenzoyl)-5-ethylthiophen-2-yl)-1,2,3,4-tetrazol-5-ylmethyl)-N'-(3-methylphenyl)urea.

EXAMPLE 95

N-(4-(2-Chlorophenyl)-2-ethyl-6H-thieno[3,2-f] [1,2,4] triazolo[4,3-a] [1,4]diazepin-9-ylmethyl)-3,4-dimethylbenzamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 3,4-dimethylbenzoic acid.

EXAMPLE 96

N-(4-(2-Chlorophenyl)-2-ethyl-6H-thieno[3,2-f] [1,2,4] triazolo[4,3-a] [1,4]diazepin-9-ylmethyl)-4-chlorobenzamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 4-chlorobenzoic acid.

EXAMPLE 97

N-(4-(2-Chlorophenyl)-2-ethyl-6H-thieno[3,2-f] [1,2,4] triazolo[4,3-a] [1,4]diazepin-9-ylmethyl)-3-chlorobenzamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 3-chlorobenzoic acid.

EXAMPLE 98

N-(4-(2-Chlorophenyl)-2-ethyl-6H-thieno[3,2-f] [1,2,4] triazolo[4,3-a] [1,4]diazepin-9-ylmethyl)-4-bromobenzamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 4-bromobenzoic acid.

EXAMPLE 99

N-(4-(2-Chlorophenyl)-2-ethyl-6H-thieno[3,2-f] [1,2,4] triazolo[4,3-a] [1,4]diazepin-9-ylmethyl)-3-bromobenzamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 3-bromobenzoic acid.

EXAMPLE 100

N-(4-(2-Chlorophenyl)-2-ethyl-6H-thieno[3,2-f] [1,2,4] triazolo[4,3-a] [1,4]diazepin-9-ylmethyl)-4-iodobenzamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 4-iodobenzoic acid.

EXAMPLE 101

N-(4-(2-Chlorophenyl)-2-ethyl-6H-thieno[3,2-f] [1,2,4] triazolo[4,3-a] [1,4]diazepin-9-ylmethyl)-3-iodobenzamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 3-iodobenzoic acid.

EXAMPLE 102

N-(4-(2-Chlorophenyl)-2-ethyl-6H-thieno[3,2-f] [1,2,4] triazolo[4,3-a] [1,4]diazepin-9-ylmethyl)naphthalene-2-carboxamide (0.60 g) was obtained in the same manner as in Example 59 using 9-aminomethyl-4-(2-chlorophenyl)-2-ethyl-6H-thieno[3,2-f] [1,2,4]triazolo[4,3-a] [1,4]diazepine (1.0 g), dimethylformamide (10 ml), 2-naphthoyl chloride (0.59 g) and triethylamine (0.39 ml).

m.p. 146°–149° C.

EXAMPLE 103

Methyl 3-(2-(4-(2-chlorophenyl)-2-ethyl-6H-thieno[3,2-f] [1,2,4]triazolo[4,3-a] [1,4]diazepin-9-ylmethylcarbamoyl)indol-1-yl)propionate is obtained in the same manner as in Example 61 using 6-aminomethyl-4-(2-chlorophenyl)-2-ethyl-6H-thieno[3,2-f] [1,2,4]triazolo[4,3-a] [1,4]diazepine and 1-(2-methoxycarbonylethyl)indole-2-carboxylic acid.

EXAMPLE 104

Methyl 3-(2-(4-(2-chlorophenyl)-2-ethyl-6H-thieno[3,2-f] [1,2,4]triazolo[4,3-a] [1,4]diazepin-9-ylmethylcarbamoyl)indol-1-yl)propionate is subjected to alkali hydrolysis to give 3-(2-(4-(2-chlorophenyl)-2-ethyl-6H-thieno[3,2-f] [1,2,4]triazolo[4,3-a] [1,4]diazepin-9-ylmethylcarbamoyl)indol-1-yl)propionic acid.

EXAMPLE 105

N-(4-(2-Chlorophenyl)-2-ethyl-6H-thieno[3,2-f] [1,2,4] triazolo[4,3-a] [1,4]diazepin-9-ylmethyl)-5-chloroindole-2- carboxamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 5-chloroindole-2-carboxylic acid.

EXAMPLE 106

N-(4-(2-Chlorophenyl)-2-ethyl-6H-thieno[3,2-f] [1,2,4]triazolo[4,3-a] [1,4]diazepin-9-ylmethyl)-5-fluoroindole-2-carboxamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 5-fluoroindole-2-carboxylic acid.

EXAMPLE 107

N-(4-(2-Chlorophenyl)-2-ethyl-6H-thieno[3,2-f] [1,2,4]triazolo[4,3-a] [1,4]diazepin-9-ylmethyl)-5-methoxyindole-2-carboxamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and 5-methoxyindole-2-carboxylic acid.

EXAMPLE 108

N-(4-(2-Chlorophenyl)-2-ethyl-6H-thieno[3,2-f] [1,2,4]triazolo[4,3-a] [1,4]diazepin-9-ylmethyl)benzofuran-2-carboxamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and benzofuran-2-carboxylic acid.

EXAMPLE 109

N-(4-(2-Chlorophenyl)-2-ethyl-6H-thieno[3,2-f] [1,2,4]triazolo[4,3-a] [1,4]diazepin-9-ylmethyl)benzothiophene-2-carboxamide is obtained in the same manner as in Example 61 using 9-aminomethyl-4-(2-chlorophenyl)-2-ethyl-6H-thieno[3,2-f] [1,2,4]triazolo[4,3-a] [1,4]diazepine and benzothiophene-2-carboxylic acid.

EXAMPLE 110

N-(4-(2-Chlorophenyl)-2-ethyl-6H-thieno[3,2-f] [1,2,4]triazolo[4,3-a] [1,4]diazepin-9-ylmethyl)-N'-(4-methylphenyl)urea is obtained in the same manner as in Example 64 using 9-aminomethyl-4-(2-chlorophenyl)-2-ethyl-6H-thieno[3,2-f] [1,2,4]triazolo[4,3-a] [1,4]diazepine and 4-methylphenyl isocyanate.

EXAMPLE 111

N-(4-(2-Chlorophenyl)-2-ethyl-6H-thieno[3,2-f] [1,2,4]triazolo[4,3-a] [1,4]diazepin-9-ylmethyl)-N'-(2-methoxyphenyl)urea (1.24 g) was obtained in the same manner as in Example 64 using 9-aminomethyl-4-(2-chlorophenyl)-2-ethyl-6H-thieno[3,2-f] [1,2,4]triazolo[4,3-a] [1,4]diazepine (1.0 g), 2-methoxyphenyl isocyanate (0.41 ml) and chloroform (50 ml).

m.p. 153°–155° C.

EXAMPLE 112

N-(4-(2-Chlorophenyl)-2-ethyl-6H-thieno[3,2-f] [1,2,4]triazolo[4,3-a] [1,4]diazepin-9-ylmethyl)-N'-(4-methoxyphenyl)urea is obtained in the same manner as in Example 64 using 9-aminomethyl-4-(2-chlorophenyl)-2-ethyl-6H-thieno[3,2-f] [1,2,4]triazolo[4,3-a] [1,4]diazepine and 4-methoxyphenyl isocyanate.

EXAMPLE 113

Methyl 3-aminophenylacetate is reacted with carbonyldiimidazole, and then with 9-aminomethyl-4-(2-chlorophenyl)-2-ethyl-6H-thieno[3,2-f] [1,2,4]triazolo[4,3-a] [1,4]diazepine to give methyl 3-(3-(4-(2-chlorophenyl)-2-ethyl-6H-thieno[3,2-f] [1,2,4]triazolo[4,3-a] [1,4]diazepin-9-ylmethyl)ureido)phenylacetate.

EXAMPLE 114

Methyl 3-(3-(4-(2-chlorophenyl)-2-ethyl-6H-thieno[3,2-f] [1,2,4]triazolo[4,3-a] [1,4]diazepin-9-ylmethyl)ureido)phenylacetate is subjected to alkali hydrolysis to give 3-(3-(4-(2-chlorophenyl)-2-ethyl-6H-thieno[3,2-f] [1,2,4]triazolo[4,3-a] [1,4]diazepin-9-ylmethyl)ureido)phenylacetic acid.

EXAMPLE 115

N-(4-(2-Chlorophenyl)-2-ethyl-6H-thieno[3,2-f] [1,2,4]triazolo[4,3-a] [1,4]diazepin-9-ylmethyl)-3,4-dichlorobenzenesulfonamide is obtained in the same manner as in Example 48 using 9-aminomethyl-4-(2-chlorophenyl)-2-ethyl-6H-thieno[3,2-f] [1,2,4]triazolo[4,3-a] [1,4]diazepine and 3,4-dichlorobenzenesulfonyl chloride.

EXAMPLE 116

N-(4-(2-Chlorophenyl)-2-ethyl-6H-thieno[3,2-f] [1,2,4]triazolo[4,3-a] [1,4]diazepin-9-ylmethyl)naphthalene-2-sulfonamide is obtained in the same manner as in Example 48 using 9-aminomethyl-4-(2-chlorophenyl)-2-ethyl-6H-thieno[3,2-f] [1,2,4]triazolo[4,3-a] [1,4]diazepine and 2-naphthalenesulfonyl chloride.

EXAMPLE 117

N-(4-(2-Chlorophenyl)-2-ethyl-6H-thieno[3,2-f] [1,2,4]triazolo[4,3-a] [1,4]diazepin-9-ylmethyl)-N'-phenylthiourea is obtained in the same manner as in Example 64 using 9-aminomethyl-4-(2-chlorophenyl)-2-ethyl-6H-thieno[3,2-f] [1,2,4]triazolo[4,3-a] [1,4]diazepine and phenyl isothiocyanate.

EXAMPLE 118

N-(4-Phenyl-6H-thieno[3,2-f] [1,2,4]triazolo[4,3-a] [1,4]diazepin-9-ylmethyl)-3,4-dichlorobenzamide is obtained in the same manner as in Example 61 using 9-aminomethyl-4-phenyl-6H-thieno[3,2-f] [1,2,4]triazolo[4,3-a] [1,4]diazepine and 3,4-dichlorobenzoic acid.

EXAMPLE 119

N-(4-Phenyl-6H-thieno[3,2-f] [1,2,4]triazolo[4,3-a] [1,4]diazepin-9-ylmethyl)indole-2-carboxamide is obtained in the same manner as in Example 61 using 9-aminomethyl-4-phenyl-6H-thieno[3,2-f] [1,2,4]-triazolo[4,3-a] [1,4]diazepine and indole-2-carboxylic acid.

EXAMPLE 120

Ethyl 2-(4-phenyl-6H-thieno[3,2-f] [1,2,4]triazolo[4,3-a] [1,4]diazepin-9-ylmethyl)indole-1-acetate is obtained in the same manner as in Example 61 using 9-aminomethyl-4-phenyl-6H-thieno[3,2-f] [1,2,4]triazolo[4,3-a] [1,4]diazepine and 1-ethoxycarbonylmethylindole-2-carboxylic acid.

EXAMPLE 121

Ethyl 2-(4-phenyl-6H-thieno[3,2-f] [1,2,4]triazolo[4,3-a] [1,4]diazepin-9-ylmethylcarbamoyl)indole-1-acetate is subjected to alkali hydrolysis to give 2-(4-phenyl-6H-thieno[3,2-f] [1,2,4]triazolo[4,3-a] [1,4]diazepin-9-ylmethylcarbamoyl)indole-1-acetic acid.

EXAMPLE 122

N-(3-Methylphenyl)-N'-(4-phenyl-6H-thieno[3,2-f] [1,2,4]triazolo[4,3-a] [1,4]diazepin-9-ylmethyl)urea is obtained in the same manner as in Example 64 using 9-aminomethyl-4-phenyl-6H-thieno[3,2-f] [1,2,4]triazolo[4,3-a] [1,4] diazepine and 3-methylphenyl isocyanate.

EXAMPLE 123

N-(2-Chlorophenyl)-N'-(4-phenyl-6H-thieno[3,2-f] [1,2,4]triazolo[4,3-a] [1,4]diazepin-9-ylmethyl)urea is obtained in the same manner as in Example 64 using 9-aminomethyl-4-phenyl-6H-thieno[3,2-f] [1,2,4]triazolo[4,3-a] [1,4] diazepine and 2-chlorophenyl isocyanate.

EXAMPLE 124

N-(3-Methoxyphenyl)-N'-(4-phenyl-6H-thieno[3,2-f] [1,2,4]triazolo[4,3-a] [1,4]diazepin-9-ylmethyl)urea is obtained in the same manner as in Example 64 using 9-aminomethyl-4-phenyl-6H-thieno[3,2-f] [1,2,4]triazolo[4,3-a] [1,4]diazepine and 3-methoxyphenyl isocyanate.

EXAMPLE 125

N-(4-(4-Chlorophenyl)-2-ethyl-6H-thieno[3,2-f] [1,2,4] triazolo[4,3-a] [1,4]diazepin-9-ylmethyl)-3,4-dichlorobenzamide (0.52 g) was obtained in the same manner as in Example 59 using 9-aminomethyl-4-(4-chlorophenyl)-2-ethyl-6H-thieno[3,2-f] [1,2,4]triazolo[4,3-a] [1,4]diazepine (0.5 g), dichloroethane (25 ml), triethylamine (0.21 ml) and 3,4-dichlorobenzoyl chloride (0.31 g).

m.p. 191°–192° C.

EXAMPLE 126

N-(4-(4-Chlorophenyl)-2-ethyl-6H-thieno[3,2-f] [1,2,4] triazolo[4,3-a] [1,4]diazepin-9-ylmethyl)indole-2-carboxamide is obtained in the same manner as in Example 61 using 9-aminomethyl-4-(4-chlorophenyl)-2-ethyl-6H-thieno[3,2-f] [1,2,4]triazolo[4,3-a] [1,4]diazepine and indole-2-carboxylic acid.

EXAMPLE 127

Ethyl 2-(4-(4-chlorophenyl)-2-ethyl-6H-thieno[3,2-f] [1,2,4]triazolo[4,3-a] [1,4]diazepin-9-ylmethylcarbamoyl) indole-1-acetate is obtained in the same manner as in Example 61 using 9-aminomethyl-4-(4-chlorophenyl)-2-ethyl-6H-thieno[3,2-f] [1,2,4]triazolo[4,3-a] [1,4]diazepine and 1-ethoxycarbonylmethylindole-2-carboxylic acid.

EXAMPLE 128

Ethyl 2-(4-(4-chlorophenyl)-2-ethyl-6H-thieno[3,2-f] [1,2,4]triazolo[4,3-a] [1,4]diazepin-9-ylmethylcarbamoyl) indole-1-acetate is subjected to alkali hydrolysis to give 2-(4-(4-chlorophenyl)-2-ethyl-6H-thieno[3,2-f] [1,2,4] triazolo[4,3-a] [1,4]diazepin-9-ylmethylcarbamoyl)indole-1-acetic acid.

EXAMPLE 129

N-(4-(4-Chlorophenyl)-2-ethyl-6H-thieno[3,2-f] [1,2,4] triazolo[4,3-a] [1,4]diazepin-9-ylmethyl)-N'-(3-methylphenyl)urea is obtained in the same manner as in Example 64 using 9-aminomethyl-4-(4-chlorophenyl)-2-ethyl-6H-thieno[3,2-f] [1,2,4]triazolo[4,3-a] [1,4]diazepine and 3-methylphenyl isocyanate.

EXAMPLE 130

N-(2-Chlorophenyl)-N'-(4-(4-chlorophenyl)-2-ethyl-6H-thieno[3,2-f] [1,2,4]triazolo[4,3-a] [1,4]diazepin-9-ylmethyl)urea is obtained in the same manner as in Example 64 using 9-aminomethyl-4-(4-chlorophenyl)-2-ethyl-6H-thieno[3,2-f] [1,2,4]triazolo[4,3-a] [1,4]diazepine and 2-chlorophenyl isocyanate.

EXAMPLE 131

N-(4-(4-Chlorophenyl)-2-ethyl-6H-thieno[3,2-f] [1,2,4] triazolo[4,3-a] [1,4]diazepin-9-ylmethyl)-N'-(2-methoxyphenyl)urea (0.64 g) was obtained in the same manner as in Example 64 using 9-aminomethyl-4-(4-chlorophenyl)-2-ethyl-6H-thieno[3,2-f] [1,2,4]triazolo[4,3-a] [1,4]diazepine (0.75 g) and 2-methoxyphenyl isocyanate (0.31 ml).

m.p. 173°–176° C.

EXAMPLE 132

N-(2-Ethyl-4-phenyl-6H-thieno[3,2-f] [1,2,4]triazolo[4,3-a] [1,4]diazepin-9-ylmethyl)-3,4-dichlorobenzamide (0.82 g) was obtained in the same manner as in Example 59 using 9-aminomethyl-2-ethyl-4-phenyl-6H-thieno[3,2-f] [1,2,4]triazolo[4,3-a] [1,4]diazepine (0.66 g), dichloroethane (35 ml), triethylamine (0.30 ml) and 3,4-dichlorobenzoyl chloride (0.45 g).

m.p. 195°–196° C.

EXAMPLE 133

N-(2-Ethyl-4-phenyl-6H-thieno[3,2-f] [1,2,4]triazolo[4,3-a] [1,4]diazepin-9-ylmethyl)indole-2-carboxamide is obtained in the same manner as in Example 61 using 9-aminomethyl-2-ethyl-4-phenyl-6H-thieno[3,2-f] [1,2,4] triazolo[4,3-a] [1,4]diazepine and indole-2-carboxylic acid.

EXAMPLE 134

Ethyl 2-(2-ethyl-4-phenyl-6H-thieno[3,2-f] [1,2,4] triazolo[4,3-a] [1,4]diazepin-9-ylmethylcarbamoyl)indole-1-acetate is obtained in the same manner as in Example 61 using 9-aminomethyl-2-ethyl-4-phenyl-6H-thieno[3,2-f] [1,2,4]triazolo[4,3-a] [1,4]diazepine and 1-ethoxycarbonylmethylindole-2-carboxylic acid.

EXAMPLE 135

Ethyl 2-(2-ethyl-4-phenyl-6H-thieno[3,2-f] [1,2,4] triazolo[4,3-a] [1,4]diazepin-9-ylmethylcarbamoyl)indole-1-acetate is subjected to alkali hydrolysis to give 2-(2-ethyl-4-phenyl-6H-thieno[3,2-f] [1,2,4]triazolo[4,3-a] [1,4] diazepin-9-ylmethylcarbamoyl)indole-1-acetic acid.

EXAMPLE 136

N-(2-Ethyl-4-phenyl-6H-thieno[3,2-f] [1,2,4]triazolo[4,3-a] [1,4]diazepin-9-ylmethyl)-N'-(3-methylphenyl)urea is obtained in the same manner as in Example 64 using 9-aminomethyl-2-ethyl-4-phenyl-6H-thieno[3,2-f] [1,2,4] triazolo[4,3-a] [1,4]diazepine and 3-methylphenyl isocyanate.

EXAMPLE 137

N-(2-Chlorophenyl)-N'-(2-ethyl-4-phenyl-6H-thieno[3,2-f] [1,2,4]triazolo[4,3-a] [1,4]diazepin-9-ylmethyl)urea is obtained in the same manner as in Example 64 using 9-aminomethyl-2-ethyl-4-phenyl-6H-thieno[3,2-f] [1,2,4] triazolo[4,3-a] [1,4]diazepine and 2-chlorophenyl isocyanate.

EXAMPLE 138

N-(2-Ethyl-4-phenyl-6H-thieno[3,2-f] [1,2,4]triazolo[4,3-a] [1,4]diazepin-9-ylmethyl)-N'-(3-methoxyphenyl)urea is obtained in the same manner as in Example 64 using 9-aminomethyl-2-ethyl-4-phenyl-6H-thieno[3,2-f] [1,2,4] triazolo[4,3-a] [1,4]diazepine and 3-methoxyphenyl isocyanate.

EXAMPLE 139

N-(2-Methyl-4-phenyl-6H-thieno[3,2-f] [1,2,4]triazolo[4,3-a] [1,4]diazepin-9-ylmethyl)-3,4-dichlorobenzamide is obtained in the same manner as in Example 61 using 9-aminomethyl-2-methyl-4-phenyl-6H-thieno[3,2-f] [1,2,4] triazolo[4,3-a] [1,4]diazepine and 3,4-dichlorobenzoic acid.

EXAMPLE 140

N-(2-Methyl-4-phenyl-6H-thieno[3,2-f] [1,2,4]triazolo[4,3-a] [1,4]diazepin-9-ylmethyl)indole-2-carboxamide is obtained in the same manner as in Example 61 using 9-aminomethyl-2-methyl-4-phenyl-6H-thieno[3,2-f] [1,2,4] triazolo[4,3-a] [1,4]diazepine and indole-2-carboxylic acid.

EXAMPLE 141

Ethyl 2-(2-methyl-4-phenyl-6H-thieno[3,2-f] [1,2,4] triazolo[4,3-a] [1,4]diazepin-9-ylmethylcarbamoyl)indole-1-acetate is obtained in the same manner as in Example 61 using 9-aminomethyl-2-methyl-4-phenyl- 6H-thieno[3,2-f] [1,2,4]triazolo[4,3-a] [1,4]diazepine and 1-ethoxycarbonylmethylindole-2-carboxylic acid.

EXAMPLE 142

Ethyl 2-(2-methyl-4-phenyl-6H-thieno[3,2-f] [1,2,4] triazolo[4,3-a] [1,4]diazepin-9-ylmethylcarbamoyl)indole-1-acetate is subjected to alkali hydrolysis to give 2-(2-methyl-4-phenyl-6H-thieno[3,2-f] [1,2,4]triazolo[4,3-a] [1,4]diazepin-9-ylmethylcarbamoyl)indole-1-acetic acid.

EXAMPLE 143

N-(2-Methyl-4-phenyl-6H-thieno[3,2-f] [1,2,4]triazolo[4,3-a] [1,4]diazepin-9-ylmethyl)-N'-(3-methylphenyl)urea is obtained in the same manner as in Example 64 using 9-aminomethyl-2-methyl-4-phenyl-6H-thieno[3,2-f] [1,2,4] triazolo[4,3-a] [1,4]diazepine and 3-methylphenyl isocyanate.

EXAMPLE 144

N-(2-Chlorophenyl)-N'-(2-methyl-4-phenyl-6H-thieno[3,2-f] [1,2,4]triazolo[4,3-a] [1,4]diazepin-9-ylmethyl)urea is obtained in the same manner as in Example 64 using 9-aminomethyl-2-methyl-4-phenyl-6H-thieno[3,2-f] [1,2,4] triazolo[4,3-a] [1,4]diazepine and 2-chlorophenyl isocyanate.

EXAMPLE 145

N-(3-Methoxyphenyl)-N'-(2-methyl-4-phenyl-6H-thieno [3,2-f] [1,2,4]triazolo[4,3-a] [1,4]diazepin-9-ylmethyl)urea is obtained in the same manner as in Example 64 using 9-aminomethyl-2-methyl-4-phenyl-6H-thieno[3,2-f] [1,2,4] triazolo[4,3-a] [1,4]diazepine and 3-methoxyphenyl isocyanate.

EXAMPLE 146

N-(2,3-Dimethyl-4-phenyl-6H-thieno[3,2-f] [1,2,4] triazolo[4,3-a] [1,4]diazepin-9-ylmethyl)-3,4-dichlorobenzamide is obtained in the same manner as in Example 61 using 9-aminomethyl-2,3-dimethyl-4-phenyl-6H-thieno[3,2-f] [1,2,4]triazolo[4,3-a] [1,4]diazepine and 3,4-dichlorobenzoic acid.

EXAMPLE 147

N-(2,3-Dimethyl-4-phenyl-6H-thieno[3,2-f] [1,2,4] triazolo[4,3-a] [1,4]diazepin-9-ylmethyl)indole-2-carboxamide is obtained in the same manner as in Example 61 using 9-aminomethyl-2,3-dimethyl-4-phenyl-6H-thieno [3,2-f] [1,2,4]triazolo[4,3-a] [1,4]diazepine and indole-2-carboxylic acid.

EXAMPLE 148

Ethyl 2-(2,3-dimethyl-4-phenyl-6H-thieno[3,2-f] [1,2,4] triazolo[4,3-a] [1,4]diazepin-9-ylmethylcarbamoyl)indole-1-acetate is obtained in the same manner as in Example 61 using 9-aminomethyl-2,3-dimethyl-4-phenyl-6H-thieno[3,2-f] [1,2,4]triazolo[4,3-a] [1,4]diazepine and 1-ethoxycarbonylmethylindole-2-carboxylic acid.

EXAMPLE 149

Ethyl 2-(2,3-dimethyl-4-phenyl-6H-thieno[3,2-f] [1,2,4] triazolo[4,3-a] [1,4]diazepin-9-ylmethylcarbamoyl)indole-1-acetate is subjected to alkali hydrolysis to give 2-(2,3-dimethyl-4-phenyl-6H-thieno[3,2-f] [1,2,4]triazolo[4,3-a] [1,4]diazepin-9-ylmethylcarbamoyl)indole-1-acetic acid.

EXAMPLE 150

N-(2,3-Dimethyl-4-phenyl-6H-thieno[3,2-f] [1,2,4] triazolo[4,3-a] [1,4]diazepin-9-ylmethyl)-N'-(3-methylphenyl)urea is obtained in the same manner as in Example 64 using 9-aminomethyl-2,3-dimethyl-4-phenyl-6H-thieno[3,2-f] [1,2,4]triazolo[4,3-a] [1,4]diazepine and 3-methylphenyl isocyanate.

EXAMPLE 151

N-(2-Chlorophenyl)-N'-(2,3-dimethyl-4-phenyl-6H-thieno[3,2-f] [1,2,4]triazolo[4,3-a] [1,4]diazepin-9-ylmethyl)urea is obtained in the same manner as in Example 64 using 9-aminomethyl-2,3-dimethyl-4-phenyl-6H-thieno [3,2-f] [1,2,4]triazolo[4,3-a] [1,4]diazepine and 2-chlorophenyl isocyanate.

EXAMPLE 152

N-(2,3-Dimethyl-4-phenyl-6H-thieno[3,2-f] [1,2,4] triazolo[4,3-a] [1,4]diazepin-9-ylmethyl)-N'-(3-methoxyphenyl)urea is obtained in the same manner as in Example 64 using 9-aminomethyl-2,3-dimethyl-4-phenyl-6H-thieno[3,2-f] [1,2,4]triazolo[4,3-a] [1,4]diazepine and 3-methoxyphenyl isocyanate.

EXAMPLE 153

Methyl (4-(2-chlorophenyl)-9-(3,4-dichlorobenzoylaminomethyl)-6H-thieno[3,2-f] [1,2,4] triazolo[4,3-a] [1,4]diazepin-2-yl)acetate is obtained in the same manner as in Example 61 using methyl (9-aminomethyl-4-(2-chlorophenyl)-6H-thieno[3,2-f] [1,2,4]triazolo[4,3-a] [1,4]diazepin-2-yl)acetate and 3,4-dichlorobenzoic acid.

EXAMPLE 154

Methyl (4-(2-chlorophenyl)-9-(indole-2-carbonylaminomethyl)-6H-thieno[3,2-f] [1,2,4]triazolo[4,3- a] [1,4]diazepin-2-yl)acetate is obtained in the same manner as in Example 61 using methyl (9-aminomethyl-4-(2-chlorophenyl)-6H-thieno[3,2-f] [1,2,4]triazolo[4,3-a] [1,4] diazepin-2-yl)acetate and indole-2-carboxylic acid.

EXAMPLE 155

Methyl (4-(2-chlorophenyl)-9-(3-(3-methylphenyl) ureidomethyl)-6H-thieno[3,2-f] [1,2,4]triazolo[4,3-a] [1,4] diazepin-2-yl)acetate is obtained in the same manner as in Example 64 using methyl (9-aminomethyl-4-(2-chlorophenyl)-6H-thieno[3,2-f] [1,2,4]triazolo[4,3-a] [1,4] diazepin-2-yl)acetate and 3-methylphenyl isocyanate.

EXAMPLE 156

Methyl (4-(2-chlorophenyl)-9-(3-(2-chlorophenyl) ureidomethyl)-6H-thieno[3,2-f] [1,2,4]triazolo[4,3-a] [1,4] diazepin-2-yl)acetate is obtained in the same manner as in Example 64 using methyl (9-aminomethyl-4-(2-chlorophenyl)-6H-thieno[3,2-f] [1,2,4]triazolo[4,3-a] [1,4] diazepin-2-yl)acetate and 2-chlorophenyl isocyanate.

EXAMPLE 157

Methyl (4-(2-chlorophenyl)-9-(3-(3-methoxyphenyl) ureidomethyl)-6H-thieno[3,2-f] [1,2,4]triazolo[4,3-a] [1,4] diazepin-2-yl)acetate is obtained in the same manner as in Example 64 using methyl (9-aminomethyl-4-(2-chlorophenyl)-6H-thieno[3,2-f] [1,2,4]triazolo[4,3-a] [1,4] diazepin-2-yl)acetate and 3-methoxyphenyl isocyanate.

EXAMPLE 158

Methyl (4-(2-chlorophenyl)-9-(3,4-dichlorobenzoylaminomethyl)-6H-thieno[3,2-f] [1,2,4] triazolo[4,3-a] [1,4]diazepin-2-yl)acetate is subjected to alkali hydrolysis to give (4-(2-chlorophenyl)-9-(3,4-dichlorobenzoylaminomethyl)-6H-thieno[3,2-f] [1,2,4] triazolo[4,3-a] [1,4]diazepin-2-yl)acetic acid.

EXAMPLE 159

Methyl (9-aminomethyl-4-(2-chlorophenyl)-6H-thieno[3,2-f] [1,2,4]triazolo[4,3-a] [1,4]diazepin-2-yl)acetate is subjected to alkali hydrolysis to give (4-(2-chlorophenyl)-9-(indole-2-carbonylaminomethyl)-6H-thieno[3,2-f] [1,2,4] triazolo[4,3-a] [1,4]diazepin-2-yl)acetic acid.

EXAMPLE 160

Methyl (4-(2-chlorophenyl)-9-(3-(3-methylphenyl) ureidomethyl)-6H-thieno[3,2-f] [1,2,4]triazolo[4,3-a] [1,4] diazepin-2-yl)acetate is subjected to alkali hydrolysis to give (4-(2-chlorophenyl)-9-(3-(3-methylphenyl)ureidomethyl)-6H-thieno[3,2-f] [1,2,4]triazolo[4,3-a] [1,4]diazepin-2-yl) acetic acid.

EXAMPLE 161

Methyl (4-(2-chlorophenyl)-9-(3-(2-chlorophenyl) ureidomethyl)-6H-thieno[3,2-f] [1,2,4]triazolo[4,3-a] [1,4] diazepin-2-yl)acetate is subjected to alkali hydrolysis to give (4-(2-chlorophenyl)-9-(3-(2-chlorophenyl)ureidomethyl)-6H-thieno[3,2-f] [1,2,4]triazolo[4,3-a] [1,4]diazepin-2-yl) acetic acid.

EXAMPLE 162

Methyl (4-(2-chlorophenyl)-9-(3-(3-methoxyphenyl) ureidomethyl)-6H-thieno[3,2-f] [1,2,4]triazolo[4,3-a] [1,4] diazepin-2-yl)acetate is subjected to alkali hydrolysis to give (4-(2-chlorophenyl)-9-(3-(3-methoxyphenyl)ureidomethyl)-6H-thieno[3,2-f] [1,2,4]triazolo[4,3-a] [1,4]diazepin-2-yl) acetic acid.

EXAMPLE 163

Ethyl 4-(2-chlorophenyl)-9-(3,4-dichlorobenzoylaminomethyl)-6H-thieno[3,2-f] [1,2,4] triazolo[4,3-a] [1,4]diazepine-2-carboxylate (0.81 g) was obtained in the same manner as in Example 61 using ethyl 9-aminomethyl- 4-(2-chlorophenyl)-6H-thieno[3,2-f] [1,2,4]triazolo[4,3-a] [1,4]diazepine-2-carboxylate (1.19 g), dichloroethane (60 ml), triethylamine (0.44 ml) and 3,4-dichlorobenzoyl chloride (0.65 g).

m.p. 171°–173° C.

EXAMPLE 164

Ethyl 4-(2-chlorophenyl)-9-((1H-indol-2-yl) carbonylaminomethyl)-6H-thieno[3,2-f] [1,2,4]triazolo[4,3-a] [1,4]diazepine-2-carboxylate (0.81 g) was obtained in the same manner as in Example 61 using ethyl 9-aminomethyl-4-(2-chlorophenyl)-6H-thieno[3,2-f] [1,2,4]triazolo[4,3-a] [1,4]diazepine-2-carboxylate (0.96 g), dimethylformamide (10 ml), indole-2-carboxylic acid (0.42 g), triethylamine (0.67 ml) and Bop reagent (1.16 g).

m.p. 257°–258° C.

EXAMPLE 165

4-(2-chlorophenyl)-9-(3-(3-methylphenyl)ureidomethyl)-6H-thieno[3,2-f] [1,2,4]triazolo[4,3-a] [1,4]diazepine-2-carboxylate is obtained in the same manner as in Example 64 using ethyl 9-aminomethyl-4-(2-chlorophenyl)-6H-thieno [3,2-f] [1,2,4]triazolo[4,3-a] [1,4]diazepine-2-carboxylate and 3-methylphenyl isocyanate.

EXAMPLE 166

Ethyl 4-(2-chlorophenyl)-9-(3-(2-chlorophenyl) ureidomethyl)-6H-thieno[3,2-f] [1,2,4]triazolo[4,3-a] [1,4] diazepine-2-carboxylate is obtained in the same manner as in Example 64 using ethyl 9-aminomethyl-4-(2-chlorophenyl)-6H-thieno[3,2-f] [1,2,4]triazolo[4,3-a] [1,4] diazepine-2-carboxylate and 2-chlorophenyl isocyanate.

EXAMPLE 167

Ethyl 4-(2-chlorophenyl)-9-(3-(3-methoxyphenyl) ureidomethyl)-6H-thieno[3,2-f] [1,2,4]triazolo[4,3-a] [1,4] diazepine-2-carboxylate is obtained in the same manner as in Example 64 using ethyl 9-aminomethyl-4-(2-chlorophenyl)-6H-thieno[3,2-f] [1,2,4]triazolo[4,3-a] [1,4] diazepine-2-carboxylate and 3-methoxyphenyl isocyanate.

EXAMPLE 168

4-(2-Chlorophenyl)-9-(3,4-dichlorobenzoylaminomethyl)-6H-thieno[3,2-f] [1,2,4] triazolo[4,3-a] [1,4]diazepine-2-carboxylic acid (0.15 g) was obtained in the same manner as in Example 63 using ethyl 4-(2-chlorophenyl)-9-(3,4-dichlorobenzoylaminomethyl)-6H-thieno[3,2-f] [1,2,4] triazolo[4,3-a] [1,4]diazepine-2-carboxylate (0.4 g), methanol (8 ml) and a 2N aqueous sodium hydroxide solution (0.7 ml).

m.p. 294°–296° C.

EXAMPLE 169

4-(2-Chlorophenyl)-9-((indol-2-yl) carbonylaminomethyl)-6H-thieno[3,2-f] [1,2,4]triazolo[4,3- a] [1,4]diazepine-2-carboxylic acid (0.19 g) was obtained in the same manner as in Example 63 using ethyl 4-(2-chlorophenyl)-9((1H-indol-2-yl)carbonylaminomethyl)-6H-thieno[3,2-f] [1,2,4]triazolo[4,3-a] [1,4]diazepine-2-carboxylate (0.4 g), methanol (5 ml) and a 2N aqueous sodium hydroxide solution (0.8 ml).

m.p. 279°–280° C.

EXAMPLE 170

Ethyl 4-(2-chlorophenyl)-9-(3-(3-methylphenyl) ureidomethyl)-6H-thieno[3,2-f] [1,2,4]triazolo[4,3-a] [1,4] diazepine-2-carboxylate is subjected to alkali hydrolysis to give 4-(2-chlorophenyl)-9-(3-(3-methylphenyl) ureidomethyl)-6H-thieno[3,2-f] [1,2,4]triazolo[4,3-a] [1,4] diazepine-2-carboxylic acid.

EXAMPLE 171

Ethyl 4-(2-chlorophenyl)-9-(3-(2-chlorophenyl) ureidomethyl)-6H-thieno[3,2-f] [1,2,4]triazolo[4,3-a] [1,4] diazepine-2-carboxylate is subjected to alkali hydrolysis to give 4-(2-chlorophenyl)-9-(3-(2-chlorophenyl) ureidomethyl)-6H-thieno[3,2-f] [1,2,4]triazolo[4,3-a] [1,4] diazepine-2-carboxylic acid.

EXAMPLE 172

Ethyl 4-(2-chlorophenyl)-9-(3-(3-methoxyphenyl) ureidomethyl)-6H-thieno[3,2-f] [1,2,4]triazolo[4,3-a] [1,4] diazepine-2-carboxylate is subjected to alkali hydrolysis to give 4-(2-chlorophenyl)-9-(3-(3-methoxyphenyl) ureidomethyl)-6H-thieno[3,2-f] [1,2,4]triazolo[4,3-a] [1,4] diazepine-2-carboxylic acid.

EXAMPLE 173

N-(4-(3-(2-Chlorobenzoyl)-5-ethylthiophen-2-yl)-5-methyl[1,2,4]triazol-3-ylmethyl)-3,4-dimethylbenzamide is obtained in the same manner as in Example 1 using 3,4-dimethylbenzoyl chloride and 3-aminomethyl-4-(3-(2-chlorobenzoyl)-5-ethylthiophen-2-yl)-5-methyl[1,2,4] triazole.

EXAMPLE 174

N-(4-(3-(2-Chlorobenzoyl)-5-ethylthiophen-2-yl)-5-methyl[1,2,4]triazol-3-ylmethyl)-4-chlorobenzamide is obtained in the same manner as in Example 1 using 4-chlorobenzoyl chloride and 3-aminomethyl-4-(3-(2-chlorobenzoyl)-5-ethylthiophen-2-yl)-5-methyl[1,2,4] triazole.

EXAMPLE 175

N-(4-(3-(2-Chlorobenzoyl)-5-ethylthiophen-2-yl)-5-methyl[1,2,4]-triazol-3-ylmethyl)-3-chlorobenzamide is obtained in the same manner as in Example 1 using 3-chlorobenzoyl chloride and 3-aminomethyl-4-(3-(2-chlorobenzoyl)-5-ethylthiophen-2-yl)-5-methyl[1,2,4] triazole.

EXAMPLE 176

N-(4-(3-(2-Chlorobenzoyl)-5-ethylthiophen-2-yl)-5-methyl[1,2,4]triazol-3-ylmethyl)-2-chlorobenzamide is obtained in the same manner as in Example 1 using 2-chlorobenzoyl chloride and 3-aminomethyl-4-(3-(2-chlorobenzoyl)-5-ethylthiophen-2-yl)-5-methyl[1,2,4] triazole.

EXAMPLE 177

N-(4-(3-(2-Chlorobenzoyl)-5-ethylthiophen-2-yl)-5-methyl[1,2,4]triazol-3-ylmethyl)-4-bromobenzamide is obtained in the same manner as in Example 1 using 4-bromobenzoyl chloride and 3-aminomethyl-4-(3-(2-chlorobenzoyl)-5-ethylthiophen-2-yl)-5-methyl[1,2,4] triazole.

EXAMPLE 178

N-(4-(3-(2-Chlorobenzoyl)-5-ethylthiophen-2-yl)-5-methyl[1,2,4]triazol-3-ylmethyl)-3-bromobenzamide is obtained in the same manner as in Example 1 using 3-bromobenzoyl chloride and 3-aminomethyl-4-(3-(2-chlorobenzoyl)-5-ethylthiophen-2-yl)-5-methyl[1,2,4] triazole.

EXAMPLE 179

N-(4-(3-(2-Chlorobenzoyl)-5-ethylthiophen-2-yl)-5-methyl[1,2,4]triazol- 3-ylmethyl)-4-iodobenzamide is obtained in the same manner as in Example 1 using 4-iodobenzoyl chloride and 3-aminomethyl-4-(3-(2-chlorobenzoyl)-5-ethylthiophen-2-yl)-5-methyl[1,2,4] triazole.

EXAMPLE 180

N-(4-(3-(2-Chlorobenzoyl)-5-ethylthiophen-2-yl)-5-methyl[1,2,4]-triazol-3-ylmethyl)-3-iodobenzamide is obtained in the same manner as in Example 1 using 3-iodobenzoyl chloride and 3-aminomethyl-4-(3-(2-chlorobenzoyl)-5-ethylthiophen-2-yl)-5-methyl[1,2,4] triazole.

EXAMPLE 181

1-(2-Methoxycarbonylethyl)indole-2-carboxylic acid (0.81 g) and thionyl chloride (2.6 ml) were dissolved in dichloroethane (10 ml), and the mixture was refluxed for 4 hours. The reaction mixture was concentrated, and the residue was dissolved in dimethylformamide (15 ml). 3-Aminomethyl-4-(3-(2-chlorobenzoyl)-5-ethylthiophen-2-yl)-5-methyl[1,2,4]triazole ditosylate (2.22 g) and triethylamine (2.1 ml) were added at room temperature, and the mixture was stirred for 3 hours. The reaction mixture was partitioned between ethyl acetate and water. The organic layer was washed with an aqueous citric acid solution, a saturated aqueous sodium hydrogencarbonate solution and saturated brine, and dried over magnesium sulfate. The solvent was evaporated, and the obtained residue was purified by silica gel column chromatography using a mixed solvent of ethyl acetate and methanol as an eluent to give 180 mg of methyl 3-(2-(4-(3-(2-chlorobenzoyl)-5-ethylthiophen-2-yl)-5-methyl[1,2,4]triazol-3-ylmethylcarbamoyl)indol-1-yl)propionate.

m.p. 67°–68° C.

EXAMPLE 182

Methyl 3-(2-(4-(3-(2-chlorobenzoyl)-5-ethylthiophen-2-yl)-5-methyl[1,2,4]triazol-3-ylmethylcarbamoyl)indol-1-yl) propionate (100 mg) was subjected to alkali hydrolysis and treated in the same manner as in Example 19 to give 85 mg of 3-(2-(4-(3-(2-chlorobenzoyl)-5-ethylthiophen-2-yl)-5-methyl[1,2,4]triazol-3-ylmethylcarbamoyl)indol-1-yl) propionic acid.

m.p. 224°–225° C.

EXAMPLE 183

N-(4-(3-(2-Chlorobenzoyl)-5-ethylthiophen-2-yl)-5-methyl[1,2,4]-triazol-3-ylmethyl)-5-chloroindole-2- carboxamide is obtained in the same manner as in Example 1 using 5-chloroindole-2-carbonyl chloride and 3-aminomethyl-4-(3-(2-chlorobenzoyl)-5-ethylthiophen-2-yl)-5-methyl[1,2,4]triazole.

EXAMPLE 184

5-Fluoroindole-2-carboxylic acid (0.50 g) and 3-aminomethyl-4-(3-(2-chlorobenzoyl)-5-ethylthiophen-2-yl)-5-methyl[1,2,4]triazole ditosylate (2.07 g) were dissolved in dimethylformamide (40 ml). Triethylamine (1.6 ml) and 1-benzotriazolyloxytris(dimethylamino) phosphonium hexafluorophosphate (Bop reagent, 1.29 g) were added under ice-cooling, and the mixture was stirred for 4 hours. The reaction mixture was partitioned between water and ethyl acetate. The organic layer was washed with an aqueous citric acid solution, a saturated aqueous sodium hydrogencarbonate solution and saturated brine, and dried over magnesium sulfate. The solvent was evaporated, and the obtained residue was crystallized from ethyl acetate to give 0.23 g of N-(4-(3-(2-chlorobenzoyl)-5-ethylthiophen-2-yl)-5-methyl[1,2,4]triazol-3-ylmethyl)-5-fluoroindole-2-carboxamide.

m.p. 248°–265° C. (decomposition)

EXAMPLE 185

N-(4-(3-(2-Chlorobenzoyl)-5-ethylthiophen-2-yl)-5-methyl[1,2,4]triazol-3-ylmethyl)-5-methoxyindole-2-carboxamide is obtained in the same manner as in Example 1 using 5-methoxyindole-2-carbonyl chloride and 3-aminomethyl-4-(3-(2-chlorobenzoyl)-5-ethylthiophen-2-yl)-5-methyl[1,2,4]triazole.

EXAMPLE 186 trans-Cinnamic acid (1.48 g), 3-aminomethyl-4-(3-(2-chlorobenzoyl)-5-ethylthiophen-2-yl)-5-methyl[1,2,4] triazole di-p-toluenesulfonate (7.42 g) and triethylamine (5.6 ml) were dissolved in dimethylformamide (50 ml). 1-Benzotriazolyloxytris(dimethylamino)phosphonium hexafluorophosphate (Bop reagent, 4.42 g) was added, and the mixture was stirred for one day. The reaction mixture was partitioned between ethyl acetate and water. The organic layer was washed with a saturated aqueous sodium hydrogencarbonate solution and saturated brine, and dried over magnesium sulfate. The solvent was evaporated to give 5.05 g of crude crystals. The crystals were recrystallized from ethyl acetate to give 3.25 g of trans-N-(4-(3-(2-chlorobenzoyl)-5-ethylthiophen-2-yl)-5-methyl[1,2,4] triazol-3-ylmethyl)-3-phenylacrylamide.

m.p. 150°–151° C.

EXAMPLE 187

N-(4-(3-(2-Chlorobenzoyl)-5-ethylthiophen-2-yl)-5-methyl[1,2,4]triazol-3-ylmethyl)benzofuran-2-carboxamide is obtained in the same manner as in Example 1 using benzofuran-2-carbonyl chloride and 3-aminomethyl-4-(3-(2-chlorobenzoyl)-5-ethylthiophen-2-yl)-5-methyl[1,2,4] triazole.

EXAMPLE 188

N-(4-(3-(2-Chlorobenzoyl)-5-ethylthiophen-2-yl)-5-methyl[1,2,4]triazol-3-ylmethyl)benzothiophene-2-carboxamide is obtained in the same manner as in Example 1 using benzothiophene-2-carbonyl chloride and 3-aminomethyl-4-(3-(2-chlorobenzoyl)-5-ethylthiophen-2-yl)-5-methyl[1,2,4]triazole.

EXAMPLE 189

N-(4-(3-(2-Chlorobenzoyl)-5-ethylthiophen-2-yl)-5-methyl[1,2,4]triazol-3-ylmethyl)-N'-(2-methylphenyl)urea is obtained in the same manner as in Example 22 using 2-methylphenyl isocyanate and 3-aminomethyl-4-(3-(2-chlorobenzoyl)-5-ethylthiophen-2-yl)-5-methyl[1,2,4] triazole.

EXAMPLE 190

N-(4-(3-(2-Chlorobenzoyl)-5-ethylthiophen-2-yl)-5-methyl[1,2,4]triazol-3-ylmethyl)-N'-(4-methylphenyl)urea is obtained in the same manner as in Example 22 using 4-methylphenyl isocyanate and 3-aminomethyl-4-(3-(2-chlorobenzoyl)-5-ethylthiophen-2-yl)-5-methyl[1,2,4] triazole.

EXAMPLE 191

N-(4-(3-(2-Chlorobenzoyl)-5-ethylthiophen-2-yl)-5-methyl[1,2,4]triazol-3-ylmethyl)-N'-(2-methoxyphenyl) urea is obtained in the same manner as in Example 22 using 2-methoxyphenyl isocyanate and 3-aminomethyl-4-(3-(2-chlorobenzoyl)-5-ethylthiophen-2-yl)-5-methyl[1,2,4] triazole.

EXAMPLE 192

N-(4-(3-(2-Chlorobenzoyl)-5-ethylthiophen-2-yl)-5-methyl[1,2,4]triazol-3-ylmethyl)-N'-(4-methoxyphenyl) urea is obtained in the same manner as in Example 22 using 4-methoxyphenyl isocyanate and 3-aminomethyl-4-(3-(2-chlorobenzoyl)-5-ethylthiophen-2-yl)-5-methyl[1,2,4] triazole.

EXAMPLE 193 tert-Butyl 3-aminophenylacetate (2.07 g) was dissolved in tetrahydrofuran (70 ml), and N,N'-carbonyldiimidazole (1.7 g) was added under ice-cooling. One hour later, triethylamine (2.8 ml) and 3-aminomethyl-4-(3-(2-chlorobenzoyl) -5-ethylthiophen-2-yl)-5-methyl[1,2,4]triazole di-p-toluenesulfonate (7.42 g) were added, and the mixture was stirred at room temperature for one day. The reaction mixture was concentrated, and partitioned between ethyl acetate and water. The organic layer was washed with a 5% aqueous citric acid solution, a saturated aqueous sodium hydrogencarbonate solution and saturated brine, and dried over magnesium sulfate. The solvent was evaporated, and crude crystals (2.58 g) were precipitated from a small amount of ethyl acetate. The crystals were recrystallized from ethyl acetate to give 1.66 g of tert-butyl 3-(3-(4-(3-(2-chlorobenzoyl)-5-ethylthiophen-2-yl)-5-methyl[1,2,4] triazol-3-ylmethyl)ureido)phenylacetate.

m.p. 178°–179° C.

EXAMPLE 194 tert-Butyl 3-(3-(4-(3-(2-chlorobenzoyl)-5-ethylthiophen-2-yl)-5-methyl[1,2,4]triazol-3-ylmethyl)ureido) phenylacetate (0.92 g) was dissolved in formic acid (20 ml), and the solution was allowed to stand at room temperature for one day. The reaction mixture was concentrated, and the obtained residue was recrystallized from ethyl acetate and isopropyl ether to give 0.66 g of 3-(3-(4-(3-(2-chlorobenzoyl)-5-ethylthiophen-2-yl)-5-methyl[1,2,4] triazol-3-ylmethyl)ureido)phenylacetic acid.

m.p. 162°–164° C.

EXAMPLE 195

3,4-Dichlorobenzenesulfonyl chloride and 3-aminomethyl-4-(3-(2-chlorobenzoyl)-5-ethylthiophen-2- yl)-5-methyl[1,2,4]triazole are reacted, and treated in the same manner as in Example 48 to give N-(4-(3-(2-chlorobenzoyl)-5-ethylthiophen-2-yl)-5-methyl[1,2,4]triazol-3-ylmethyl)-3,4-dichlorobenzenesulfonamide.

EXAMPLE 196

N-(4-(3-(2-Chlorobenzoyl)-5-ethylthiophen-2-yl)-5-methyl[1,2,4]triazol-3-ylmethyl)-N'-phenylthiourea is obtained in the same manner as in Example 22 using phenyl isothiocyanate and 3-aminomethyl-4-(3-(2-chlorobenzoyl)-5-ethylthiophen-2-yl)-5-methyl[1,2,4]triazole.

EXAMPLE 197

N-(4-(3-(2-Chlorobenzoyl)-5-methylthiophen-2-yl)-5-methyl[1,2,4]triazol-3-ylmethyl)-3,4-dichlorobenzamide is obtained in the same manner as in Example 36 using 3,4-dichlorobenzoyl chloride and 3-aminomethyl-4-(3-(2-chlorobenzoyl)-5-methylthiophen-2-yl)-5-methyl[1,2,4]triazole.

EXAMPLE 198

N-(4-(3-(2-Chlorobenzoyl)-5-methylthiophen-2-yl)-5-methyl[1,2,4]triazol-3-ylmethyl)indole-2-carboxamide (115 mg) was obtained in the same manner as in Example 2 using 3-aminomethyl-4-(3-(2-chlorobenzoyl)-5-methylthiophen-2-yl)-5-methyl[1,2,4]triazole di-p-toluenesulfonate (500 mg) obtained in the same manner as in Production Example 1 and indole-2-carbonyl chloride (148 mg).

m.p. 251°–252° C.

EXAMPLE 199

4-(2-Chlorophenyl)-2,9-dimethyl-6H-thieno[3,2-f] [1,2,4]triazolo[4,3-a] [1,4]diazepine (4.15 g) was dissolved in 5% hydrochloric acid (50 ml), and the solution was stirred at 60° C. for 4 hours. The reaction mixture was cooled in a water bath, and chloroform (60 ml) and sodium hydrogencarbonate (12.6 g) were added with vigorous stirring. Then, 1-ethoxycarbonylmethylindole-2-carbonyl chloride (3.52 g) was added, and the mixture was stirred for 1 hour. The chloroform layer was washed with saturated brine and dried over magnesium sulfate. The solvent was evaporated, and the residue was purified by silica gel column chromatography using a mixed solvent of ethyl acetate and methanol as eluent and crystallized from a mixed solvent of ethyl acetate and hexane to give 6.23 g of ethyl 2-(4-(3-(2-chlorobenzoyl)-5-methylthiophen-2-yl)-5-methyl[1,2,4]triazol-3-ylmethylcarbamoyl)indole-1-acetate.

m.p. 153°–154° C.

EXAMPLE 200

Ethyl 2-(4-(3-(2-chlorobenzoyl)-5-methylthiophen-2-yl)-5-methyl[1,2,4]triazol-3-ylmethylcarbamoyl)indole-1-acetate (2.0 g) was subjected to alkali hydrolysis in the same manner as in Example 19 to give 1.34 g of 2-(4-(3-(2-chlorobenzoyl)-5-methylthiophen-2-yl)-5-methyl[1,2,4]triazol-3-ylmethylcarbamoyl)indole-1-acetic acid.

m.p. 194°–196° C.

EXAMPLE 201

N-(4-(3-(2-Chlorobenzoyl)-5-methylthiophen-2-yl)-5-methyl[1,2,4]triazol-3-ylmethyl)-N'-(2-chlorophenyl)urea is obtained in the same manner as in Example 31 using 2-chlorophenyl isocyanate and 3-aminomethyl-4-(3-(2-chlorobenzoyl)-5-methylthiophen-2-yl)-5-methyl[1,2,4]triazole.

EXAMPLE 202

N-(4-(3-(2-Chlorobenzoyl)-5-methylthiophen-2-yl)-5-methyl[1,2,4]triazol-3-ylmethyl)-N'-(3-methylphenyl)urea is obtained in the same manner as in Example 31 using 3-methylphenyl isocyanate and 3-aminomethyl-4-(3-(2-chlorobenzoyl)-5-methylthiophen-2-yl)-5-methyl[1,2,4]triazole.

EXAMPLE 203

N-(4-(3-(2-Chlorobenzoyl)-5-methylthiophen-2-yl)-5-methyl[1,2,4]triazol-3-ylmethyl)-N'-(3-methoxyphenyl)urea is obtained in the same manner as in Example 31 using 3-methoxyphenyl isocyanate and 3-aminomethyl-4-(3-(2-chlorobenzoyl)-5-methylthiophen-2-yl)-5-methyl[1,2,4]triazole.

EXAMPLE 204

N-(4-(3-(2-Chlorobenzoyl)thiophen-2-yl)-5-methyl[1,2,4]triazol-3-ylmethyl)-3,4-dichlorobenzamide is obtained in the same manner as in Example 36 using 3,4-dichlorobenzoyl chloride and 3-aminomethyl-4-(3-(2-chlorobenzoyl)thiophen-2-yl)-5-methyl[1,2,4]triazole.

EXAMPLE 205

N-(4-(3-(2-Chlorobenzoyl)thiophen-2-yl)-5-methyl[1,2,4]triazol-3-ylmethyl)indole-2-carboxamide is obtained in the same manner as in Example 36 using indole-2-carbonyl chloride and 3-aminomethyl-4-(3-(2-chlorobenzoyl)thiophen-2-yl)-5-methyl[1,2,4]triazole.

EXAMPLE 206

Ethyl 2-(4-(3-(2-chlorobenzoyl)thiophen-2-yl)-5-methyl[1,2,4]triazol-3-ylmethylcarbamoyl)indole-1-acetate is obtained in the same manner as in Example 36 using 1-ethoxycarbonylmethylindole-2-carbonyl chloride and 3-aminomethyl-4-(3-(2-chlorobenzoyl)thiophen-2-yl)-5-methyl[1,2,4]triazole.

EXAMPLE 207

Ethyl 2-(4-(3-(2-chlorobenzoyl)thiophen-2-yl)-5-methyl[1,2,4]triazol-3-ylmethylcarbamoyl)indole-1-acetate is subjected to alkali hydrolysis to give 2-(4-(3-(2-chlorobenzoyl)thiophen-2-yl)-5-methyl[1,2,4]triazol-3-ylmethylcarbamoyl)indole-1-acetic acid.

EXAMPLE 208

N-(4-(3-(2-Chlorobenzoyl)thiophen-2-yl)-5-methyl[1,2,4]triazol-3-ylmethyl)-N'-(2-chlorophenyl)urea is obtained in the same manner as in Example 31 using 2-chlorophenyl isocyanate and 3-aminomethyl-4-(3-(2-chlorobenzoyl)thiophen-2-yl)-5-methyl[1,2,4]triazole.

EXAMPLE 209

N-(4-(3-(2-Chlorobenzoyl)thiophen-2-yl)-5-methyl[1,2,4]triazol-3-ylmethyl)-N'-(3-methylphenyl)urea is obtained in the same manner as in Example 31 using 3-methylphenyl isocyanate and 3-aminomethyl-4-(3-(2-chlorobenzoyl)thiophen-2-yl)-5-methyl[1,2,4]triazole.

EXAMPLE 210

N-(4-(3-(2-Chlorobenzoyl)thiophen-2-yl)-5-methyl[1,2,4]triazol-3-ylmethyl)-N'-(3-methoxyphenyl)urea is obtained in the same manner as in Example 31 using 3-methoxyphenyl isocyanate and 3-aminomethyl-4-(3-(2-chlorobenzoyl)thiophen-2-yl)-5-methyl[1,2,4]triazole.

EXAMPLE 211

N-(4-(3-(2-Chlorobenzoyl)-4,5-dimethylthiophen-2-yl)-5-methyl[1,2,4]triazol-3-ylmethyl)-3,4-dichlorobenzamide is obtained in the same manner as in Example 36 using 3,4-dichlorobenzoyl chloride and 3-aminomethyl-4-(3-(2-chlorobenzoyl)-4,5-dimethylthiophen-2-yl)-5-methyl[1,2,4] triazole.

EXAMPLE 212

N-(4-(3-(2-Chlorobenzoyl)-4,5-dimethylthiophen-2-yl)-5-methyl[1,2,4]triazol-3-ylmethyl)indole-2-carboxamide (160 mg) was obtained in the same manner as in Example 2 using 3-aminomethyl-4-(3-(2-chlorobenzoyl)-4,5-dimethylthiophen-2-yl)-5-methyl[1,2,4]triazole di-p-toluenesulfonate (1.0 g) and indole-2-carbonyl chloride (0.27 g).

m.p. 273° C. (dec.)

EXAMPLE 213

Ethyl 2-(4-(3-(2-chlorobenzoyl)-4,5-dimethylthiophen-2-yl)-5-methyl[1,2,4]triazol-3-ylmethylcarbamoyl)indole-1-acetate is obtained in the same manner as in Example 36 using 1-ethoxycarbonylmethylindole-2-carbonyl chloride and 3-aminomethyl-4-(3-(2-chlorobenzoyl)-4,5-dimethylthiophen-2-yl)-5-methyl[1,2,4]triazole.

EXAMPLE 214

Ethyl 2-(4-(3-(2-chlorobenzoyl)-4,5-dimethylthiophen-2-yl)-5-methyl[1,2,4]triazol-3-ylmethylcarbamoyl)indole-1-acetate is subjected to alkali hydrolysis to give 2-(4-(3-(2-chlorobenzoyl)-4,5-dimethylthiophen- 2-yl)-5-methyl[1,2,4]triazol-3-ylmethylcarbamoyl)indole-1-acetic acid.

EXAMPLE 215

N-(4-(3-(2-Chlorobenzoyl)-4,5-dimethylthiophen-2-yl)-5-methyl[1,2,4]triazol-3-ylmethyl)-N'-(2-chlorophenyl)urea is obtained in the same manner as in Example 31 using 2-chlorophenyl isocyanate and 3-aminome thyl-4-(3-(2-chlorobenzoyl)-4,5-dimethylthiophen-2-yl)-5-methyl[1,2,4] triazole.

EXAMPLE 216

N-(4-(3-(2-Chlorobenzoyl)-4,5-dimethylthiophen-2-yl)-5-methyl[1,2,4]triazol-3-ylmethyl)-N'-(3-methylphenyl) urea is obtained in the same manner as in Example 31 using 3-methylphenyl isocyanate and 3-aminomethyl-4-(3-(2-chlorobenzoyl)-4,5-dimethylthiophen-2-yl)-5-methyl[1,2,4] triazole.

EXAMPLE 217

N-(4-(3-(2-Chlorobenzoyl)-4,5-dimethylthiophen-2-yl)-5-methyl[1,2,4]triazol-3-ylmethyl)-N'-(3-methoxyphenyl) urea is obtained in the same manner as in Example 31 using 3-methoxyphenyl isocyanate and 3-aminomethyl-4-(3-(2-chlorobenzoyl)-4,5-dimethylthiophen-2-yl)-5-methyl[1,2,4] triazole.

EXAMPLE 218

N-(4-(3-Benzoyl-5-ethylthiophen-2-yl)-5-methyl[1,2,4] triazol-3-ylmethyl)-3,4-dichlorobenzamide is obtained in the same manner as in Example 36 using 3,4-dichlorobenzoyl chloride and 3-aminomethyl-4-(3-benzoyl-5-ethylthiophen-2-yl)-5-methyl[1,2,4]triazole.

EXAMPLE 219

2-Ethyl-9-methyl-4-phenyl-6H-thieno[3,2-f] [1,2,4] triazolo[4,3-a] [1,4]diazepine (924 mg) and 10-camphorsulfonic acid (2.1 g) were dissolved in a mixed solvent (25 ml) of ethanol:water (9:1), and the solution was refluxed for 3 hours. The reaction mixture was concentrated under reduced pressure, and the obtained residue was dissolved in dimethylformamide (10 ml). Indole-2-carbonyl chloride (538 mg) and triethylamine (1.4 ml) were added, and the mixture was stirred at room temperature for one day. The reaction mixture was partitioned between ethyl acetate and water. The organic layer was washed with a saturated aqueous sodium hydrogencarbonate solution and saturated brine, and dried over magnesium sulfate. The solvent was concentrated under reduced pressure, and the obtained solid was recrystallized from a mixed solvent of ethyl acetate and methanol to give 0.57 g of N-(4-(3-benzoyl-5-ethylthiophen-2-yl)-5-methyl[1,2,4]triazol-3-ylmethyl) indole-2-carboxamide.

m.p. 214°–215° C.

EXAMPLE 220

2-Ethyl-9-methyl-4-phenyl-6H-thieno[3,2-f] [1,2,4] triazolo[4,3-a] [1,4]diazepine (1.07 g) and 10-camphorsulfonic acid (2.55 g) were dissolved in a mixed solvent (25 ml) of ethanol:water (9:1), and the solution was refluxed for 3 hours. The reaction mixture was concentrated under reduced pressure, and the obtained residue was dissolved in dimethylformamide (10 ml). 1-Ethoxycarbonylmethylindole-2-carbonyl chloride (1.06 g) and triethylamine (2.55 ml) were added, and the mixture was stirred at room temperature for one day. The reaction mixture was partitioned between ethyl acetate and water. The organic layer was washed with a saturated aqueous sodium hydrogencarbonate solution and saturated brine, and dried over magnesium sulfate. The solvent was concentrated under reduced pressure, and the obtained solid was crystallized from a small amount of ethyl acetate to give 1.1 g of ethyl (2-(4-(3-benzoyl-5-ethylthiophen-2-yl)-5-methyl[1,2,4]triazol-3-ylmethylcarbamoyl)indol-1-yl)acetate.

m.p. 129°–131° C.

EXAMPLE 221

Ethyl 2-(4-(3-benzoyl-5-ethylthiophen-2-yl)-5-methyl[1,2,4]triazol-3-ylmethylcarbamoyl)indole-1-acetate (0.74 g) was subjected to alkali hydrolysis in the same manner as in Example 19 to give 0.50 g of 2-(4-(3-benzoyl-5-ethylthiophen-2-yl)-5-methyl[1,2,4]triazol-3-ylmethylcarbamoyl)indole-1-acetic acid.

m.p. 130° C. (decomposition)

EXAMPLE 222

2-Ethyl-9-methyl-4-phenyl-6H-thieno[3,2-f] [1,2,4] triazolo[4,3-a] [1,4]diazepine is subjected to hydrolysis in the same manner as in Example 89, and reacted with 2-chlorophenyl isocyanate to give N-(4-(3-benzoyl-5-ethylthiophen-2-yl)-5-methyl[1,2,4]triazol-3-ylmethyl)-N'-(2-chlorophenyl)urea.

EXAMPLE 223

2-Ethyl-9-methyl-4-phenyl-6H-thieno[3,2-f] [1,2,4] triazolo[4,3-a] [1,4]diazepine is subjected to hydrolysis in the same manner as in Example 89, and reacted with 3-methylphenyl isocyanate to give N-(4-(3-benzoyl-5-ethylthiophen-2-yl)-5-methyl[1,2,4]triazol-3-ylmethyl)-N'-(3-methylphenyl)urea.

EXAMPLE 224

2-Ethyl-9-methyl-4-phenyl-6H-thieno[3,2-f] [1,2,4] triazolo[4,3-a] [1,4]diazepine is subjected to hydrolysis in the same manner as in Example 89, and reacted with 3-methoxyphenyl isocyanate to give N-(4-(3-benzoyl-5-ethylthiophen-2-yl)-5-methyl[1,2,4]triazol-3-ylmethyl)-N'-(3-methoxyphenyl)urea.

EXAMPLE 225

2-Ethyl-4-(2-fluorophenyl)-9-methyl-6H-thieno[3,2-f] [1,2,4]triazolo[4,3-a] [1,4]diazepine is subjected to hydrolysis in the same manner as in Example 226, and reacted with 3,4-dichlorobenzoyl chloride to give N-(4-(5-ethyl-3-(2-fluorobenzoyl)thiophen-2-yl)-5-methyl[1,2,4]triazol-3-ylmethyl)-3,4-dichlorobenzamide.

EXAMPLE 226

2-Ethyl-4-(2-fluorophenyl)-9-methyl-6H-thieno[3,2-f] [1,2,4]triazolo[4,3-a] [1,4]diazepine (500 mg) and p-toluenesulfonic acid monohydrate (874 mg) were dissolved in a mixed solvent (15 ml) of ethanol:water (9:1), and the solution was refluxed for 4 hours. The reaction mixture was concentrated under reduced pressure, and the obtained residue was dissolved in dimethylformamide (15 ml). Indole-2-carbonyl chloride (407 mg) and triethylamine (1.07 ml) were added, and the mixture was stirred at room temperature for one day. The reaction mixture was partitioned between ethyl acetate and water. The organic layer was washed with a saturated aqueous sodium hydrogencarbonate solution and saturated brine, and dried over magnesium sulfate. The solvent was concentrated under reduced pressure, and the obtained solid was recrystallized from ethyl acetate to give 0.40 g of N-(4-(5-ethyl-3-(2-fluorobenzoyl)thiophen-2-yl)-5-methyl[1,2,4]triazol-3-ylmethyl)indole-2-carboxamide.

m.p. 255°–256° C.

EXAMPLE 227

2-Ethyl-4-(2-fluorophenyl)-9-methyl-6H-thieno[3,2-f] [1,2,4]triazolo[4,3-a] [1,4]diazepine is subjected to hydrolysis in the same manner as in Example 226, and reacted with 1-ethoxycarbonylmethylindole-2-carbonyl chloride to give ethyl 2-(4-(5-ethyl-3-(2-fluorobenzoyl)thiophen-2-yl)-5-methyl[1,2,4]triazol-3-ylmethylcarbamoyl)indole-1-acetate.

EXAMPLE 228

Ethyl 2-(4-(5-ethyl-3-(2-fluorobenzoyl)thiophen-2-yl)-5-methyl[1,2,4]triazol-3-ylmethylcarbamoyl)indole-1-acetate is subjected to alkali hydrolysis to give 2-(4-(5-ethyl-3-(2-fluorobenzoyl)thiophen-2-yl)-5-methyl[1,2,4]triazol-3-ylmethylcarbamoyl)indole-1-acetic acid.

EXAMPLE 229

2-Ethyl-4-(2-fluorophenyl)-9-methyl-6H-thieno[3,2-f] [1,2,4]triazolo[4,3-a] [1,4]diazepine is subjected to hydrolysis in the same manner as in Example 226, and reacted with 2-chlorophenyl isocyanate to give N-(2-chlorophenyl)-N'-(4-(5-ethyl-3-(2-fluorobenzoyl)thiophen-2-yl)-5-methyl[1,2,4]triazol-3-ylmethyl)urea.

EXAMPLE 230

2-Ethyl-4-(2-fluorophenyl)-9-methyl-6H-thieno[3,2-f] [1,2,4]triazolo[4,3-a] [1,4]diazepine is subjected to hydrolysis in the same manner as in Example 226, and reacted with 3-methylphenyl isocyanate to give N-(4-(5-ethyl-3-(2-fluorobenzoyl)thiophen-2-yl)-5-methyl[1,2,4]triazol-3-ylmethyl)-N'-(3-methylphenyl)urea.

EXAMPLE 231

2-Ethyl-4-(2-fluorophenyl)-9-methyl-6H-thieno[3,2-f] [1,2,4]triazolo[4,3-a] [1,4]diazepine is subjected to hydrolysis in the same manner as in Example 226, and reacted with 3-methoxyphenyl isocyanate to give N-(4-(5-ethyl-3-(2-fluorobenzoyl)thiophen-2-yl)-5-methyl[1,2,4]triazol-3-ylmethyl)-N'-(3-methoxyphenyl)urea.

EXAMPLE 232

5-(2-Chlorophenyl)-7-ethyl-1,3-dihydro-2H-thieno[2,3-e] [1,4]diazepine-2-thione (32 g) synthesized by the method disclosed in Arzneim.-Forsch./Drug Res. 28 (II), Heft, 1153–1158 (1978) and dimethylaminoacetyl hydrazide (12.3 g) were dissolved in toluene (300 ml), and the solution was stirred at room temperature for 5 hours. Then, acetic acid (9 g) was added to the reaction mixture, and the mixture was refluxed for 2 hours. The reaction mixture was washed with a 5% aqueous sodium hydrogencarbonate solution and dried over magnesium sulfate. The solvent was evaporated, and the obtained residue was crystallized from ethyl acetate and isopropyl ether to give 26.3 g of 4-(2-chlorophenyl)-9-dimethylaminomethyl-2-ethyl-6H-thieno[3,2-f] [1,2,4] triazolo[4,3-a] [1,4]diazepine. This compound (3.85 g) was dissolved in a 5% aqueous hydrochloric acid solution (40 ml), and the solution was stirred at 60° C. for 3 hours. Then, sodium hydrogencarbonate was added to the reaction mixture to make the mixture alkaline. Chloroform (80 ml) and 3,4-dichlorobenzoyl chloride (2.3 g) were added, and the mixture was stirred under ice-cooling for 1 hour. The organic layer was washed with an aqueous citric acid solution, a saturated aqueous sodium hydrogencarbonate solution and saturated brine, and dried over magnesium sulfate. The solvent was evaporated, and the obtained crude product was recrystallized from ethyl acetate to give 2.22 g of N-(4-(3-(2-chlorobenzoyl)-5-ethylthiophen-2-yl)-5-dimethylaminomethyl[1,2,4]triazol-3-ylmethyl)-3,4-dichlorobenzamide.

m.p. 186°–187° C.

EXAMPLE 233

N-(4-(3-(2-Chlorobenzoyl)-5-ethylthiophen-2-yl)-5-dimethylaminomethyl[1,2,4]triazol-3-ylmethyl)indole-2-carboxamide (1.83 g) was obtained in the same manner as in Example 232 using indole-2-carbonyl chloride (1.97 g) and 4-(2-chlorophenyl)-9-dimethylaminomethyl-2-ethyl-6H-thieno[3,2-f] [1,2,4]triazolo[4,3-a] [1,4]diazepine (3.85 g).

m.p. 205°–207° C.

EXAMPLE 234

Ethyl 2-(4-(3-(2-chlorobenzoyl)-5-ethylthiophen-2-yl)-5-dimethylaminomethyl[1,2,4]triazol-3-ylmethylcarbamoyl) indole-1-acetate is obtained in the same manner as in Example 36 using 1-ethoxycarbonylmethylindole-2-carbonyl chloride and 3-aminomethyl-4-(3-(2-chlorobenzoyl)-5-ethylthiophen-2-yl)-5-dimethylaminomethyl[1,2,4]triazole.

EXAMPLE 235

Ethyl 2-(4-(3-(2-chlorobenzoyl)-5-ethylthiophen-2-yl)-5-dimethylaminomethyl[1,2,4]triazol-3-ylmethylcarbamoyl) indole-1-acetate is subjected to alkali hydrolysis to give 2-(4-(3-(2-chlorobenzoyl)-5-ethylthiophen-2-yl)-5-dimethylaminomethyl[1,2,4]triazol-3-ylmethylcarbamoyl) indole-1-acetic acid.

EXAMPLE 236

N-(4-(3-(2-Chlorobenzoyl)-5-ethylthiophen-2-yl)-5-dimethylaminomethyl[1,2,4]triazol-3-ylmethyl)-N'-(2-chlorophenyl)urea is obtained in the same manner as in Example 31 using 2-chlorophenyl isocyanate and 3-aminomethyl-4-(3-(2-chlorobenzoyl)-5-ethylthiophen-2-yl)-5-dimethylaminomethyl[1,2,4]triazole.

EXAMPLE 237

N-(4-(3-(2-Chlorobenzoyl)-5-ethylthiophen-2-yl)-5-dimethylaminomethyl[1,2,4]triazol-3-ylmethyl)-N'-(3-methylphenyl)urea is obtained in the same manner as in Example 31 using 3-methylphenyl isocyanate and 3-aminomethyl-4-(3-(2-chlorobenzoyl)-5-ethylthiophen-2-yl)-5-dimethylaminomethyl[1,2,4]triazole.

EXAMPLE 238

N-(4-(3-(2-Chlorobenzoyl)-5-ethylthiophen-2-yl)-5-dimethylaminomethyl[1,2,4]triazol-3-ylmethyl)-N'-(3-methoxyphenyl)urea is obtained in the same manner as in Example 31 using 3-methoxyphenyl isocyanate and 3-aminomethyl-4-(3-(2-chlorobenzoyl)-5-ethylthiophen-2-yl)-5-dimethylaminomethyl[1,2,4]triazole.

EXAMPLE 239

N-(4-(3-(2-Chlorobenzoyl)-5-ethylthiophen-2-yl)-5-isopropyl[1,2,4]triazol-3-ylmethyl)-3,4-dichlorobenzamide is obtained in the same manner as in Example 36 using 3,4-dichlorobenzoyl chloride and 3-aminomethyl-4-(3-(2-chlorobenzoyl)-5-ethylthiophen-2-yl)-5-isopropyl[1,2,4] triazole.

EXAMPLE 240

4-(2-Chlorophenyl)-2-ethyl-9-isopropyl-6H-thieno[3,2-f] [1,2,4]triazolo[4,3-a] [1,4]diazepine (1.11 g) and p-toluenesulfonic acid monohydrate (1.71 g) were dissolved in a mixed solvent (25 ml) of ethanol and water (9:1), and the solution was refluxed for 3 hours. The reaction mixture was concentrated under reduced pressure, and the obtained residue was dissolved in dimethylformamide (10 ml). Indole-2-carbonyl chloride (1.06 g) and triethylamine (2.5 ml) were added, and the mixture was stirred at room temperature for one day. The reaction mixture was partitioned between ethyl acetate and water. The organic layer was washed with a saturated aqueous sodium hydrogencarbonate solution and saturated brine, and dried over magnesium sulfate. The solvent was concentrated under reduced pressure, and the obtained solid was recrystallized from ethyl acetate to give 0.42 g of N-(4-(3-(2-chlorobenzoyl)-5-ethylthiophen-2-yl)-5-isopropyl[1,2,4]triazol-3-ylmethyl) indole-2-carboxamide.

m.p. 209°–211° C.

EXAMPLE 241

Ethyl 2-(4-(3-(2-chlorobenzoyl)-5-ethylthiophen-2-yl)-5-isopropyl[1,2,4]triazol-3-ylmethylcarbamoyl)indole-1-acetate is obtained in the same manner as in Example 36 using 1-ethoxycarbonylmethylindole-2-carbonyl chloride and 3-aminomethyl-4-(3-(2-chlorobenzoyl)-5-ethylthiophen-2-yl)-5-isopropyl[1,2,4]triazole.

EXAMPLE 242

Ethyl 2-(4-(3-(2-chlorobenzoyl)-5-ethylthiophen-2-yl)-5-isopropyl[1,2,4]triazol-3-ylmethylcarbamoyl)indole-1-acetate is subjected to alkali hydrolysis to give 2-(4-(3-(2-chlorobenzoyl)-5-ethylthiophen-2-yl)-5-isopropyl[1,2,4] triazol-3-ylmethylcarbamoyl)indole-1-acetic acid.

EXAMPLE 243

N-(4-(3-(2-Chlorobenzoyl)-5-ethylthiophen-2-yl)-5-isopropyl[1,2,4]triazol-3-ylmethyl)-N'-(2-chlorophenyl) urea is obtained in the same manner as in Example 31 using 2-chlorophenyl isocyanate and 3-aminomethyl-4-(3-(2-chlorobenzoyl)-5-ethylthiophen-2-yl)-5-isopropyl[1,2,4] triazole.

EXAMPLE 244

N-(4-(3-(2-Chlorobenzoyl)-5-ethylthiophen-2-yl)-5-isopropyl[1,2,4]triazol-3-ylmethyl)-N'-(3-methylphenyl) urea is obtained in the same manner as in Example 31 using 3-methylphenyl isocyanate and 3-aminomethyl-4-(3-(2-chlorobenzoyl)-5-ethylthiophen-2-yl)-5-isopropyl[1,2,4] triazole.

EXAMPLE 245

N-(4-(3-(2-Chlorobenzoyl)-5-ethylthiophen-2-yl)-5-isopropyl[1,2,4]triazol-3-ylmethyl)-N'-(3-methoxyphenyl) urea is obtained in the same manner as in Example 31 using 3-methoxyphenyl isocyanate and 3-aminomethyl-4-(3-(2-chlorobenzoyl)-5-ethylthiophen-2-yl)-5-isopropyl[1,2,4] triazole.

Production Example 10

Production of ethyl (4-(2-chlorophenyl)-9-methyl-6H-thieno[3,2-f] [1,2,4]triazolo[4,3-a] [1,4]diazepin-2-yl) carboxylate Using a known method such as Monatshefte fur Chemie, 104, 973–978 (1973), the compound was synthesized as follows. Potassium hydroxide (263.5 g) and a 40% methylamine aqueous solution (344 ml) were added to water (400 ml). Carbon disulfide (240 ml) was dropwise added under ice-cooling, and the mixture was stirred for 1.5 hours. An aqueous solution of chloroacetic acid (378 g), water (800 ml) and potassium carbonate (276 g) was added, and the mixture was added to conc. hydrochloric acid (800 ml) with vigorous stirring. The precipitated crystals were collected by filtration, washed with water and dried to give 403 g of 3-methyl-4-oxo-thiazolidine-2-thione.

3-Methyl-4-oxo-thiazolidine-2-thione (403 g) and ethyl orthoformate (1370 ml) were added to acetic anhydride (775 ml), and the mixture was refluxed for 6 hours. The mixture was allowed to stand, and the resulting crystals were collected by filtration and washed with diisopropyl ether to give 342 g of 5-ethoxymethylene-3-methyl-4-oxo-thiazolidine-2-thione.

5-Ethoxymethylene-3-methyl-4-oxo-thiazolidine-2-thione (422 g) was dissolved in dichloromethane (3 l). 3-(2-Chlorophenyl)-3-oxo-propionitrile (410.7 g) and triethylamine (289.4 ml) were added under ice-cooling, and the mixture was stirred at room temperature overnight.

Then, the solvent was evaporated and ethyl acetate was added. The precipitated crystals were collected by filtration and washed with ethyl acetate to give 692 g of 2-(2-chlorobenzoyl)-3-(3-methyl-4-oxo-2-thioxo-thiazolidine) propionitrile.

2-(2-Chlorobenzoyl)-3-(3-methyl-4-oxo-2-thioxo-thiazolidine)propylnitrile (494 g) was added to a 15% aqueous sodium hydroxide solution (2000 ml), and the mixture was refluxed for 30 minutes. The mixture was cooled, and the mixture was added to conc. hydrochloric acid (3000 ml). The precipitated crystals were collected by filtration and washed with water to give 299 g of 5-amino-4-(2-chlorobenzoyl)thiophene-2-carboxylic acid.

5-Amino-4-(2-chlorobenzoyl)thiophene-2-carboxylic acid (240 g), potassium carbonate (176 g) and ethyl iodide (150 ml) were added to acetone (5 l), and the mixture was refluxed overnight. The solvent was evaporated, and ethyl acetate and a saturated aqueous sodium hydrogencarbonate solution were added. The precipitated layer was taken out, washed with brine, dried over sodium sulfate and concentrated. The resulting crystals were collected by filtration and washed with ethyl acetate to give 126 g of ethyl 5-amino-4-(2-chlorobenzoyl)thiophene-2-carboxylate.

Ethyl 5-amino-4-(2-chlorobenzoyl)thiophene-2-carboxylate (280 g) and chloroacetyl chloride (218 ml) were added to chloroform (4 l), and the mixture was refluxed under heating for 2.5 hours. Water was added thereto. The organic layer was taken out, and dried over magnesium sulfate. The solvent was evaporated. Then, diisopropyl ether was added, and the resulting crystals were collected by filtration and washed with diisopropyl ether to give 325 g of ethyl 5-(2-chloroacetylamino)-4-(2-chlorobenzoyl) thiophene-2-carboxylate.

Ethyl 5-(2-chloroacetylamino)-4-(2-chlorobenzoyl) thiophene-2-carboxylate (325 g) and sodium iodide (151.3 g) were added to tetrahydrofuran (3500 ml), and the mixture was refluxed under heating for 1.5 hours. The mixture was cooled to −65° C., and ammonia (164 ml) was added. The reaction temperature was raised slowly to room temperature. The solvent was evaporated, and chloroform and water were added. The organic layer was taken out, washed with water and dried over sodium sulfate. The solvent was evaporated. Toluene (7 l) and silica gel (1365 g) were added thereto, and the mixture was refluxed under heating for 1.5 hours. The silica gel was collected by filtration, and a mixed solvent of chloroform-methanol (10:1) was added to elute the obtained product. The solvent was evaporated, and ethyl acetate was added. The resulting crystals were collected by filtration and washed with ethyl acetate to give 70.0 g of ethyl (5-(2-chlorophenyl)-1,2-dihydro-3H-thieno[2,3-e] [1,4]diazepin-2-on-7-yl)-carboxylate.

Ethyl (5-(2-chlorophenyl)-1,2-dihydro-3H-thieno[2,3-e] [1,4]diazepin-2-on-7-yl)carboxylate (40.0 g) and diphosphorus pentasulfide (76.5 g) were added to chloroform (4 l), and the mixture was refluxed under heating for 2 hours. The mixture was cooled, methanol (1 l) was added and the insoluble matter was filtered off. The filtrate was washed with a saturated aqueous sodium hydrogencarbonate solution and dried over magnesium sulfate. The solvent was evaporated, and diisopropyl ether was added. The resulting crystals were collected by filtration and washed with diisopropyl ether. The mixture was added to methanol (330 ml), and hydrazine monohydrate (16.4 ml) was added under ice-cooling with stirring. The mixture was further stirred at room temperature for 1.5 hours. The obtained product was collected by filtration and washed with methanol. This product was dissolved in toluene (600 ml), and ethyl orthoacetate (28.1 ml) was added. The mixture was stirred at 80° C. for 1 hour and concentrated. The resulting crystals were collected by filtration, washed with diisopropyl ether and recrystallized from a mixed solvent of ethyl acetate-diisopropyl ether to give 20.4 g of ethyl (4-(2-chlorophenyl)-9-methyl-6H-thieno[3,2-f] [1,2,4]triazolo[4,3-a] [1,4]diazepin-2-yl)carboxylate.

m.p. 148°–150° C.

Ethyl (4-(2-chlorophenyl)-9-methyl-6H-thieno[3,2-f] [1,2,4]triazolo[4,3-a] [1,4]diazepin-2-yl)carboxylate can be also synthesized by the following method.

2-Acetyl-4-(2-chlorophenyl)-9-methyl-6H-thieno[3,2-f] [1,2,4]triazolo[4,3-a] [1,4]diazepine (1.0 g) synthesized by the method described in Artneim.-Forsch./Drug Res. 28 (II), Heft 7, 1153–1158 (1978) was added to a 10% aqueous sodium hypochlorite solution (21 ml), and the mixture was stirred at 60° C. for 1.5 hours. Sodium hydrogensulfite (2.9 g) was added to the reaction mixture. Then, an aqueous citric acid solution was added to adjust the reaction mixture to pH 3. The obtained crystals were collected by filtration, and washed with water to give 0.5 g of (4-(2-chlorophenyl)-9-methyl-6H-thieno[3,2-f] [1,2,4]triazolo[4,3-a] [1,4] diazepin-2-yl)carboxylic acid.

The obtained (4-(2-chlorophenyl)-9-methyl-6H-thieno[3,2-f] [1,2,4]triazolo[4,3-a] [1,4]diazepin-2-yl)carboxylic acid was dissolved in dimethylformamide. Potassium carbonate and ethyl iodide were added, and the mixture was stirred overnight to give ethyl (4-(2-chlorophenyl)-9-methyl-6H-thieno[3,2-f] [1,2,4]triazolo[4,3-a] [1,4]diazepin-2-yl) carboxylate.

EXAMPLE 246

Ethyl (4-(2-chlorophenyl)-9-methyl-6H-thieno[3,2-f] [1,2,4]triazolo[4,3-a] [1,4]diazepin-2-yl)carboxylate is hydrolyzed in the same manner as in Example 250, and reacted with 3,4-dichlorobenzoyl chloride to give ethyl (3-(2-chlorobenzoyl)-2-(3-(3,4-dichlorobenzoylaminomethyl)-5-methyl[1,2,4]triazol-4-yl) thiophen-5-yl)carboxylate.

EXAMPLE 247

Ethyl (4-(2-chlorophenyl)-9-methyl-6H-thieno[3,2-f] [1,2,4]triazolo[4,3-a] [1,4]diazepin-2-yl)carboxylate (0.5 g) and p-toluenesulfonic acid (0.75 g) were dissolved in a mixed solvent (5 ml) of methanol:water (9:1), and the solution was refluxed for 3.5 hours. The solvent was evaporated, and the residue was dissolved in dimethylformamide (5 ml). Indole-2-carbonyl chloride (0.27 g) and triethylamine (1.0 ml) were added under ice-cooling, and the mixture was stirred for 1 hour. The reaction mixture was partitioned between ethyl acetate and a saturated aqueous sodium hydrogencarbonate solution. The organic layer was washed with brine, an aqueous citric acid solution and brine, and dried over magnesium sulfate. The solvent was evaporated. The residue was crystallized from ethyl acetate to give 230 mg of ethyl (3-(2-chlorobenzoyl)-2-(3-(2-indolecarbonylaminomethyl)-5-methyl[1,2,4]triazol-4-yl) thiophen-5-yl)carboxylate.

m.p. 135°–140° C.

EXAMPLE 248

Ethyl (4-(2-chlorophenyl)-9-methyl-6H-thieno[3,2-f] [1,2,4]triazolo[4,3-a] [1,4]diazepin-2-yl)carboxylate is hydrolyzed in the same manner as in Example 250, and reacted with 2-chlorophenyl isocyanate to give ethyl (3-(2-chlorobenzoyl)-2-(3-(3-(2-chlorophenyl)ureidomethyl)-5-methyl[1,2,4]triazol-4-yl)thiophen-5-yl)carboxylate.

EXAMPLE 249

Ethyl (4-(2-chlorophenyl)-9-methyl-6H-thieno[3,2-f] [1,2,4]triazolo[4,3-a] [1,4]diazepin-2-yl)carboxylate is hydrolyzed in the same manner as in Example 250, and reacted with 3-methylphenyl isocyanate to give ethyl (3-(2-chlorobenzoyl)-2-(3-(3-(3-methylphenyl)ureidomethyl)-5-methyl[1,2,4]triazol-4-yl)thiophen-5-yl)carboxylate.

EXAMPLE 250

Ethyl (4-(2-chlorophenyl)-9-methyl-6H-thieno[3,2-f] [1,2,4]triazolo[4,3-a] [1,4]diazepin-2-yl)carboxylate (4.0 g) and p-toluenesulfonic acid monohydrate (6.0 g) were dissolved in a mixed solvent (40 ml) of ethanol-water (9:1), and the mixture was refluxed under heating for 1 hour. The solvent was evaporated, and the residue was dissolved in dimethylformamide (40 ml). 3-Methoxyphenyl isocyanate (1.44 ml) and triethylamine (8.3 ml) were added under ice-cooling, and the mixture was stirred for 1 hour. The reaction mixture was partitioned between ethyl acetate and a saturated aqueous sodium hydrogencarbonate solution. The organic layer was washed with brine, an aqueous citric acid solution and brine, and dried over magnesium sulfate. The solvent was evaporated. The residue was purified by silica gel column chromatography (developing solvent:ethyl acetate) and recrystallized from ethyl acetate to give 2.18 g of ethyl (3-(2-chlorobenzoyl)-2-(3-(3-(3-methoxyphenyl)ureidomethyl)-5-methyl[1,2,4]triazol-4-yl)thiophen-5-yl)carboxylate.

m.p. 132°–134° C.

EXAMPLE 251

Ethyl (3-(2-chlorobenzoyl)-2-(3-(3,4-dichlorobenzoylaminomethyl)-5-methyl[1,2,4]triazol-4-yl)thiophen-5-yl)carboxylate is hydrolyzed to give (3-(2-chlorobenzoyl)-2-(3-(3,4-dichlorobenzoylaminomethyl)-5-methyl[1,2,4]triazol-4-yl)thiophen-5-yl)carboxylic acid.

EXAMPLE 252

Ethyl (3-(2-chlorobenzoyl)-2-(3-(2-indolecarbonylaminomethyl)-5-methyl[1,2,4]triazol-4-yl)thiophen-5-yl)carboxylate (0.16 g) was hydrolyzed using a 2M aqueous sodium hydroxide solution (0.22 ml) and methanol (1 ml) to give 0.053 g of (3-(2-chlorobenzoyl)-2-(3-(2-indolecarbonylaminomethyl)-5-methyl[1,2,4]triazol-4-yl)thiophen-5-yl)carboxylic acid.

m.p. 270° C. (decomposition)

This compound can be also synthesized by the following method.

(4-(2-Chlorophenyl)-9-methyl-6H-thieno[3,2-f] [1,2,4] triazolo[4,3-a] [1,4]diazepin-2-yl)carboxylic acid (0.50 g) was dissolved in a mixed solvent (5 ml) of methanol:water (9:1). p-Toluenesulfonic acid monohydrate (0.81 g) was added, and the mixture was refluxed under heating for 3 hours. The solvent was evaporated, and dimethylformamide (5 ml), indole-2-carbonyl chloride (0.28 g) and triethylamine (1.0 ml) were added. The mixture was stirred for 1 hour. A saturated aqueous sodium hydrogencarbonate solution was added, and the mixture was extracted with ethyl acetate. The extract was washed with an aqueous citric acid solution and brine, dried over magnesium sulfate and concentrated to give (3-(2-chlorobenzoyl)-2-(3-(2-indolecarbonylaminomethyl)-5-methyl[1,2,4]triazol-4-yl)thiophen-5-yl)carboxylic acid.

EXAMPLE 253

(4-(2-Chlorophenyl)-9-methyl-6H-thieno[3,2-f] [1,2,4] triazolo[4,3-a] [1,4]diazepin-2-yl)carboxylic acid and p-toluenesulfonic acid are dissolved in a mixed solvent of methanol:water (9:1), and the solution is refluxed for 3 hours. The solvent is evaporated, and the residue is dissolved in dimethylformamide. 2-Chlorophenyl isocyanate and triethylamine are added under ice-cooing, and the mixture is stirred for 1 hour to give (3-(2-chlorobenzoyl)-2-(3-(3-(2-chlorophenyl)ureidomethyl)-5-methyl[1,2,4]triazol-4-yl)thiophen-5-yl)carboxylic acid.

EXAMPLE 254

(3-(2-Chlorobenzoyl)-2-(3-(3-(3-methylphenyl)ureidomethyl)-5-methyl[1,2,4]triazol-4-yl)thiophen-5-yl)carboxylic acid is obtained in the same manner as in Example 253 using (4-(2-chlorophenyl)-9-methyl-6H-thieno[3,2-f] [1,2,4]triazolo[4,3-a] [1,4]diazepin-2-yl)carboxylic acid and 3-methylphenyl isocyanate.

EXAMPLE 255

(4-(2-Chlorophenyl)-9-methyl-6H-thieno[3,2-f] [1,2,4] triazolo[4,3-a] [1,4]diazepin-2-yl)carboxylic acid (0.47 g) and p-toluenesulfonic acid (0.76 g) were dissolved in a mixed solvent (5 ml) of methanol:water (9:1), and the solution was refluxed for 1 hour. The solvent was evaporated, and the residue was dissolved in dimethylformamide (5 ml). 3-Methoxyphenyl isocyanate (0.19 ml) and triethylamine (0.94 ml) were added under ice-cooling, and the mixture was stirred for 30 minutes. Ethyl acetate was added thereto, and the mixture was extracted. An aqueous citric acid solution was added to adjust the reaction mixture to pH 3. The obtained crystals were collected by filtration and washed with water to give 0.42 g of (3-(2-chlorobenzoyl)-2-(3-(3-(3-methoxyphenyl)ureidomethyl)-5-methyl[1,2,4]triazol-4-yl)thiophen-5-yl)carboxylic acid.

m.p. 206°–208° C.

EXAMPLE 256

3,4-Dichlorobenzoyl chloride and methyl (2-(3-aminomethyl-5-methyl[1,2,4]triazol-4-yl)-3-(2-chlorobenzoyl)thiophen-5-yl)acetate are reacted to give methyl (3-(2-chlorobenzoyl)-2-(3-(3,4-dichlorobenzoylaminomethyl)-5-methyl[1,2,4]triazol-4-yl)thiophen-5-yl)acetate.

EXAMPLE 257

Indole-2-carbonyl chloride and methyl (2-(3-aminomethyl-5-methyl[1,2,4]triazol-4-yl)-3-(2-chlorobenzoyl)thiophen-5-yl)acetate are reacted to give methyl (3-(2-chlorobenzoyl)-2-(3-(2-indolecarbonylaminomethyl)-5-methyl[1,2,4]triazol-4-yl)thiophen-5-yl)acetate.

EXAMPLE 258

2-Chlorophenyl isocyanate and methyl (2-(3-aminomethyl-5-methyl[1,2,4]triazol-4-yl)-3-(2-chlorobenzoyl)thiophen-5-yl)acetate are reacted to give methyl (3-(2-chlorobenzoyl)-2-(3-(3-(2-chlorophenyl)ureidomethyl)-5-methyl[1,2,4]triazol-4-yl)thiophen-5-yl)acetate.

EXAMPLE 259

3-Methylphenyl isocyanate and methyl (2-(3-aminomethyl-5-methyl[1,2,4]triazol-4-yl)-3-(2-chlorobenzoyl)thiophen-5-yl)acetate are reacted to give methyl (3-(2-chlorobenzoyl)-2-(3-(3-(3-methylphenyl) ureidomethyl)-5-methyl[1,2,4]triazol-4-yl)thiophen-5-yl) acetate.

EXAMPLE 260

3-Methoxyphenyl isocyanate and methyl (2-(3-aminomethyl-5-methyl[1,2,4]triazol-4-yl)-3-(2-chlorobenzoyl)thiophen-5-yl)acetate are reacted to give methyl (3-(2-chlorobenzoyl)-2-(3-(3-(3-methoxyphenyl) ureidomethyl)-5-methyl[1,2,4]triazol-4-yl)thiophen-5-yl) acetate.

EXAMPLE 261

Methyl (3-(2-chlorobenzoyl)-2-(3-(3,4-dichlorobenzoylaminomethyl)-5-methyl[1,2,4]triazol-4-yl) thiophen-5-yl)acetate is subjected to hydrolysis to give (3-(2-chlorobenzoyl)-2-(3-(3,4-dichlorobenzoylaminomethyl)-5-methyl[1,2,4]triazol-4-yl) thiophen-5-yl)acetic acid.

EXAMPLE 262

Methyl (3-(2-chlorobenzoyl)-2-(3-(2-indolecarbonylaminomethyl)-5-methyl[1,2,4]triazol-4-yl) thiophen-5-yl)acetate is subjected to hydrolysis to give (3-(2-chlorobenzoyl)-2-(3-(2-indolecarbonylaminomethyl)-5-methyl[1,2,4]triazol-4-yl)thiophen-5-yl)acetic acid.

EXAMPLE 263

Methyl (3-(2-chlorobenzoyl)-2-(3-(3-(2-chlorophenyl) ureidomethyl)-5-methyl[1,2,4]triazol-4-yl)thiophen-5-yl) acetate is subjected to hydrolysis to give (3-(2-chlorobenzoyl)-2-(3-(3-(2-chlorophenyl)ureidomethyl)-5-methyl[1,2,4]triazol-4-yl)thiophen-5-yl)acetic acid.

EXAMPLE 264

Methyl (3-(2-chlorobenzoyl)-2-(3-(3-(3-methylphenyl) ureidomethyl)-5-methyl[1,2,4]triazol-4-yl)thiophen-5-yl) acetate is subjected to hydrolysis to give (3-(2-chlorobenzoyl)-2-(3-(3-(3-methylphenyl)ureidomethyl)-5-methyl[1,2,4]triazol-4-yl)thiophen-5-yl)acetic acid.

EXAMPLE 265

Methyl (3-(2-chlorobenzoyl)-2-(3-(3-(3-methoxyphenyl) ureidomethyl)-5-methyl[1,2,4]triazol-4-yl)thiophen-5-yl) acetate is subjected to hydrolysis to give (3-(2-chlorobenzoyl)-2-(3-(3-(3-methoxyphenyl)ureidomethyl)-5-methyl[1,2,4]triazol-4-yl)thiophen-5-yl)acetic acid.

EXAMPLE 266

5-(2-Chlorophenyl)-7-ethyl-2-hydrazino-1,3-dihydro-2H-thieno[2,3-e] [1,4]diazepine (15.9 g) was suspended in chloroform (200 ml) under ice-cooling. 3-Phthalimidepropionyl chloride (12.5 g) was added, and the mixture was stirred for 1 hour. The reaction mixture was washed with a saturated aqueous sodium hydrogencarbonate solution and dried over magnesium sulfate. The solvent was evaporated. The residue was dissolved in a mixed solvent of toluene (150 ml) and acetic acid (4.5 ml), and the solution was refluxed for 3 hours. The reaction mixture was concentrated. The residue was purified by silica gel column chromatography (eluted with ethyl acetate and methanol), and N-(2-(4-(2-chlorophenyl)-2-ethyl-6H-thieno[3,2-f] [1,2,4] triazolo[4,3-a] [1,4]diazepin-9-yl)ethyl)phthalimide was obtained from a fraction containing the objective compound. This compound was dissolved in ethanol (200 ml). Hydrazine monohydrate (2.18 g) was added and the mixture was refluxed for 6 hours. The reaction mixture was concentrated, and partitioned between water and chloroform. The organic layer was washed with saturated brine, and dried over magnesium sulfate. The solvent was evaporated, and the obtained product was purified by silica gel column chromatography using a mixed solvent of chloroform and methanol as an eluent to give 5.2 g of 9-(2-aminoethyl)-4-(2-chlorophenyl)-2-ethyl-6H-thieno[3,2-f] [1,2,4]triazolo[4,3-a] [1,4]diazepine as an oil.

9-(2-Aminoethyl)-4-(2-chlorophenyl)-2-ethyl-6H-thieno [3,2-f] [1,2,4]triazolo[4,3-a] [1,4]diazepine (1.0 g) thus obtained, indole-2-carboxylic acid (0.455 g), Bop reagent (1.25 g) and triethylamine (0.75 g) were dissolved in dimethylformamide (10 ml), and the solution was stirred overnight. The reaction mixture was partitioned between ethyl acetate and water. The organic layer was washed with an aqueous citric acid solution, a saturated aqueous sodium hydrogencarbonate solution and saturated brine, and dried over magnesium sulfate. The solvent was evaporated, and the obtained residue was purified by silica gel column chromatography using a mixed solvent of ethyl acetate and methanol as an eluent to give 0.68 g of N-(2-(4-(2-chlorophenyl)-2-ethyl-6H-thieno[3,2-f] [1,2,4]triazolo[4,3-a] [1,4]diazepin-9-yl)ethyl)-indole-2-carboxamide.

m.p. 174°–178° C.

EXAMPLE 267

4-(2-Chlorophenyl)-2-(2-(4-isobutylphenyl)ethyl)-9-methyl-6H-thieno[3,2-f] [1,2,4]triazolo[4,3-a] [1,4] diazepine described in Example 1 of Japanese Patent Publication No. 55510/1993 was dissolved in a 5% aqueous hydrochloric acid solution, and the solution was stirred at 60° C. for 5 hours. A saturated aqueous sodium hydrogencarbonate solution was added to the reaction mixture to make the mixture alkaline. Chloroform and 3,4-dichlorobenzoyl chloride were added, and the mixture was stirred under ice-cooling for 1 hour. The organic layer was washed with an aqueous citric acid solution, a saturated aqueous sodium hydrogencarbonate solution and saturated brine, and dried over magnesium sulfate. The solvent was evaporated, and the residue was purified to give N-(4-(3-(2-chlorobenzoyl)-5-(2-(4-isobutylphenyl)ethyl)thiophen-2-yl)-5-methyl[1,2,4]triazol-3-ylmethyl)-3,4-dichlorobenzamide.

EXAMPLE 268

N-(2-(4-(2-Chlorophenyl)-2-ethyl-6H-thieno[3,2-f] [1,2,4]triazolo[4,3-a] [1,4]diazepin-9-yl)ethyl)-3,4-dichlorobenzamide (0.98 g) was obtained in the same manner as in Example 59 using 9-(2-aminoethyl)-4-(2-chlorophenyl)-2-ethyl-6H-thieno[3,2-f] [1,2,4]triazolo[4,3-a] [1,4]diazepine (2.0 g), dichloroethane (100 ml), triethylamine (0.79 ml) and 3,4-dichlorobenzoyl chloride (1.18 g).

m.p. 141°–142° C.

EXAMPLE 269

5-(2-Chlorophenyl)-7-ethyl-2-hydrazino-1,3-dihydro-2H-thieno[2,3-e] [1,4]diazepine (9.56 g) was suspended in chloroform (100 ml) under ice-cooling. 4-Phthalimidebutanoyl chloride (7.93 g) was added, and the mixture was stirred for 1 hour. The reaction mixture was washed with a saturated aqueous sodium hydrogencarbonate solution and dried over magnesium sulfate. The solvent was evaporated. The residue was dissolved in a mixed solvent of toluene (200 ml) and acetic acid (2.7 ml) and the mixture was refluxed for 3 hours. The reaction mixture was concentrated and the residue was purified by silica gel column chromatography (eluted with ethyl acetate and methanol) to give 10.13 g of 4-(2-chlorophenyl)-2-ethyl-9-(3-phthalimidepropyl)-6H-thieno[3,2-f] [1,2,4]triazolo[4,3-a] [1,4]diazepine.

4-(2-Chlorophenyl)-2-ethyl-9-(3-phthalimidepropyl)-6H-thieno[3,2-f] [1,2,4]triazolo[4,3-a] [1,4]diazepine (4.64 g) thus obtained was dissolved in ethanol (90 ml). Hydrazine monohydrate (0.87 ml) was added, and the mixture was refluxed for 2.5 hours. The reaction mixture was filtered, and the solvent was evaporated. Water was added, and the mixture was extracted with chloroform. The extract was washed with saturated brine and dried over magnesium sulfate. The solvent was evaporated, and the residue was purified by silica gel column chromatography using a mixed solvent of chloroform and methanol as an eluent to give 1.67 g of 9-(3-aminopropyl)-4-(2-chlorophenyl)-2-ethyl-6H-thieno[3,2-f] [1,2,4]triazolo[4,3-a] [1,4]diazepine.

N-(3-(4-(2-Chlorophenyl)-2-ethyl-6H-thieno[3,2-f] [1,2,4]triazolo[4,3-a] [1,4]diazepin-9-yl)propyl)-3,4-dichlorobenzamide (0.87 g) was obtained in the same manner as in Example 268 using 9-(3-aminopropyl)-4-(2-chlorophenyl)-2-ethyl-6H-thieno[3,2-f] [1,2,4]triazolo[4,3-a] [1,4]diazepine (1.67 g) thus obtained, dimethylformamide (80 ml), triethylamine (0.64 ml) and 3,4-dichlorobenzoyl chloride (0.95 g).

m.p. 143°–144° C.

EXAMPLE 270

β-Cyclohexyl N-α-tert-butoxycarbonyl-L-aspartate (4.0 g) was dissolved in tetrahydrofuran (50 ml), and triethylamine (1.8 ml) was added. Isobutyl chloroformate (1.6 ml) was gradually added dropwise under cooling with ice-salt. Thirty minutes later, 5-(2-chlorophenyl)-7-ethyl-2-hydrazine-3H-thieno[2,3-e] [1,4]diazepine (2.0 g) was dissolved in dimethylformamide (20 ml), and the solution was dropwise added to the mixture. The mixture was stirred at room temperature. Ethyl acetate was added to the reaction mixture. The organic layer was washed with a saturated aqueous sodium hydrogencarbonate solution and dried over magnesium sulfate. The solvent was evaporated, and the residue was dissolved in toluene (60 ml). Acetic acid (1 ml) was added, and the mixture was refluxed for 5 hours. Ethyl acetate was added to the reaction mixture. The mixture was washed with a saturated aqueous sodium hydrogencarbonate solution and dried over magnesium sulfate. The solvent was evaporated, and the residue was purified by silica gel column chromatography using ethyl acetate as an eluent to give 1.26 g of cyclohexyl (S)-3-(tert-butoxycarbonylamino)-3-(4-(2-chlorophenyl)-2-ethyl-6H-thieno[3,2-f] [1,2,4]triazolo[4,3-a] [1,4]diazepin-9-yl)propionate.

Cyclohexyl (S)-3-(tert-butoxycarbonylamino)-3-(4-(2-chlorophenyl)-2-ethyl-6H-thieno[3,2-f] [1,2,4]triazolo[4,3-a] [1,4]diazepin-9-yl)propionate (1.26 g) obtained was dissolved in trifluoroacetic acid (13 ml), and the solution was stirred under ice-cooling for 30 minutes. The solvent was evaporated, and chloroform was added. The mixture was washed with a saturated aqueous sodium hydrogencarbonate solution and saturated brine and dried over magnesium sulfate. The solvent was evaporated to give 1.01 g of cyclohexyl (S)-3-amino-3-(4-(2-chlorophenyl)-2-ethyl-6H-thieno[3,2-f] [1,2,4]triazolo[4,3-a] [1,4]diazepin-9-yl) propionate.

Cyclohexyl (S)-(+)-3-(3,4-dichlorobenzoylamino)-3-(4-(2-chlorophenyl)-2-ethyl-6H-thieno[3,2-f] [1,2,4]triazolo[4,3-a] [1,4]diazepin-9-yl)propionate (0.43 g) was obtained in the same manner as in Example 59 using cyclohexyl (S)-3-(4-(2-chlorophenyl)-2-ethyl-6H-thieno[3,2-f] [1,2,4]triazolo [4,3-a] [1,4]diazepin-9-yl)propionate (1.01 g) thus obtained, dichloroethane (50 ml), triethylamine (0.30 ml) and 3,4-dichlorobenzoyl chloride (0.45 g).

m.p. 165°–166° C., $[\alpha]_D$=+61.3° (c=1, dimethylformamide)

EXAMPLE 271

Cyclohexyl (S)-(+)-3-(3,4-dichlorobenzoylamino)-3-(4-(2-chlorophenyl)-2-ethyl-6H-thieno[3,2-f] [1,2,4]triazolo[4,3-a] [1,4]diazepin-9-yl)propionate (0.40 g) obtained in Example 270 was dissolved in methanol (5 ml). A 2N aqueous sodium hydroxide solution (0.6 ml) was added, and the mixture was stirred for 3 hours. The solvent was evaporated. Water was added and the mixture was washed with ethyl acetate. Citric acid was added to the aqueous layer to make the layer acidic. The mixture was extracted with ethyl acetate and the extract was dried over magnesium sulfate. The solvent was evaporated, and the residue was purified by silica gel column chromatography using a mixed solvent of chloroform, methanol and acetic acid as an eluent to give 96 mg of (S)-(+)-3-(3,4-dichlorobenzoylamino)-3-(4-(2-chlorophenyl)-2-ethyl-6H-thieno[3,2-f] [1,2,4]triazolo[4,3-a] [1,4]diazepin-9-yl)propionic acid.

NMR (270 MHz, $CD_3OD$):1.23(3H,t,J=7.4 Hz), 2.81(2H, q,J=7.4 Hz), 3.08–3.45(2H,m), 5.93–5.96(1H,m), 6.06(1H, s), 6.45(1H,s), 7.36–7.93(8H,m)

$[\alpha]_D$=+65.5° (c=1, dimethylformamide)

EXAMPLE 272

Cyclohexyl (R)-(−)-3-(3,4-dichlorobenzoylamino)-3-(4-(2-chlorophenyl)-2-ethyl-6H-thieno[3,2-f] [1,2,4]triazolo[4,3-a] [1,4]diazepin-9-yl)propionate (0.73 g) was obtained in the same manner as in Example 270 using β-cyclohexyl N-α-tert-butoxycarbonyl-D-aspartate (5.0 g), tetrahydrofuran (80 ml), triethylamine (2.2 ml), isobutyl chloroformate (2.1 ml) and 5-(2-chlorophenyl)-7-ethyl-2-hydrazine-3H-thieno[2,3-e] [1,4]diazepine (3.4 g).

m.p. 170°–171° C., $[\alpha]_D$=−64.90 (c=1, dimethylformamide)

EXAMPLE 273

(R)-(−)-3-(3,4-Dichlorobenzoylamino)-3-(4-(2-chlorophenyl)-2-ethyl-6H-thieno[3,2-f] [1,2,4]triazolo[4,3-a] [1,4]diazepin-9-yl)propionic acid (67 mg) was obtained in the same manner as in Example 271 using cyclohexyl (R)-(−)-3-(3,4-dichlorobenzoylamino)-3-(4-(2-chlorophenyl)-2-ethyl-6H-thieno[3,2-f] [1,2,4]triazolo[4,3-a] [1,4]diazepin-9-yl)propionate (0.50 g) obtained in Example 272, methanol (5 ml) and a 2N sodium hydroxide aqueous solution (0.7 ml).

$[\alpha]_D$=−67.0° (c=1, dimethylformamide)

EXAMPLE 274

Cyclohexyl (S)-(+)-4-(3,4-dichlorobenzoylamino)-4-(4-(2-chlorophenyl)-2-ethyl-6H-thieno[3,2-f] [1,2,4]triazolo[4, 3-a] [1,4]diazepin-9-yl)butanoate (1.22 g) was obtained in the same manner as in Example 270 using γ-cyclohexyl N-α-tert-butoxycarbonyl-L-glutamate (4.1 g), tetrahydrofuran (50 ml), triethylamine (1.8 ml), isobutyl chloroformate (1.6 ml) and 5-(2-chlorophenyl)-7-ethyl-2-hydrazine-3H-thieno[2,3-e] [1,4]diazepine (2.0 g).

m.p. 157°–159° C., $[\alpha]_D$=+70.2° (c=1, dimethylformamide)

EXAMPLE 275

(S)-(+)-4-(3,4-Dichlorobenzoylamino)-4-(4-(2-chlorophenyl)-2-ethyl-6H-thieno[3,2-f] [1,2,4]triazolo[4,3-a] [1,4]diazepin-9-yl)butanoic acid (0.40 g) was obtained in the same manner as in Example 271 using cyclohexyl (S)-(+)-4-(3,4-dichlorobenzoylamino)-4-(4-(2-chlorophenyl)-2-ethyl-6H-thieno[3,2-f] [1,2,4]triazolo[4,3-a] [1,4]diazepin-9-yl)butanoate (1.0 g) obtained in Example 274, methanol (10 ml) and a 2N sodium hydroxide aqueous solution (1.7 ml).

NMR (270 MHz, $CDCl_3$):1.29(3H,t,J=7.3 Hz), 2.41–2.54 (4H,m), 2.81(2H,q,J=7.3 Hz), 4.69–5.11(2H,m), 5.93–5.96 (1H,m), 7.26(1H,s), 7.30–7.92(7H,m), 8.98(1H,m)

$[\alpha]_D$=+84.3° (c=1, dimethylformamide)

EXAMPLE 276

Cyclohexyl (R)-(−)-4-(3,4-dichlorobenzoylamino)-4-(4-(2-chlorophenyl)-2-ethyl-6H-thieno[3,2-f] [1,2,4]triazolo[4,3-a] [1,4]diazepin-9-yl)butanoate (0.92 g) was obtained in the same manner as in Example 270 using γ-cyclohexyl N-α-tert-butoxycarbonyl-D-glutamate (5.0 g), tetrahydrofuran (80 ml), triethylamine (2.1 ml), isobutyl chloroformate (2.1 ml) and 5-(2-chlorophenyl)-7-ethyl-2-hydrazine-3H-thieno[2,3-e] [1,4]diazepine (3.2 g).

m.p. 158°–160° C., $[\alpha]_D$=−70.9° (c=1, dimethylformamide)

EXAMPLE 277

(R)-(−)-4-(3,4-Dichlorobenzoylamino)-4-(4-(2-chlorophenyl)-2-ethyl-6H-thieno[3,2-f] [1,2,4]triazolo[4,3-a] [1,4]diazepin-9-yl)butanoic acid (0.36 g) was obtained in the same manner as in Example 271 using cyclohexyl (R)-(−)-4-(3,4-dichlorobenzoylamino)-4-(4-(2-chlorophenyl)-2-ethyl-6H-thieno[3,2-f] [1,2,4]triazolo[4,3-a] [1,4]diazepin- 9-yl)butanoate (0.7 g) obtained in Example 276, methanol (7 ml) and a 2N sodium hydroxide aqueous solution (1 ml).

$[\alpha]_D$=−82.1° (c=1, dimethylformamide)

Production Example 11

γ-Benzyl N-α-tert-butoxycarbonyl-L-aspartate (25.0 g) was dissolved in tetrahydrofuran (250 ml), and triethylamine (11.4 ml) was added. Isobutyl chloroformate (10.7 ml) was gradually added dropwise at −10° C. Thirty minutes later, a solution of 5-(2-chlorophenyl)-7-ethyl-2-hydrazino-3H-thieno[2,3-e] [1,4]diazepine (23.65 g) dissolved in dimethylformamide (50 ml) was dropwise added to the reaction mixture. The mixture was stirred at room temperature. Ethyl acetate was added to the reaction mixture. The mixture was washed with a saturated aqueous sodium hydrogencarbonate solution and dried over magnesium sulfate. The solvent was evaporated, and the residue was dissolved in toluene (1500 ml). Acetic acid (25 ml) was added, and the mixture was refluxed for 5 hours. The reaction mixture was cooled, washed with a saturated aqueous sodium hydrogencarbonate solution and saturated brine, and dried over magnesium sulfate. The solvent was evaporated, and the residue was purified by silica gel column chromatography using ethyl acetate as an eluent to give 30.1 g of benzyl (R)-4-(4-(2-chlorophenyl)-2-ethyl-6H-thieno[3,2-f] [1,2,4]triazolo[4,3-a] [1,4]diazepin-9-yl)-4-(tert-butoxycarbonylamino) butanoate.

Benzyl (R)-4-(4-(2-chlorophenyl)-2-ethyl-6H-thieno[3,2-f] [1,2,4]triazolo[4,3-a] [1,4]diazepin-9-yl)-4-(tert-butoxycarbonylamino)butanoate (3.14 g) thus obtained was dissolved in trifluoroacetic acid (35 ml), and the solution was stirred under ice-cooling for 30 minutes. The solvent was evaporated, and chloroform was added. The mixture was washed with a saturated aqueous sodium hydrogencarbonate solution and saturated brine, and dried over magnesium sulfate. The solvent was evaporated, and the residue was dissolved in ethyl acetate. A solution of p-toluenesulfonic acid monohydrate (1.82 g) in ethanol was added, and the precipitated crystals were collected by filtration to give 3.42 g of benzyl (R)-4-amino-4-(4-(2-chlorophenyl)-2-ethyl-6H-thieno[3,2-f] [1,2,4]triazolo[4,3-a] [1,4]diazepin-9-yl)butanoate di-p-toluenesulfonate.

EXAMPLE 278

Benzyl (R)-4-amino-4-(4-(2-chlorophenyl)-2-ethyl-6H-thieno[3,2-f] [1,2,4]triazolo[4,3-a] [1,4]diazepin-9-yl) butanoate di-p-toluenesulfonate (3.0 g) and triethylamine (1.46 ml) were dissolved in dichloroethane (50 ml). Indole-2-carbonyl chloride (923 mg) was added, and the mixture was stirred at room temperature for 1 hour. Chloroform was added to the reaction mixture. The mixture was washed with a 10% aqueous citric acid solution, a saturated aqueous sodium hydrogencarbonate solution and saturated brine, and dried over magnesium sulfate. The solvent was concentrated under reduced pressure, and the residue was purified by silica gel column chromatography using ethyl acetate as an eluent to give 1.44 g of benzyl (R)-4-(4-(2-chlorophenyl)-2-ethyl-6H-thieno[3,2-f] [1,2,4]triazolo[4,3-a] [1,4] diazepin-9-yl)-4-(1H-indole-2-carboxamide)butanoate.

NMR (270 MHz, DMSO-$d_6$):1.07(3H,t,J=7.9 Hz), 2.3–2.8(6H), 4.80(2H,bs), 5.08(2H,s), 5.68(1H,m), 6.36(1H, s), 7.03(1H,t,J=7.3 Hz), 7.10–7.55(12H), 7.59(1H,d,J=5.3 Hz), 9.06(1H,m), 11.58(1H,s)

EXAMPLE 279

Cyclohexyl (R)-4-amino-4-(4-(2-chlorophenyl)-2-ethyl-6H-thieno[3,2-f] [1,2,4]triazolo[4,3-a] [1,4]diazepin-9-yl) butanoate (6.57 g) was synthesized in the same manner as in Example 270 using γ-cyclohexyl N-α-tert-butoxycarbonyl-D-glutamate (10.0 g), tetrahydrofuran (97 ml), triethylamine (4.6 ml), isobutyl chloroformate (4.7 ml) and 5-(2-chlorophenyl)-7-ethyl-2-hydrazine-3H-thieno[2,3-e] [1,4] diazepine (9.7 g).

Cyclohexyl (R)-4-amino-4-(4-(2-chlorophenyl)-2-ethyl-6H-thieno[3,2-f] [1,2,4]triazolo[4,3-a] [1,4]diazepin-9-yl) butanoate (2.77 g) thus obtained and indole-2-carboxylic acid (1.0 g) were dissolved in dimethylformamide (30 ml). Triethylamine (1.5 ml) and Bop reagent (2.65 g) were added, and the mixture was stirred for 4 hours. The reaction mixture was partitioned between ethyl acetate and water. The organic layer was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using ethyl acetate as an eluent to give 1.87 g of cyclohexyl (R)-(−)-4-(4-(2-chlorophenyl)-2-ethyl-6H-thieno[3,2-f] [1,2,4]triazolo[4,3-a] [1,4]diazepin-9-yl)-4-(indole-2-carboxamide)butanoate.

m.p. 133°–137° C., $[\alpha]_D$=−91.9° (c=1, dimethylformamide)

EXAMPLE 280

(R)-(−)-4-(4-(2-Chlorophenyl)-2-ethyl-6H-thieno[3,2-f] [1,2,4]triazolo[4,3-a] [1,4]diazepin-9-yl)-4-(indole-2-carboxamide)butanoic acid (0.37 g) was obtained in the same manner as in Example 271 using cyclohexyl (R)-(−)-4-(4-(2-chlorophenyl)-2-ethyl-6H-thieno[3,2-f] [1,2,4] triazolo[4,3-a] [1,4]diazepin-9-yl)-4-(1H-indole-2-carboxamide)butanoate (1.42 g) obtained in Example 279, methanol (14 ml) and a 2N sodium hydroxide aqueous solution (2 ml).

m.p. 276°–283° C. (dec.), $[\alpha]_D$=−115.8° (c=1, dimethylformamide)

EXAMPLE 281

Benzyl (R)-4-amino-4-(4-(2-chlorophenyl)-2-ethyl-6H-thieno[3,2-f] [1,2,4]triazolo[4,3-a] [1,4]diazepin-9-yl) butanoate di-p-toluenesulfonate (3.0 g) and 3-quinolinecarboxylic acid (0.66 g) were dissolved in DMF (30 ml). Triethylamine (1.94 ml) and Bop reagent (1.69 g) were added and the mixture was stirred. Water was added to the reaction mixture. The mixture was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using a mixed solvent of ethyl acetate and methanol as an eluent to give 1.76 g of benzyl (R)-(−)-4-(4-(2-chlorophenyl)-2-ethyl-6H-thieno[3,2-f] [1,2,4]triazolo [4,3-a] [1,4]diazepin-9-yl)-4-(quinoline-3-carboxamide) butanoate.

NMR (270 MHz, DMSO-$d_6$):1.05(3H,t,J=7.4 Hz), 2.25–2.54(4H,m), 2.70(2H,q,J=7.4 Hz), 5.09(2H,s), 5.70–5.75(1H,q),6.37(1H,s), 7.29–8.10(13H,m), 8.77(1H, s), 9.22(1H,s), 9.43(1H,s)

$[\alpha]_D$=−83.6° (c=1, dimethylformamide)

EXAMPLE 282

(R)-(−)-4-(4-(2-Chlorophenyl)-2-ethyl-6H-thieno[3,2-f] [1,2,4]triazolo[4,3-a] [1,4]diazepin-9-yl)-4-(quinoline-3-carboxamide)butanoic acid (0.32 g) was obtained in the same manner as in Example 271 using benzyl (R)-(−)-4-(4-(2-chlorophenyl)-2-ethyl-6H-thieno[3,2-f] [1,2,4]triazolo[4, 3-a] [1,4]diazepin-9-yl)-4-(quinoline-3-carboxamide) butanoate (1.65 g), methanol (16.5 ml) and a 2N sodium hydroxide aqueous solution (2.4 ml).

NMR (270 MHz, DMSO-$d_6$):1.08(3H,t,J=7.3 Hz), 2.32–2.68(4H,m), 2.75(2H,q,J=7.3 Hz), 4.91(2H,s), 5.70–5.71(1H,q), 6.37(1H,s), 7.34–8.10(8H,m), 8.77(1H,s), 9.21(1H,s), 9.40(1H,d)

$[\alpha]_D$=−102.3° (c=1, dimethylformamide)

EXAMPLE 283

Benzyl (R)-(−)-4-(2-amino-4-chlorobenzoylamino)-4-(4-(2-chlorophenyl)-2-ethyl-6H-thieno[3,2-f] [1,2,4]triazolo[4, 3-a] [1,4]diazepin-9-yl)butanoate (1.73 g) was obtained in the same manner as in Example 281 using benzyl (R)-4-amino-4-(4-(2-chlorophenyl)-2-ethyl-6H-thieno[3,2-f] [1,2, 4]triazolo[4,3-a] [1,4]diazepin-9-yl)butanoate di-p-toluenesulfonate (3.0 g), 2-amino-4-chlorobenzoic acid (0.66 g), dimethylformamide (30 ml), triethylamine (1.94 ml) and Bop reagent (1.69 g).

NMR (270 MHz, DMSO-$d_6$):1.08(3H,t,J=7.5 Hz), 2.24–2.59(4H,m), 2.71(2H,q,J=7.5 Hz), 4.81(2H,s), 5.03–5.13(2H,q), 5.51–5.59(1H,q), 6.39(1H,s), 6.41–7.48 (12H,m), 8.81–8.83(1H,d)

$[\alpha]_D$=−53.6° (c=1, dimethylformamide)

EXAMPLE 284

(R)-(−)-4-(2-Amino-4-chlorobenzoylamino)-4-(4-(2-chlorophenyl)-2-ethyl-6H-thieno[3,2-f] [1,2,4]triazolo[4,3-a] [1,4]diazepin-9-yl)butanoic acid (0.23 g) was obtained in the same manner as in Example 271 using benzyl (R)-(−)-4-(2-amino-4-chlorobenzoylamino)-4-(4-(2-chlorophenyl)-2-ethyl-6H-thieno[3,2-f] [1,2,4]triazolo[4,3-a] [1,4] diazepin-9-yl)butanoate (1.28 g), methanol (13 ml) and a 2N sodium hydroxide aqueous solution (1.9 ml).

NMR (270 MHz, DMSO-$d_6$):1.11(3H,t,J=7.5 Hz), 2.22–2.42(4H,m), 2.74(2H,q,J=7.5 Hz), 4.82(2H,s), 5.51–5.53(1H,q), 6.39(1H,s), 6.42–7.46(7H,m), 8.86(1H,d)

$[\alpha]_D$=−31.4° (c–1, dimethylformamide)

Production Example 12

9-Aminomethyl-4-(2-chlorophenyl)-2-ethyl-6H-thieno[3, 2-f] [1,2,4]triazolo[4,3-a] [1,4]diazepine (20 g) was dissolved in chloroform (200 ml). tert-Butyl dicarbonate (13.4 g) was added under ice-cooling, and the mixture was stirred at room temperature for 4 hours. The mixture was washed with a saturated aqueous sodium hydrogen-carbonate solution and saturated brine, and dried over magnesium sulfate. The solvent was evaporated, and the residue was recrystallized from a mixed solvent of ethyl acetate and hexane to give 23.85 g of 9-(tert-butoxycarbonylaminomethyl)-4-(2-chlorophenyl)-2-ethyl-6H-thieno[3,2-f] [1,2,4]triazolo[4,3-a] [1,4]diazepine.

9-(tert-Butoxycarbonylaminomethyl)-4-(2-chlorophenyl)-2-ethyl-6H-thieno[3,2-f] [1,2,4]triazolo[4,3-a] [1,4]diazepine (21.79 g) thus obtained was dissolved in THF (220 ml). A 2N lithium diisopropylamide-hexane solution (49.8 ml) was dropwise added at −78° C., and the mixture was stirred for 1 hour. Ethyl bromoacetate (5.8 ml) was added. The reaction temperature was raised slowly to room temperature, and the mixture was stirred for 2 hours. A saturated aqueous ammonium chloride solution was added to the reaction mixture. The mixture was extracted with ethyl acetate. The extract was washed with saturated brine, and dried over magnesium sulfate. The solvent was evaporated, and the residue was purified by silica gel column chromatography using a mixed solvent of ethyl acetate and hexane as an eluent to give 3.91 g of ethyl 9-(tert-butoxycarbonylaminomethyl)-4-(2-chlorophenyl)-2-ethyl-6H-thieno[3,2-f] [1,2,4]triazolo[4,3-a] [1,4]-diazepine-6-acetate.

Ethyl 9-(tert-butoxycarbonylaminomethyl)-4-(2-chlorophenyl)-2-ethyl-6H-thieno[3,2-f] [1,2,4]triazolo[4,3-a] [1,4]diazepine-6-acetate (3.91 g) thus obtained was dissolved in trifluoroacetic acid (40 ml), and the solution was stirred under ice-cooling. The solvent was evaporated and chloroform was added. The mixture was washed with a saturated aqueous sodium hydrogencarbonate solution and saturated brine, and dried over magnesium sulfate. The solvent was evaporated to give 2.55 g of ethyl 9-(aminomethyl)-4-(2-chlorophenyl)-2-ethyl-6H-thieno[3, 2-f] [1,2,4]triazolo[4,3-a] [1,4]diazepine-6-acetate.

EXAMPLE 285

Ethyl 9-(aminomethyl)-4-(2-chlorophenyl)-2-ethyl-6H-thieno[3,2-f] [1,2,4]triazolo[4,3-a] [1,4]diazepine-6-acetate (1.2 g) obtained in Production Example 12 and 3,4-dichlorobenzoyl chloride (0.59 g) were dissolved in dichloroethane (60 ml). Triethylamine (0.40 ml) was added and the mixture was stirred for 1 hour. The reaction mixture was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using ethyl acetate as an eluent to give 0.88 g of ethyl 9-((3,4-dichlorobenzoylamino) methyl)-4-(2-chlorophenyl)-2-ethyl-6H-thieno[3,2-f] [1,2,4]triazolo[4,3-a] [1,4]diazepine-6-acetate.

m.p. 183°–184° C.

EXAMPLE 286

Ethyl 9-((3,4-dichlorobenzoylamino)methyl)-4-(2-chlorophenyl)-2-ethyl-6H-thieno[3,2-f] [1,2,4]triazolo[4,3-a] [1,4]diazepine-6-acetate (0.4 g) was dissolved in methanol (4 ml). 2N Sodium hydroxide (1 ml) was added and the mixture was stirred. The solvent was evaporated. Water was added and the mixture was washed with ethyl acetate. Citric acid was added to the aqueous layer to make the layer acidic. The solution was extracted with ethyl acetate and the extract was dried over magnesium sulfate. The solvent was evaporated, and the residue was recrystallized from a mixed solvent of diisopropyl alcohol and methanol to give 0.17 g of 9-((3,4-dichlorobenzoylamino)methyl)-4-(2-chlorophenyl)-2-ethyl-6H-thieno[3,2-f] [1,2,4]triazolo[4,3-a] [1,4]-diazepine-6-acetic acid isopropyl alcoholate.

m.p. 167°–169° C.

EXAMPLE 287

Ethyl 3-(3-(4-(3-(2-chlorobenzoyl)-5-ethylthiophen-2-yl)-5-methyl[1,2,4]triazol-3-ylmethyl)ureido)benzoate (130 mg) was obtained in the same manner as in Example 193 using ethyl 3-aminobenzoate (0.15 ml), N,N'-carbonyldiimidazole (170 mg), 3-aminomethyl-4-(3-(2-chlorobenzoyl)-5-ethylthiophen-2-yl)-5-methyl[1,2,4] triazole di-p-toluenesulfonate (0.74 g) and triethylamine (1.4 ml).

m.p. 185°–187° C.

EXAMPLE 288 tert-Butyl 3-(N-benzyloxycarbonylamino)benzoate (2.18 g) and ammonium formate (2.1 g) were dissolved in methanol (30 ml). Catalyst (1 g) of 10% palladium/carbon was added, and the mixture was stirred at 60° C. for 2 hours. The reaction mixture was filtered through Celite to remove catalyst and the filtrate was concentrated. The residue was partitioned between chloroform and water. The organic layer was washed with water, dried over magnesium sulfate, and concentrated under reduced pressure to give tert-butyl 3-aminobenzoate. This compound was dissolved in tetrahydrofuran (30 ml). N,N'-Carbonyldiimidazole (1.05 g) was added, and the mixture was stirred at room temperature for 3 hours. Triethylamine (1.82 ml) and 3-aminomethyl-4-(3-(2-chlorobenzoyl)-5-ethylthiophen-2-yl)-5-methyl[1,2,4] triazole di-p-toluenesulfonate (4.82 g) were added to the reaction mixture, and the mixture was further stirred at room temperature for 3 hours. The reaction mixture was concentrated. The residue was partitioned between ethyl acetate and water. The organic layer was washed with a 5% aqueous citric acid solution, a saturated aqueous sodium hydrogencarbonate solution and saturated brine, and dried over magnesium sulfate. The solvent was evaporated. The residue was purified by silica gel column chromatography using a mixed solvent of ethyl acetate and methanol (10:1) as an eluent, and crystallized from isopropyl ether to give 0.95 g of tert-butyl 3-(3-(4-(3-(2-chlorobenzoyl)-5-ethylthiophen-2-yl)-5-methyl[1,2,4]triazol-3-ylmethyl)ureido)benzoate.

m.p. 194°–195° C.

EXAMPLE 289 tert-Butyl 3-(3-(4-(3-(2-chlorobenzoyl)-5-ethylthiophen-2-yl)-5-methyl[1,2,4]triazol-3-ylmethyl)ureido)benzoate (800 mg) was dissolved in formic acid (20 ml), and the solution was allowed to stand for one day. The reaction mixture was concentrated, and the obtained crude crystals were recrystallized from isopropyl alcohol to give 580 mg of 3-(3-(4-(3-(2-chlorobenzoyl)-5-ethylthiophen-2-yl)-5-methyl[1,2,4]triazol-3-ylmethyl)ureido)benzoic acid.

m.p. 178°–180° C.

EXAMPLE 290

Ethyl indole-2-carboxylate (6.0 g) was dissolved in dimethylformamide (60 ml) and sodium hydride (60% in oil, 1.4 g) was added under ice-cooling. After stirring for 30 minutes, bromoacetonitrile (2.3 ml) was added and the mixture was stirred. Water was added to the reaction mixture, and the mixture was extracted with ethyl acetate. The extract was washed with saturated brine and dried over magnesium sulfate. The solvent was evaporated, and the residue was recrystallized from ethyl acetate to give 6.6 g of ethyl 1-cyanomethylindole-2-carboxylate.

m.p. 92°–94° C.

Ethyl 1-cyanomethylindole-2-carboxylate (5.35 g) obtained was dissolved in dimethylformamide (55 ml). Sodium azide (1.68 g) and ammonium chloride (1.38 g) were added and the mixture was stirred at 80° C. for 2.5 hours. Water was added to the reaction mixture and the mixture was washed with ethyl acetate. Citric acid was added, and the mixture was extracted with ethyl acetate and the extract was dried over magnesium sulfate. The solvent was evaporated, and the residue was recrystallized from ethyl acetate to give 3.61 g of ethyl 1-(1H-tetrazol- 5-yl) methylindole-2-carboxylate.

m.p. 165°–170° C.

Ethyl 1-(1H-tetrazol-5-yl)methylindole-2-carboxylate (1.17 g) thus obtained was dissolved in dichloroethane (12 ml). Triethylamine (1.44 ml) was added and the mixture was stirred under ice-cooling. A solution of triphenylmethyl chloride (1.44 g) in dichloroethane (6 ml) was dropwise added, and the mixture was stirred for 1 hour. The reaction mixture was extracted with chloroform. The extract was washed with an aqueous citric acid solution and dried over magnesium sulfate. The solvent was evaporated, and the residue was recrystallized from ethyl acetate to give 1.8 g of ethyl 1-(1-triphenylmethyltetrazol-5-yl)methylindole-2-carboxylate.

m.p. 142°–144° C.

Ethyl 1-(1-triphenylmethyltetrazol-5-yl)methylindole-2-carboxylate (1.71 g) obtained was dissolved in dimethylformamide (15 ml). A 2N sodium hydroxide aqueous solution (3.3 ml) was added, and the mixture was stirred. An aqueous citric acid solution was added to the reaction mixture, and the mixture was extracted with ethyl acetate. The extract was dried over magnesium sulfate. The solvent was evaporated, and the residue was recrystallized from ethyl acetate to give 1.53 g of 1-(1-triphenylmethyltetrazol-5-yl)methylindole-2-carboxylic acid.

m.p. 210°–212° C.

1-(1-Triphenylmethyltetrazol-5-yl)methylindole-2-carboxylic acid (1.50 g) thus obtained and 3-aminomethyl-4-(3-(2-chlorobenzoyl)-5-ethylthiophen-2-yl)-5-methyl[1,2,4]triazole di-p-toluenesulfonate (2.23 g) were dissolved in dimethylformamide (45 ml). Triethylamine (1.68 ml) and Bop reagent (1.33 g) were added under ice-cooling, and the mixture was stirred at room temperature. The reaction mixture was partitioned between water and ethyl acetate. The organic layer was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using a mixed solvent of ethyl acetate and methanol as an eluent to give 0.68 g of N-(4-(3-(2-chlorobenzoyl)-5-ethylthiophen-2-yl)-5-methyl[1,2,4]triazol-3-ylmethyl)-1-(1-triphenylmethyltetrazol-5-yl)methylindole-2-carboxamide.

m.p. 90°–105° C.

N-(4-(3-(2-Chlorobenzoyl)-5-ethylthiophen-2-yl)-5-methyl[1,2,4]triazol-3-ylmethyl)-1-(1-triphenylmethyltetrazol-5-yl)methylindole-2-carboxamide (0.5 g) thus obtained was dissolved in tetrahydrofuran (10 ml). Conc. hydrochloric acid (2 ml) was added and the mixture was stirred at room temperature for 1 hour. The reaction mixture was extracted with ethyl acetate, and the extract was dried over magnesium sulfate. The solvent was evaporated, and the residue was crystallized from isopropyl alcohol to give 0.24 g of N-(4-(3-(2-chlorobenzoyl)-5-ethylthiophen-2-yl)-5-methyl[1,2,4]triazol-3-ylmethyl)-1-(1H-tetrazol-5-yl)methylindole-2-carboxamide.

m.p. 238°–241° C.

EXAMPLE 291

N-(3-(tert-Butoxycarbonylamino)phenyl)-N'-(4-(3-(2-chlorobenzoyl)-5-ethylthiophen-2-yl)-5-methyl[1,2,4]triazol-3-ylmethyl)urea (5.39 g) was obtained in the same manner as in Example 193 using 3-(N-tert-butoxycarbonylamino)aniline (4.94 g), N,N'-carbonyldiimidazole (4.04 g), 3-aminomethyl-4-(3-(2-chlorobenzoyl)-5-ethylthiophen-2-yl)-5-methyl[1,2,4]triazole di-p-toluenesulfonate (17.62 g) and triethylamine (8.31 ml).

m.p. 214°–215° C.

Then, this compound (595 mg) was dissolved in trifluoroacetic acid (6 ml), and the mixture was allowed to stand at room temperature for one day. The reaction mixture was concentrated. The residue was partitioned between ethyl acetate and water. The organic layer was washed with a saturated aqueous sodium hydrogencarbonate solution and saturated brine, and dried over magnesium sulfate. The solvent was concentrated under reduced pressure, and the residue was crystallized from isopropanol and recrystallized from ethanol to give 270 mg of N-(3-aminophenyl)-N'-(4-(3-(2-chlorobenzoyl)-5-ethylthiophen-2-yl)-5-methyl[1,2,4]triazol-3-ylmethyl)urea.

m.p. 189°–191° C.

EXAMPLE 292

3-Dimethylaminobenzoic acid (1.65 g), diphenylphosphoryl azide (2.16 ml) and triethylamine (1.4 ml) were dissolved in tetrahydrofuran (20 ml), and the reaction mixture was kept at 60° C. for 1 hour to give 3-dimethylaminophenyl isocyanate. The reaction mixture was cooled to 0° C. Triethylamine (4.2 ml) and 3-aminomethyl-4-(3-(2-chlorobenzoyl)-5-ethylthiophen-2-yl)-5-methyl[1,2,4]triazole di-p-toluenesulfonate (7.42 g) were added, and the mixture was stirred for 2 hours. The reaction mixture was concentrated. The residue was partitioned between ethyl acetate and water. The organic layer was washed with a saturated aqueous sodium hydrogencarbonate solution and saturated brine, and dried over magnesium sulfate. The solvent was evaporated. The obtained residue was purified by silica gel column chromatography using a mixed solvent of ethyl acetate and methanol (10:1) as an eluent and by silica gel column chromatography using a mixed solvent of chloroform and methanol (50:1) as an eluent, and crystallized from ethyl acetate to give 140 mg of N-((4-(3-(2-chlorobenzoyl)-5-ethylthiophen-2-yl)-5-methyl[1,2,4]triazol-3-yl)methyl)-N'-(3-dimethylaminophenyl)urea.

m.p. 179°–181° C.

EXAMPLE 293

N-((4-(3-(2-Chlorobenzoyl)-5-ethylthiophen-2-yl)-5-methyl[1,2,4]triazol-3-yl)methyl)-N'-(3- nitrophenyl)urea (4.07 g) was obtained in the same manner as in Example 23 using 3-nitrophenyl isocyanate (1.64 g), 3-aminomethyl-4-(3-(2-chlorobenzoyl)-5-ethylthiophen-2-yl)-5-methyl[1,2,4]triazole di-p-toluenesulfonate (7.42 g) and triethylamine (2.8 ml).

m.p. 157°–159° C.

EXAMPLE 294

2,3,9-Trimethyl-4-(4-chlorophenyl)-6H-thieno[3,2-f][1,2,4]triazolo[4,3-a] [1,4]diazepine (1.0 g) and 10-camphorsulfonic acid (2.1 g) was dissolved in a mixed solvent (25 ml) of ethanol and water (9:1), and the mixture was refluxed for 3 hours. The reaction mixture was concentrated under reduced pressure, and the obtained residue was dissolved in dimethylformamide (10 ml). 2-Methoxyphenyl isocyanate (0.40 ml) and triethylamine (1.47 ml) were added, and the mixture was stirred at room temperature for one day. The reaction mixture was partitioned between chloroform and water. The organic layer was washed with a 10% aqueous citric acid solution and saturated brine, and dried over magnesium sulfate. The solvent was concentrated under reduced pressure. The obtained solid was subjected to silica gel column chromatography using a mixed solvent of ethyl acetate and methanol as an eluent, and N-((4-(3-(4-chlorobenzoyl)-4,5-dimethylthiophen-2-yl)-5-methyl[1,2,4]triazol-3-yl)methyl)-N'-(2-methoxyphenyl)urea (900 mg) was obtained from a fraction containing the objective compound.

m.p. 228°–230° C.

EXAMPLE 295

2,9-Dimethyl-4-phenyl-6H-thieno[3,2-f] [1,2,4]triazolo[4,3-a] [1,4]diazepine (882 mg) and 10-camphorsulfonic acid (2.1 g) was dissolved in a mixed solvent (25 ml) of ethanol and water (9:1), and the mixture was refluxed for 3 hours. The reaction mixture was concentrated under reduced pressure. The obtained residue was dissolved in dimethylformamide (10 ml). Indole-2-carbonyl chloride (538 mg) and triethylamine (1.4 ml) were added and the mixture was stirred at room temperature for one day. The reaction mixture was partitioned between ethyl acetate and water. The organic layer was washed with a saturated aqueous sodium hydrogencarbonate solution and saturated brine, and dried over magnesium sulfate. The solvent was concentrated under reduced pressure. The obtained solid was recrystallized from a mixed solvent of ethyl acetate and methanol to give 0.61 g of N-(4-(3-benzoyl-5-methylthiophen-2-yl)-5-methyl[1,2,4]triazol- 3-ylmethyl)indole-2-carboxamide.

m.p. 231°–233° C.

EXAMPLE 296

3-Methylindole-2-carboxylic acid (0.5 g) and 3-aminomethyl-4-(3-(2-chlorobenzoyl)-5-ethylthiophen-2-yl)-5-methyl[1,2,4]triazole di-p-toluenesulfonate (2.1 g) was dissolved in DMF (42 ml). Triethylamine (1.6 ml) and Bop reagent (1.32 g) were added under ice-cooling, and the mixture was stirred for 6 hours. Water was added, and the mixture was extracted with ethyl acetate. The extract was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using a mixed solvent of ethyl acetate and methanol as an eluent and recrystallized from a mixed solvent of ethyl acetate and hexane to give 0.22 g of N-(4-(3-(2-chlorobenzoyl)-5-ethylthiophen-2-yl)-5-methyl[1,2,4]triazol-3-yl-methyl)-3-methyl-1H-indole-2-carboxamide.

m.p. 143°–147° C.

EXAMPLE 297

N-(4-(3-(2-Chlorobenzoyl)-5-ethylthiophen-2-yl)-5-methyl[1,2,4]triazol-3-ylmethyl)indole-2-carboxamide (1.0 g, Example 14) was dissolved in acetic acid (12 ml). Bromine (0.1 ml) dissolved in acetic acid (1 ml) was dropwise added under water-cooling, and the mixture was stirred for 1 hour. The solvent was evaporated, and an aqueous sodium thiosulfate solution was added. The mixture was extracted with chloroform. The extract was washed with saturated brine, a saturated aqueous sodium hydrogencarbonate solution and saturated brine, and dried over magnesium sulfate. The solvent was evaporated, and the residue was recrystallized from methanol to give 0.36 g of N-(4-(3-(2-chlorobenzoyl)-5-ethylthiophen-2-yl)-5-methyl[1,2,4]triazol-3-ylmethyl)-3-bromoindole-2-carboxamide.

m.p. 200°–202° C.

EXAMPLE 298

N-(4-(3-(2-Chlorobenzoyl)-5-ethylthiophen-2-yl)-5-methyl[1,2,4]triazol-3-ylmethyl)-3-chloroindole-2-carboxamide is obtained in the same manner as in Example 186 using 3-chloroindole-2-carboxylic acid synthesized according to *Nippon Kagaku Zasshi*, Vol. 81, No. 9, 1431 (1960). 3-aminomethyl-4-(3-(2-chlorobenzoyl)-5-ethylthiophen-2-yl)-5-methyl[1,2,4]triazole di-p-toluenesulfonate, dimethylformamide, triethylamine and Bop reagent.

EXAMPLE 299

N-(4-(3-(2-Chlorobenzoyl)-5-ethylthiophen-2-yl)-5-methyl[1,2,4]triazol-3-ylmethyl)-indole-2-carboxamide is dissolved in dichloroethane, and reacted with 1-fluoro-2,6-dichloropyridinium triflate to give N-(4-(3-(2-chlorobenzoyl)-5-ethylthiophen-2-yl)-5-methyl[1,2,4]triazol-3-ylmethyl)-3-fluoroindole-2-carboxamide.

EXAMPLE 300

In the same manner as in Example 186, 1-(2-ethoxycarbonylethyl)indole-2-carboxylic acid (3.22 g), 3-aminomethyl-4-(3-(2-chlorobenzoyl)-5-ethylthiophen-2-yl)-5-methyl[1,2,4]triazole di-p-toluenesulfonate (9.15 g), triethylamine (6.9 ml) and 1-benzotriazolyloxytris(dimethylamino)phosphonium hexafluorophosphate (Bop reagent, 5.44 g) were reacted, and the reaction mixture was purified by silica gel column chromatography using a mixed solvent of ethyl acetate and methanol (10:1) as an eluent, followed by crystallization from acetone to give 5.07 g of ethyl 3-((2-(4-(3-(2-chlorobenzoyl)-5-ethylthiophen-2-yl)-5-methyl[1,2,4]triazol-3-yl)methylcarbamoyl)indol-1-yl)propionate.

m.p. 99°–101° C.

EXAMPLE 301

Benzyl indole-2-carboxylate (50.2 g) was dissolved in DMF (500 ml). Sodium hydride (60% oil, 1.8 g) was added under ice-cooling and the mixture was stirred for 30 minutes. Ethyl 4-bromobutanoate (30.1 ml) was further added and the mixture was stirred for 4 hours. The reaction mixture was concentrated under reduced pressure. The obtained residue was partitioned between ethyl acetate and water. The organic layer was washed with saturated brine and dried over magnesium sulfate. The solvent was evaporated, and the residue was crystallized from ethyl acetate to give a crude product of benzyl 1-(3-ethoxy-carbonylbutyl)indole-2-carboxylate. This product was dissolved in ethanol (350 ml) and hydrogenated by blowing a hydrogen gas in the presence of 10% palladium/carbon (25 g). The reaction mixture was filtered through Celite, and the filtrate was concentrated under reduced pressure. The residue was crystallized from isopropyl alcohol to give 39.1 g of 1-(3-ethoxycarbonylpropyl)indole-2-carboxylic acid.

In the same manner as in Example 186, the reaction was carried out using 1-(3-ethoxycarbonylpropyl)indole-2-carboxylic acid (0.52 g) obtained, 3-aminomethyl-4-(3-(2-chlorobenzoyl)-5-ethylthiophen-2-yl)-5-methyl[1,2,4]triazole di-p-toluenesulfonate (1.4 g), triethylamine (1.06 ml) and 1-benzotriazolyloxytris(dimethylamino)phosphonium hexafluorophosphate (Bop reagent, 0.84 g). Purification of the reaction mixture by silica gel column chromatography using a mixed solvent of ethyl acetate and methanol (10:1) as an eluent and crystallization from a mixed solvent of hexane-ethyl acetate gave 0.56 g of ethyl 4-((2-(4-(3-(2-chlorobenzoyl)-5-ethylthiophen-2-yl)-5-methyl[1,2,4]triazol-3-yl)methylcarbamoyl)indol-1-yl)butanoate.

m.p. 105°–106° C.

EXAMPLE 302

Ethyl 4-((2-(4-(3-(2-chlorobenzoyl)-5-ethylthiophen-2-yl)-5-methyl[1,2,4]triazol-3-yl)methylcarbamoyl)indol-1-yl)butanoate (0.54 g) was dissolved in methanol (10 ml). A 2N sodium hydroxide aqueous solution (0.87 ml) was added and the mixture was allowed to stand at room temperature for one day. Treatment in the same manner as in Example 19 gave 0.35 g of 4-((2-(4-(3-(2-chlorobenzoyl)-5-ethylthiophen-2-yl)-5-methyl[1,2,4]triazol-3-yl)methylcarbamoyl)indol-1-yl)butanoic acid.

m.p. 176°–177° C.

EXAMPLE 303

Benzyl indole-2-carboxylate (10 g) was dissolved in DMF (100 ml). Sodium hydride (60% oil, 1.8 g) was added under ice-cooling, and the mixture was stirred for 30 minutes. Ethyl 5-bromopentanoate (6.7 ml) was further added and the mixture was stirred for 6 hours. Water was added to the reaction mixture, and the mixture was extracted with ethyl acetate. The mixture was washed with saturated brine and dried over magnesium sulfate. The solvent was evaporated, and the residue was purified by silica gel column chromatography using a mixed solvent of ethyl acetate and hexane as an eluent to give 12.44 g of benzyl 1-(4-ethoxycarbonylbutyl)indole-2-carboxylate.

Benzyl 1-(4-ethoxycarbonylbutyl)indole-2-carboxylate (12.44 g) was dissolved in ethanol (120 ml). The mixture was subjected to catalytic reduction by blowing a hydrogen gas in the presence of 10% palladium/carbon. The reaction mixture was filtered through Celite to remove catalyst. The solvent was evaporated, and the residue was purified by silica gel column chromatography using a mixed solvent of ethyl acetate and hexane as an eluent to give 2.19 g of 1-(4-ethoxycarbonylbutyl)indole-2-carboxylic acid.

1-(4-Ethoxycarbonylbutyl)indole-2-carboxylic acid (2.19 g) thus obtained and 3-aminomethyl-4-(3-(2-chlorobenzoyl)-5-ethylthiophen-2-yl)-5-methyl[1,2,4] triazole di-p-toluenesulfonate (5.62 g) were dissolved in DMF (100 ml). Triethylamine (4.2 ml) and Bop reagent (3.35 g) were added under ice-cooling, and the mixture was stirred at room temperature for one day. Water was added, and the mixture was extracted with ethyl acetate. The extract was washed with an aqueous citric acid solution, saturated brine, a saturated aqueous sodium hydrogencarbonate solution and saturated brine and dried over magnesium sulfate. The solvent was evaporated, and the residue was purified by silica gel column chromatography using a mixed solvent of ethyl acetate and methanol as an eluent and recrystallized from a mixed solvent of ethyl acetate and hexane to give 0.295 g of ethyl 5-(2-((4-(3-(2-chlorobenzoyl)-5-ethylthiophen-2-yl)-5-methyl[1,2,4]-triazol-3-yl) methylcarbamoyl)indol-1-yl)pentanoate 1/2 hydrate.

m.p. 85°–87° C.

EXAMPLE 304

5-(2-((4-(3-(2-Chlorobenzoyl)-5-ethylthiophen-2-yl)-5-methyl[1,2,4]triazol-3-yl)methylcarbamoyl)indol-1-yl) pentanoic acid (0.10 g) was obtained in the same manner as in Example 271 using ethyl 5-(2-((4-(3-(2-chlorobenzoyl)-5-ethylthiophen-2-yl)-5-methyl[1,2,4]triazol-3-yl) methylcarbamoyl)indol-1-yl)pentanoate (0.25 g) thus obtained, methanol (3 ml) and a 2N sodium hydroxide aqueous solution (0.4 ml).

NMR (270 MHz, $CDCl_3$):1.33(3H,t,J=7.5 Hz), 1.49–1.53 (2H,m), 1.77–1.82(2H,m), 2.29(2H,t), 2.34(3H,s), 2.82(2H, q,J=7.5 Hz), 4.40–4.55(2H,m), 4.53–4.82(2H,m), 6.76(1H, s), 6.93–7.61(10H,m)

EXAMPLE 305

1-(5-Ethoxycarbonylpentyl)indole-2-carboxylic acid was prepared using benzyl indole-2-carboxylate, DMF, sodium hydride (60% in oil) and ethyl 5-bromohexanoate, and ethyl 6-(2-((4-(3-(2-chlorobenzoyl)-5-ethylthiophen-2-yl)-5-methyl[1,2,4]triazol-3-yl)methylcarbamoyl)indol-1-yl) hexanoate was synthesized in the same manner as in Example 186 using 3-aminomethyl-4-(3-(2-chlorobenzoyl) -5-ethylthiophen-2-yl)-5-methyl[1,2,4]triazole di-p-toluenesulfonate, triethylamine and Bop reagent.

EXAMPLE 306

6-(2-((4-(3-(2-Chlorobenzoyl)-5-ethylthiophen-2-yl)-5-methyl[1,2,4]triazol-3-yl)methylcarbamoyl)indol-1-yl) hexanoic acid is obtained in the same manner as in Example 271 using ethyl 6-(2-((4-(3-(2-chlorobenzoyl)-5-ethylthiophen-2-yl)-5-methyl[1,2,4]triazol-3-yl) methylcarbamoyl)indol-1-yl)hexanoate obtained, methanol and a 2N sodium hydroxide aqueous solution.

EXAMPLE 307

Benzyl 5-fluoroindole-2-carboxylate (9.4 g) was dissolved in DMF (94 ml). Potassium carbonate (9.7 g) and bromoethyl acetate (4.0 ml) were added and the mixture was stirred for 5 hours. The reaction mixture was partitioned between ethyl acetate and water. The organic layer was washed with saturated brine and dried over magnesium sulfate. The solvent was evaporated, and the residue was recrystallized from isopropyl alcohol to give 9.59 g of benzyl 1-ethoxycarbonylmethyl-5-fluoroindole-2-carboxylate.

m.p. 75°–76° C.

Benzyl 1-ethoxycarbonylmethyl-5-fluoroindole-2-carboxylate (8.53 g) thus obtained was dissolved in ethanol (85 ml). The solution was subjected to catalytic reduction by blowing a hydrogen gas in the presence of 5% palladium/carbon (8.5 g). After filtration through Celite, the solvent was evaporated, and the obtained solid was recrystallized form isopropyl ether to give 2.96 g of 1-ethoxycarbonylmethyl-5-fluoroindole-2-carboxylic acid.

1-Ethoxycarbonylmethyl-5-fluoroindole-2-carboxylic acid (1.0 g) obtained and 3-aminomethyl-4-(3-(2-chlorobenzoyl)-5-ethylthiophen-2-yl)-5-methyl[1,2,4] triazole di-p-toluenesulfonate (2.8 g) were dissolved in DMF (56 ml). Triethylamine (2.1 ml) and Bop reagent (1.8 g) were added under ice-cooling, and the mixture was stirred at room temperature for 4 hours. Water was added, and the mixture was extracted with ethyl acetate. The organic layer was washed with an aqueous citric acid solution, saturated brine, a saturated aqueous sodium hydrogencarbonate solution and saturated brine and dried over magnesium sulfate. The solvent was evaporated, and the residue was crystallized from ethyl acetate to give 1.97 g of ethyl (2-(4-(3-(2-chlorobenzoyl)-5-ethylthiophen-2-yl)-5-methyl[1,2,4] triazol-3-ylmethyl)carbamoyl-5-fluoroindol-1-yl)acetate.

m.p. 125°–127° C.

EXAMPLE 308

(2-(4-(3-(2-Chlorobenzoyl)-5-ethylthiophen-2-yl)-5-methyl[1,2,4]triazol-3-ylmethyl)carbamoyl-5-fluoroindol-1-yl)acetic acid (0.24 g) was obtained in the same manner as in Example 271 using ethyl (2-(4-(3-(2-chlorobenzoyl)-5-ethylthiophen-2-yl)-5-methyl[1,2,4]triazol-3-ylmethyl) carbamoyl-5-fluoroindol-1-yl)acetate (1.64 g), methanol (16 ml) and a 2N sodium hydroxide aqueous solution (2.7 ml).

m.p. 174°–175° C.

EXAMPLE 309

1-(4-Ethoxycarbonylbutyl)indole-2-carboxylic acid was obtained in the same manner as in Example 301 using benzyl 5-fluoroindole-2-carboxylate (5.0 g), DMF (50 ml), sodium hydride (60% oil, 0.82 g) and ethyl bromobutaneacetate (2.8 ml). Reaction with 3-aminomethyl-4-(3-(2-chlorobenzoyl)-5-ethylthiophen-2-yl)-5-methyl[1,2,4]triazole di-p-toluenesulfonate (4.9 g), Bop reagent (2.92 g) and triethylamine (3.7 ml) gave 1.84 g of ethyl 4-(2-(4-(3-(2-chlorobenzoyl)-5-ethylthiophen-2-yl)-5-methyl[1,2,4] triazol-3-ylmethyl)carbamoyl-5-fluoroindol-1-yl)butanoate.

m.p. 127°–128° C.

EXAMPLE 310

4-(2-(4-(3-(2-Chlorobenzoyl)-5-ethylthiophen-2-yl)-5-methyl[1,2,4]triazol-3-ylmethyl)carbamoyl-5-fluoroindol-1-yl)butanoic acid (0.79 g) was obtained in the same manner as in Example 271 using ethyl 4-(2-(4-(3-(2-chlorobenzoyl)-5-ethylthiophen-2-yl)-5-methyl[1,2,4]triazol-3-ylmethyl) carbamoyl-5-fluoroindol-1-yl)butanoate (1.6 g), methanol (16 ml) and a 2N sodium hydroxide aqueous solution (2.5 ml).

m.p. 177°–179° C.

EXAMPLE 311

Ethyl (3-bromo-2-(4-(3-(2-chlorobenzoyl)-5-ethylthiophen-2-yl)-5-methyl[1,2,4]triazol-3-ylmethyl) carbamoyl-indol-1-yl)acetate (1.02 g) was obtained in the same manner as in Example 297 using ethyl 2-(4-(3-(2-chlorobenzoyl)-5-ethylthiophen-2-yl)-5-methyl[1,2,4] triazol-3-ylmethylcarbamoyl)indole-1-acetate (1.76 g, Example 18), acetic acid (23 ml) and bromine (0.15 ml).

m.p. 56°–58° C.

EXAMPLE 312

(3-Bromo-2-(4-(3-(2-chlorobenzoyl)-5-ethylthiophen-2-yl)-5-methyl[1,2,4]triazol-3-ylmethyl)carbamoyl-indol-1-yl)acetic acid is obtained in the same manner as in Example 271 using ethyl (3-bromo-2-(4-(3-(2-chlorobenzoyl)-5-ethylthiophen-2-yl)-5-methyl[1,2,4]triazol- 3-ylmethyl) carbamoyl-indol-1-yl)acetate obtained, methanol and a 2N sodium hydroxide aqueous solution.

EXAMPLE 313

Ethyl 2-(4-(3-(2-chlorobenzoyl)-5-ethylthiophen-2-yl)-5-methyl[1,2,4]triazol-3-ylmethylcarbamoyl)indole-1-acetate is dissolved in dichloroethane, and reacted with 1-fluoro-2,6-dichloropyridiniumtriflate to give ethyl 2-(4-(3-(2-chlorobenzoyl)-5-ethylthiophen-2-yl)-5-methyl[1,2,4] triazol-3-ylmethylcarbamoyl)-3-fluoroindole-1-acetate.

EXAMPLE 314

Ethyl 2-(4-(3-(2-chlorobenzoyl)-5-ethylthiophen-2-yl)-5-methyl[1,2,4]triazol-3-ylmethylcarbamoyl)-3-fluoroindole-1-acetate is subjected to alkali hydrolysis to give 2-(4-(3-(2-chlorobenzoyl)-5-ethylthiophen-2-yl)-5-methyl[1,2,4] triazol-3-ylmethylcarbamoyl)-3-fluoroindole-1-acetic acid.

Production Example 13

4-(2-Chlorophenyl)-2-ethyl-6H-thieno[3,2-f] [1,2,4] triazolo[4,3-a] [1,4]diazepine (10.0 g) and N-chlorosuccinimide (4.55 g) were dissolved in dimethylformamide (50 ml), and the mixture was stirred at room temperature overnight. Ethyl acetate and water were added thereto. The organic layer was washed with water and dried over magnesium sulfate. The solvent was concentrated under reduced pressure, and the obtained residue was purified by silica gel column chromatography to give 1.8 g of 9-chloro-4-(2-chlorophenyl)-2-ethyl-6H-thieno[3,2-f] [1,2,4]triazolo[4,3-a] [1,4]diazepine.

m.p. 133°–135° C.

EXAMPLE 315

9-Chloro-4-(2-chlorophenyl)-2-ethyl-6H-thieno[3,2-f] [1,2,4]triazolo[4,3-a] [1,4]diazepine (0.5 g) was stirred with 2M hydrochloric acid (12.5 ml) at 60° C. for 2.5 hours. The reaction mixture was cooled to room temperature. Sodium hydrogencarbonate was added to make the reaction mixture alkaline. Chloroform and indole-2-carbonyl chloride (0.33 g) were added, and the mixture was stirred for 0.5 hour. The organic layer was washed with saturated brine and dried over magnesium sulfate. The solvent was concentrated under reduced pressure, and the obtained residue was crystallized from ethyl acetate to give 0.2 g of N-(3-chloro-4-(3-(2-chlorobenzoyl)-5-ethylthiophen-2-yl) [1,2,4]triazol-5-ylmethyl)indole-2-carboxamide.

m.p. 254°–256° C.

EXAMPLE 316

N-(3-Chloro-4-(3-(2-chlorobenzoyl)-5-ethylthiophen-2-yl) [1,2,4]triazol-5-ylmethyl)-3,4-dichlorobenzamide is obtained in the same manner as in Example 315 using 9-chloro-4-(2-chlorophenyl)-2-ethyl-6H-thieno[3,2-f] [1,2,4]triazolo[4,3-a] [1,4]diazepine and 3,4-dichlorobenzoyl chloride.

EXAMPLE 317

Ethyl 2-(5-chloro-4-(3-(2-chlorobenzoyl)-5-ethylthiophen-2-yl) [1,2,4]triazol-3-ylmethylcarbamoyl) indole-1-acetate is obtained in the same manner as in Example 315 from 9-chloro-4-(2-chlorophenyl)-2-ethyl-6H-thieno[3,2-f] [1,2,4]triazolo[4,3-a] [1,4]diazepine and 1-(ethoxycarbonylmethyl)indole-2-carbonyl chloride.

EXAMPLE 318

Ethyl 2-(5-chloro-4-(3-(2-chlorobenzoyl)-5-ethylthiophen-2-yl) [1,2,4]triazol-3-ylmethylcarbamoyl) indole-1-acetate is subjected to alkali hydrolysis to give 2-(5-chloro-4-(3-(2-chlorobenzoyl)-5-ethylthiophen-2-yl) [1,2,4]triazol-3-ylmethylcarbamoyl)indole-1-acetic acid.

EXAMPLE 319

1-Ethoxycarbonylmethyl-3-methylindole-2-carboxylic acid is obtained in the same manner as in Example 307 using benzyl 3-methylindole-2-carboxylate, DMF, potassium carbonate and bromoethyl acetate, and reacted with Bop reagent to give ethyl (2-(4-(3-(2-chlorobenzoyl)-5-ethylthiophen-2-yl)-5-methyl[1,2,4]triazol-3-ylmethyl) carbamoyl-3-methylindol-1-yl)acetate.

EXAMPLE 320

(2-(4-(3-(2-Chlorobenzoyl)-5-ethylthiophen-2-yl)-5-methyl[1,2,4]triazol-3-ylmethyl)carbamoyl-3-methylindol-1-yl)acetic acid is obtained in the same manner as in Example 271 using ethyl (2-(4-(3-(2-chlorobenzoyl)-5-ethylthiophen-2-yl)-5-methyl[1,2,4]triazol-3-ylmethyl) carbamoyl-3-methylindol-1-yl)acetate thus obtained, methanol and a 2N sodium hydroxide aqueous solution.

EXAMPLE 321

1-(3-Ethoxycarbonylpropyl)-3-methylindole-2-carboxylic acid was obtained in the same manner as in Example 303 using benzyl 3-methylindole-2-carboxylate, and reacted in the same manner as in Example 186 using 3-aminomethyl-4-(3-(2-chlorobenzoyl)-5-ethylthiophen-2-yl)-5-methyl[1,2,4]triazole di-p-toluenesulfonate (2.43 g), triethylamine (1.8 ml) and 1-benzotriazolyloxytris (dimethylamino)phosphonium hexafluorophosphate (Bop reagent, 1.45 g). Purification by silica gel column chromatography using a mixed solvent of ethyl acetate and methanol (10:1) as an eluent and crystallization from a mixed solvent of hexane-ethyl acetate gave 1.07 g of ethyl 4-(2-(4-(3-(2-chlorobenzoyl)-5-ethylthiophen-2-yl)-5-methyl[1,2,4]triazol-3-ylmethyl)carbamoyl-3-methylindol-1-yl) butanoate 1/2 hydrate.

m.p. 96°–98° C.

EXAMPLE 322

4-(2-(4-(3-(2-Chlorobenzoyl)-5-ethylthiophen-2-yl)-5-methyl[1,2,4]triazol-3-ylmethyl)carbamoyl-3-methylindol-1-yl)butanoic acid (0.37 g) was obtained in the same manner as in Example 271 using ethyl 4-(2-(4-(3-(2-chlorobenzoyl)-5-ethylthiophen-2-yl)-5-methyl[1,2,4]triazol-3-ylmethyl) carbamoyl-3-methylindol-1-yl)butanoate (0.80 g) thus obtained, methanol (8 ml) and a 2N sodium hydroxide aqueous solution (1.2 ml).

NMR (270 MHz, $CDCl_3$):1.33(3H,t,J=7.4 Hz), 2.04–2.23 (4H,m), 2.35(3H,s), 2.48(3H,s), 2.85(2H,q,J=7.4 Hz), 4.34–4.51(2H,m), 4.56–4.87(2H,m), 6.79(1H,s), 7.08–7.58 (10H,m)

EXAMPLE 323

Ethyl 2-(4-(2-chlorophenyl)-2-ethyl-9-methyl-6H-thieno [3,2-f] [1,2,4]triazolo[4,3-a] [1,4]diazepin-6-yl)acetate (1.0 g) synthesized by a known method such as WO94/06802 was added to 2M hydrochloric acid (24 ml), and the mixture was stirred at 60° C. for 0.5 hour. The reaction mixture was cooled to 0° C. A saturated aqueous sodium hydrogencarbonate solution, chloroform and 3,4-dichlorobenzoyl chloride (0.53 g) were added and the mixture was stirred for 1 hour. The organic layer was taken out and dried over magnesium sulfate. The residue was purified by silica gel column chromatography (developing solvent:ethyl acetate-hexane) and crystallized from diisopropyl ether to give 0.06 g of ethyl 3-(4-(3-(2-chlorobenzoyl)-5-ethylthiophen-2-yl)-5-methyl[1,2,4]triazol-3-yl)-3-(3,4-dichlorobenzoylamino) propionate.

NMR (270 MHz, DMSO-$d_6$):0.85–1.27(6H), 2.18–2.22 (3H), 2.56–3.65(4H), 3.93–4.09(2H), 5.54–5.74(1H), 6.56–7.99(8H), 9.07–9.12(1H)

EXAMPLE 324

Ethyl 3-(4-(3-(2-chlorobenzoyl)-5-ethylthiophen-2-yl)-5-methyl[1,2,4]triazol-3-yl)-3-(3,4-dichlorobenzoylamino) propionate (0.55 g) was subjected to alkali hydrolysis to give 3-(4-(3-(2-chlorobenzoyl)-5-ethylthiophen-2-yl)-5-methyl [1,2,4]triazol-3-yl)-3-(3,4-dichlorobenzoylamino)propionic acid (0.23 g).

NMR (270 MHz, DMSO-$d_6$):0.88–1.26(3H), 2.17–2.21 (3H), 2.57–3.35(4H), 5.48–5.70(1H), 6.65–8.00(8H), 9.04–9.10(1H), 12.34(1H)

EXAMPLE 325

Ethyl 3-(4-(3-(2-chlorobenzoyl)-5-ethylthiophen-2-yl)-5-methyl[1,2,4]triazol-3-yl)-3-((indol-2-yl)carbonylamino) propionate (1.63 g) was obtained in the same manner as in Example 323 using ethyl 2-(4-(2-chlorophenyl)-2-ethyl-9-methyl-6H-thieno[3,2-f] [1,2,4]triazolo[4,3-a] [1,4] diazepin-6-yl)acetate (6.9 g) and indole-2-carbonyl chloride (3.18 g).

NMR (270 MHz, DMSO-$d_6$):0.68–1.26(6H), 2.18–2.22 (3H), 2.42–3.45(4H), 3.93–4.11(2H), 5.59–5.83(1H), 6.53–7.69(10H), 8.81–8.89(1H), 11.46–11.48(1H)

EXAMPLE 326

Ethyl 3-(4-(3-(2-chlorobenzoyl)-5-ethylthiophen-2-yl)-5-methyl[1,2,4]triazol-3-yl)-3-((indol-2-yl)carbonylamino)

propionate (1.0 g) was subjected to alkali hydrolysis to give 3-(4-(3-(2-chlorobenzoyl)-5-ethylthiophen-2-yl)-5-methyl [1,2,4]triazol-3-yl)-3-((indol-2-yl)carbonylamino)propionic acid (0.81 g).

NMR (270 MHz, DMSO-$d_6$):0.73–1.25(3H), 2.19–2.21 (3H), 2.45–3.42(4H), 5.53–5.80(1H), 6.57–7.67(10H), 8.79–8.87(1H), 11.48(1H), 12.34(1H)

Production Example 14

4-(2-Chlorophenyl)-2-ethyl-9-methyl-6H-thieno[3,2-f] [1,2,4]triazolo[4,3-a] [1,4]diazepine (10.0 g) and 60% sodium hydride (2.0 g) were added to diethyl carbonate (150 ml), and the mixture was refluxed under heating under a nitrogen atmosphere for 2 hours. The reaction mixture was cooled to 50° C. Ethyl acrylate (5.37 ml) was added and the mixture was further stirred for 3 hours. The reaction mixture was added to water. 1M Hydrochloric acid was added with vigorous stirring to adjust the aqueous solution to pH 4. The solution was extracted with ethyl acetate. The extract was washed with a saturated aqueous sodium hydrogencarbonate solution and brine, and dried over magnesium sulfate. The residue was purified by silica gel column chromatography (developing solvent:ethyl acetate-hexane) to give 3.2 g of ethyl 4-(2-chlorophenyl)-6-(2-ethoxycarbonylethyl)-2-ethyl-9-methyl-6H-thieno[3,2-f] [1,2,4]triazolo[4,3-a] [1,4] diazepine-6-carboxylate.

Ethyl 4-(2-chlorophenyl)-6-(2-ethoxycarbonylethyl)-2-ethyl-9-methyl-6H-thieno[3,2-f] [1,2,4]triazolo[4,3-a] [1,4] diazepine-6-carboxylate (23 g) was dissolved in ethanol (92 ml). A 4M sodium hydroxide aqueous solution (92 ml) was added and the mixture was stirred at 60° C. for 6 hours. 2M Hydrochloric acid was added to adjust the aqueous solution to pH 2. The solution was extracted with ethyl acetate. The extract was dried over magnesium sulfate, and concentrated. The obtained crystals were taken out, and washed with diisopropyl ether to give 13.5 g of 3-(4-(2-chlorophenyl)-2-ethyl-9-methyl-6H-thieno[3,2-f] [1,2,4]triazolo[4,3-a] [1,4] diazepin-6-yl)propionic acid.

3-(4-(2-Chlorophenyl)-2-ethyl-9-methyl-6H-thieno[3,2-f] [1,2,4]triazolo[4,3-a] [1,4]diazepin-6-yl)propionic acid (13.5 g) was dissolved in dimethylformamide (140 ml). Potassium carbonate (9.1 g) and iodoethane (2.9 ml) were added, and the mixture was stirred for 4 hours. Ethyl acetate and water were added thereto. The organic layer was taken out, washed with brine and dried over magnesium sulfate. The solvent was evaporated, and the residue was crystallized from diisopropyl ether to give 11.2 g of ethyl 3-(4-(2-chlorophenyl)-2-ethyl-9-methyl-6H-thieno[3,2-f] [1,2,4] triazolo[4,3-a] [1,4]diazepin-6-yl)propionate.

EXAMPLE 327

Ethyl 3-(4-(2-chlorophenyl)-2-ethyl-9-methyl-6H-thieno [3,2-f] [1,2,4]triazolo[4,3-a] [1,4]diazepin-6-yl)propionate (4.0 g) was added to 2M hydrochloric acid (100 ml), and the mixture was stirred at 60° C. for 1 hour. The reaction mixture was cooled to 0° C. A saturated aqueous sodium hydrogencarbonate solution, chloroform and 3,4-dichlorobenzoyl chloride (2.1 g) were added, and the mixture was stirred for 0.5 hour. The organic layer was taken out, dried over magnesium sulfate and concentrated under reduced pressure. The obtained residue was purified by silica gel column chromatography (developing solvent: ethyl acetate) and crystallized from a mixed solvent of ethyl acetate-diisopropyl ether to give 0.56 g of ethyl 4-(4-(3-(2-chlorobenzoyl)-5-ethylthiophen-2-yl)-5-methyl[1,2,4] triazol-3-yl)-4-(3,4-dichlorobenzoylamino)butanoate.

NMR (270 MHz, DMSO-$d_6$):0.66–1.24(6H), 2.17–2.23 (3H), 2.32–2.87(6H), 3.89–4.07(2H), 5.17–5.38(1H), 6.63–8.02(8H), 8.93–8.99(1H)

EXAMPLE 328

Ethyl 4-(4-(3-(2-chlorobenzoyl)-5-ethylthiophen-2-yl)-5-methyl[1,2,4]triazol-3-yl)-4-(3,4-dichlorobenzoylamino) butanoate (0.47 g) was subjected to alkali hydrolysis to give 4-(4-(3-(2-chlorobenzoyl)-5-ethylthiophen-2-yl)-5-methyl [1,2,4]triazol-3-yl)-4-(3,4-dichlorobenzoylamino)butanoic acid (0.17 g).

NMR (270 MHz, DMSO-$d_6$):0.88–1.24(3H), 2.09–2.86 (9H), 5.14–5.34(1H), 6.63–8.02(8H), 8.91–8.98(1H), 12.08 (1H)

EXAMPLE 329

Ethyl 4-(4-(3-(2-chlorobenzoyl)-5-ethylthiophen-2-yl)-5-methyl[1,2,4]triazol-3-yl)-4-((1H-indol-2-yl) carbonylamino)butanoate (0.12 g) was obtained in the same manner as in Example 327 from ethyl 3-(4-(2-chlorophenyl)-2-ethyl-9-methyl-6H-thieno[3,2-f] [1,2,4] triazolo[4,3-a] [1,4]diazepin-6-yl)propionate (4.0 g) and indole-2-carbonyl chloride (1.8 g).

NMR (270 MHz, DMSO-$d_6$):0.71–1.23(6H), 2.17–2.22 (3H), 2.26–3.57(6H), 3.96–4.07(2H), 5.21–5.45(1H), 6.58–7.63(10H), 8.65–8.78(1H), 11.46(1H)

EXAMPLE 330

Ethyl 4-(4-(3-(2-chlorobenzoyl)-5-ethylthiophen-2-yl)-5-methyl[1,2,4]triazol-3-yl)-4-((indol-2-yl)carbonylamino) butanoate (0.21 g) was subjected to alkali hydrolysis to give 4-(4-(3-(2-chlorobenzoyl)-5-ethylthiophen-2-yl)-5-methyl [1,2,4]triazol-3-yl)-4-((indol-2-yl)carbonylamino)butanoic acid (0.11 g).

NMR (270 MHz, DMSO-$d_6$):0.73–1.23(3H), 2.10–2.85 (9H), 5.18–5.40(1H), 6.58–7.63(10H), 8.63–8.77(1H), 11.45(1H), 12.08(1H)

Production Example 15

Ethyl indole-2-carboxylate (22 g) was dissolved in dimethylformamide (150 ml), and sodium hydride (including 60% oil, 5.12 g) was gradually added with stirring. Then, benzyl bromoacetate (19.2 ml) was added, and the mixture was stirred for 3 hours. The reaction mixture was partitioned between ethyl acetate and water. The organic layer was washed with saturated brine and dried over magnesium sulfate. The solvent was concentrated under reduced pressure. The residue thus obtained as a solid was subjected to silica gel column chromatography and eluted with a mixed solvent of ethyl acetate and hexane to give benzyl 2-ethoxycarbonyl-indole-1-acetate (28.9 g) as an oil. This compound (32.5 g) was dissolved in ethanol (350 ml), and hydrogenated in the presence of palladium/carbon (10%) catalyst at 1 atm. The catalyst was filtered off, and the solvent was concentrated under reduced pressure. The obtained residue was crystallized from isopropyl ether to give 10.22 g of 2-ethoxycarbonyl-indole-1-acetic acid.

In the same manner as in the above, 3-ethoxycarbonyl-indole-1-acetic acid can be prepared using ethyl indole-3-carboxylate; 3-tert-butoxycarbonyl-indole-1-acetic acid can be prepared using tert-butyl indole-3-carboxylate; and 3-methoxycarbonylmethyl-indole-1-acetic acid can be prepared using methyl indole-3-acetate.

EXAMPLE 331

N-((4-(3-(2-Chlorobenzoyl)-5-ethylthiophen-2-yl)-5-methyl[1,2,4]triazol-3-yl)methyl)indole-1-acetamide (1.5 g) was obtained in the same manner as in Example 186 using indole-1-acetic acid (1.0 g), 3-aminomethyl-4-(3-(2-chlorobenzoyl)-5-ethylthiophen-2-yl)-5-methyl[1,2,4] triazole di-p-toluenesulfonate (3.3 g), triethylamine (2.7 ml) and 1-benzotriazolyloxytris(dimethylamino)phosphonium hexafluorophosphate (Bop reagent, 2.5 g).

m.p. 176°–177° C.

EXAMPLE 332

Ethyl 1-((4-(3-(2-chlorobenzoyl)-5-ethylthiophen-2-yl)-5-methyl[1,2,4]triazol-3-yl)methylcarbamoylmethyl) indole-2-carboxylate (16.45 g) was obtained in the same manner as in Example 186 using 2-ethoxycarbonyl-indole-1-acetic acid (9.0 g), 3-aminomethyl-4-(3-(2-chlorobenzoyl) -5-ethylthiophen-2-yl)-5-methyl[1,2,4]triazole di-p-toluenesulfonate (27.37 g), triethylamine (20.7 ml) and 1-benzotriazolyloxytris(dimethylamino)phosphonium hexafluorophosphate (Bop reagent, 17.94 g).

m.p. 176°–177° C.

EXAMPLE 333

Ethyl 1-((4-(3-(2-chlorobenzoyl)-5-ethylthiophen-2-yl)-5-methyl[1,2,4]triazol-3-yl)methylcarbamoylmethyl) indole-3-carboxylate (250 mg) was obtained in the same manner as in Example 186 using 3-ethoxycarbonyl-indole-1-acetic acid (1.22 g), 3-aminomethyl-4-(3-(2-chlorobenzoyl)-5-ethylthiophen-2-yl)-5-methyl[1,2,4] triazole di-p-toluenesulfonate (3.71 g), triethylamine (2.8 ml), 1-benzotriazolyloxytris(dimethylamino)phosphonium hexafluorophosphate (Bop reagent, 2.43 g).

m.p. 182°–183° C.

EXAMPLE 334 tert-Butyl 1-((4-(3-(2-chlorobenzoyl)-5-ethylthiophen-2-yl)-5-methyl[1,2,4]triazol-3-yl)methylcarbamoylmethyl) indole-3-carboxylate (2.86 g) was obtained in the same manner as in Example 186 using 3-tert-butoxycarbonyl-indole-1-acetic acid (2.75 g), 3-aminomethyl-4-(3-(2-chlorobenzoyl)-5-ethylthiophen-2-yl)-5-methyl[1,2,4] triazole di-p-toluenesulfonate (7.42 g), triethylamine (7.0 ml) and 1-benzotriazolyloxytris(dimethylamino) phosphonium hexafluorophosphate (Bop reagent, 4.64 g).

m.p. 129°–130° C.

EXAMPLE 335 tert-Butyl 1-((4-(3-(2-chlorobenzoyl)-5-ethylthiophen-2-yl)-5-methyl[1,2,4]triazol-3-yl)methylcarbamoylmethyl) indole-3-carboxylate (500 mg) was dissolved in formic acid (5 ml), and the solution was allowed to stand for one day. The reaction mixture was concentrated, and the obtained residue was crystallized from ethyl acetate to give 184 mg of 1-((4-(3-(2-chlorobenzoyl)-5-ethylthiophen-2-yl)-5-methyl[1,2,4]triazol-3-yl)methylcarbamoylmethyl)indole-3-carboxylic acid.

m.p. 253° C. (dec.)

EXAMPLE 336

Methyl 1-((4-(3-(2-chlorobenzoyl)-5-ethylthiophen-2-yl) -5-methyl[1,2,4]triazol-3-yl)methylcarbamoylmethyl) indole-3-acetate (0.44 g) was obtained in the same manner as in Example 186 using 3-methoxycarbonylmethyl-indole-1-acetic acid (562 mg), 3-aminomethyl-4-(3-(2-chlorobenzoyl)-5-ethylthiophen-2-yl)-5-methyl[1,2,4] triazole di-p-toluenesulfonate (1.69 g), triethylamine (1.28 ml) and 1-benzotriazolyloxytris(dimethylamino) phosphonium hexafluorophosphate (Bop reagent, 1.06 g).

m.p. 143°–145° C.

EXAMPLE 337

Methyl 1-((4-(3-(2-chlorobenzoyl)-5-ethylthiophen-2-yl)-5-methyl[1,2,4]triazol-3-yl)methylcarbamoylmethyl)-indole-3-acetate is subjected to hydrolysis in the same manner as in Example 19 to give 1-((4-(3-(2-chlorobenzoyl)-5-ethylthiophen-2-yl)-5-methyl[1,2,4]-triazol-3-yl)methylcarbamoylmethyl)indole-3-acetic acid.

EXAMPLE 338

Crude crystals of 2-amino-4-chloro-N-(4-(3-(2-chlorobenzoyl)-5-ethylthiophen-2-yl)-5-methyl[1,2,4] triazol-3-ylmethyl)benzamide (3.7 g) were obtained in the same manner as in Example 186 using 2-amino-4-chlorobenzoic acid (1.72 g), 3-aminomethyl-4-(3-(2-chlorobenzoyl)-5-ethylthiophen-2-yl)-5-methyl[1,2,4] triazole di-p-toluenesulfonate (7.42 g), triethylamine (5.6 ml) and 1-benzotriazolyloxytris(dimethylamino) phosphonium hexafluorophosphate (Bop reagent, 4.42 g). The crystals were recrystallized from ethyl acetate to give 1.83 g of the objective compound.

m.p. 211°–213° C.

EXAMPLE 339

3-Amino-4-chloro-N-(4-(3-(2-chlorobenzoyl)-5-ethylthiophen-2-yl)-5-methyl[1,2,4]triazol-3-ylmethyl) benzamide (1.81 g) was obtained in the same manner as in Example 186 using 3-amino-4-chlorobenzoic acid (1.72 g), 3-aminomethyl-4-(3-(2-chlorobenzoyl)-5-ethylthiophen-2-yl)-5-methyl[1,2,4]triazole di-p-toluenesulfonate (7.42 g), triethylamine (5.6 ml) and 1-benzotriazolyloxytris (dimethylamino)phosphonium hexafluorophosphate (Bop reagent, 4.64 g).

m.p. 231°–233° C.

EXAMPLE 340

4-Amino-3-chloro-N-(4-(3-(2-chlorobenzoyl)-5-ethylthiophen-2-yl)-5-methyl[1,2,4]triazol-3-ylmethyl) benzamide (2.51 g) was obtained in the same manner as in Example 186 using 4-amino-3-chlorobenzoic acid (1.71 g), 3-aminomethyl-4-(3-(2-chlorobenzoyl)-5-ethylthiophen-2-yl)-5-methyl[1,2,4]triazole di-p-toluenesulfonate (7.42 g), triethylamine (5.6 ml) and 1-benzotriazolyloxytris (dimethylamino)phosphonium hexafluorophosphate (Bop reagent, 4.64 g). This compound (2.40 g) was dissolved in methanol, and methanesulfonic acid (0.302 ml) was added. The reaction mixture was concentrated under reduced pressure, and the residue was crystallized from ethyl acetate. The obtained crude crystals were recrystallized from ethanol (30 ml) to give 1.57 g of 4-amino-3-chloro-N-(4-(3-(2-chlorobenzoyl)-5-ethylthiophen-2-yl)-5-methyl[1,2,4] triazol-3-ylmethyl)benzamide methansulfonate.

m.p. 211°–213° C.

EXAMPLE 341

Reaction was carried out in the same manner as in Example 186 using trans-3-(2-hydroxyphenyl)propenoic acid (1.64 g), 3-aminomethyl-4-(3-(2-chlorobenzoyl)-5-ethylthiophen-2-yl)-5-methyl[1,2,4]triazole di-p-toluenesulfonate (7.42 g), triethylamine (5.6 ml) and 1-benzotriazolyloxytris(dimethylamino)phosphonium hexafluorophosphate (Bop reagent, 4.42 g), and the obtained product was purified by silica gel column chromatography using a mixed solvent of ethyl acetate and methanol as an eluent to give 0.90 g of trans-N-(4-(3-(2-chlorobenzoyl)-5-ethylthiophen-2-yl)-5-methyl[1,2,4]triazol-3-ylmethyl)-3-(2-hydroxyphenyl)propenamide. NMR (270 MHz, $CDCl_3$) :1.17(3H,t,J=7.6 Hz), 2.21(3H,s), 2.78(2H,q, J=7.6 Hz), 4.33(1H,dd,J=4.3 Hz,15.5 Hz), 4.51(1H,dd,J=6.3 Hz,15.5 Hz), 6.60(1H,d,J=16.8 Hz), 6.75–6.90(3H), 7.18(1H,m), 7.35–7.65(6H), 8.52(1H,m), 10.01(1H,s)

EXAMPLE 342

Reaction was carried out in the same manner as in Example 186 using trans-3-(2-nitrophenyl)propenoic acid (1.93 g), 3-aminomethyl-4-(3-(2-chlorobenzoyl)-5-ethylthiophen-2-yl)-5-methyl[1,2,4]triazole di-p-toluenesulfonate (7.42 g), triethylamine (5.6 ml) and 1-benzotriazolyloxytris(dimethylamino)phosphonium hexafluorophosphate (Bop reagent, 4.42 g), and the obtained crude crystals were recrystallized from ethyl acetate to give 3.65 g of trans-N-(4-(3-(2-chlorobenzoyl)-5-ethylthiophen-2-yl)-5-methyl[1,2,4]triazol-3-ylmethyl)-3-(2-nitrophenyl) propenamide.

m.p. 180°–182° C.

EXAMPLE 343

Ammonium chloride (118 mg) and iron powder (1.0 g) were dissolved in a mixed solvent of ethanol (15 ml) and water (5 ml). trans-N-(4-(3-(2-Chlorobenzoyl)-5-ethylthiophen-2-yl)-5-methyl[1,2,4]triazol-3-ylmethyl)-3-(2-nitrophenyl)propenamide (1.07 g) was carefully added under reflux to the reaction mixture, and the mixture was refluxed for 1 hour. The reaction mixture was filtered through Celite, and the filtrate was concentrated. The residue was partitioned between ethyl acetate and water. The organic layer was washed with a saturated aqueous sodium hydrogencarbonate solution and saturated brine, and dried over magnesium sulfate. The solvent was concentrated under reduced pressure. The obtained solid was recrystallized from ethyl acetate to give 0.60 g of trans-N-(4-(3-(2-chlorobenzoyl)-5-ethylthiophen-2-yl)-5-methyl[1,2,4] triazol-3-ylmethyl)-3-(2-aminophenyl)propenamide.

m.p. 141°–143° C.

EXAMPLE 344

4-(2-Chlorophenyl)-2-ethyl-9-phenyl-6H-thieno[3,2-f] [1,2,4]triazolo[4,3-a] [1,4]diazepine (405 mg) and p-toluenesulfonic acid monohydrate (570 mg) were dissolved in a mixed solvent (15 ml) of ethanol and water (9:1), and the solution was refluxed for 3 hours. The reaction mixture was concentrated under reduced pressure. The obtained residue was dissolved in dimethylformamide (10 ml). Indole-2-carbonyl chloride (293 mg) and triethylamine (0.7 ml) were added, and the mixture was stirred at room temperature for one day. The reaction mixture was partitioned between ethyl acetate and water. The organic layer was washed with a saturated aqueous sodium hydrogencarbonate solution and saturated brine, and dried over magnesium sulfate. The solvent was concentrated under reduced pressure. The obtained solid was recrystallized from ethyl acetate to give 0.29 g of N-(4-(3-(2-chlorobenzoyl)-5-ethylthiophen-2-yl)-5-phenyl[1,2,4]triazol-3-ylmethyl) indole-2-carboxamide.

m.p. 230°–232° C.

EXAMPLE 345

9-(1-Adamantyl)-4-(2-chlorophenyl)-2-ethyl-6H-thieno [3,2-f] [1,2,4]triazolo[4,3-a] [1,4]diazepine (926 mg) and p-toluenesulfonic acid monohydrate (1.14 g) were dissolved in a mixed solvent (25 ml) of ethanol and water (9:1), and the solution was refluxed for 3 hours. The reaction mixture was concentrated under reduced pressure, and the obtained residue was dissolved in dimethylformamide (10 ml). Indole-2-carbonyl chloride (585 mg) and triethylamine (1.4 ml) were added, and the mixture was stirred at room temperature for one day. The reaction mixture was partitioned between ethyl acetate and water. The organic layer was washed with a saturated aqueous sodium hydrogencarbonate solution and saturated brine, and dried over magnesium sulfate. The solvent was concentrated under reduced pressure, and the obtained solid was recrystallized from a mixed solvent of ethyl acetate and methanol to give 0.64 g of N-(4-(3-(2-chlorobenzoyl)-5-ethylthiophen-2-yl)-5-(1-adamantyl) [1,2,4]triazol-3-ylmethyl)indole-2-carboxamide.

m.p. 283°–286° C.

EXAMPLE 346

1-Dimethylaminoethylindole-2-carboxylic acid (0.55 g) synthesized by a known method such as the method disclosed in Japanese Patent Unexamined Publication No. 155871/1993 and 3-aminomethyl-4-(3-(2-chlorobenzoyl)-5-ethylthiophen-2-yl)-5-methyl[1,2,4]triazole di-p-toluenesulfonate (1.76 g) were dissolved in DMF (20 ml). Triethylamine (1.33 ml) and Bop reagent (1.05 g) were added under ice-cooling, and the mixture was stirred at room temperature. The reaction mixture was partitioned between water and ethyl acetate. The organic layer was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using a mixed solvent of ethyl acetate, methanol and triethylamine as an eluent, and crystallized to give hydrochloride, whereby 0.27 g of N-(4-(3-(2-chlorobenzoyl)-5-ethylthiophen-2-yl)-5-methyl[1,2,4]triazol-3-ylmethyl)-1-(2-dimethylaminoethyl)indole-2-carboxamide hydrochloride was obtained.

m.p. 213°–215° C.

EXAMPLE 347

Monomethyl isophthalate (2.86 g) and thionyl chloride (12 ml) were added to dichloroethane (30 ml), and the mixture was refluxed with stirring for 5 hours. The solvent was evaporated and the residue was dissolved in dimethylformamide (40 ml). 3-Aminomethyl-4-(3-(2-chlorobenzoyl)-5-ethylthiophen-2-yl)-5-methyl[1,2,4]triazole di-p-toluenesulfonate (10.0 g) and triethylamine (12 ml) were added under ice-cooling, and the mixture was stirred at room temperature for 2.5 hours. A saturated aqueous sodium hydrogencarbonate solution was added to the reaction mixture. The mixture was extracted with ethyl acetate. The organic layer was washed with an aqueous citric acid solution and saturated brine, and dried over magnesium sulfate. The solvent was evaporated, and the residue was purified by silica gel column chromatography (developing solvent:ethyl acetate) and recrystallized from a mixed solvent of ethyl acetate and diisopropyl ether to give 1.58 g of methyl 3-(4-(3-(2-chlorobenzoyl)-5-ethylthiophen-2-yl)-5-methyl[1,2,4]triazol-3-ylmethylcarbamoyl)benzoate.

m.p. 111°–114° C.

EXAMPLE 348

Methanol (13 ml) and a 2M sodium hydroxide aqueous solution (2.5 ml) were added to methyl 3-(4-(3-(2-chlorobenzoyl)-5-ethylthiophen-2-yl)-5-methyl[1,2,4]triazol-3-ylmethylcarbamoyl)benzoate (1.3 g), and the mixture was stirred at room temperature for 2 hours. The reaction mixture was evaporated, and the residue was partitioned between water and ethyl acetate. The aqueous layer was taken out, and citric acid was added to adjust the aqueous solution to pH 3. The solution was extracted with ethyl acetate. The organic layer was washed with saturated brine, and dried over magnesium sulfate. The solvent was evaporated, and the residue was recrystallized from a mixed solvent of ethyl acetate and diisopropyl ether to give 1.05 g of 3-(4-(3-(2-chlorobenzoyl)-5-ethylthiophen-2-yl)-5-methyl[1,2,4]triazol-3-ylmethylcarbamoyl)benzoic acid.

m.p. 133°–136° C.

Production Example 16

Methyl 3-(4-(2-chlorophenyl)-9-methyl-6H-thieno[3,2-f][1,2,4]triazolo[4,3-a] [1,4]diazepin-2-yl)propionate was prepared by the following method.

3-(2-Chlorophenyl)-3-oxo-propionitrile (53.5 g) and sulfur (9.5 g) were dissolved in dimethylformamide (120 ml). Diethyl 2-(3-oxo-propyl)malonate (71 g) synthesized by the method disclosed in J. Am. Chem. Soc. 70, 3470 (1948) was added under ice-cooling, and the mixture was heated at 60° C. for 3 hours. The mixture was poured into ice water (300 ml). The mixture was extracted with ethyl acetate to give a product. The organic layer was washed 3 times with water and dried over magnesium sulfate. The solvent was evaporated, and isopropyl alcohol was added. The obtained crystals were collected by filtration to give 78 g of diethyl 2-(5-amino-4-(2-chlorobenzoyl)thiophen-2-ylmethyl) malonate.

Diethyl 2-(5-amino-4-(2-chlorobenzoyl)thiophen-2-ylmethyl)malonate (20 g) and a 4M potassium hydroxide aqueous solution (30 ml) were added to ethanol (120 ml), and the mixture was refluxed under heating for 2 hours. The solvent was evaporated, and the residue was dissolved in water. 1.2M Hydrochloric acid was added to adjust the solution to pH 3. The mixture was extracted with ethyl acetate to give a product and the product was washed with brine, and dried over magnesium sulfate. The solvent was evaporated. Dimethylformamide (30 ml) and toluene (70 ml) were added to the residue, and the mixture was heated at 80° C. for 1 hour. The mixture was washed with water, dried over magnesium sulfate and concentrated to give 11.0 g of 3-(5-amino-4-(2-chlorobenzoyl)thiophen-2-yl) propionic acid.

3-(5-Amino-4-(2-chlorobenzoyl)thiophen-2-yl)propionic acid was treated in the same manner as in Production Example 10 to give methyl (4-(2-chlorophenyl)-9-methyl-6H-thieno[3,2-f] [1,2,4]triazolo[4,3-a] [1,4]diazepin-2-yl) propionate.

EXAMPLE 349

Methyl (4-(2-chlorophenyl)-9-methyl-6H-thieno[3,2-f] [1,2,4]triazolo[4,3-a] [1,4]diazepin-2-yl)propionate (1.0 g) was stirred in 2M hydrochloric acid (12 ml) at 60° C. for 3.5 hours. Then, sodium hydrogencarbonate was added to the reaction mixture to make the mixture alkaline. Chloroform and indole-2-carbonyl chloride (0.55 g) were added, and the mixture was stirred at room temperature for 2 hours. An aqueous citric acid solution was added to adjust the solution to pH 3. The obtained crystals were collected by filtration, washed with water and ethyl acetate, and dried to give 3-(3-(2-chlorobenzoyl)-2-(3-(2-indolecarbonylaminomethyl)-5-methyl[1,2,4]triazol-4-yl) thiophen-5-yl)propionic acid.

m.p. 240° C. (dec.)

EXAMPLE 350

N-(4-(2-Chlorophenyl)-2-methyl-6H-thieno[3,2-f] [1,2,4] triazolo[4,3-a] [1,4]diazepin-9-ylmethyl)-3,4-dichlorobenzamide (0.45 g) was obtained in the same manner as in Example 59 using 9-aminomethyl-4-(2-chlorophenyl)-2-methyl-6H-thieno[3,2-f] [1,2,4]triazolo[4,3-a] [1,4]diazepine (0.60 g), dichloroethane (30 ml), triethylamine (0.26 ml) and 3,4-dichlorobenzoyl chloride (0.38 g).

m.p. 193°–195° C.

EXAMPLE 351

N-(4-(2-Chlorophenyl)-2,3-dimethyl-6H-thieno[3,2-f] [1,2,4]triazolo[4,3-a] [1,4]diazepin-9-ylmethyl)-3,4-dichlorobenzamide (0.43 g) was obtained in the same manner as in Example 59 using 9-aminomethyl-4-(2-chlorophenyl)-2,3-dimethyl-6H-thieno[3,2-f] [1,2,4]triazolo [4,3-a] [1,4]diazepine (1.19 g), dichloroethane (60 ml), triethylamine (0.49 ml) and 3,4-dichlorobenzoyl chloride (0.73 g).

m.p. 193°–195° C.

EXAMPLE 352

Benzyl (R)-4-(3,4-dichlorobenzoylamino)-4-(4-(2-chlorophenyl)-2-ethyl-6H-thieno[3,2-f] [1,2,4]triazolo[4,3-a] [1,4]diazepin-9-yl)butanoate (4.79 g) was obtained in the same manner as in Example 59 using benzyl (R)-4-amino-4-(4-(2-chlorophenyl)-2-ethyl-6H-thieno[3,2-f] [1,2,4] triazolo[4,3-a] [1,4]diazepin-9-yl)butanoate di-p-toluenesulfonate (8.64 g), 3,4-dichlorobenzoyl chloride (2.10 g), dichloroethane (100 ml) and triethylamine (4.2 ml).

NMR (270 MHz, $CDCl_3$):1.29(3H,t,J=7.3 Hz), 2.20–2.70 (4H), 2.80(2H,m), 4.63(1H,bs), 5.03(2H,s), 5.18(1H,bs), 5.94(1H,m), 6.40(1H,s), 7.20–7.70(11H), 7.90(1H), 8.44 (1H,m)

EXAMPLE 353

N-(4-(2-Chlorophenyl)-2-propyl-6H-thieno[3,2-f] [1,2,4] triazolo[4,3-a] [1,4]diazepin-9-ylmethyl)-3,4-dichlorobenzamide (0.56 g) was obtained in the same manner as in Example 59 using 9-aminomethyl-4-(2-chlorophenyl)-2-propyl-6H-thieno[3,2-f] [1,2,4]triazolo[4,3-a] [1,4]diazepine (2.81 g), dichloroethane (50 ml), triethylamine (1.11 ml) and 3,4-dichlorobenzoyl chloride (1.66 g).

NMR (270 MHz, DMSO-$d_6$):0.76(3H,t,J=7.3 Hz), 1.47 (2H,J=7.3 Hz), 2.68(2H,t,J=7.3 Hz), 4.88–4.90(4H,m), 6.38 (1H,s), 7.39–8.04(7H,m), 9.23–9.27(1H,t)

EXAMPLE 354

N-(4-(2-Chlorophenyl)-2-ethyl-6H-thieno[3,2-f] [1,2,4] triazolo[4,3-a] [1,4]diazepin-9-ylmethyl)quinoline-3-carboxamide (0.59 g) was obtained in the same manner as in Example 61 using 9-aminomethyl-4-(2-chlorophenyl)-2-ethyl-6H-thieno[3,2-f] [1,2,4]triazolo[4,3-a] [1,4]diazepine (1.0 g), 3-quinolinecarboxylic acid (0.53 g), Bop reagent (1.36 g), triethylamine (0.78 ml) and dimethylformamide (10 ml).

m.p. 200°–202° C.

EXAMPLE 355

N-(4-(2-Chlorophenyl)-2-ethyl-6H-thieno[3,2-f] [1,2,4] triazolo[4,3-a] [1,4]diazepin-9-ylmethyl)indole-3-carboxamide (12 mg) was obtained in the same manner as in Example 61 using 9-aminomethyl-4-(2-chlorophenyl)-2-ethyl-6H-thieno[3,2-f] [1,2,4]triazolo[4,3-a] [1,4]diazepine (1.0 g), indole-3-carboxylic acid (0.49 g), Bop reagent (1.36 g), triethylamine (0.39 ml) and dimethylformamide (10 ml).

m.p. 238°–239° C.

EXAMPLE 356

Benzyl (R)-4-amino-4-(4-(2-chlorophenyl)-2-ethyl-6H-thieno[3,2-f] [1,2,4]triazolo[4,3-a] [1,4]diazepin-9-yl) butanoate di-p-toluenesulfonate (3.0 g) and 2-naphthoyl chloride (0.73 g) were dissolved in DMF (30 ml). Triethylamine (1.46 ml) was added and the mixture was stirred. Water was added to the reaction mixture. The mixture was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using a mixed solvent of ethyl acetate and methanol as an eluent to give 1.43 g of benzyl (R)-4-(4-(2-chlorophenyl)-2-ethyl-6H-thieno[3,2-f] [1,2,4]triazolo[4,3-a] [1,4]diazepin-9-yl)-4-(naphthalene-2-carboxamide)butanoate.

NMR (270 MHz, DMSO-$d_6$):1.04(3H,t,J=7.3 Hz), 2.38–2.52(4H,m), 2.66(2H,q,J=7.3 Hz), 5.03–5.11(2H), 5.68–5.71(1H,q), 6.36(1H,s), 7.32–7.95(15H,m), 8.40(1H, s), 9.22(1H,s)

EXAMPLE 357

(R)-(−)-4-(4-(2-Chlorophenyl)-2-ethyl-6H-thieno[3,2-f] [1,2,4]triazolo[4,3-a] [1,4]diazepin-9-yl)-4-(naphthalene-2-carboxamide)butanoic acid (0.32 g) was obtained in the same manner as in Example 271 using benzyl (R)-4-(4-(2-chlorophenyl)-2-ethyl-6H-thieno[3,2-f] [1,2,4]triazolo[4,3-a] [1,4]diazepin-9-yl)-4-(naphthalene-2-carboxamide) butanoate (1.13 g), methanol (12 ml) and a 2N sodium hydroxide aqueous solution (1.7 ml).

NMR (270 MHz, DMSO-$d_6$):1.06(3H,t,J=7.5 Hz), 2.31–2.54(4H,m), 2.71(2H,q,J=7.5 Hz), 4.86(2H), 5.66–5.68(1H,q), 6.37(1H,s), 7.31–7.98 (10H,m), 8.40(1H, s), 9.22(1H,s)

$[\alpha]_D$=−101.4° (c=1, dimethylformamide)

EXAMPLE 358

Benzyl (R)-4-amino-4-(4-(2-chlorophenyl)-2-ethyl-6H-thieno[3,2-f] [1,2,4]triazolo[4,3-a] [1,4]diazepin-9-yl) butanoate di-p-toluenesulfonate (3.0 g) and 2-naphthalenesulfonyl chloride (0.87 g) were dissolved in DMF (30 ml). Triethylamine (1.46 ml) was added and the mixture was stirred. Water was added to the reaction mixture. The mixture was washed with an aqueous citric acid solution, saturated brine, a saturated aqueous sodium hydrogencarbonate solution and saturated brine and dried over magnesium sulfate. The solvent was evaporated, and the residue was purified by silica gel column chromatography using ethyl acetate as an eluent to give 1.25 g of benzyl (R)-4-(4-(2-chlorophenyl)-2-ethyl-6H-thieno[3,2-f] [1,2,4] triazolo[4,3-a] [1,4]diazepin-9-yl)-4-(naphthalene-2-sulfonamide)butanoate.

NMR (270 MHz, DMSO-$d_6$):1.13(3H,t,J=7.5 Hz), 2.07–2.39(4H,m), 2.70(2H,q,J=7.5 Hz), 4.68(2H), 4.68–4.94(2H,q), 4.97–5.02(1H,q), 6.44(1H,s), 7.21–7.98 (12H,m), 8.00–8.03(3H,t), 8.31(1H,s), 8.81–8.83(1H,s)

EXAMPLE 359

(R)-(−)-4-(4-(2-Chlorophenyl)-2-ethyl-6H-thieno[3,2-f] [1,2,4]triazolo[4,3-a] [1,4]diazepin-9-yl)-4-(naphthalene-2-sulfonamide)butanoic acid (0.50 g) was obtained in the same manner as in Example 271 using benzyl (R)-4-(4-(2-chlorophenyl)-2-ethyl-6H-thieno[3,2-f] [1,2,4]triazolo[4,3-a] [1,4]diazepin-9-yl)-4-(naphthalene-2-sulfonamide) butanoate (1.07 g), methanol (10 ml) and a 2N sodium hydroxide aqueous solution (1.5 ml).

m.p. 227°–229° C., $[\alpha]_D$=−26.8° (c=1, dimethylformamide)

EXAMPLE 360

Benzyl (R)-4-amino-4-(4-(2-chlorophenyl)-2-ethyl-6H-thieno[3,2-f] [1,2,4]triazolo[4,3-a] [1,4]diazepin-9-yl) butanoate di-p-toluenesulfonate (3.0 g) and 2-chlorophenyl isocyanate (0.46 ml) were dissolved in DMF (30 ml). Triethylamine (1.46 ml) was added and the mixture was stirred and water was added to the reaction mixture. The mixture was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using ethyl acetate as an eluent to give 2.02 g of benzyl (R)-4-(4-(2-chlorophenyl)-2-ethyl-6H-thieno[3,2-f] [1,2,4]triazolo[4,3-a] [1,4]diazepin-9-yl)-4-(3-(2-chlorophenyl)ureido) butanoate.

NMR (270 MHz, DMSO-$d_6$):1.16(3H,t,J=7.4 Hz), 2.15–2.26(4H,m), 2.78(2H,q,J=7.4 Hz), 4.79(2H), 5.01–5.11(1H,q), 5.43–5.51(1H,q), 6.46(1H,s), 6.94–8.15 (15H,m)

EXAMPLE 361

(R)-(−)-4-(4-(2-Chlorophenyl)-2-ethyl-6H-thieno[3,2-f] [1,2,4]triazolo[4,3-a] [1,4]diazepin-9-yl)-4-(3-(2-chlorophenyl)ureido)butanoic acid (0.25 g) was obtained in the same manner as in Example 271 using benzyl (R)-4-(4-(2-chlorophenyl)-2-ethyl-6H-thieno[3,2-f] [1,2,4]triazolo[4,3-a] [1,4]diazepin-9-yl)-4-(3-(2-chlorophenyl)ureido) butanoate (0.5 g), methanol (15 ml) and a IN sodium hydroxide aqueous solution (0.755 ml).

NMR (270 MHz, DMSO-$d_6$):1.18(3H,t,J=7.5 Hz), 2.06–2.33(4H,m), 2.80(2H,q,J=7.5 Hz), 4.83(2H), 5.41–5.45(1H,q), 6.45(1H,s), 6.93–8.13(10H,m)

$[\alpha]_D$=−53.6° (c=1, dimethylformamide)

EXAMPLE 362

Benzyl (R)-4-amino-4-(4-(2-chlorophenyl)-2-ethyl-6H-thieno[3,2-f] [1,2,4]triazolo[4,3-a] [1,4]diazepin-9-yl) butanoate di-p-toluenesulfonate (2.0 g) and 2-methoxyphenyl isocyanate (0.34 ml) were dissolved in DMF (20 ml). Triethylamine (0.97 ml) was added and the mixture was stirred. Water was added to the reaction mixture. The mixture was washed with an aqueous citric acid solution, saturated brine, a saturated aqueous sodium hydrogencarbonate solution and saturated brine, and dried over magnesium sulfate. The solvent was evaporated, and the residue was purified by silica gel column chromatography using ethyl acetate as an eluent to give 1.19 g of benzyl (R)-4-(4-(2-chlorophenyl)-2-ethyl-6H-thieno[3,2-f] [1,2,4] triazolo[4,3-a] [1,4]diazepin-9-yl)-4-(3-(2-methoxyphenyl) ureido)butanoate.

m.p. 179°–181° C.

EXAMPLE 363

(R)-(−)-4-(4-(2-Chlorophenyl)-2-ethyl-6H-thieno[3,2-f] [1,2,4]triazolo[4,3-a] [1,4]diazepin-9-yl)-4-(3-(2-methoxyphenyl)ureido)butanoic acid (0.17 g) was obtained in the same manner as in Example 271 using benzyl (R)-4-(4-(2-chlorophenyl)-2-ethyl-6H-thieno[3,2-f] [1,2,4]triazolo [4,3-a] [1,4]diazepin-9-yl)-4-(3-(2-methoxyphenyl)ureido) butanoate (0.7 g), methanol (10 ml) and a 1N sodium hydroxide aqueous solution (1.05 ml).

NMR (270 MHz, $CDCl_3$):1.25(3H,t,J=7.4 Hz), 2.31–2.52 (4H,m), 2.77(2H,q,J=7.4 Hz), 3.72(3H,s), 4.65–5.13(2H,d), 5.86–5.89(1H,q), 6.36(1H,s), 6.71–8.13(10H,m)

EXAMPLE 364

Benzyl alcohol (2.8 ml) was added to a solution of D-α-aminoadipic acid (4.0 g) in 60% sulfuric acid (3.24 ml), and the mixture was heated at 70° C. for 1 hour. The reaction mixture was concentrated under reduced pressure to remove moisture. The reaction mixture was added to ice water (300 ml) containing sodium hydrogen-carbonate (4.58 g) to give δ-benzyl D-α-aminoadipate (2.09 g). δ-Benzyl D-α-aminoadipate (2.47 g) and triethylamine (2.06 ml) were mixed with water (15 ml). A solution of tert-butyl dicarbonate (2.36 g) in dioxane (15 ml) was added, and the mixture was stirred at room temperature for 7 hours. Water (50 ml) was added to the reaction mixture and the mixture was washed with ethyl acetate (50 ml). Citric acid was added to make the mixture acidic. The mixture was extracted with ethyl acetate. The extract was dried over magnesium sulfate. The solvent was evaporated to give 2.93 g of δ-benzyl N-α-tert-butoxycarbonylamino-D-adipate.

Benzyl (R)-(−)-5-(3,4-dichlorobenzoylamino)-5-(4-(2-chlorophenyl)-2-ethyl-6H-thieno[3,2-f] [1,2,4]triazolo[4,3-a] [1,4]diazepin-9-yl)pentanoate (0.47 g) was obtained in the same manner as in Example 270 using δ-benzyl N-α-tert-butoxycarbonylamino-D-adipate (2.93 g) thus obtained, tetrahydrofuran (30 ml), triethylamine (1.3 ml), isobutyl chloroformate (1.2 ml) and 5-(2-chlorophenyl)-7-ethyl-2-hydrazine-3H-thieno[2,3-e] [1,4]diazepine (2.66 g).

NMR (270 MHz, $CDCl_3$):1.29(3H,t,J=7.3 Hz), 1.70–2.41 (6H,m), 2.80(2H,q,J=7.3 Hz), 4.62–5.19(2H,d), 5.04(2H,s), 5.80–5.88(1H,q), 6.39(1H,s), 7.23–7.87(12H,m), 8.59(1H, d)

$[\alpha]_D$=−61.6° (c=1, chloroform)

EXAMPLE 365

(R)-(−)-5-(3,4-Dichlorobenzoylamino)-5-(4-(2-chlorophenyl)-2-ethyl-6H-thieno[3,2-f] [1,2,4]triazolo[4,3-a] [1,4]diazepin-9-yl)pentanoic acid (72 mg) was obtained in the same manner as in Example 271 using benzyl (R)-(−)-5-(3,4-dichlorobenzoylamino)-5-(4-(2-chlorophenyl)-2-ethyl-6H-thieno[3,2-f] [1,2,4]triazolo[4,3-a] [1,4]diazepin-9-yl)pentanoate (0.41 g), methanol (10 ml) and a 1N sodium hydroxide aqueous solution (1.16 ml).

NMR (270 MHz, DMSO-$d_6$):1.33(3H,t,J=7.5 Hz), 1.74–2.60(6H,m), 2.86(2H,q,J=7.5 Hz), 4.77–5.03(2H,d), 5.96–6.02(1H,t), 6.44(1H,s), 7.24–8.14(7H,m), 9.41–9.34 (1H,d)

$[\alpha]_D$=−87.5° (c=1, dimethylformamide)

EXAMPLE 366

N-(4-(3-Chlorophenyl)-2-methyl-6H-thieno[3,2-f] [1,2,4] triazolo[4,3-a] [1,4]diazepin-9-ylmethyl)-3,4- dichlorobenzamide is obtained in the same manner as in Example 59 using 9-aminomethyl-4-(3-chlorophenyl)-2-methyl-6H-thieno[3,2-f] [1,2,4]triazolo[4,3-a] [1,4] diazepine, dichloroethane, triethylamine and 3,4-dichlorobenzoyl chloride.

EXAMPLE 367

N-(4-(3-Chlorophenyl)-2-ethyl-6H-thieno[3,2-f] [1,2,4] triazolo[4,3-a] [1,4]diazepin-9-ylmethyl)-N'-(2-methoxyphenyl)urea is obtained in the same manner as in Example 64 using 9-aminomethyl-4-(3-chlorophenyl)-2-ethyl-6H-thieno[3,2-f] [1,2,4]triazolo[4,3-a] [1,4]diazepine, 2-methoxyphenyl isocyanate and chloroform.

EXAMPLE 368

4-(2-Chlorophenyl)-9-methyl-2-propyl-6H-thieno[3,2-f] [1,2,4]triazolo[4,3-a] [1,4]diazepine is dissolved in a mixed solvent of methanol and water (9:1). p-Toluenesulfonic acid monohydrate is added, and the mixture is refluxed under heating for 3 hours. The solvent is evaporated. Dimethylformamide, indole-2-carbonyl chloride and triethylamine are added, and the mixture is stirred for 1 hour to give N-(4-(3-(2-chlorobenzoyl)-5-propylthiophen-2-yl)-5-methyl[1,2,4]triazol-3-ylmethyl)indole-2-carboxamide.

EXAMPLE 369

4-(2-Chlorophenyl)-2-isopropyl-9-methyl-6H-thieno[3,2-f] [1,2,4]triazolo[4,3-a] [1,4]diazepine is dissolved in a mixed solvent of methanol and water (9:1). p-Toluenesulfonic acid monohydrate is added, and the mixture is refluxed under heating for 3 hours. The solvent is evaporated. Dimethylformamide, indole-2-carbonyl chloride and triethylamine are added, and the mixture is stirred for 1 hour to give N-(4-(3-(2-chlorobenzoyl)-5-isopropylthiophen-2-yl)-5-methyl[1,2,4]triazol-3-ylmethyl) indole-2-carboxamide.

EXAMPLE 370

4-(2-Chlorophenyl)-2-cyclopropyl-9-methyl-6H-thieno [3,2-f] [1,2,4]triazolo[4,3-a] [1,4]diazepine is dissolved in a mixed solvent of methanol and water (9:1). p-Toluenesulfonic acid monohydrate is added, and the mixture is refluxed under heating for 3 hours. The solvent is evaporated. Dimethylformamide, indole-2-carbonyl chloride and triethylamine are added, and the mixture is stirred for 1 hour to give N-(4-(3-(2-chlorobenzoyl)-5-cyclopropylthiophen-2-yl)-5-methyl[1,2,4]triazol-3-ylmethyl)indole-2-carboxamide.

EXAMPLE 371

4-(2-Chlorophenyl)-9-methyl-2-propyl-6H-thieno[3,2-f] [1,2,4]triazolo[4,3-a] [1,4]diazepine is dissolved in a mixed solvent of methanol and water (9:1). p-Toluenesulfonic acid monohydrate is added, and the mixture is refluxed under heating for 3 hours. The solvent is evaporated. Dimethylformamide, 3-methoxyphenyl isocyanate and triethylamine are added, and the mixture is stirred for 1 hour to give N-(4-(3-(2-chlorobenzoyl)-5-propylthiophen-2-yl)-5-methyl[1,2,4]triazol-3-ylmethyl)-N'-(3-methoxyphenyl) urea.

EXAMPLE 372

4-(2-Chlorophenyl)-2-isopropyl-9-methyl-6H-thieno[3,2-f] [1,2,4]triazolo[4,3-a] [1,4]diazepine is dissolved in a mixed solvent of methanol and water (9:1). p-Toluenesulfonic acid monohydrate is added, and the mixture is refluxed under heating for 3 hours. The solvent is evaporated. Dimethylformamide, 3-methoxyphenyl isocyanate and triethylamine are added, and the mixture is stirred for 1 hour to give N-(4-(3-(2-chlorobenzoyl)-5-isopropylthiophen-2-yl)-5-methyl[1,2,4]triazol-3-ylmethyl)-N'-(3-methoxyphenyl)urea.

EXAMPLE 373

4-(2-Chlorophenyl)-2-cyclopropyl-9-methyl-6H-thieno [3,2-f] [1,2,4]triazolo[4,3-a] [1,4]diazepine is dissolved in a mixed solvent of methanol and water (9:1). p-Toluenesulfonic acid monohydrate is added, and the mixture is refluxed under heating for 3 hours. The solvent is evaporated. Dimethylformamide, 3-methoxyphenyl isocyanate and triethylamine are added, and the mixture is stirred for 1 hour to give N-(4-(3-(2-chlorobenzoyl)-5-cyclopropylthiophen-2-yl)-5-methyl[1,2,4]triazol-3-ylmethyl)-N'-(3-methoxyphenyl)urea.

EXAMPLE 374

(4-(2-Chlorophenyl)-9-methyl-6H-thieno[3,2-f] [1,2,4] triazolo[4,3-a] [1,4]diazepin-2-yl)carboxylic acid and p-toluenesulfonic acid are dissolved in a mixed solvent of methanol and water (9:1), and the solution is refluxed for 3 hours. The solvent is evaporated. The residue is dissolved in dimethylformamide. 3-Chlorophenyl isocyanate and triethylamine are added under ice-cooling, and the mixture is stirred for 1 hour to give (3-(2-chlorobenzoyl)-2-(3-(3-(3-chlorophenyl)ureidomethyl)- 5-methyl[1,2,4]triazol-4-yl) thiophen-5-yl)carboxylic acid.

EXAMPLE 375

N-(4-(2-Chlorophenyl)-2-propyl-6H-thieno[3,2-f] [1,2,4] triazolo[4,3-a] [1,4]diazepin-9-ylmethyl)indole-2-carboxamide is obtained in the same manner as in Example 59 using 9-aminomethyl-4-(2-chlorophenyl)-2-propyl-6H-thieno[3,2-f] [1,2,4]triazolo[4,3-a] [1,4]diazepine, dimethylformamide, triethylamine and indole-2-carboxylic acid chloride.

EXAMPLE 376

N-(4-(2-Chlorophenyl)-2-isopropyl-6H-thieno[3,2-f] [1,2,4]triazolo[4,3-a] [1,4]diazepin-9-ylmethyl)indole-2-carboxamide is obtained in the same manner as in Example 59 using 9-aminomethyl-4-(2-chlorophenyl)-2-isopropyl-6H-thieno[3,2-f] [1,2,4]triazolo[4,3-a] [1,4]diazepine, dimethylformamide, triethylamine and indole-2-carboxylic acid chloride.

EXAMPLE 377

N-(4-(2-Chlorophenyl)-2-cyclopropyl-6H-thieno[3,2-f] [1,2,4]triazolo[4,3-a] [1,4]diazepin-9-ylmethyl)indole-2-carboxamide is obtained in the same manner as in Example 59 using 9-aminomethyl-4-(2-chlorophenyl)-2-cyclopropyl-6H-thieno[3,2-f] [1,2,4]triazolo[4,3-a] [1,4]diazepine, dimethylformamide, triethylamine and indole-2-carboxylic acid chloride.

EXAMPLE 378

N-(2-Chlorophenyl)-N'-(4-(2-chlorophenyl)-2-propyl-6H-thieno[3,2-f] [1,2,4]triazolo[4,3-a] [1,4]diazepin-9-ylmethyl)urea is obtained in the same manner as in Example 64 using 9-aminomethyl-4-(2-chlorophenyl)-2-propyl-6H-thieno[3,2-f] [1,2,4]triazolo[4,3-a] [1,4]diazepine, 2-chlorophenyl isocyanate and chloroform.

EXAMPLE 379

N-(2-Chlorophenyl)-N'-(4-(2-chlorophenyl)-2-isopropyl-6H-thieno[3,2-f] [1,2,4]triazolo[4,3-a] [1,4]diazepin-9-ylmethyl)urea is obtained in the same manner as in Example 64 using 9-aminomethyl-4-(2-chlorophenyl)- 2-isopropyl-6H-thieno[3,2-f] [1,2,4]triazolo[4,3-a] [1,4]diazepine, 2-chlorophenyl isocyanate and chloroform.

EXAMPLE 380

N-(2-Chlorophenyl)-N'-(4-(2-chlorophenyl)-2-cyclopropyl-6H-thieno[3,2-f] [1,2,4]triazolo[4,3-a] [1,4] diazepin-9-ylmethyl)urea is obtained in the same manner as in Example 64 using 9-aminomethyl-4-(2-chlorophenyl)-2-cyclopropyl-6H-thieno[3,2-f] [1,2,4]triazolo[4,3-a] [1,4] diazepine, 2-chlorophenyl isocyanate and chloroform.

EXAMPLE 381

Benzyl (R)-4-(4-(2-chlorophenyl)-2-propyl-6H-thieno[3,2-f] [1,2,4]triazolo[4,3-a] [1,4]diazepin-9-yl)-4-(indole-2-carboxamide)butanoate is obtained in the same manner as in Example 278 using benzyl (R)-4-amino-4-(4-(2-chlorophenyl)-2-propyl-6H-thieno[3,2-f] [1,2,4]triazolo[4,3-a] [1,4]diazepin-9-yl)butanoate di-p-toluenesulfonate, triethylamine, dichloroethane and indole-2-carboxylic acid chloride.

EXAMPLE 382

Benzyl (R)-4-(4-(2-chlorophenyl)-2-propyl-6H-thieno[3,2-f] [1,2,4]triazolo[4,3-a] [1,4]diazepin-9-yl)-4-(indole-2-carboxamide)butanoate is subjected to alkali hydrolysis to give (R)-4-(4-(2-chlorophenyl)-2-propyl-6H-thieno[3,2-f] [1,2,4]triazolo[4,3-a] [1,4]diazepin-9-yl)-4-(indole-2-carboxamide)butanoic acid.

EXAMPLE 383

Benzyl (R)-4-(4-(2-chlorophenyl)-2-isopropyl-6H-thieno [3,2-f] [1,2,4]triazolo[4,3-a] [1,4]diazepin-9-yl)-4-(indole-2-carboxamide)butanoate is obtained in the same manner as in Example 278 using benzyl (R)-4-amino-4-(4-(2-chlorophenyl)-2-isopropyl-6H-thieno[3,2-f] [1,2,4]triazolo [4,3-a] [1,4]diazepin-9-yl)butanoate di-p-toluenesulfonate, triethylamine, dichloroethane and indole-2-carboxylic acid chloride.

EXAMPLE 384

Benzyl (R)-4-(4-(2-chlorophenyl)-2-isopropyl-6H-thieno [3,2-f] [1,2,4]triazolo[4,3-a] [1,4]diazepin-9-yl)-4-(indole-2-carboxamide)butanoate is subjected to alkali hydrolysis to give (R)-4-(4-(2-chlorophenyl)-2-isopropyl-6H-thieno[3,2-f] [1,2,4]triazolo[4,3-a] [1,4]diazepin-9-yl)-4-(indole-2-carboxamide)butanoic acid.

EXAMPLE 385

Benzyl (R)-4-(4-(2-chlorophenyl)-2-cyclopropyl-6H-thieno[3,2-f] [1,2,4]triazolo[4,3-a] [1,4]diazepin-9-yl)-4-(indole-2-carboxamide)butanoate is obtained in the same manner as in Example 278 using benzyl (R)-4-amino-4-(4-(2-chlorophenyl)-2-cyclopropyl-6H-thieno[3,2-f] [1,2,4] triazolo[4,3-a] [1,4]diazepin-9-yl)butanoate di-p-toluenesulfonate, triethylamine, dichloroethane and indole-2-carboxylic acid chloride.

EXAMPLE 386

Benzyl (R)-4-(4-(2-chlorophenyl)-2-cyclopropyl-6H-thieno[3,2-f] [1,2,4]triazolo[4,3-a] [1,4]diazepin-9-yl)-4-(indole-2-carboxamide)butanoate is subjected to alkali hydrolysis to give (R)-4-(4-(2-chlorophenyl)-2-cyclopropyl-6H-thieno[3,2-f] [1,2,4]triazolo[4,3-a] [1,4]diazepin-9-yl)-4-(indole-2-carboxamide)butanoic acid.

EXAMPLE 387

Benzyl (R)-4-(4-(2-chlorophenyl)-2-propyl-6H-thieno[3,2-f] [1,2,4]triazolo[4,3-a] [1,4]diazepin-9-yl)-4-(3-(2-chlorophenyl)ureido)butanoate is obtained in the same manner as in Example 360 using benzyl (R)-4-amino-4-(4-(2-chlorophenyl)-2-propyl-6H-thieno[3,2-f] [1,2,4]triazolo[4,3-a] [1,4]diazepin-9-yl)butanoate di-p-toluenesulfonate, 2-chlorophenyl isocyanate, dimethylformamide and triethylamine.

EXAMPLE 388

Benzyl (R)-4-(4-(2-chlorophenyl)-2-propyl-6H-thieno[3,2-f] [1,2,4]triazolo[4,3-a] [1,4]diazepin-9-yl)-4-(3-(2-chlorophenyl)ureido)butanoate is subjected to alkali hydrolysis to give (R)-4-(4-(2-chlorophenyl)-2-propyl-6H-thieno[3,2-f] [1,2,4]triazolo[4,3-a] [1,4]diazepin-9-yl)-4-(3-(2-chlorophenyl)ureido)butanoic acid.

EXAMPLE 389

Benzyl (R)-4-(4-(2-chlorophenyl)-2-isopropyl-6H-thieno [3,2-f] [1,2,4]triazolo[4,3-a] [1,4]diazepin-9-yl)-4-(3-(2-chlorophenyl)ureido)butanoate is obtained in the same manner as in Example 360 using benzyl (R)-4-amino-4-(4-(2-chlorophenyl)-2-isopropyl-6H-thieno[3,2-f] [1,2,4]triazolo [4,3-a] [1,4]diazepin-9-yl)butanoate di-p-toluenesulfonate, 2-chlorophenyl isocyanate, dimethylformamide and triethylamine.

EXAMPLE 390

Benzyl (R)-4-(4-(2-chlorophenyl)-2-isopropyl-6H-thieno [3,2-f] [1,2,4]triazolo[4,3-a] [1,4]diazepin-9-yl)-4-(3-(2-chlorophenyl)ureido)butanoate is subjected to alkali hydrolysis to give (R)-4-(4-(2-chlorophenyl)-2-isopropyl-6H-thieno[3,2-f] [1,2,4]triazolo[4,3-a] [1,4]diazepin-9-yl)-4-(3-(2-chlorophenyl)ureido)butanoic acid.

EXAMPLE 391

Benzyl (R)-4-(4-(2-chlorophenyl)-2-cyclopropyl-6H-thieno[3,2-f] [1,2,4]triazolo[4,3-a] [1,4]diazepin-9-yl)-4-(3-(2-chlorophenyl)ureido)butanoate is obtained in the same manner as in Example 360 using benzyl (R)-4-amino-4-(4-(2-chlorophenyl)-2-cyclopropyl-6H-thieno[3,2-f] [1,2,4] triazolo[4,3-a] [1,4]diazepin-9-yl)butanoate di-p-toluenesulfonate, 2-chlorophenyl isocyanate, dimethylformamide and triethylamine.

EXAMPLE 392

Benzyl (R)-4-(4-(2-chlorophenyl)-2-cyclopropyl-6H-thieno[3,2-f] [1,2,4]triazolo[4,3-a] [1,4]diazepin-9-yl)-4-(3-(2-chlorophenyl)ureido)butanoate is subjected to alkali hydrolysis to give (R)-4-(4-(2-chlorophenyl)-2-cyclopropyl-6H-thieno[3,2-f] [1,2,4]triazolo[4,3-a] [1,4]diazepin-9-yl)-4-(3-(2-chlorophenyl)ureido)butanoic acid.

The structural formulas of the thienylazole compounds of the above Examples are shown in Table I-1 to Table I-26. The structural formulas of the thienotriazolodiazepine compounds are shown in Table II-1 to Table II-16. In the Tables, Me means methyl, Et means ethyl, t-Bu means tert-butyl, Bn means benzyl, and cHex means cyclohexyl.

TABLE I-1
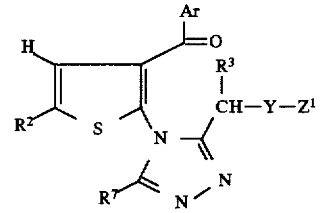
| Example No. | $R^2$ | $R^3$ | $R^7$ | Ar | Y | $Z^1$ |
|---|---|---|---|---|---|---|
| 1 | $C_2H_5$ | H | H | 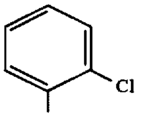 | $-NHCO-$ | 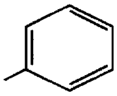 |
| 2 | $C_2H_5$ | H | H | 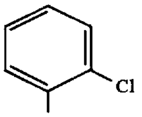 | $-NHCO-$ | 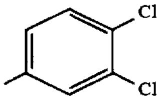 |
| 3 | $C_2H_5$ | H | H | 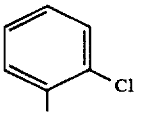 | $-NHCO-$ | 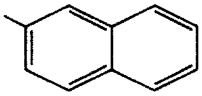 |
| 4 | $C_2H_5$ | H | H | 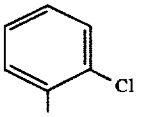 | $-NHCO-$ | 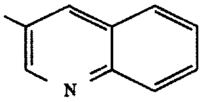 |
| 5 | $C_2H_5$ | H | H | 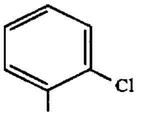 | $-NHCO-$ | 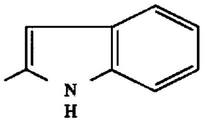 |
| 6 | $C_2H_5$ | H | H | 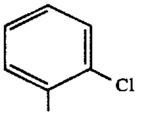 | $-NHCO-$ | 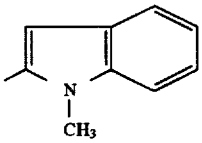 |
| 7 | $C_2H_5$ | H | H | 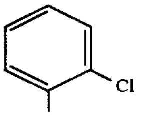 | $-NHCO-$ | 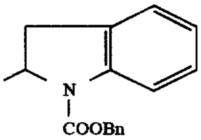 |
| 8 | $C_2H_5$ | H | H | 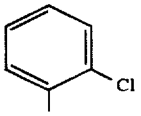 | $-NHCO-$ | 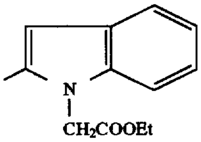 |
| 9 | $C_2H_5$ | H | H | 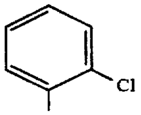 | $-NHCO-$ | 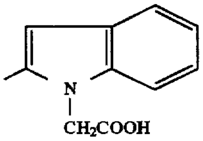 |

TABLE I-1-continued
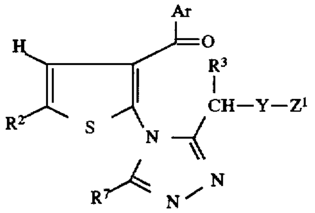
| Example No. | $R^2$ | $R^3$ | $R^7$ | Ar | Y | $Z^1$ |
|---|---|---|---|---|---|---|
| 10 | $C_2H_5$ | H | $CH_3$ | 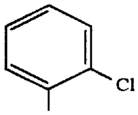 | $-NHCO-$ | 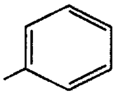 |
TABLE I-2
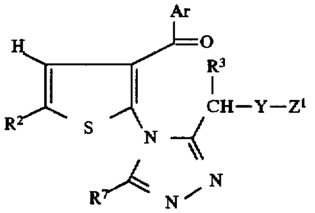
| Example No. | $R^2$ | $R^3$ | $R^7$ | Ar | Y | $Z^1$ |
|---|---|---|---|---|---|---|
| 11 | $C_2H_5$ | H | $CH_3$ | 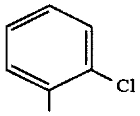 | $-NHCO-$ | 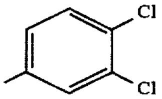 |
| 12 | $C_2H_5$ | H | $CH_3$ | 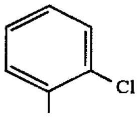 | $-NHCO-$ | 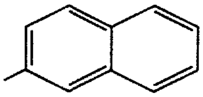 |
| 13 | $C_2H_5$ | H | $CH_3$ | 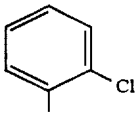 | $-NHCO-$ | 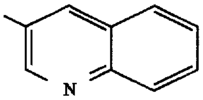 |
| 14 | $C_2H_5$ | H | $CH_3$ | 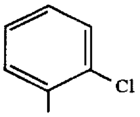 | $-NHCO-$ | 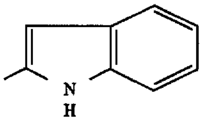 |
| 15 | $C_2H_5$ | H | $CH_3$ | 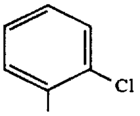 | $-NHCO-$ | 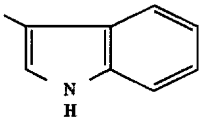 |
| 16 | $C_2H_5$ | H | $CH_3$ | 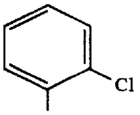 | $-NHCO-$ | 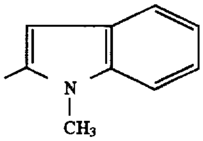 |

TABLE I-2-continued
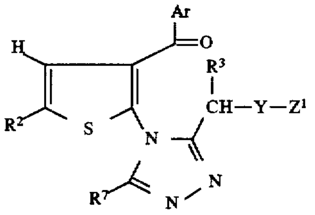
| Example No. | $R^2$ | $R^3$ | $R^7$ | Ar | Y | $Z^1$ |
|---|---|---|---|---|---|---|
| 17 | $C_2H_5$ | H | $CH_3$ | 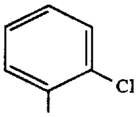 | $-NHCO-$ | 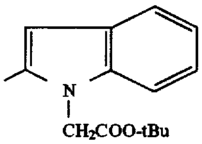 |
| 18 | $C_2H_5$ | H | $CH_3$ | 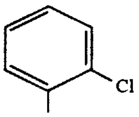 | $-NHCO-$ | 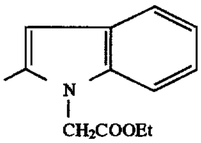 |
| 19 | $C_2H_5$ | H | $CH_3$ | 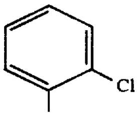 | $-NHCO-$ | 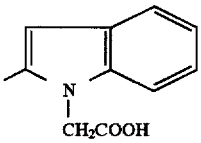 |
| 20 | $C_2H_5$ | H | $CH_3$ | 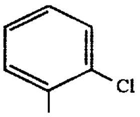 | $-NHCO-$ | 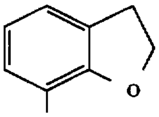 |
TABLE I-3
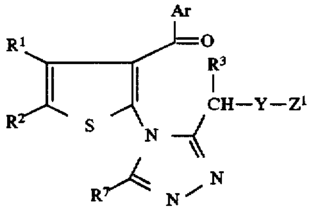
| Example No. | $R^1$ | $R^2$ | $R^3$ | $R^7$ | Ar | Y | $Z^1$ |
|---|---|---|---|---|---|---|---|
| 21 | H | $C_2H_5$ | H | $CH_3$ | 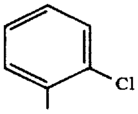 | $-NHCO-$ | 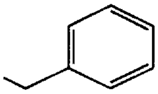 |
| 22 | H | $C_2H_5$ | H | $CH_3$ | 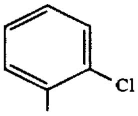 | $-NHCONH-$ | 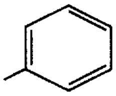 |
| 23 | H | $C_2H_5$ | H | $CH_3$ | 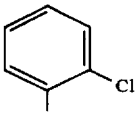 | $-NHCONH-$ | 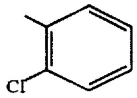 |

TABLE I-3-continued
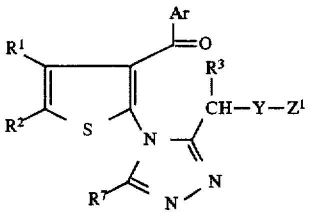
| Example No. | $R^1$ | $R^2$ | $R^3$ | $R^7$ | Ar | Y | $Z^1$ |
|---|---|---|---|---|---|---|---|
| 24 | H | $C_2H_5$ | H | $CH_3$ | 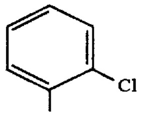 | —NHCONH— | 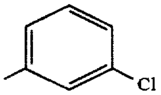 |
| 25 | H | $C_2H_5$ | H | $CH_3$ | 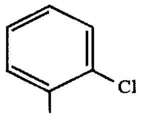 | —NHCONH— | 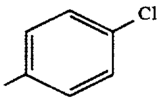 |
| 26 | H | $C_2H_5$ | H | $CH_3$ | 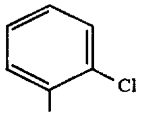 | —NHCONH— | 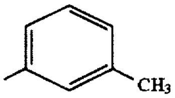 |
| 27 | H | $C_2H_5$ | H | $CH_3$ | 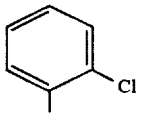 | —NHCONH— | 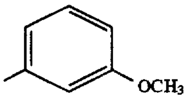 |
| 28 | $CH_3$ | $CH_3$ | H | $CH_3$ | 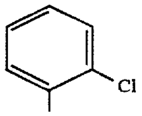 | —NHCONH— | 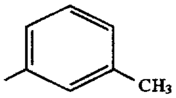 |
| 29 | | $(C_4H_8)$ | H | $CH_3$ | 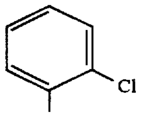 | —NHCONH— | 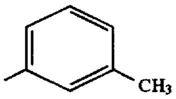 |
| 30 | H | $C_2H_5$ | H | H | 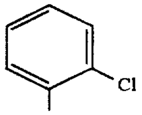 | —NHCONH— | 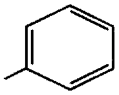 |

TABLE I-4
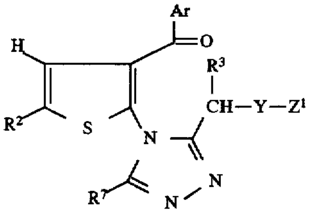
| Example No. | $R^2$ | $R^3$ | $R^7$ | Ar | Y | $Z^1$ |
|---|---|---|---|---|---|---|
| 31 | $C_2H_5$ | H | COOEt | 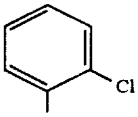 | —NHCONH— | 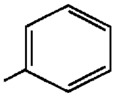 |
| 32 | $C_2H_5$ | H | $C_2H_5$ | 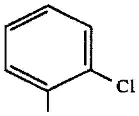 | —NHCO— | 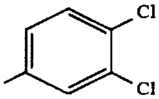 |
| 33 | $C_2H_5$ | H | $C_2H_5$ | 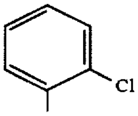 | —NHCO— | 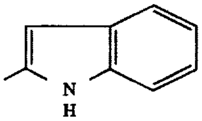 |
| 34 | $C_2H_5$ | H | $C_2H_5$ | 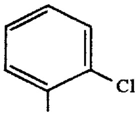 | —NHCO— | 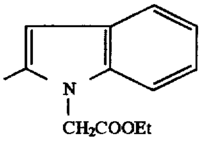 |
| 35 | $C_2H_5$ | H | $C_2H_5$ | 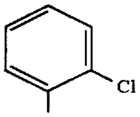 | —NHCO— | 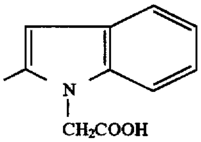 |
| 36 | $C_2H_5$ | H | 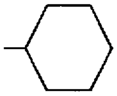 | 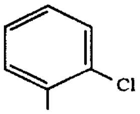 | —NHCO— | 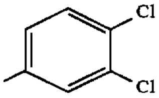 |
| 37 | $C_2H_5$ | H | 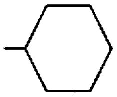 | 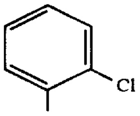 | —NHCO— | 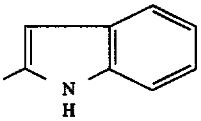 |
| 38 | $C_2H_5$ | H | 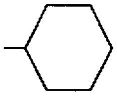 | 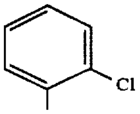 | —NHCO— | 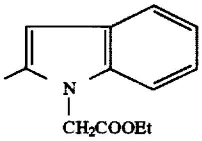 |
| 39 | $C_2H_5$ | H | 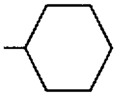 | 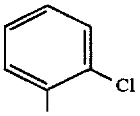 | —NHCO— | 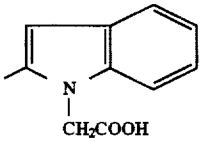 |

TABLE I-4-continued
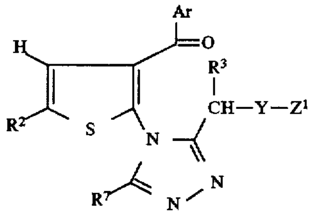
| Example No. | $R^2$ | $R^3$ | $R^7$ | Ar | Y | $Z^1$ |
|---|---|---|---|---|---|---|
| 40 | $C_2H_5$ | H | $CF_3$ | 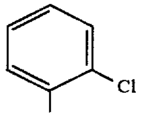 | —NHCO— | 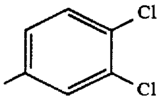 |
TABLE I-5
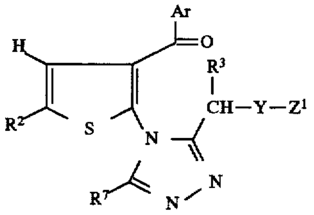
| Example No. | $R^2$ | $R^3$ | $R^7$ | Ar | Y | $Z^1$ |
|---|---|---|---|---|---|---|
| 41 | $C_2H_5$ | H | $CF_3$ | 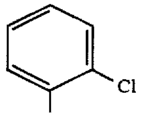 | —NHCO— | 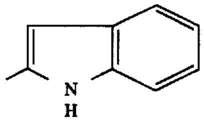 |
| 42 | $C_2H_5$ | H | $CF_3$ | 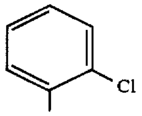 | —NHCO— | 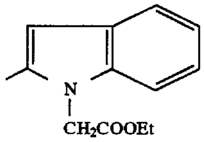 |
| 43 | $C_2H_5$ | H | $CF_3$ | 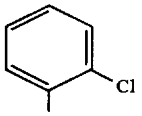 | —NHCO— | 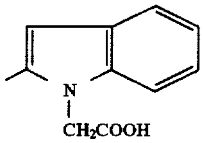 |
| 44 | $C_2H_5$ | H | COOEt | 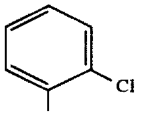 | —NHCO— | 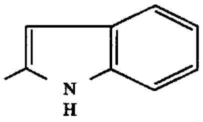 |
| 45 | $C_2H_5$ | H | $(CH_2)_2CO_2Et$ | 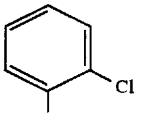 | —NHCO— | 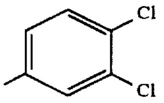 |
| 46 | $C_2H_5$ | H | $(CH_2)_2CO_2H$ | 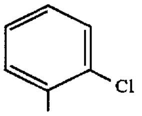 | —NHCO— | 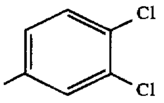 |

TABLE I-5-continued
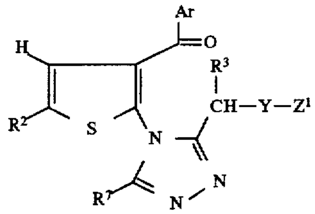
| Example No. | $R^2$ | $R^3$ | $R^7$ | Ar | Y | $Z^1$ |
|---|---|---|---|---|---|---|
| 47 | $C_2H_5$ | H | $(CH_2)_2CO_2H$ | 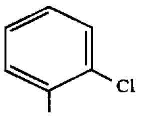 | $-NHCO-$ | 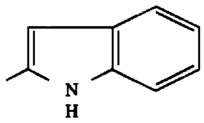 |
| 48 | $C_2H_5$ | H | H | 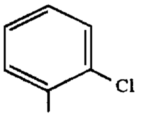 | $-NHSO_2-$ | 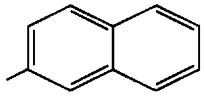 |
| 49 | $C_2H_5$ | H | $CH_3$ | 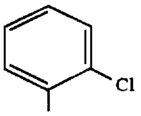 | $-NHSO_2-$ | 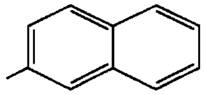 |
| 50 | $C_2H_5$ | H | $CH_3$ | 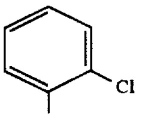 | $-OCONH-$ | 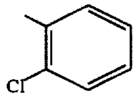 |
TABLE I-6
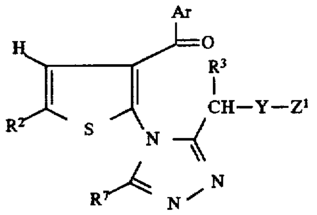
| Example No. | $R^2$ | $R^3$ | $R^7$ | Ar | Y | $Z^1$ |
|---|---|---|---|---|---|---|
| 51 | $C_2H_5$ | H | $CH_3$ | 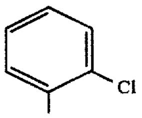 | $-OCONH-$ | 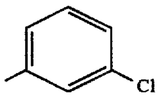 |
| 52 | $C_2H_5$ | H | $CH_3$ | 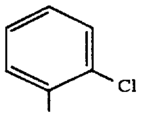 | $-OCONH-$ | 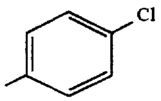 |
| 53 | $C_2H_5$ | H | $CH_3$ | 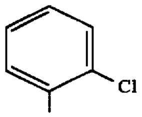 | $-OCONH-$ | 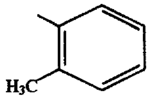 |

TABLE I-6-continued
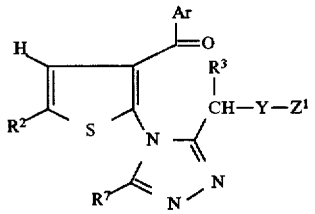
| Example No. | $R^2$ | $R^3$ | $R^7$ | Ar | Y | $Z^1$ |
|---|---|---|---|---|---|---|
| 54 | $C_2H_5$ | H | $CH_3$ | 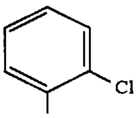 | $-OCONH-$ | 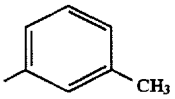 |
| 55 | $C_2H_5$ | H | $CH_3$ | 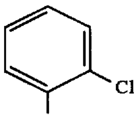 | $-OCONH-$ | 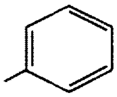 |
| 56 | $C_2H_5$ | H | $CH_3$ | 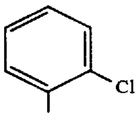 | $-OCONH-$ | 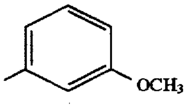 |
| 57 | $C_2H_5$ | H | $CH_3$ | 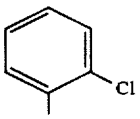 | $-OCO-$ | 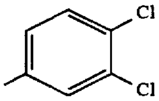 |
| 58 | $C_2H_5$ | H | $CH_3$ | 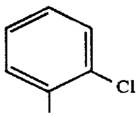 | $-OCO-$ | 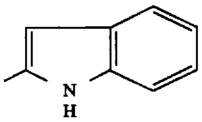 |
| 71 | $C_2H_5$ | H | Br | 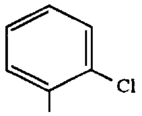 | $-NHCO-$ | 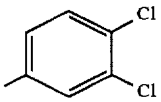 |
| 72 | $C_2H_5$ | H | Br | 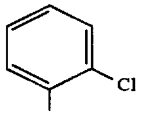 | $-NHCO-$ | 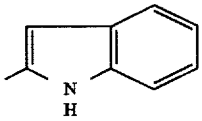 |

TABLE I-7
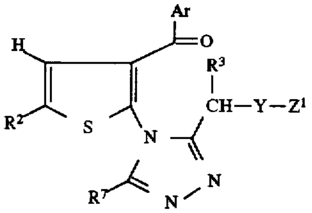
| Example No. | $R^2$ | $R^3$ | $R^7$ | Ar | Y | $Z^1$ |
|---|---|---|---|---|---|---|
| 73 | $C_2H_5$ | H | Br | 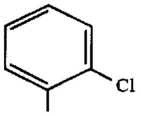 | —NHCO— | 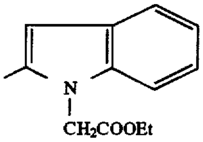 |
| 74 | $C_2H_5$ | H | Br | 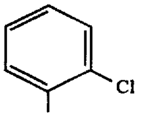 | —NHCO— | 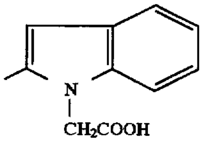 |
| 75 | $C_2H_5$ | H | Br | 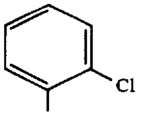 | —NHCONH— | 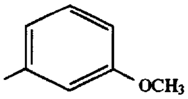 |
| 76 | $C_2H_5$ | H | $CH_2OH$ | 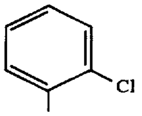 | —NHCO— | 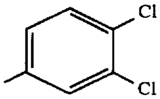 |
| 77 | $C_2H_5$ | H | $CH_2OH$ | 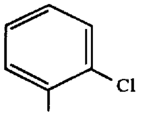 | —NHCO— | 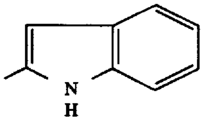 |
| 78 | $C_2H_5$ | H | $CH_2OH$ | 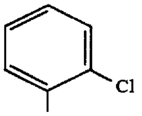 | —NHCO— | 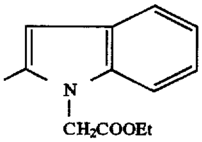 |
| 79 | $C_2H_5$ | H | $CH_2OH$ | 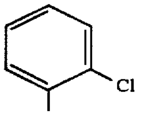 | —NHCO— | 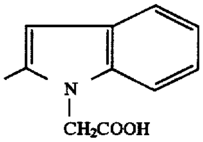 |
| 80 | $C_2H_5$ | H | $CH_2OH$ | 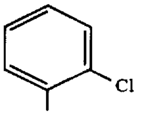 | —NHCONH— | 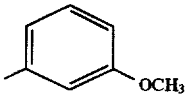 |
| 173 | $C_2H_5$ | H | $CH_3$ | 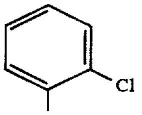 | —NHCO— | 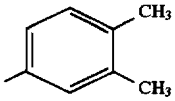 |

TABLE I-7-continued
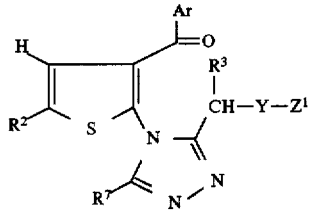
| Example No. | $R^2$ | $R^3$ | $R^7$ | Ar | Y | $Z^1$ |
|---|---|---|---|---|---|---|
| 174 | $C_2H_5$ | H | $CH_3$ | 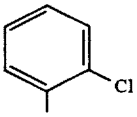 | $-NHCO-$ | 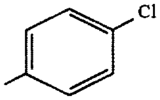 |
TABLE I-8
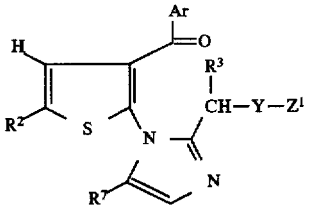
| Example No. | $R^2$ | $R^3$ | $R^7$ | Ar | Y | $Z^1$ |
|---|---|---|---|---|---|---|
| 81 | $C_2H_5$ | H | H | 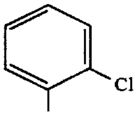 | $-NHCO-$ | 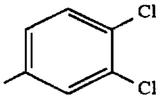 |
| 82 | $C_2H_5$ | H | H | 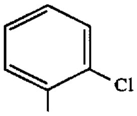 | $-NHCO-$ | 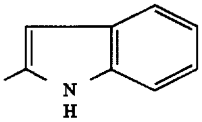 |
| 83 | $C_2H_5$ | H | H | 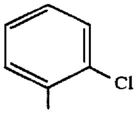 | $-NHCO-$ | 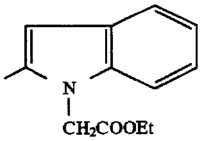 |
| 84 | $C_2H_5$ | H | H | 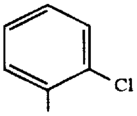 | $-NHCO-$ | 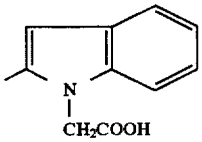 |
| 85 | $C_2H_5$ | H | H | 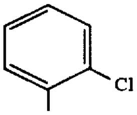 | $-NHCONH-$ | 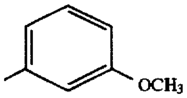 |
| 86 | $C_2H_5$ | H | H | 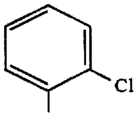 | $-NHCONH-$ | 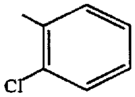 |

TABLE I-8-continued
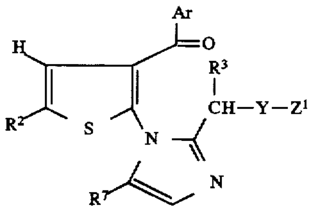
| Example No. | $R^2$ | $R^3$ | $R^7$ | Ar | Y | $Z^1$ |
|---|---|---|---|---|---|---|
| 87 | $C_2H_5$ | H | H | 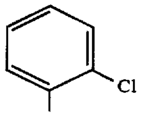 | $-NHCONH-$ | 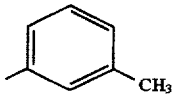 |
TABLE I-9
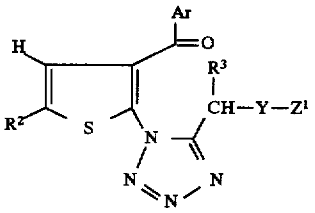
| Example No. | $R^2$ | $R^3$ | Ar | Y | $Z^1$ |
|---|---|---|---|---|---|
| 88 | $C_2H_5$ | H | 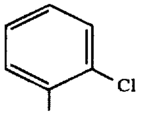 | $-NHCO-$ | 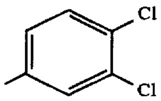 |
| 89 | $C_2H_5$ | H | 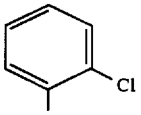 | $-NHCO-$ | 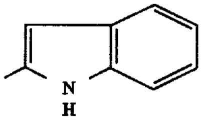 |
| 90 | $C_2H_5$ | H | 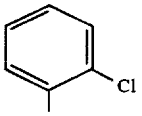 | $-NHCO-$ | 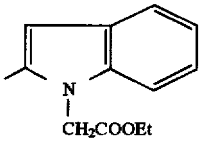 |
| 91 | $C_2H_5$ | H | 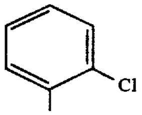 | $-NHCO-$ | 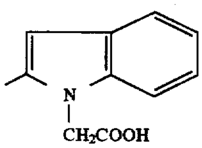 |
| 92 | $C_2H_5$ | H | 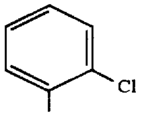 | $-NHCONH-$ | 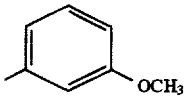 |
| 93 | $C_2H_5$ | H | 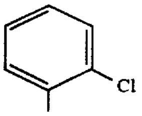 | $-NHCONH-$ | 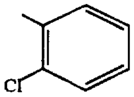 |

TABLE I-9-continued
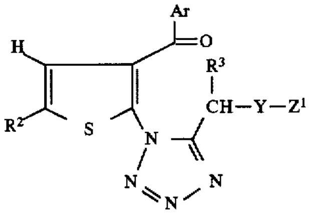
| Example No. | $R^2$ | $R^3$ | Ar | Y | $Z^1$ |
|---|---|---|---|---|---|
| 94 | $C_2H_5$ | H | 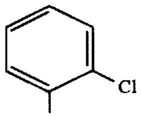 | —NHCONH— | 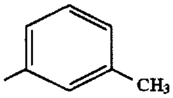 |
TABLE I-10
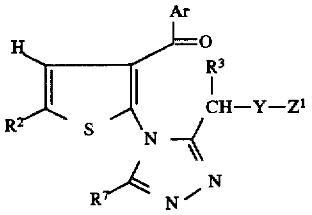
| Example No. | $R^2$ | $R^3$ | $R^7$ | Ar | Y | $Z^1$ |
|---|---|---|---|---|---|---|
| 175 | $C_2H_5$ | H | $CH_3$ | 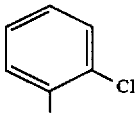 | —NHCO— | 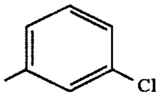 |
| 176 | $C_2H_5$ | H | $CH_3$ | 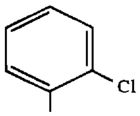 | —NHCO— | 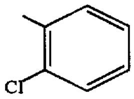 |
| 177 | $C_2H_5$ | H | $CH_3$ | 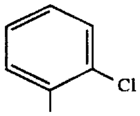 | —NHCO— | 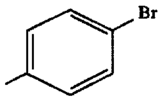 |
| 178 | $C_2H_5$ | H | $CH_3$ | 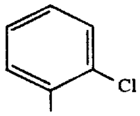 | —NHCO— | 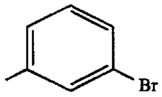 |
| 179 | $C_2H_5$ | H | $CH_3$ | 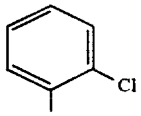 | —NHCO— | 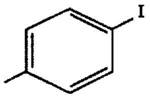 |
| 180 | $C_2H_5$ | H | $CH_3$ | 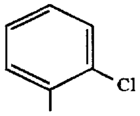 | —NHCO— | 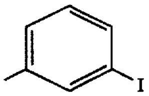 |

TABLE I-10-continued
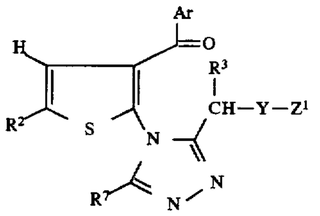
| Example No. | $R^2$ | $R^3$ | $R^7$ | Ar | Y | $Z^1$ |
|---|---|---|---|---|---|---|
| 181 | $C_2H_5$ | H | $CH_3$ | 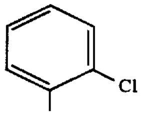 | −NHCO− | 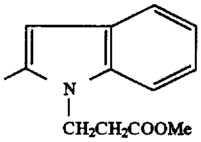 |
| 182 | $C_2H_5$ | H | $CH_3$ | 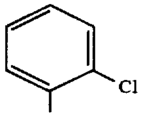 | −NHCO− | 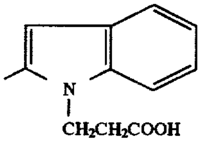 |
| 183 | $C_2H_5$ | H | $CH_3$ | 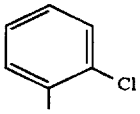 | −NHCO− | 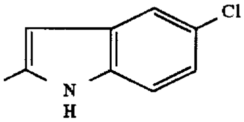 |
| 184 | $C_2H_5$ | H | $CH_3$ | 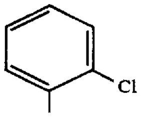 | −NHCO− | 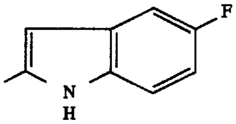 |
TABLE I-11
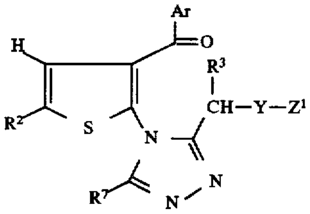
| Example No. | $R^2$ | $R^3$ | $R^7$ | Ar | Y | $Z^1$ |
|---|---|---|---|---|---|---|
| 185 | $C_2H_5$ | H | $CH_3$ | 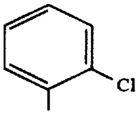 | −NHCO− | 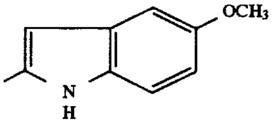 |
| 186 | $C_2H_5$ | H | $CH_3$ | 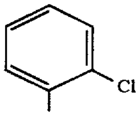 | −NHCO− | 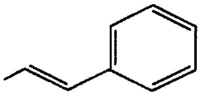 |
| 187 | $C_2H_5$ | H | $CH_3$ | 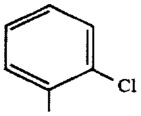 | −NHCO− | 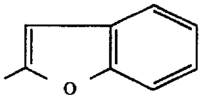 |

TABLE I-11-continued
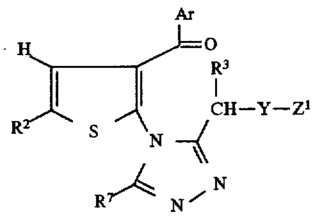
| Example No. | $R^2$ | $R^3$ | $R^7$ | Ar | Y | $Z^1$ |
|---|---|---|---|---|---|---|
| 188 | $C_2H_5$ | H | $CH_3$ | 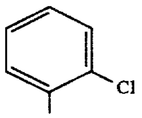 | —NHCO— | 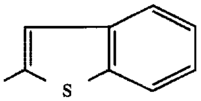 |
| 189 | $C_2H_5$ | H | $CH_3$ | 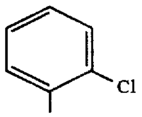 | —NHCONH— | 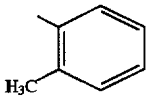 |
| 190 | $C_2H_5$ | H | $CH_3$ | 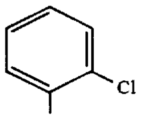 | —NHCONH— | 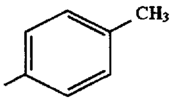 |
| 191 | $C_2H_5$ | H | $CH_3$ | 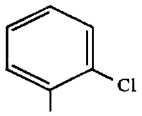 | —NHCONH— | 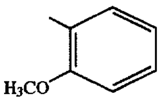 |
| 192 | $C_2H_5$ | H | $CH_3$ | 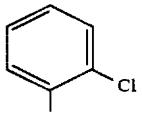 | —NHCONH— | 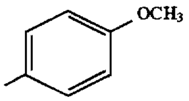 |
| 193 | $C_2H_5$ | H | $CH_3$ | 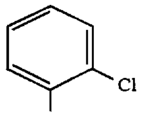 | —NHCONH— | 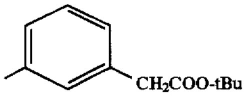 |
| 194 | $C_2H_5$ | H | $CH_3$ | 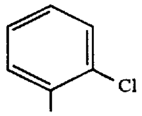 | —NHCONH— | 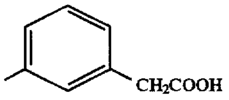 |

TABLE I-12
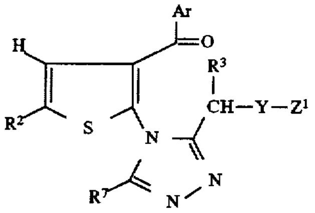
| Example No. | $R^2$ | $R^3$ | $R^7$ | Ar | Y | $Z^1$ |
|---|---|---|---|---|---|---|
| 195 | $C_2H_5$ | H | $CH_3$ | 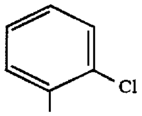 | $-NHSO_2-$ | 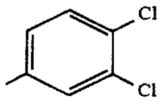 |
| 196 | $C_2H_5$ | H | $CH_3$ | 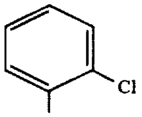 | $-NHCSNH$ | 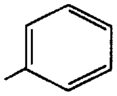 |
| 197 | $CH_3$ | H | $CH_3$ | 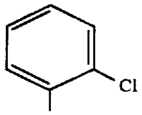 | $-NHCO-$ | 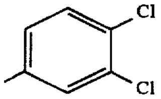 |
| 198 | $CH_3$ | H | $CH_3$ | 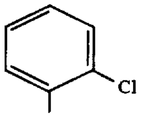 | $-NHCO-$ | 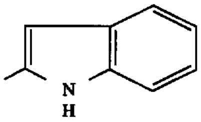 |
| 199 | $CH_3$ | H | $CH_3$ | 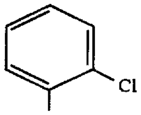 | $-NHCO-$ | 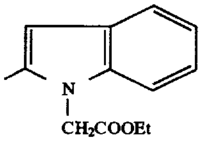 |
| 200 | $CH_3$ | H | $CH_3$ | 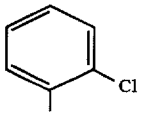 | $-NHCO-$ | 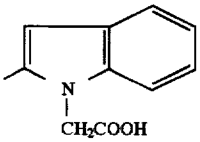 |
| 201 | $CH_3$ | H | $CH_3$ | 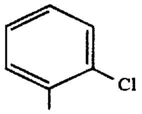 | $-NHCONH-$ | 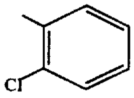 |
| 202 | $CH_3$ | H | $CH_3$ | 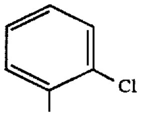 | $-NHCONH-$ | 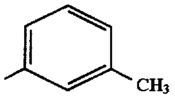 |
| 203 | $CH_3$ | H | $CH_3$ | 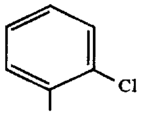 | $-NHCONH-$ | 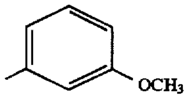 |

TABLE I-12-continued
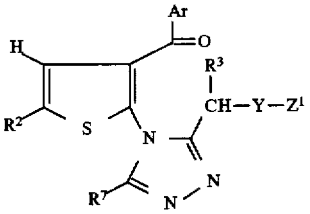
| Example No. | $R^2$ | $R^3$ | $R^7$ | Ar | Y | $Z^1$ |
|---|---|---|---|---|---|---|
| 204 | H | H | $CH_3$ | 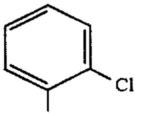 | —NHCO— | 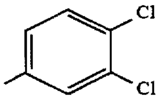 |
TABLE I-13
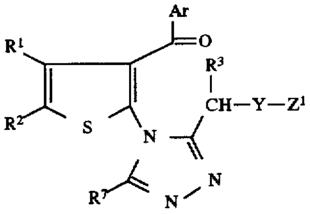
| Example No. | $R^1$ | $R^2$ | $R^3$ | $R^7$ | Ar | Y | $Z^1$ |
|---|---|---|---|---|---|---|---|
| 205 | H | H | H | $CH_3$ | 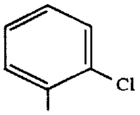 | —NHCO— | 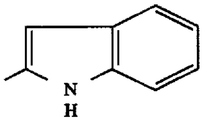 |
| 206 | H | H | H | $CH_3$ | 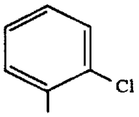 | —NHCO— | 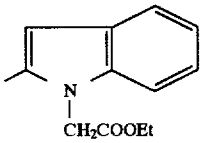 |
| 207 | H | H | H | $CH_3$ | 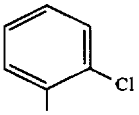 | —NHCO— | 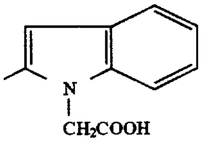 |
| 208 | H | H | H | $CH_3$ | 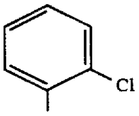 | —NHCONH— | 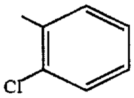 |
| 209 | H | H | H | $CH_3$ | 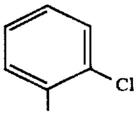 | —NHCONH— | 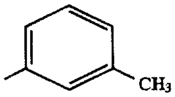 |
| 210 | H | H | H | $CH_3$ | 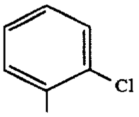 | —NHCONH— | 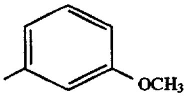 |

TABLE I-13-continued
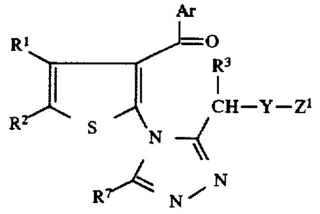
| Example No. | $R^1$ | $R^2$ | $R^3$ | $R^7$ | Ar | Y | $Z^1$ |
|---|---|---|---|---|---|---|---|
| 211 | $CH_3$ | $CH_3$ | H | $CH_3$ | 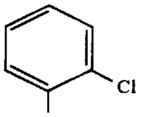 | —NHCO— | 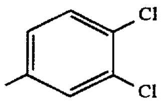 |
| 212 | $CH_3$ | $CH_3$ | H | $CH_3$ | 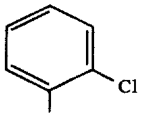 | —NHCO— | 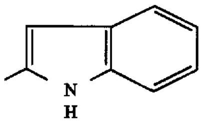 |
| 213 | $CH_3$ | $CH_3$ | H | $CH_3$ | 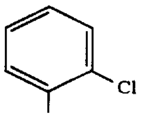 | —NHCO— | 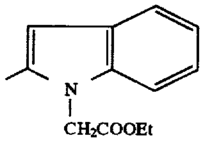 |
| 214 | $CH_3$ | $CH_3$ | H | $CH_3$ | 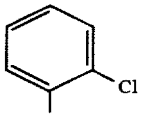 | —NHCO— | 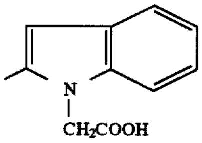 |
TABLE I-14
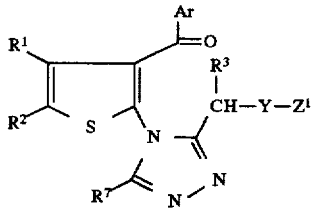
| Example No. | $R^1$ | $R^2$ | $R^3$ | $R^7$ | Ar | Y | $Z^1$ |
|---|---|---|---|---|---|---|---|
| 215 | $CH_3$ | $CH_3$ | H | $CH_3$ | 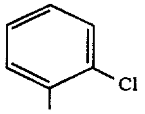 | —NHCONH— | 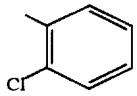 |
| 216 | $CH_3$ | $CH_3$ | H | $CH_3$ | 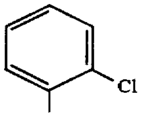 | —NHCONH— | 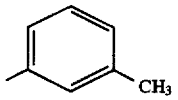 |
| 217 | $CH_3$ | $CH_3$ | H | $CH_3$ | 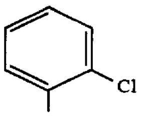 | —NHCONH— | 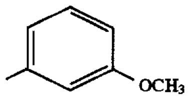 |

TABLE I-14-continued
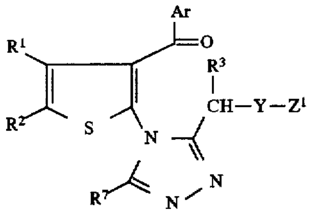
| Example No. | $R^1$ | $R^2$ | $R^3$ | $R^7$ | Ar | Y | $Z^1$ |
|---|---|---|---|---|---|---|---|
| 218 | H | $C_2H_5$ | H | $CH_3$ | 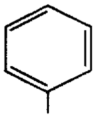 | $-NHCO-$ | 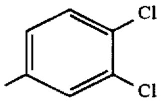 |
| 219 | H | $C_2H_5$ | H | $CH_3$ | 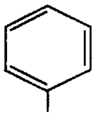 | $-NHCO-$ | 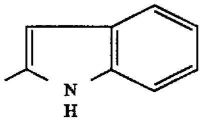 |
| 220 | H | $C_2H_5$ | H | $CH_3$ | 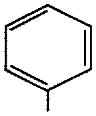 | $-NHCO-$ | 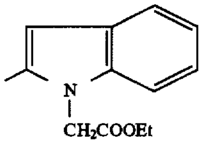 |
| 221 | H | $C_2H_5$ | H | $CH_3$ | 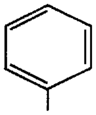 | $-NHCO-$ | 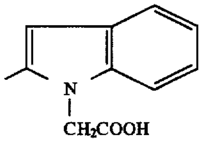 |
| 222 | H | $C_2H_5$ | H | $CH_3$ | 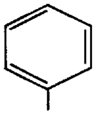 | $-NHCONH-$ | 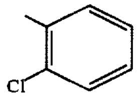 |
| 223 | H | $C_2H_5$ | H | $CH_3$ | 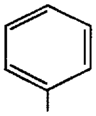 | $-NHCONH-$ | 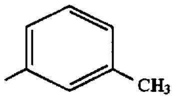 |
| 224 | H | $C_2H_5$ | H | $CH_3$ | 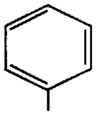 | $-NHCONH-$ | 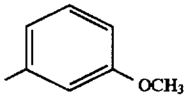 |

TABLE I-15
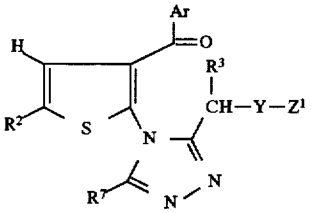
| Example No. | $R^2$ | $R^3$ | $R^7$ | Ar | Y | $Z^1$ |
|---|---|---|---|---|---|---|
| 225 | $C_2H_5$ | H | $CH_3$ | 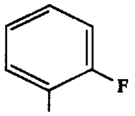 | —NHCO— | 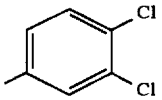 |
| 226 | $C_2H_5$ | H | $CH_3$ | 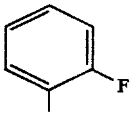 | —NHCO— | 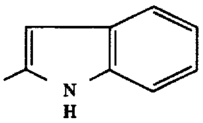 |
| 227 | $C_2H_5$ | H | $CH_3$ | 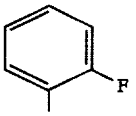 | —NHCO— | 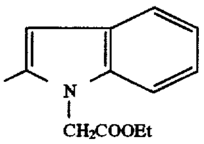 |
| 228 | $C_2H_5$ | H | $CH_3$ | 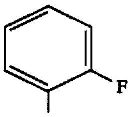 | —NHCO— | 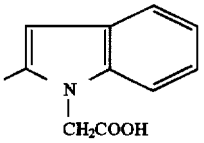 |
| 229 | $C_2H_5$ | H | $CH_3$ | 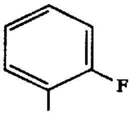 | —NHCONH— | 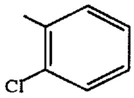 |
| 230 | $C_2H_5$ | H | $CH_3$ | 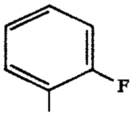 | —NHCONH— | 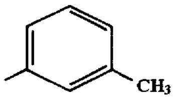 |
| 231 | $C_2H_5$ | H | $CH_3$ | 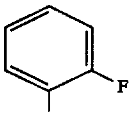 | —NHCONH— | 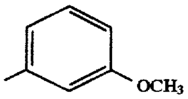 |
| 232 | $C_2H_5$ | H | $CH_2N(Me)_2$ | 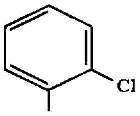 | —NHCO— | 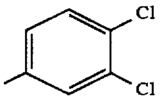 |
| 233 | $C_2H_5$ | H | $CH_2N(Me)_2$ | 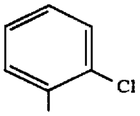 | —NHCO— | 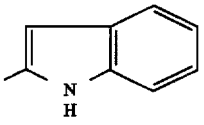 |

TABLE I-15-continued
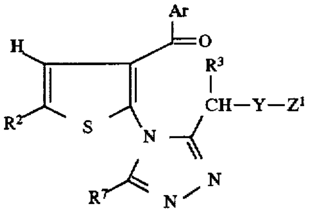
| Example No. | $R^2$ | $R^3$ | $R^7$ | Ar | Y | $Z^1$ |
|---|---|---|---|---|---|---|
| 234 | $C_2H_5$ | H | $CH_2N(Me)_2$ | 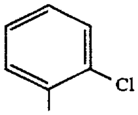 | —NHCO— | 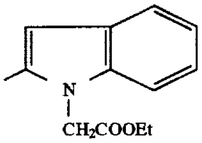 |
TABLE I-16
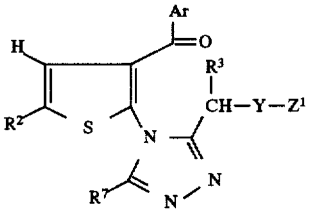
| Example No. | $R^2$ | $R^3$ | $R^7$ | Ar | Y | $Z^1$ |
|---|---|---|---|---|---|---|
| 235 | $C_2H_5$ | H | $CH_2N(Me)_2$ | 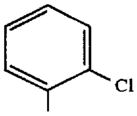 | —NHCO— | 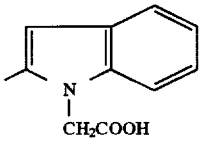 |
| 236 | $C_2H_5$ | H | $CH_2N(Me)_2$ | 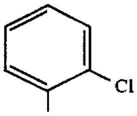 | —NHCONH— | 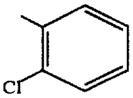 |
| 237 | $C_2H_5$ | H | $CH_2N(Me)_2$ | 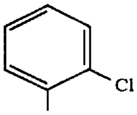 | —NHCONH— | 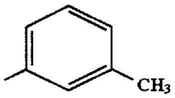 |
| 238 | $C_2H_5$ | H | $CH_2N(Me)_2$ | 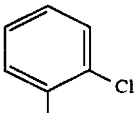 | —NHCONH— | 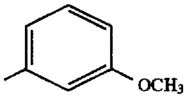 |
| 239 | $C_2H_5$ | H | $CH(CH_3)_2$ | 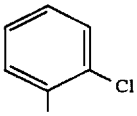 | —NHCO— | 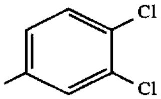 |
| 240 | $C_2H_5$ | H | $CH(CH_3)_2$ | 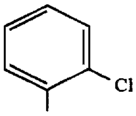 | —NHCO— | 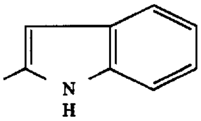 |

TABLE I-16-continued
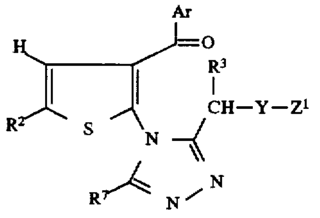
| Example No. | $R^2$ | $R^3$ | $R^7$ | Ar | Y | $Z^1$ |
|---|---|---|---|---|---|---|
| 241 | $C_2H_5$ | H | $CH(CH_3)_2$ | 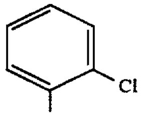 | −NHCO− | 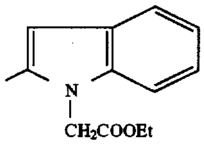 |
| 242 | $C_2H_5$ | H | $CH(CH_3)_2$ | 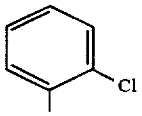 | −NHCO− | 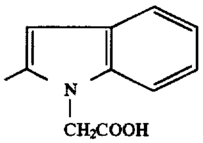 |
| 243 | $C_2H_5$ | H | $CH(CH_3)_2$ | 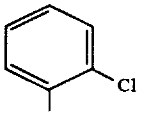 | −NHCONH− | 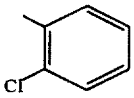 |
| 244 | $C_2H_5$ | H | $CH(CH_3)_2$ | 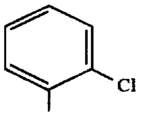 | −NHCONH− | 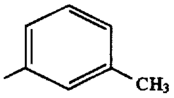 |
TABLE I-17
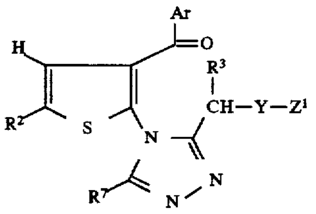
| Example No. | $R^2$ | $R^3$ | $R^7$ | Ar | Y | $Z^1$ |
|---|---|---|---|---|---|---|
| 245 | $C_2H_5$ | H | $CH(CH_3)_2$ | 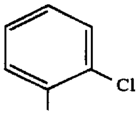 | −NHCONH− | 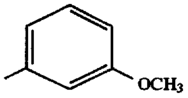 |
| 246 | COOEt | H | $CH_3$ | 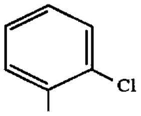 | −NHCO− | 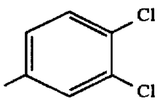 |
| 247 | COOEt | H | $CH_3$ | 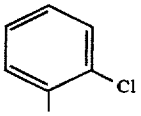 | −NHCO− | 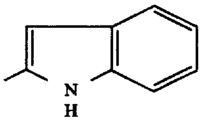 |

TABLE I-17-continued
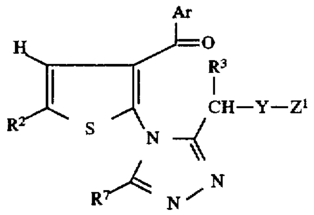
| Example No. | $R^2$ | $R^3$ | $R^7$ | Ar | Y | $Z^1$ |
|---|---|---|---|---|---|---|
| 248 | COOEt | H | $CH_3$ | 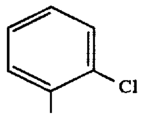 | −NHCONH− | 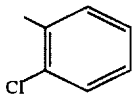 |
| 249 | COOEt | H | $CH_3$ | 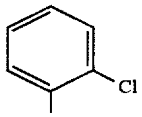 | −NHCONH− | 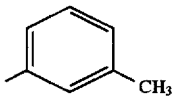 |
| 250 | COOEt | H | $CH_3$ | 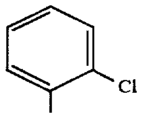 | −NHCONH− | 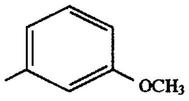 |
| 251 | COOH | H | $CH_3$ | 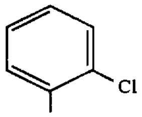 | −NHCO− | 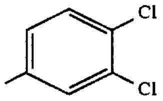 |
| 252 | COOH | H | $CH_3$ | 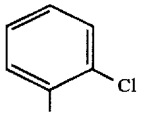 | −NHCO− | 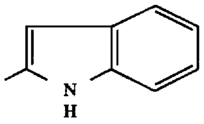 |
| 253 | COOH | H | $CH_3$ | 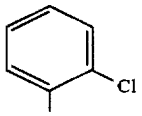 | −NHCONH− | 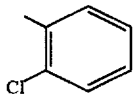 |
| 254 | COOH | H | $CH_3$ | 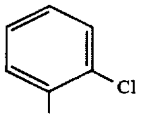 | −NHCONH− | 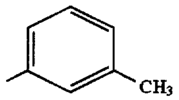 |

TABLE I-18
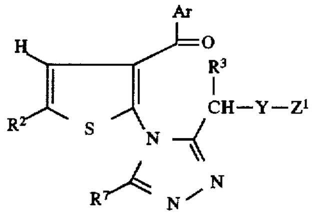
| Example No. | $R^2$ | $R^3$ | $R^7$ | Ar | Y | $Z^1$ |
|---|---|---|---|---|---|---|
| 255 | COOH | H | $CH_3$ | 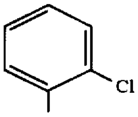 | −NHCONH− | 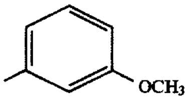 |
| 256 | $CH_2COOMe$ | H | $CH_3$ | 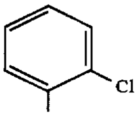 | −NHCO− | 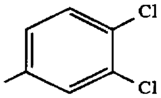 |
| 257 | $CH_2COOMe$ | H | $CH_3$ | 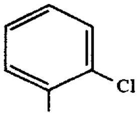 | −NHCO− | 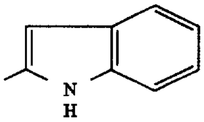 |
| 258 | $CH_2COOMe$ | H | $CH_3$ | 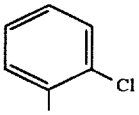 | −NHCONH− | 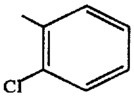 |
| 259 | $CH_2COOMe$ | H | $CH_3$ | 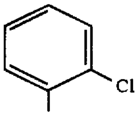 | −NHCONH− | 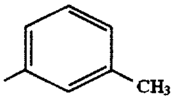 |
| 260 | $CH_2COOMe$ | H | $CH_3$ | 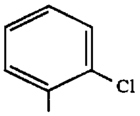 | −NHCONH− | 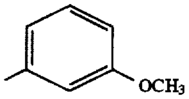 |
| 261 | $CH_2COOH$ | H | $CH_3$ | 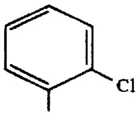 | −NHCO− | 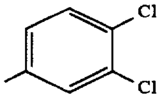 |
| 262 | $CH_2COOH$ | H | $CH_3$ | 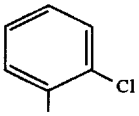 | −NHCO− | 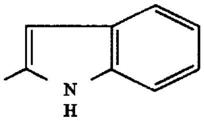 |
| 263 | $CH_2COOH$ | H | $CH_3$ | 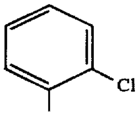 | −NHCONH− | 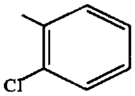 |
| 264 | $CH_2COOH$ | H | $CH_3$ | 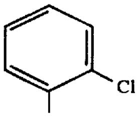 | −NHCONH− | 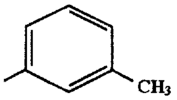 |

TABLE I-19
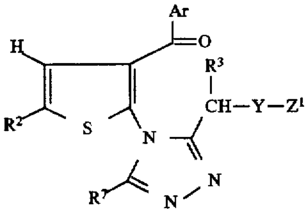
| Example No. | $R^2$ | $R^3$ | $R^7$ | Ar | Y | $Z^1$ |
|---|---|---|---|---|---|---|
| 265 | $CH_2COOH$ | H | $CH_3$ | 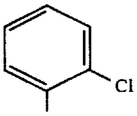 | —NHCONH— | 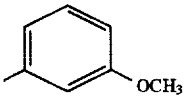 |
| 267 | * | H | $CH_3$ | 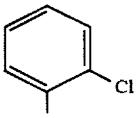 | —NHCO— | 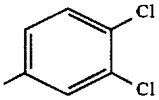 |
| 287 | $C_2H_5$ | H | $CH_3$ | 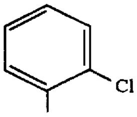 | —NHCONH— | 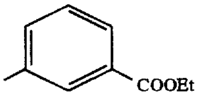 |
| 288 | $C_2H_5$ | H | $CH_3$ | 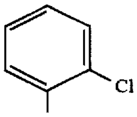 | —NHCONH— | 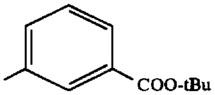 |
| 289 | $C_2H_5$ | H | $CH_3$ | 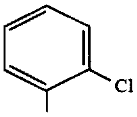 | —NHCONH— | 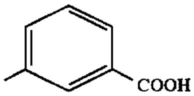 |
| 290 | $C_2H_5$ | H | $CH_3$ | 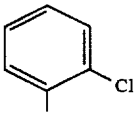 | —NHCO— | 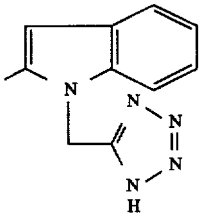 |
| 291 | $C_2H_5$ | H | $CH_3$ | 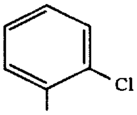 | —NHCONH— | 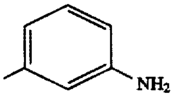 |
| 292 | $C_2H_5$ | H | $CH_3$ | 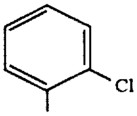 | —NHCONH— | 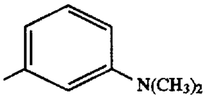 |
* 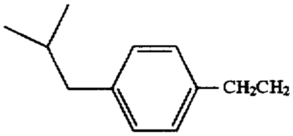

TABLE I-20
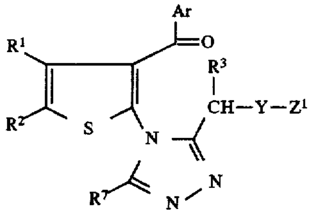
| Example No. | $R^1$ | $R^2$ | $R^3$ | $R^7$ | Ar | Y | $Z^1$ |
|---|---|---|---|---|---|---|---|
| 293 | H | $C_2H_5$ | H | $CH_3$ | 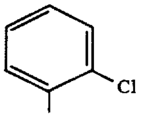 | —NHCONH— | 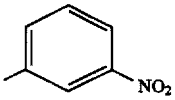 |
| 294 | $CH_3$ | $CH_3$ | H | $CH_3$ | 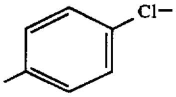 | —NHCONH— | 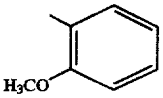 |
| 295 | H | $CH_3$ | H | $CH_3$ | 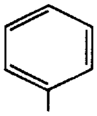 | —NHCO— | 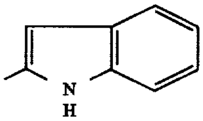 |
| 296 | H | $C_2H_5$ | H | $CH_3$ | 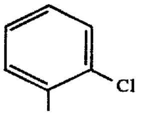 | —NHCO— | 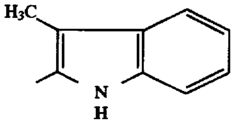 |
| 297 | H | $C_2H_5$ | H | $CH_3$ | 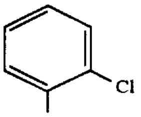 | —NHCO— | 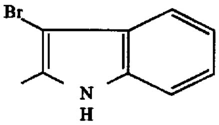 |
| 298 | H | $C_2H_5$ | H | $CH_3$ | 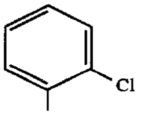 | —NHCO— | 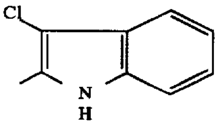 |
| 299 | H | $C_2H_5$ | H | $CH_3$ | 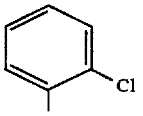 | —NHCO— | 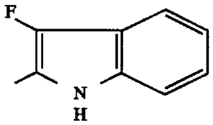 |
| 300 | H | $C_2H_5$ | H | $CH_3$ | 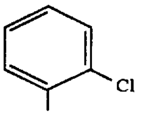 | —NHCO— | 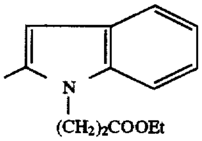 |
| 301 | H | $C_2H_5$ | H | $CH_3$ | 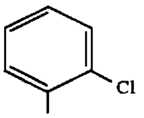 | —NHCO— | 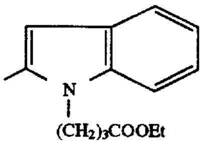 |

TABLE I-20-continued
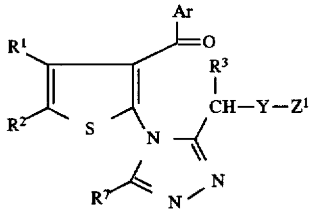
| Example No. | $R^1$ | $R^2$ | $R^3$ | $R^7$ | Ar | Y | $Z^1$ |
|---|---|---|---|---|---|---|---|
| 302 | H | $C_2H_5$ | H | $CH_3$ | 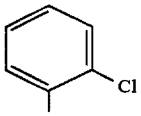 | —NHCO— | 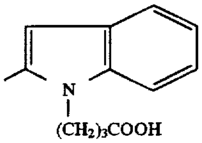 |
TABLE I-21
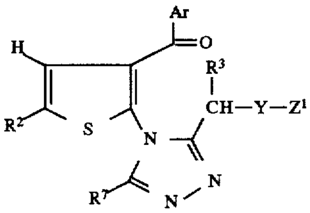
| Example No. | $R^2$ | $R^3$ | $R^7$ | Ar | Y | $Z^1$ |
|---|---|---|---|---|---|---|
| 303 | $C_2H_5$ | H | $CH_3$ | 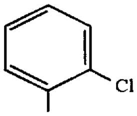 | —NHCO— | 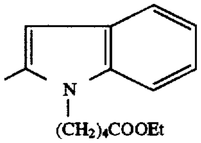 |
| 304 | $C_2H_5$ | H | $CH_3$ | 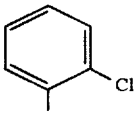 | —NHCO— | 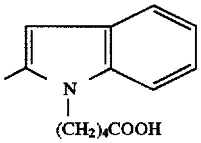 |
| 305 | $C_2H_5$ | H | $CH_3$ | 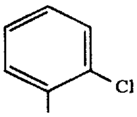 | —NHCO— | 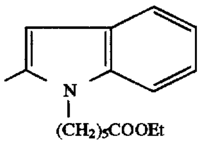 |
| 306 | $C_2H_5$ | H | $CH_3$ | 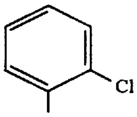 | —NHCO— | 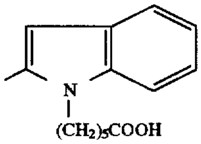 |
| 307 | $C_2H_5$ | H | $CH_3$ | 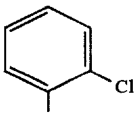 | —NHCO— | 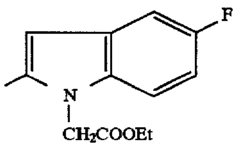 |

TABLE I-21-continued
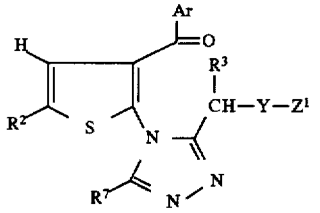
| Example No. | $R^2$ | $R^3$ | $R^7$ | Ar | Y | $Z^1$ |
|---|---|---|---|---|---|---|
| 308 | $C_2H_5$ | H | $CH_3$ | 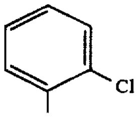 | —NHCO— | 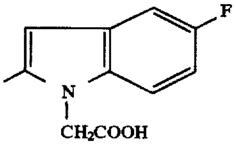 |
| 309 | $C_2H_5$ | H | $CH_3$ | 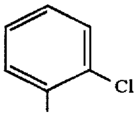 | —NHCO— | 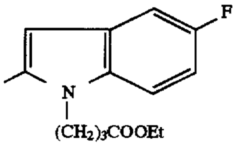 |
| 310 | $C_2H_5$ | H | $CH_3$ | 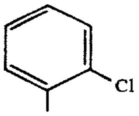 | —NHCO— | 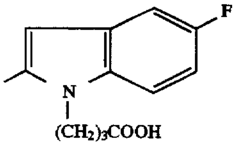 |
| 311 | $C_2H_5$ | H | $CH_3$ | 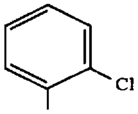 | —NHCO— | 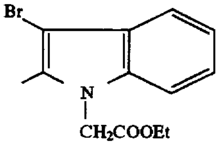 |
| 312 | $C_2H_5$ | H | $CH_3$ | 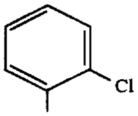 | —NHCO— | 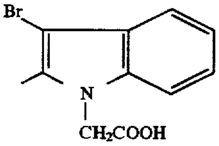 |
TABLE I-22
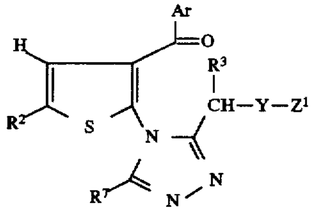
| Example No. | $R^2$ | $R^3$ | $R^7$ | Ar | Y | $Z^1$ |
|---|---|---|---|---|---|---|
| 313 | $C_2H_5$ | H | $CH_3$ | 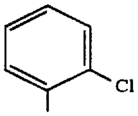 | —NHCO— | 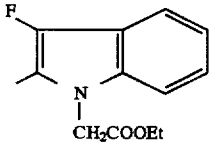 |

TABLE I-22-continued
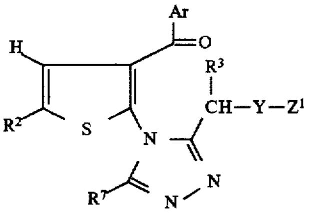
| Example No. | $R^2$ | $R^3$ | $R^7$ | Ar | Y | $Z^1$ |
| --- | --- | --- | --- | --- | --- | --- |
| 314 | $C_2H_5$ | H | $CH_3$ | 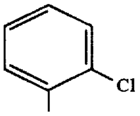 | −NHCO− | 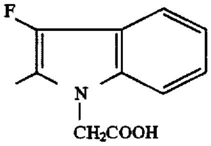 |
| 315 | $C_2H_5$ | H | Cl | 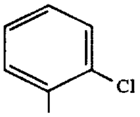 | −NHCO− | 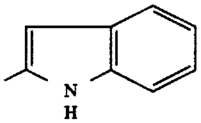 |
| 316 | $C_2H_5$ | H | Cl | 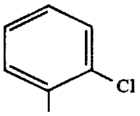 | −NHCO− | 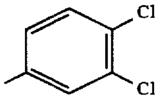 |
| 317 | $C_2H_5$ | H | Cl | 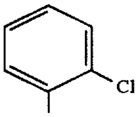 | −NHCO− | 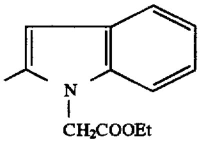 |
| 318 | $C_2H_5$ | H | Cl | 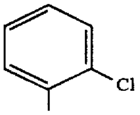 | −NHCO− | 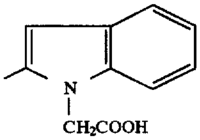 |
| 319 | $C_2H_5$ | H | $CH_3$ | 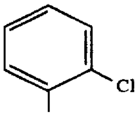 | −NHCO− | 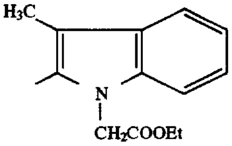 |
| 320 | $C_2H_5$ | H | $CH_3$ | 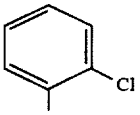 | −NHCO− | 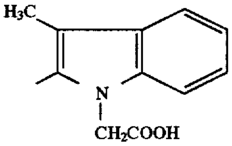 |
| 321 | $C_2H_5$ | H | $CH_3$ | 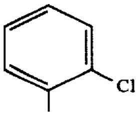 | −NHCO− | 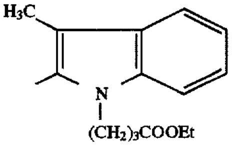 |

TABLE I-22-continued
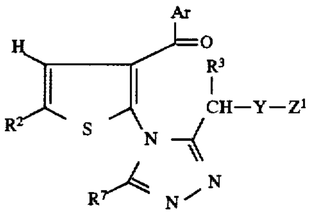
| Example No. | $R^2$ | $R^3$ | $R^7$ | Ar | Y | $Z^1$ |
|---|---|---|---|---|---|---|
| 322 | $C_2H_5$ | H | $CH_3$ | 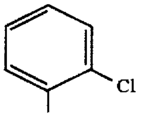 | $-NHCO-$ | 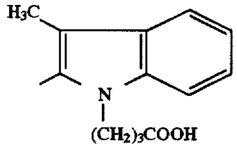 |
TABLE I-23
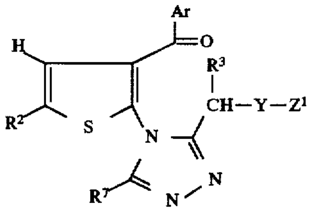
| Example No. | $R^2$ | $R^3$ | $R^7$ | Ar | Y | $Z^1$ |
|---|---|---|---|---|---|---|
| 323 | $C_2H_5$ | $CH_2COOEt$ | $CH_3$ | 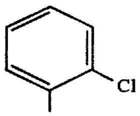 | $-NHCO-$ | 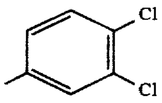 |
| 324 | $C_2H_5$ | $CH_2COOH$ | $CH_3$ | 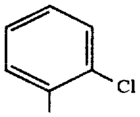 | $-NHCO-$ | 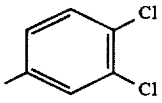 |
| 325 | $C_2H_5$ | $CH_2COOEt$ | $CH_3$ | 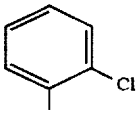 | $-NHCO-$ | 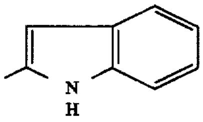 |
| 326 | $C_2H_5$ | $CH_2COOH$ | $CH_3$ | 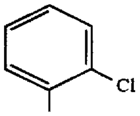 | $-NHCO-$ | 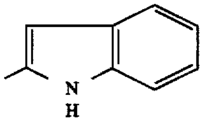 |
| 327 | $C_2H_5$ | $(CH_2)_2COOEt$ | $CH_3$ | 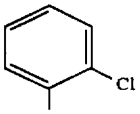 | $-NHCO-$ | 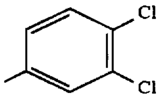 |
| 328 | $C_2H_5$ | $(CH_2)_2COOH$ | $CH_3$ | 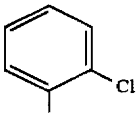 | $-NHCO-$ | 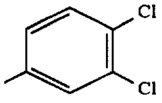 |

TABLE I-23-continued
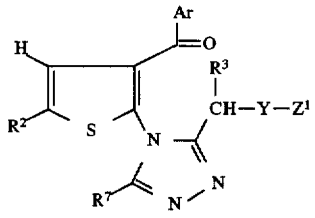
| Example No. | $R^2$ | $R^3$ | $R^7$ | Ar | Y | $Z^1$ |
|---|---|---|---|---|---|---|
| 329 | $C_2H_5$ | $(CH_2)_2COOEt$ | $CH_3$ | 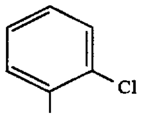 | $-NHCO-$ | 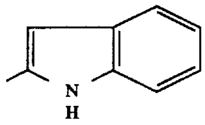 |
| 330 | $C_2H_5$ | $(CH_2)_2COOH$ | $CH_3$ | 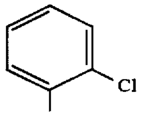 | $-NHCO-$ | 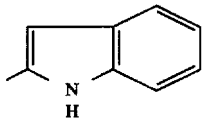 |
| 331 | $C_2H_5$ | H | $CH_3$ | 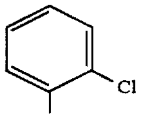 | $-NHCO-$ | 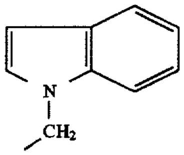 |
| 332 | $C_2H_5$ | H | $CH_3$ | 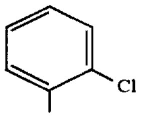 | $-NHCO-$ | 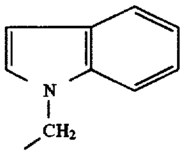 |
TABLE I-24
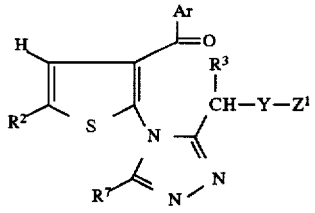
| Example No. | $R^2$ | $R^3$ | $R^7$ | Ar | Y | $Z^1$ |
|---|---|---|---|---|---|---|
| 333 | $C_2H_5$ | H | $CH_3$ | 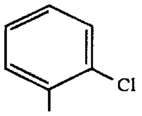 | $-NHCO-$ | 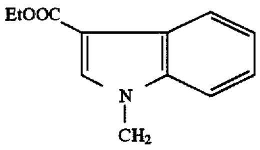 |
| 334 | $C_2H_5$ | H | $CH_3$ | 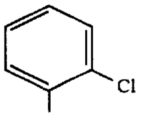 | $-NHCO-$ | 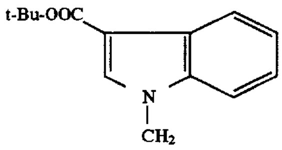 |

TABLE I-24-continued
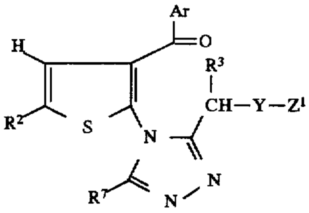
| Example No. | $R^2$ | $R^3$ | $R^7$ | Ar | Y | $Z^1$ |
|---|---|---|---|---|---|---|
| 335 | $C_2H_5$ | H | $CH_3$ | 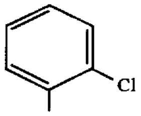 | $-NHCO-$ | 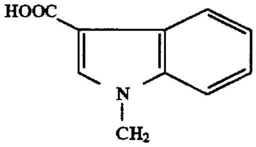 |
| 336 | $C_2H_5$ | H | $CH_3$ | 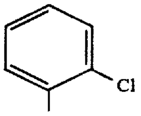 | $-NHCO-$ | 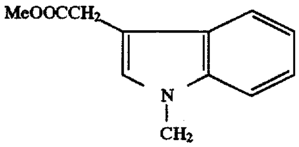 |
| 337 | $C_2H_5$ | H | $CH_3$ | 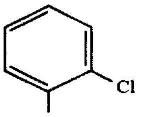 | $-NHCO-$ | 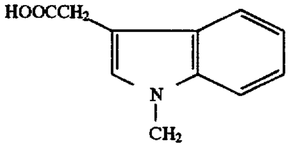 |
| 338 | $C_2H_5$ | H | $CH_3$ | 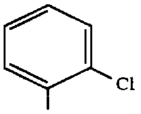 | $-NHCO-$ | 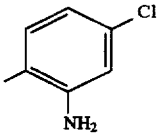 |
| 339 | $C_2H_5$ | H | $CH_3$ | 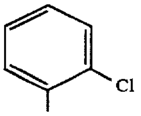 | $-NHCO-$ | 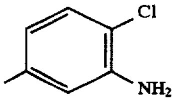 |
| 340 | $C_2H_5$ | H | $CH_3$ | 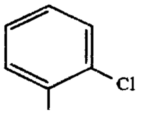 | $-NHCO-$ | 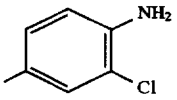 |
| 341 | $C_2H_5$ | H | $CH_3$ | 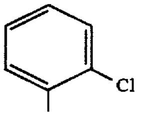 | $-NHCO-$ | 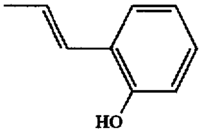 |
| 342 | $C_2H_5$ | H | $CH_3$ | 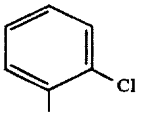 | $-NHCO-$ | 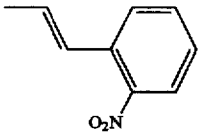 |

TABLE I-25
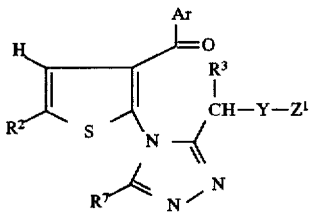
| Example No. | $R^2$ | $R^3$ | $R^7$ | Ar | Y | $Z^1$ |
|---|---|---|---|---|---|---|
| 343 | $C_2H_5$ | H | $CH_3$ | 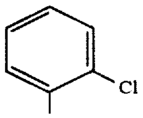 | —NHCO— | 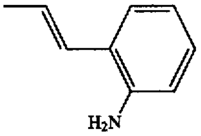 |
| 344 | $C_2H_5$ | H | 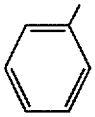 | 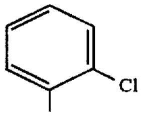 | —NHCO— | 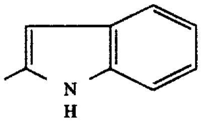 |
| 345 | $C_2H_5$ | H | 1-adamantyl | 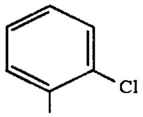 | —NHCO— | 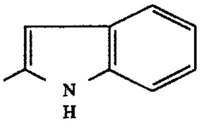 |
| 346 | $C_2H_5$ | H | $CH_3$ | 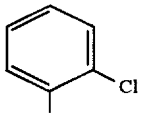 | —NHCO— | 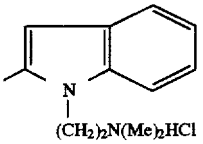 |
| 347 | $C_2H_5$ | H | $CH_3$ | 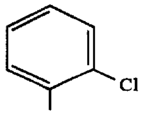 | —NHCO— | 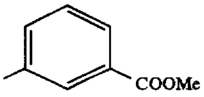 |
| 348 | $C_2H_5$ | H | $CH_3$ | 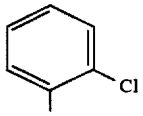 | —NHCO— | 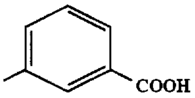 |
| 349 | $(CH_2)_2COOH$ | H | $CH_3$ | 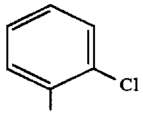 | —NHCO— | 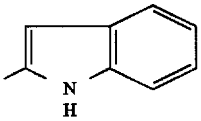 |

TABLE I-26
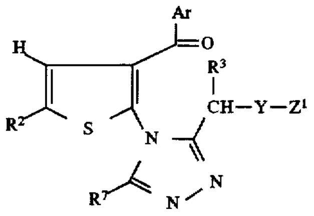
| Example No. | $R^2$ | $R^3$ | $R^7$ | Ar | Y | $Z^1$ |
|---|---|---|---|---|---|---|
| 368 | $C_3H_7$ | H | $CH_3$ | 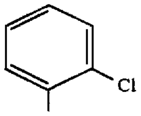 | −NHCO− | 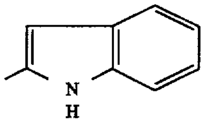 |
| 369 | $CH(CH_3)_2$ | H | $CH_3$ | 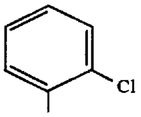 | −NHCO− | 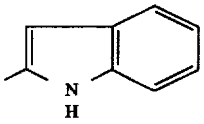 |
| 370 | 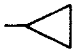 | H | $CH_3$ | 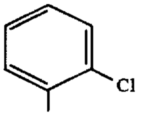 | −NHCO− | 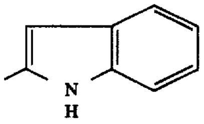 |
| 371 | $C_3H_7$ | H | $CH_3$ | 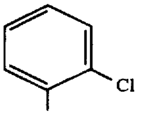 | −NHCONH− | 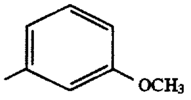 |
| 372 | $CH(CH_3)_2$ | H | $CH_3$ | 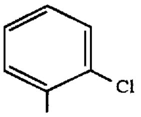 | −NHCONH− | 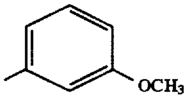 |
| 373 | 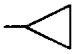 | H | $CH_3$ | 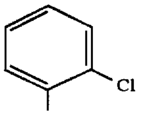 | −NHCONH− | 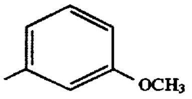 |
| 374 | COOH | H | $CH_3$ | 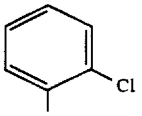 | −NHCONH− | 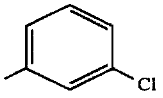 |

TABLE II-1
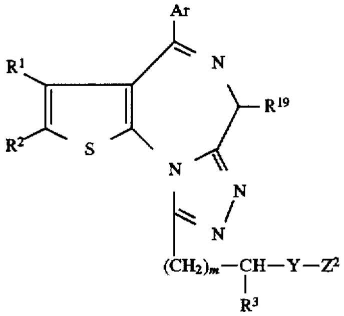
$R^1 = H$
$R^3 = H$
$R^{19} = H$
m = 0
| Example No. | $R^2$ | Ar | Y | $Z^2$ |
|---|---|---|---|---|
| 59 | $C_2H_5$ | 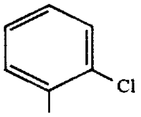 | $-NHCO-$ | 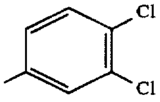 |
| 60 | $C_2H_5$ | 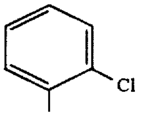 | $-NHCO-$ | 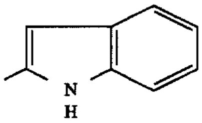 |
| 61 | $C_2H_5$ | 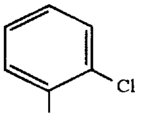 | $-NHCO-$ | 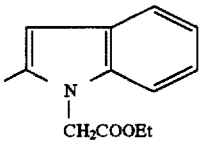 |
| 62 | $C_2H_5$ | 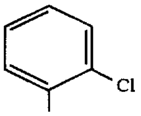 | $-NHCO-$ | 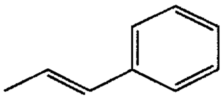 |
| 63 | $C_2H_5$ | 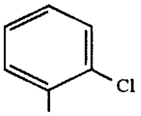 | $-NHCO-$ | 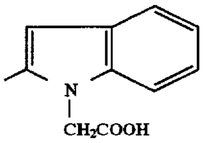 |
| 64 | $C_2H_5$ | 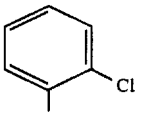 | $-NHCONH-$ | 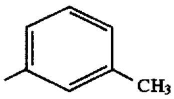 |
| 65 | $C_2H_5$ | 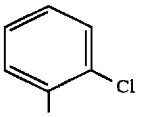 | $-NHCONH-$ | 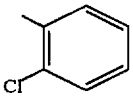 |
| 66 | $C_2H_5$ | 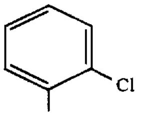 | $-NHCONH-$ | 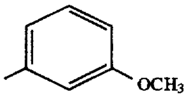 |
| 67 | $C_2H_5$ | 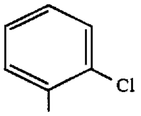 | $-NHCONH-$ | 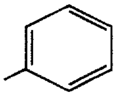 |

TABLE II-1-continued
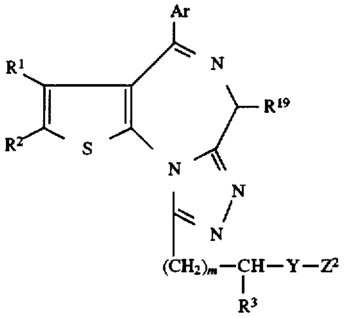
$R^1 = H$
$R^3 = H$
$R^{19} = H$
m = 0
| Example No. | $R^2$ | Ar | Y | $Z^2$ |
|---|---|---|---|---|
| 68 | $C_2H_5$ | 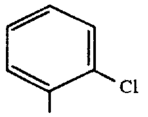 | −NHCONH− | 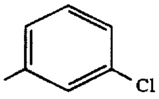 |
TABLE II-2
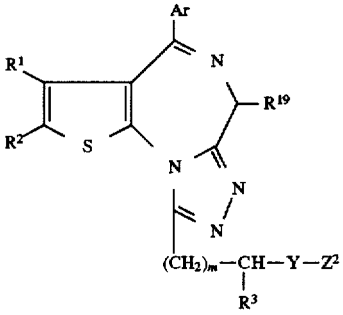
$R^1 = H$
$R^3 = H$
$R^{19} = H$
m = 0
| Example No. | $R^2$ | Ar | Y | $Z^2$ |
|---|---|---|---|---|
| 69 | $C_2H_5$ | 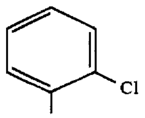 | −NHCONH− | 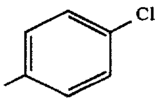 |
| 70 | $C_2H_5$ | 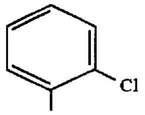 | −NHCONH− | 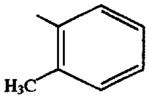 |
| 95 | $C_2H_5$ | 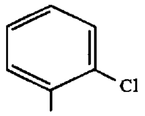 | −NHCO− | 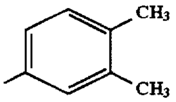 |
| 96 | $C_2H_5$ | 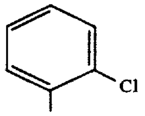 | −NHCO− | 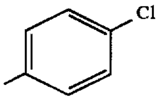 |
| 97 | $C_2H_5$ | 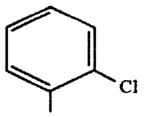 | −NHCO− | 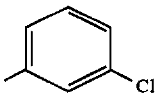 |

TABLE II-2-continued
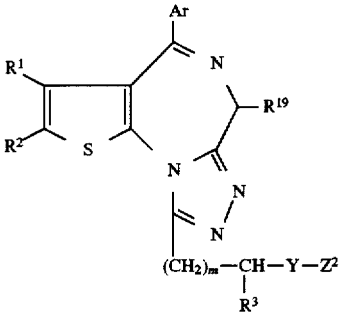
$R^1 = H$
$R^3 = H$
$R^{19} = H$
$m = 0$
| Example No. | $R^2$ | Ar | Y | $Z^2$ |
|---|---|---|---|---|
| 98 | $C_2H_5$ | 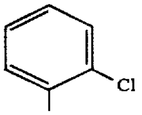 | —NHCO— | 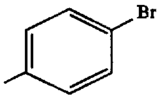 |
| 99 | $C_2H_5$ | 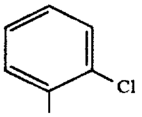 | —NHCO— | 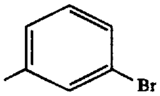 |
| 100 | $C_2H_5$ | 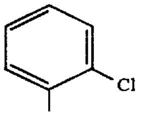 | —NHCO— | 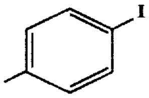 |
| 101 | $C_2H_5$ | 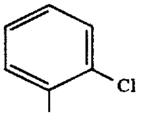 | —NHCO— | 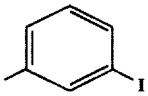 |
| 102 | $C_2H_5$ | 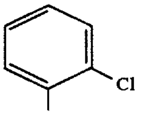 | —NHCO— | 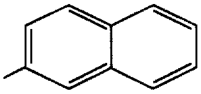 |

TABLE II-3
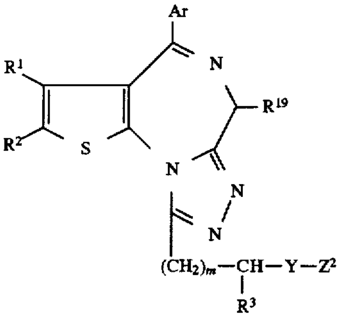
$R^1$ = H
$R^3$ = H
$R^{19}$ = H
m = 0
| Example No. | $R^2$ | Ar | Y | $Z^2$ |
|---|---|---|---|---|
| 103 | $C_2H_5$ | 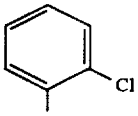 | −NHCO− | 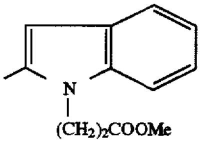 |
| 104 | $C_2H_5$ | 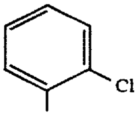 | −NHCO− | 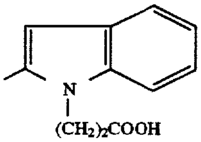 |
| 105 | $C_2H_5$ | 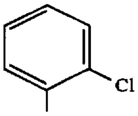 | −NHCO− | 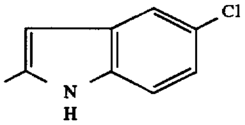 |
| 106 | $C_2H_5$ | 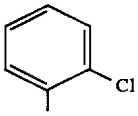 | −NHCO− | 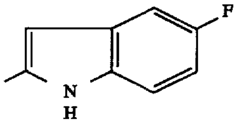 |
| 107 | $C_2H_5$ | 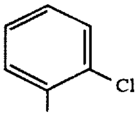 | −NHCO− | 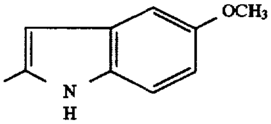 |
| 108 | $C_2H_5$ | 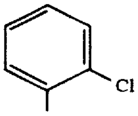 | −NHCO− | 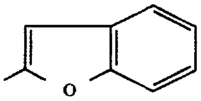 |
| 109 | $C_2H_5$ | 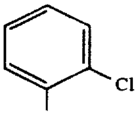 | −NHCO− | 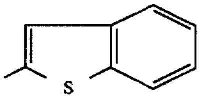 |
| 110 | $C_2H_5$ | 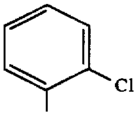 | −NHCONH− | 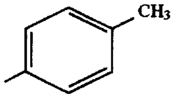 |
| 111 | $C_2H_5$ | 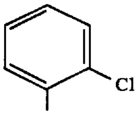 | −NHCONH− | 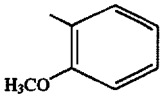 |

TABLE II-3-continued
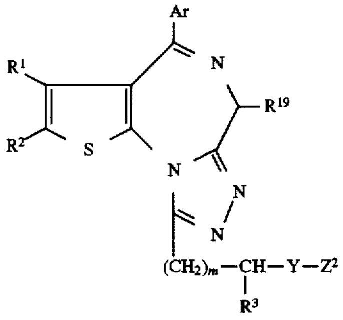
$R^1 = H$
$R^3 = H$
$R^{19} = H$
$m = 0$
| Example No. | $R^2$ | Ar | Y | $Z^2$ |
|---|---|---|---|---|
| 112 | $C_2H_5$ | 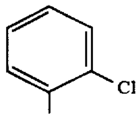 | $-NHCONH-$ | 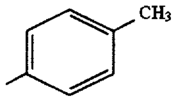 |
TABLE II-4
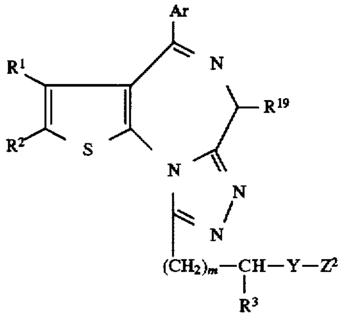
$R^1 = H$
$R^3 = H$
$R^{19} = H$
$m = 0$
| Example No. | $R^2$ | Ar | Y | $Z^2$ |
|---|---|---|---|---|
| 113 | $C_2H_5$ | 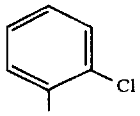 | $-NHCONH-$ | 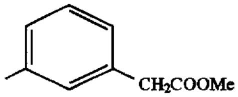 |
| 114 | $C_2H_5$ | 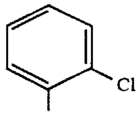 | $-NHCONH-$ | 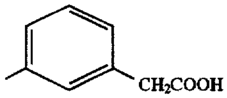 |
| 115 | $C_2H_5$ | 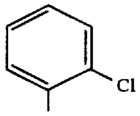 | $-NHSO_2-$ | 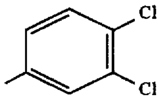 |
| 116 | $C_2H_5$ | 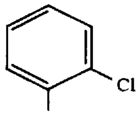 | $-NHSO_2-$ | 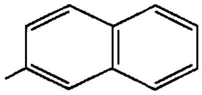 |
| 117 | $C_2H_5$ | 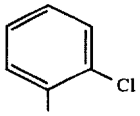 | $-NHCSNH-$ | 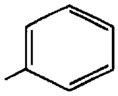 |

TABLE II-4-continued
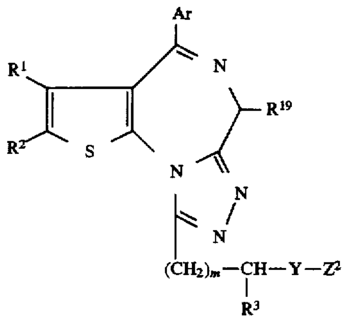
$R^1 = H$
$R^3 = H$
$R^{19} = H$
m = 0
| Example No. | $R^2$ | Ar | Y | $Z^2$ |
|---|---|---|---|---|
| 118 | H | 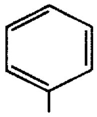 | —NHCO— | 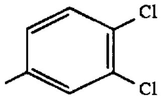 |
| 119 | H | 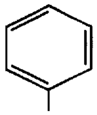 | —NHCO— | 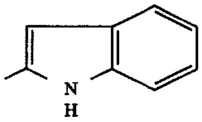 |
| 120 | H | 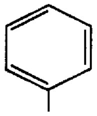 | —NHCO— | 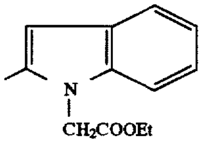 |
| 121 | H | 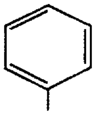 | —NHCO— | 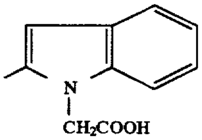 |
| 122 | H | 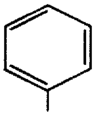 | —NHCONH— | 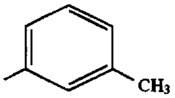 |

TABLE II-5
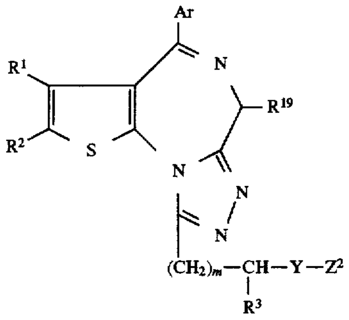
$R^1 = H$
$R^3 = H$
$R^{19} = H$
$m = 0$
| Example No. | $R^2$ | Ar | Y | $Z^2$ |
|---|---|---|---|---|
| 123 | H | 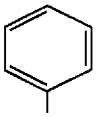 | —NHCONH— | 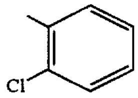 |
| 124 | H | 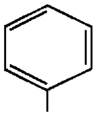 | —NHCONH— | 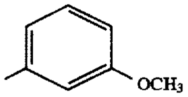 |
| 125 | $C_2H_5$ | 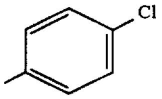 | —NHCO— | 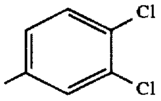 |
| 126 | $C_2H_5$ | 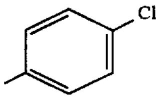 | —NHCO— | 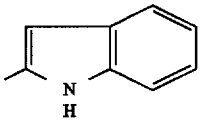 |
| 127 | $C_2H_5$ | 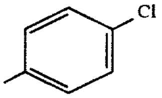 | —NHCO— | 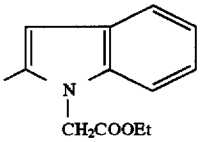 |
| 128 | $C_2H_5$ | 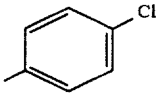 | —NHCO— | 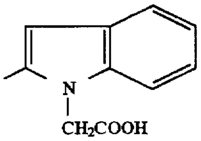 |
| 129 | $C_2H_5$ | 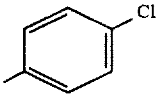 | —NHCONH— | 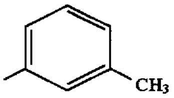 |
| 130 | $C_2H_5$ | 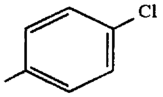 | —NHCONH— | 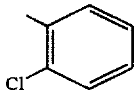 |
| 131 | $C_2H_5$ | 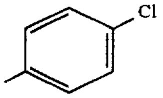 | —NHCONH— | 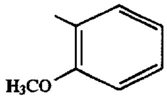 |

TABLE II-5-continued
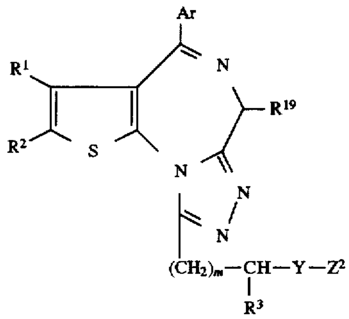
$R^1 = H$
$R^3 = H$
$R^{19} = H$
$m = 0$
| Example No. | $R^2$ | Ar | Y | $Z^2$ |
|---|---|---|---|---|
| 132 | $C_2H_5$ | 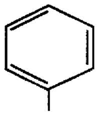 | $-NHCO-$ | 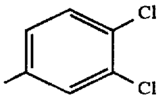 |
TABLE II-6
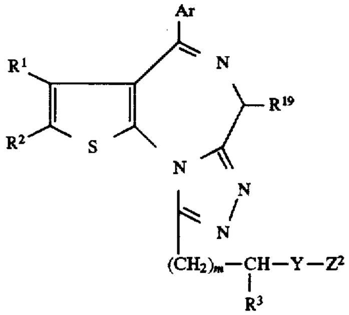
$R^1 = H$
$R^3 = H$
$R^{19} = H$
$m = 0$
| Example No. | $R^2$ | Ar | Y | $Z^2$ |
|---|---|---|---|---|
| 133 | $C_2H_5$ | 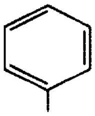 | $-NHCO-$ | 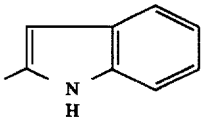 |
| 134 | $C_2H_5$ | 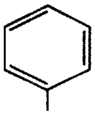 | $-NHCO-$ | 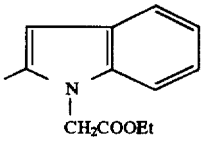 |
| 135 | $C_2H_5$ | 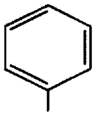 | $-NHCO-$ | 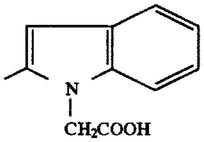 |
| 136 | $C_2H_5$ | 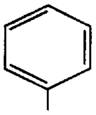 | $-NHCONH-$ | 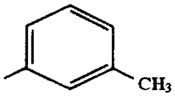 |
TABLE II-6-continued
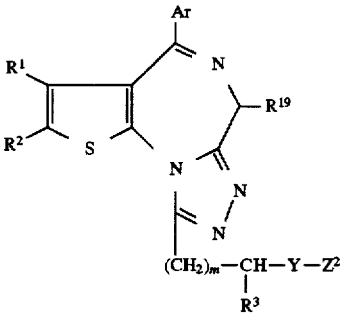
$R^1 = H$
$R^3 = H$
$R^{19} = H$
$m = 0$
| Example No. | $R^2$ | Ar | Y | $Z^2$ |
|---|---|---|---|---|
| 137 | $C_2H_5$ | 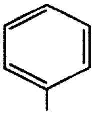 | $-NHCONH-$ | 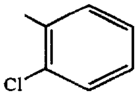 |
| 138 | $C_2H_5$ | 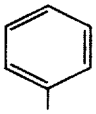 | $-NHCONH-$ | 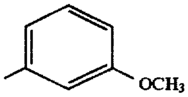 |
| 139 | $CH_3$ | 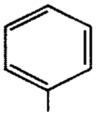 | $-NHCO-$ | 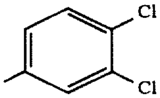 |
| 140 | $CH_3$ | 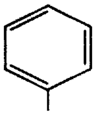 | $-NHCO-$ | 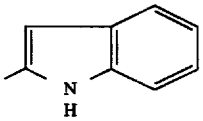 |

TABLE II-6-continued
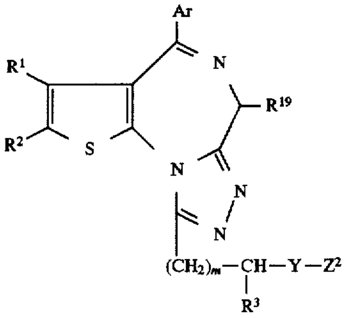
$R^1 = H$
$R^3 = H$
$R^{19} = H$
m = 0
| Example No. | $R^2$ | Ar | Y | $Z^2$ |
|---|---|---|---|---|
| 141 | $CH_3$ | 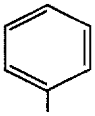 | $-NHCO-$ | 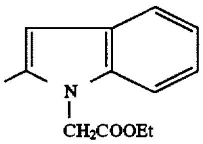 |
TABLE II-6-continued
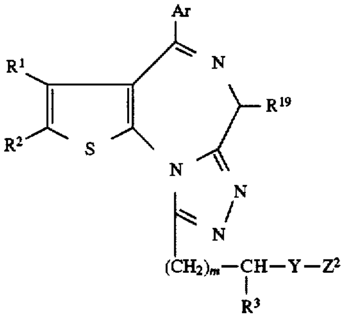
$R^1 = H$
$R^3 = H$
$R^{19} = H$
m = 0
| Example No. | $R^2$ | Ar | Y | $Z^2$ |
|---|---|---|---|---|
| 142 | $CH_3$ | 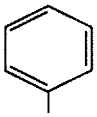 | $-NHCO-$ | 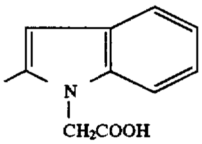 |
TABLE II-7
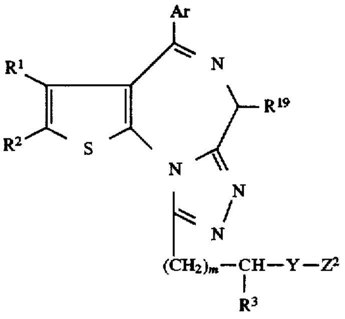
$R^3 = H$
$R^{19} = H$
m = 0
| Example No. | $R^1$ | $R^2$ | Ar | Y | $Z^2$ |
|---|---|---|---|---|---|
| 143 | H | $CH_3$ | 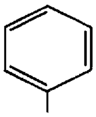 | $-NHCONH-$ | 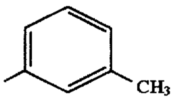 |
| 144 | H | $CH_3$ | 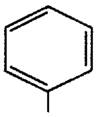 | $-NHCONH-$ | 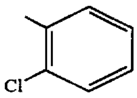 |
| 145 | H | $CH_3$ | 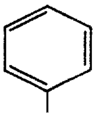 | $-NHCONH-$ | 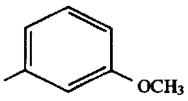 |

TABLE II-7-continued
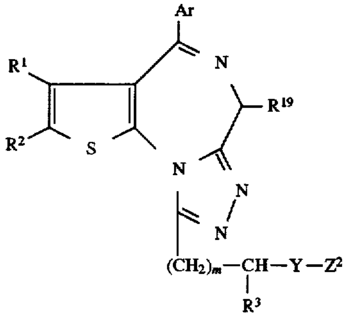
$R^3 = H$
$R^{19} = H$
m = 0
| Example No. | $R^1$ | $R^2$ | Ar | Y | $Z^2$ |
|---|---|---|---|---|---|
| 146 | $CH_3$ | $CH_3$ | 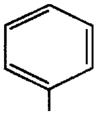 | $-NHCO-$ | 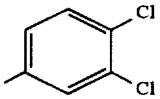 |
| 147 | $CH_3$ | $CH_3$ | 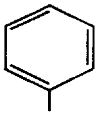 | $-NHCO-$ | 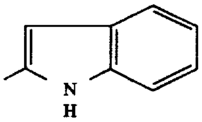 |
| 148 | $CH_3$ | $CH_3$ | 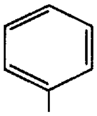 | $-NHCO-$ | 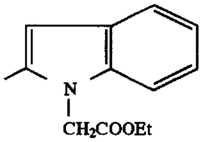 |
| 149 | $CH_3$ | $CH_3$ | 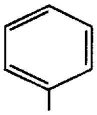 | $-NHCO-$ | 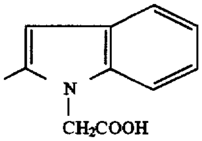 |
| 150 | $CH_3$ | $CH_3$ | 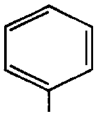 | $-NHCONH-$ | 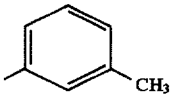 |
| 151 | $CH_3$ | $CH_3$ | 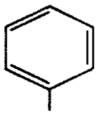 | $-NHCONH-$ | 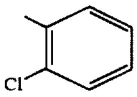 |
| 152 | $CH_3$ | $CH_3$ | 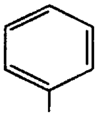 | $-NHCONH-$ | 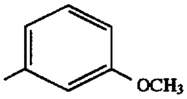 |

TABLE II-8
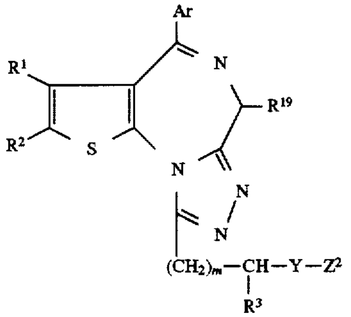
$R^1 = H$
$R^3 = H$
$R^{19} = H$
$m = 0$
| Example No. | $R^2$ | Ar | Y | $Z^2$ |
|---|---|---|---|---|
| 153 | $CH_2COOMe$ | 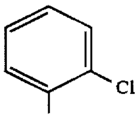 | $-NHCO-$ | 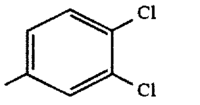 |
| 154 | $CH_2COOMe$ | 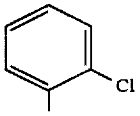 | $-NHCO-$ | 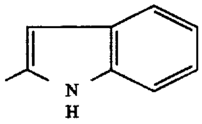 |
| 155 | $CH_2COOMe$ | 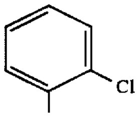 | $-NHCONH-$ | 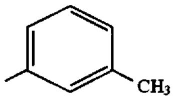 |
| 156 | $CH_2COOMe$ | 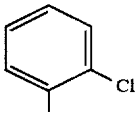 | $-NHCONH-$ | 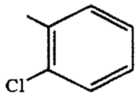 |
| 157 | $CH_2COOMe$ | 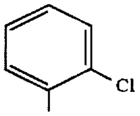 | $-NHCONH-$ | 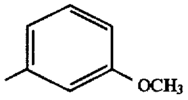 |
| 158 | $CH_2COOH$ | 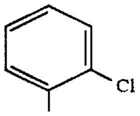 | $-NHCO-$ | 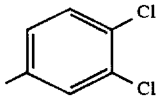 |
| 159 | $CH_2COOH$ | 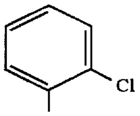 | $-NHCO-$ | 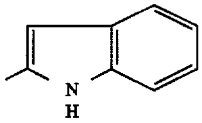 |
| 160 | $CH_2COOH$ | 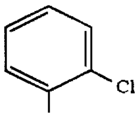 | $-NHCONH-$ | 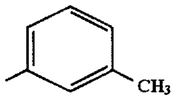 |
| 161 | $CH_2COOH$ | 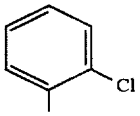 | $-NHCONH-$ | 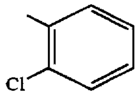 |

TABLE II-8-continued
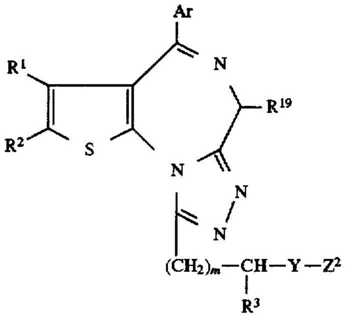
$R^1 = H$
$R^3 = H$
$R^{19} = H$
m = 0
| Example No. | $R^2$ | Ar | Y | $Z^2$ |
|---|---|---|---|---|
| 162 | $CH_2COOH$ | 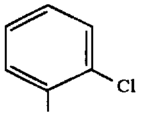 | −NHCONH− | 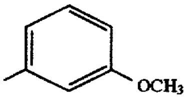 |
TABLE II-9
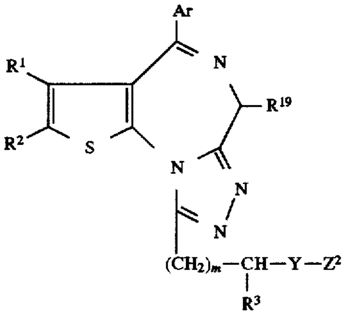
$R^1 = H$
$R^3 = H$
$R^{19} = H$
m = 0
| Example No. | $R^2$ | Ar | Y | $Z^2$ |
|---|---|---|---|---|
| 163 | COOEt | 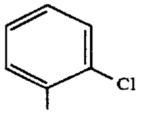 | −NHCO− | 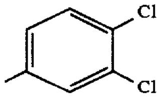 |
| 164 | COOEt | 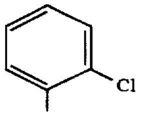 | −NHCO− | 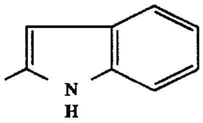 |
| 165 | COOEt | 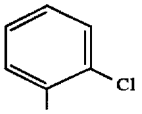 | −NHCONH− | 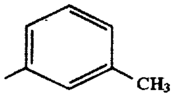 |
| 166 | COOEt | 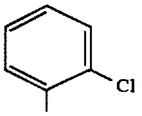 | NHCONH− | 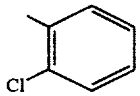 |
| 167 | COOEt | 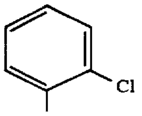 | −NHCONH− | 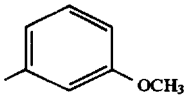 |

TABLE II-9-continued
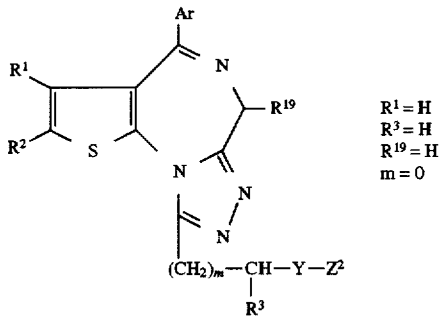
| Example No. | $R^2$ | Ar | Y | $Z^2$ |
|---|---|---|---|---|
| 168 | COOH | 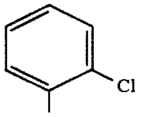 | —NHCO— | 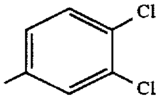 |
| 169 | COOH | 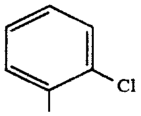 | —NHCO— | 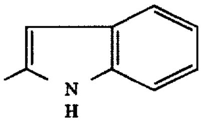 |
| 170 | COOH | 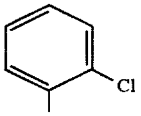 | —NHCONH— | 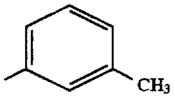 |
| 171 | COOH | 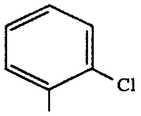 | —NHCONH— | 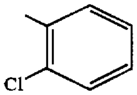 |
| 172 | COOH | 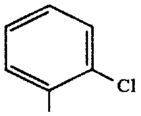 | —NHCONH— | 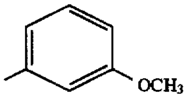 |

TABLE II-10
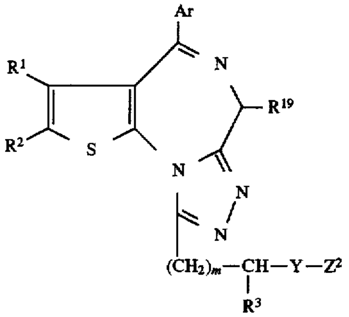
$R^1 = H$
$R^{19} = H$
| Example No. | $R^2$ | Ar | m | $R^3$ | Y | $Z^2$ |
|---|---|---|---|---|---|---|
| 266 | $C_2H_5$ | 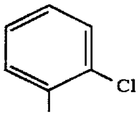 | 1 | H | −NHCO− | 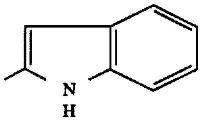 |
| 268 | $C_2H_5$ | 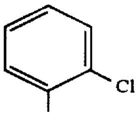 | 1 | H | −NHCO− | 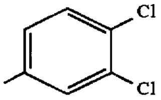 |
| 269 | $C_2H_5$ | 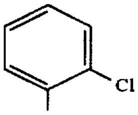 | 2 | H | −NHCO− | 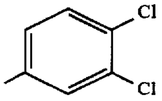 |
| 270 | $C_2H_5$ | 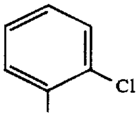 | 0 | $CH_2COOcHex$ (S) | −NHCO− | 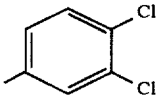 |
| 271 | $C_2H_5$ | 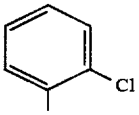 | 0 | $CH_2COOH$ (S) | −NHCO− | 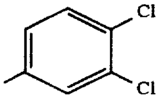 |
| 272 | $C_2H_5$ | 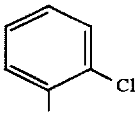 | 0 | $CH_2COOcHex$ (R) | −NHCO− | 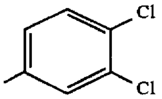 |
| 273 | $C_2H_5$ | 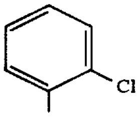 | 0 | $CH_2COOH$ (R) | −NHCO− | 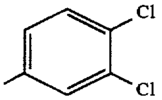 |
| 274 | $C_2H_5$ | 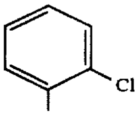 | 0 | $(CH_2)_2COOcHex$ (S) | −NHCO− | 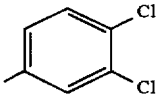 |
| 275 | $C_2H_5$ | 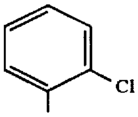 | 0 | $(CH_2)_2COOH$ (S) | −NHCO− | 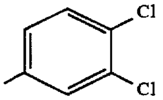 |

TABLE II-10-continued
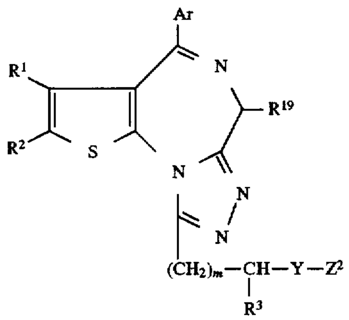
$R^1 = H$
$R^{19} = H$
| Example No. | $R^2$ | Ar | m | $R^3$ | Y | $Z^2$ |
|---|---|---|---|---|---|---|
| 276 | $C_2H_5$ | 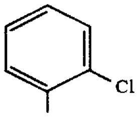 | 0 | $(CH_2)_2COOcHex$ (R) | $-NHCO-$ | 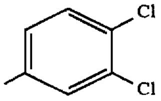 |
TABLE II-11
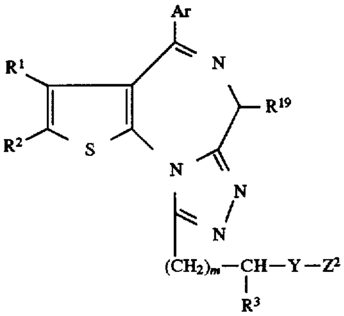
$R^1 = H$
$m = 0$
| Example No. | $R^2$ | Ar | $R^{19}$ | $R^3$ | Y | $Z^2$ |
|---|---|---|---|---|---|---|
| 277 | $C_2H_5$ | 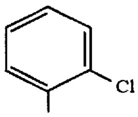 | H | $(CH_2)_2COOH$ (R) | $-NHCO-$ | 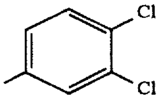 |
| 278 | $C_2H_5$ | 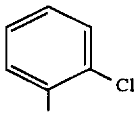 | H | $(CH_2)_2COOBn$ (R) | $-NHCO-$ | 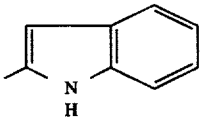 |
| 279 | $C_2H_5$ | 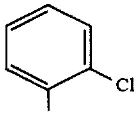 | H | $(CH_2)_2COOcHex$ (R) | $-NHCO-$ | 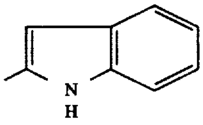 |
| 280 | $C_2H_5$ | 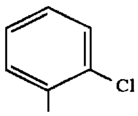 | H | $(CH_2)_2COOH$ (R) | $-NHCO-$ | 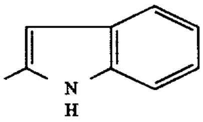 |

TABLE II-11-continued
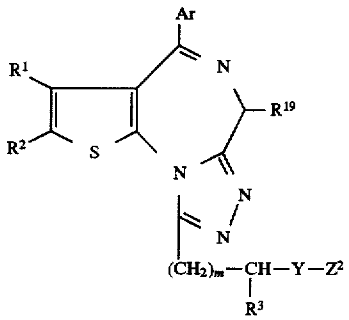
$R^1 = H$
$m = 0$
| Example No. | $R^2$ | Ar | $R^{19}$ | $R^3$ | Y | $Z^2$ |
|---|---|---|---|---|---|---|
| 281 | $C_2H_5$ | 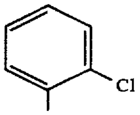 | H | $(CH_2)_2COOBn$ (R) | $-NHCO-$ | 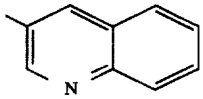 |
| 282 | $C_2H_5$ | 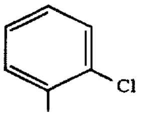 | H | $(CH_2)_2COOH$ (R) | $-NHCO-$ | 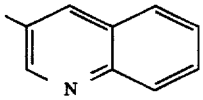 |
| 283 | $C_2H_5$ | 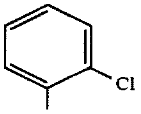 | H | $(CH_2)_2COOBn$ (R) | $-NHCO-$ | 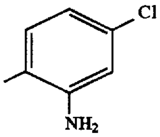 |
| 284 | $C_2H_5$ | 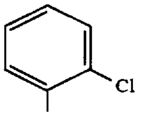 | H | $(CH_2)_2COOH$ (R) | $-NHCO-$ | 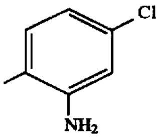 |
| 285 | $C_2H_5$ | 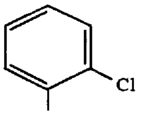 | $CH_2COOEt$ | H | $-NHCO-$ | 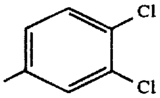 |
| 286 | $C_2H_5$ | 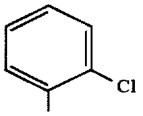 | $CH_2COOH$ | H | $-NHCO-$ | 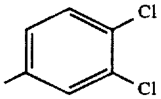 |

TABLE II-12
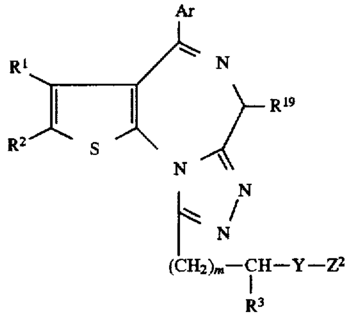
$R^{19} = H$
m = 0
| Example No. | $R^1$ | $R^2$ | Ar | $R^3$ | Y | $Z^2$ |
|---|---|---|---|---|---|---|
| 350 | H | $CH_3$ | 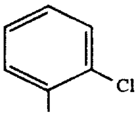 | H | $-NHCO-$ | 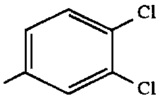 |
| 351 | $CH_3$ | $CH_3$ | 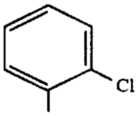 | H | $-NHCO-$ | 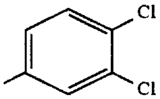 |
| 352 | H | $C_2H_5$ | 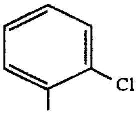 | $(CH_2)_2COOBn$ (R) | $-NHCO-$ | 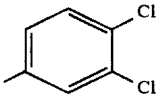 |
| 353 | H | $C_3H_7$ | 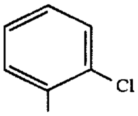 | H | $-NHCO-$ | 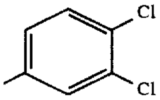 |
| 354 | H | $C_2H_5$ | 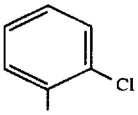 | H | $-NHCO-$ | 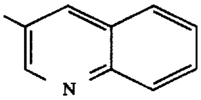 |
| 355 | H | $C_2H_5$ | 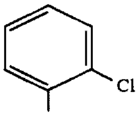 | H | $-NHCO-$ | 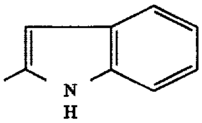 |
| 356 | H | $C_2H_5$ | 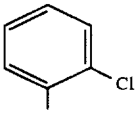 | $(CH_2)_2COOBn$ (R) | $-NHCO-$ | 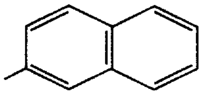 |
| 357 | H | $C_2H_5$ | 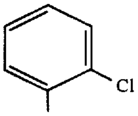 | $(CH_2)_2COOH$ (R) | $-NHCO-$ | 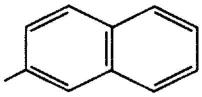 |
| 358 | H | $C_2H_5$ | 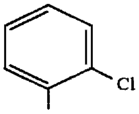 | $(CH_2)_2COOBn$ (R) | $-NHSO_2-$ | 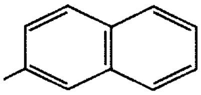 |

TABLE II-12-continued
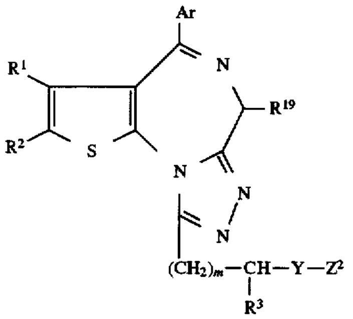
$R^{19} = H$
m = 0
| Example No. | $R^1$ | $R^2$ | Ar | $R^3$ | Y | $Z^2$ |
|---|---|---|---|---|---|---|
| 359 | H | $C_2H_5$ | 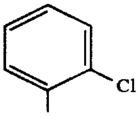 | $(CH_2)_2COOH$ (R) | $-NHSO_2-$ | 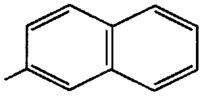 |
TABLE II-13
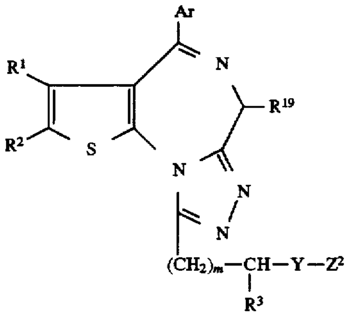
$R^1 = H$
$R^{19} = H$
m = 0
| Example No. | $R^2$ | Ar | $R^3$ | Y | $Z^2$ |
|---|---|---|---|---|---|
| 360 | $C_2H_5$ | 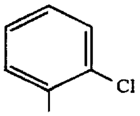 | $(CH_2)_2COOBn$ (R) | $-NHCONH-$ | 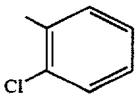 |
| 361 | $C_2H_5$ | 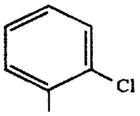 | $(CH_2)_2COOH$ (R) | $-NHCONH-$ | 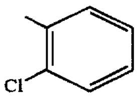 |
| 362 | $C_2H_5$ | 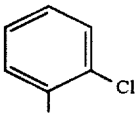 | $(CH_2)_2COOBn$ (R) | $-NHCONH-$ | 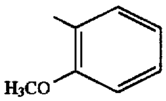 |
| 363 | $C_2H_5$ | 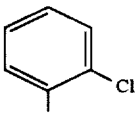 | $(CH_2)_2COOH$ (R) | $-NHCONH-$ | 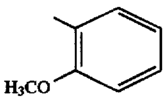 |
| 364 | $C_2H_5$ | 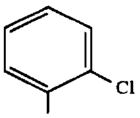 | $(CH_2)_2COOBn$ (R) | $-NHCO-$ | 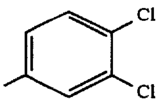 |

TABLE II-13-continued
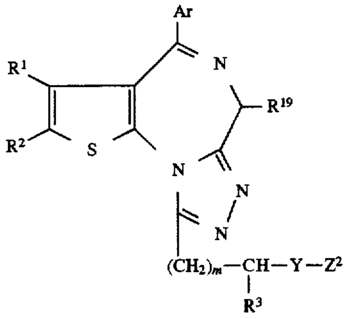
$R^1 = H$
$R^{19} = H$
$m = 0$
| Example No. | $R^2$ | Ar | $R^3$ | Y | $Z^2$ |
|---|---|---|---|---|---|
| 365 | $C_2H_5$ | 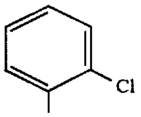 | $(CH_2)_2COOH$ (R) | —NHCO— | 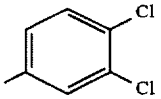 |
| 366 | $C_2H_5$ | 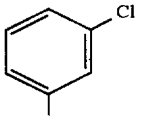 | H | —NHCO— | 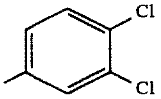 |
| 367 | $C_2H_5$ | 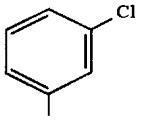 | H | —NHCONH— | 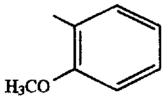 |
TABLE II-14
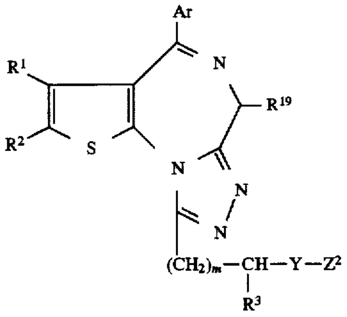
$R^1 = H$
$R^3 = H$
$R^{19} = H$
$m = 0$
| Example No. | $R^2$ | Ar | Y | $Z^2$ |
|---|---|---|---|---|
| 375 | $C_3H_7$ | 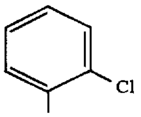 | —NHCO— | 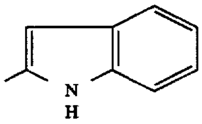 |
| 376 | $CH(CH_3)_2$ | 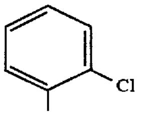 | —NHCO— | 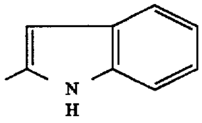 |

TABLE II-14-continued
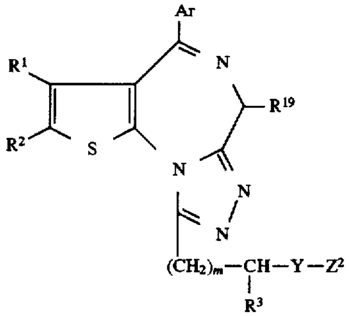
$R^1 = H$
$R^3 = H$
$R^{19} = H$
m = 0
| Example No. | $R^2$ | Ar | Y | $Z^2$ |
|---|---|---|---|---|
| 377 | 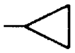 | 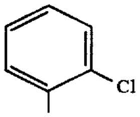 | —NHCO— | 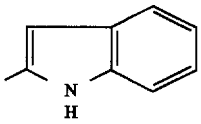 |
| 378 | $C_3H_7$ | 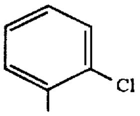 | —NHCONH— | 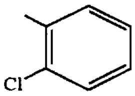 |
| 379 | $CH(CH_3)_2$ | 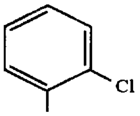 | —NHCONH— | 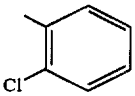 |
| 380 | 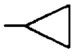 | 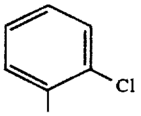 | —NHCONH— | 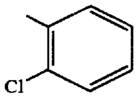 |
TABLE II-15
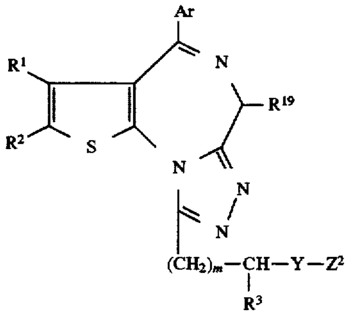
$R^1 = H$
$R^{19} = H$
m = 0
| Example No. | $R^2$ | Ar | $R^3$ | Y | $Z^2$ |
|---|---|---|---|---|---|
| 381 | $C_3H_7$ | 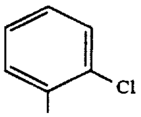 | $(CH_2)_2COOBn$ (R) | —NHCO— | 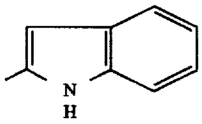 |

TABLE II-15-continued
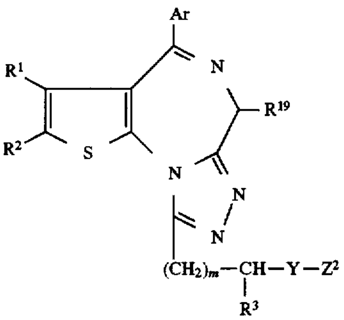
$R^1 = H$
$R^{19} = H$
$m = 0$
| Example No. | $R^2$ | Ar | $R^3$ | Y | $Z^2$ |
|---|---|---|---|---|---|
| 382 | $C_3H_7$ | 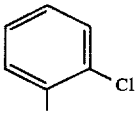 | $(CH_2)_2COOH$ (R) | $-NHCO-$ | 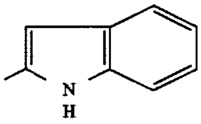 |
| 383 | $CH(CH_3)_2$ | 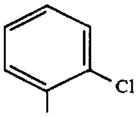 | $(CH_2)_2COOBn$ (R) | $-NHCO-$ | 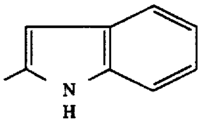 |
| 384 | $CH(CH_3)_2$ | 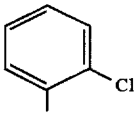 | $(CH_2)_2COOH$ (R) | $-NHCO-$ | 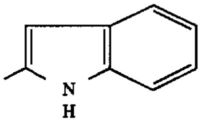 |
| 385 | 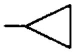 | 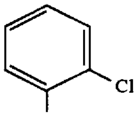 | $(CH_2)_2COOBn$ (R) | $-NHCO-$ | 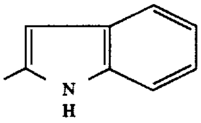 |
| 386 | 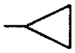 | 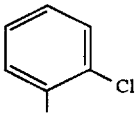 | $(CH_2)_2COOH$ (R) | $-NHCO-$ | 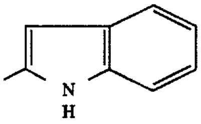 |

TABLE II-16

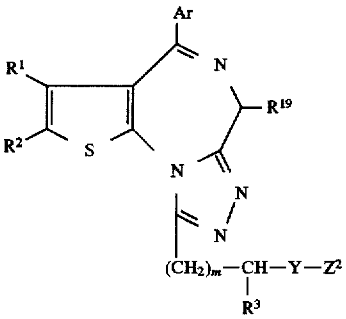

$R^1 = H$
$R^{19} = H$
$m = 0$

| Example No. | $R^2$ | Ar | $R^3$ | Y | $Z^2$ |
|---|---|---|---|---|---|
| 387 | $C_3H_7$ | 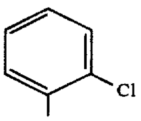 | $(CH_2)_2COOBn$ (R) | $-NHCONH-$ | 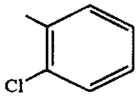 |
| 388 | $C_3H_7$ | 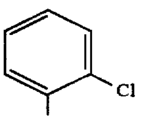 | $(CH_2)_2COOH$ (R) | $-NHCONH-$ | 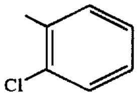 |
| 389 | $CH(CH_3)_2$ | 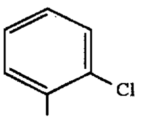 | $(CH_2)_2COOBn$ (R) | $-NHCONH-$ | 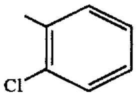 |
| 390 | $CH(CH_3)_2$ | 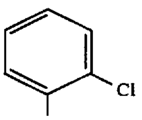 | $(CH_2)_2COOH$ (R) | $-NHCONH-$ | 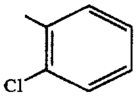 |
| 391 | 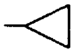 | 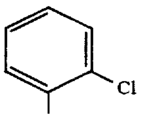 | $(CH_2)_2COOBn$ (R) | $-NHCONH-$ | 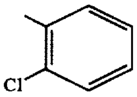 |
| 392 | 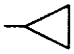 | 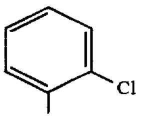 | $(CH_2)_2COOH$ (R) | $-NHCONH-$ | 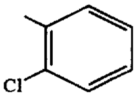 |

Thienylazole compounds shown in Table I-27 to Table I-43 and thienotriazolodiazepine compounds shown in Table II-17 to Table II-37 are obtained in the same manner as in the above Examples. The compounds of Examples are also included in the instant Tables. In the Tables, Me means methyl, Et means ethyl, t-Bu means tert-butyl, Bn means benzyl, and cHex means cyclohexyl.

TABLE I-27
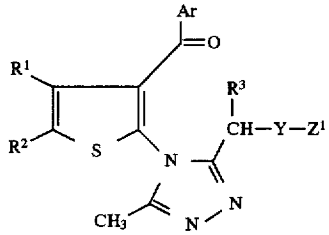
| $R^1$ | $R^2$ | $R^3$ | Ar | Y | $Z^1$ |
|---|---|---|---|---|---|
| Cl | $C_2H_5$ | H | 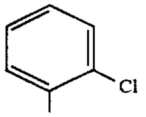 | $-NHCO-$ | 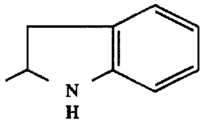 |
| Cl | $C_2H_5$ | H | 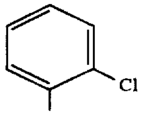 | $-NHCO-$ | 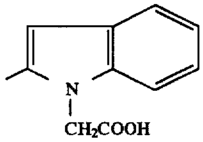 |
| Cl | $C_2H_5$ | H | 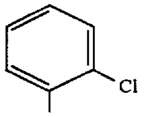 | $-NHCO-$ | 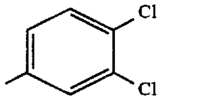 |
| Br | $C_2H_5$ | H | 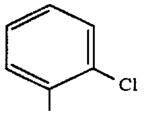 | $-NHCO-$ | 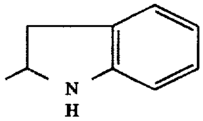 |
| Br | $C_2H_5$ | H | 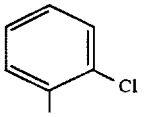 | $-NHCO-$ | 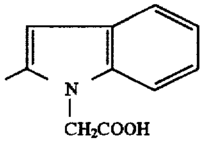 |
| Br | $C_2H_5$ | H | 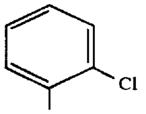 | $-NHCO-$ | 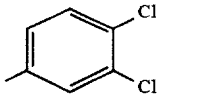 |
| Br | H | H | 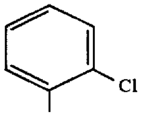 | $-NHCO-$ | 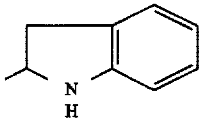 |
| Br | H | H | 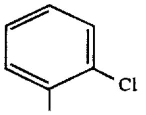 | $-NHCO-$ | 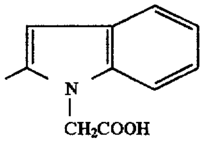 |
| Br | H | H | 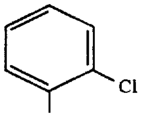 | $-NHCO-$ | 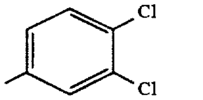 |

TABLE I-27-continued
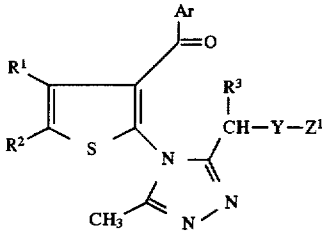
| $R^1$ | $R^2$ | $R^3$ | Ar | Y | $Z^1$ |
|---|---|---|---|---|---|
| Cl | $CH_3$ | H | 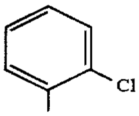 | $-$NHCONH$-$ | 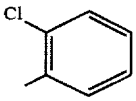 |
| Cl | $CH_3$ | H | 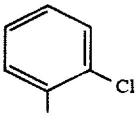 | $-$NHCONH$-$ | 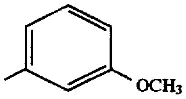 |
TABLE I-28
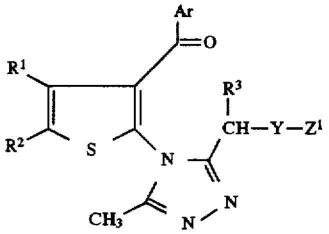
| $R^1$ | $R^2$ | $R^3$ | Ar | Y | $Z^1$ |
|---|---|---|---|---|---|
| H | H | H | 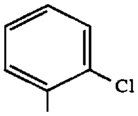 | $-$NHCO$-$ | 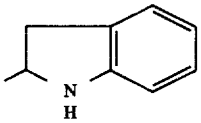 |
| H | H | H | 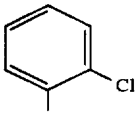 | $-$NHCO$-$ | 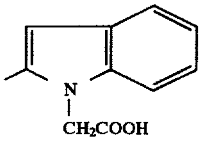 |
| H | H | H | 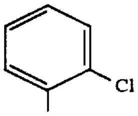 | $-$NHCO$-$ | 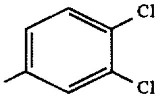 |
| H | H | H | 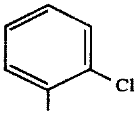 | $-$NHCONH$-$ | 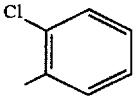 |
| H | H | H | 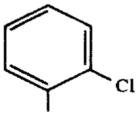 | $-$NHCONH$-$ | 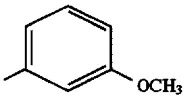 |

TABLE I-28-continued
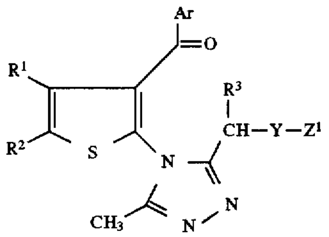
| $R^1$ | $R^2$ | $R^3$ | Ar | Y | $Z^1$ |
|---|---|---|---|---|---|
| H | Br | H | 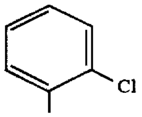 | —NHCO— | 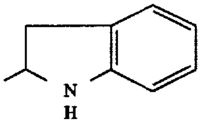 |
| H | Br | H | 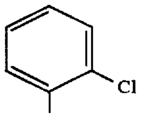 | —NHCO— | 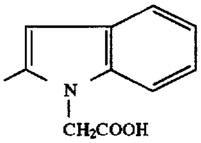 |
| H | Br | H | 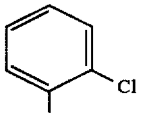 | —NHCO— | 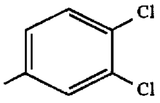 |
| H | Br | H | 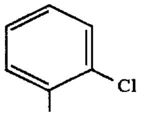 | —NHCONH— | 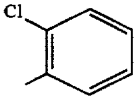 |
| H | Br | H | 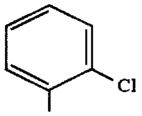 | —NHCONH— | 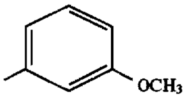 |
TABLE I-29
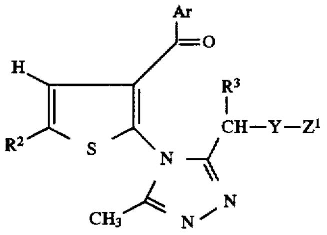
| $R^2$ | $R^3$ | Ar | Y | $Z^1$ |
|---|---|---|---|---|
| $-CH_2CONMe_2$ | H | 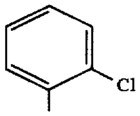 | —NHCO— | 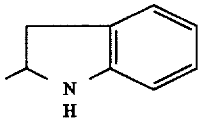 |
| $-CH_2CONMe_2$ | H | 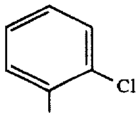 | —NHCO— | 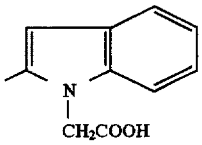 |

TABLE I-29-continued
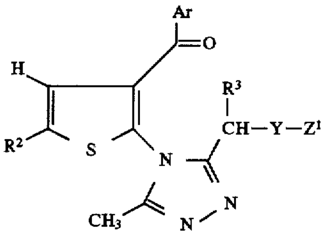
| $R^2$ | $R^3$ | Ar | Y | $Z^1$ |
|---|---|---|---|---|
| $-CH_2CONMe_2$ | H | 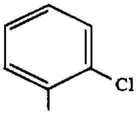 | −NHCO− | 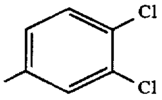 |
| $-CH_2CONMe_2$ | H | 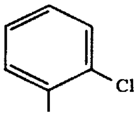 | −NHCONH− | 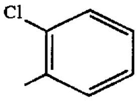 |
| $-CONMe_2$ | H | 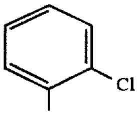 | −NHCO− | 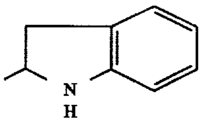 |
| $-CH_2CH_2CONMe_2$ | H | 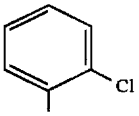 | −NHCO− | 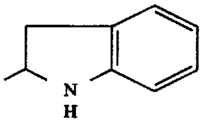 |
| $-CH_2CONEt_2$ | H | 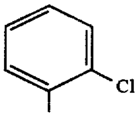 | −NHCO− | 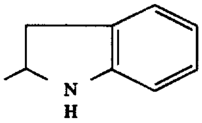 |
| $-CH_2CON$ 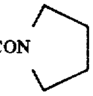 | H | 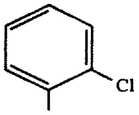 | −NHCO− | 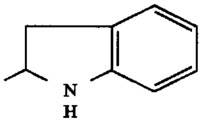 |
| $-CH_2CON$ 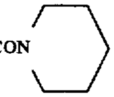 | H | 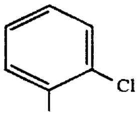 | −NHCO− | 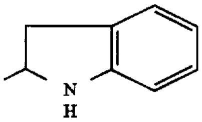 |
| $-CH_2CH_2CON$ 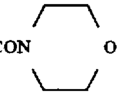 | H | 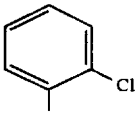 | −NHCO− | 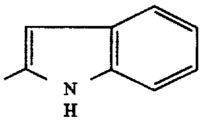 |

TABLE I-30
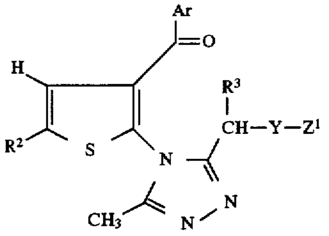
| $R^2$ | $R^3$ | Ar | Y | $Z^1$ |
|---|---|---|---|---|
| $-CH_2OH$ | H | 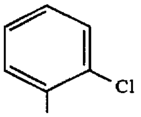 | $-NHCO-$ | 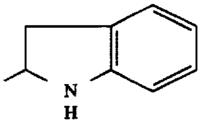 |
| $-CH_2OH$ | H | 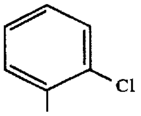 | $-NHCO-$ | 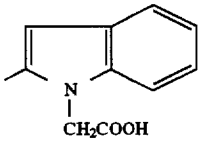 |
| $-CH_2OH$ | H | 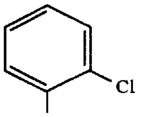 | $-NHCO-$ | 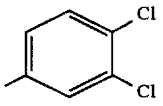 |
| $-CH_2OH$ | H | 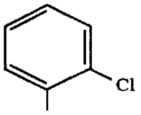 | $-NHCONH-$ | 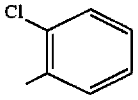 |
| $CH_3CO-$ | H | 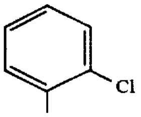 | $-NHCO-$ | 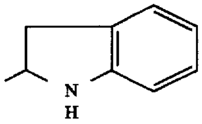 |
| $CH_3CO-$ | H | 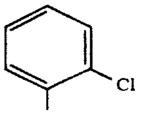 | $-NHCO-$ | 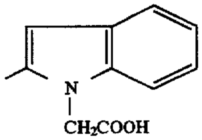 |
| $CH_3CO-$ | H | 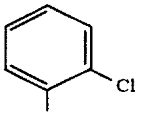 | $-NHCO-$ | 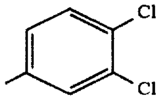 |
| $CH_3CO-$ | H | 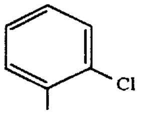 | $-NHCONH-$ | 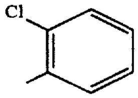 |
| $CH_3CH(OH)-$ | H | 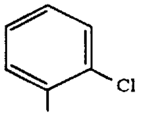 | $-NHCO-$ | 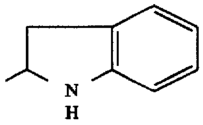 |

TABLE I-30-continued
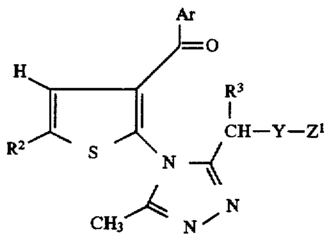
| $R^2$ | $R^3$ | Ar | Y | $Z^1$ |
|---|---|---|---|---|
| $CH_3CH_2CO-$ | H | 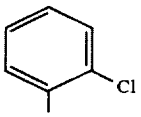 | —NHCO— | 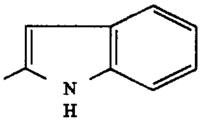 |
TABLE I-31
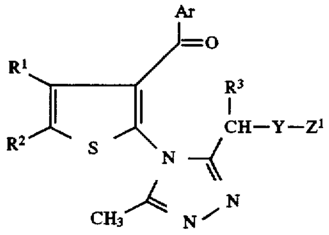
| $R^1$ | $R^2$ | $R^3$ | Ar | Y | $Z^1$ |
|---|---|---|---|---|---|
| H | 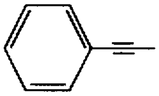 | H | 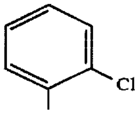 | —NHCO— | 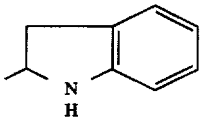 |
| H | 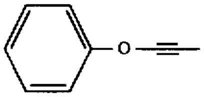 | H | 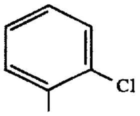 | —NHCO— | 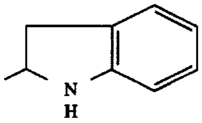 |
| 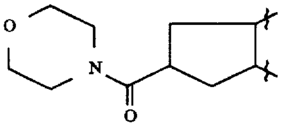 | | H | 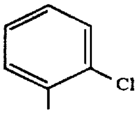 | —NHCO— | 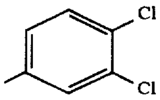 |
| 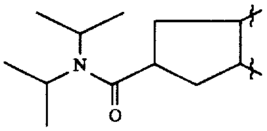 | | H | 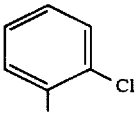 | —NHCONH— | 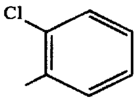 |
| 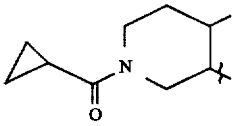 | | H | 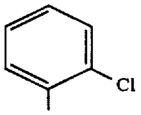 | —NHCO— | 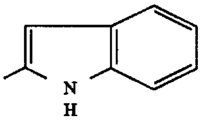 |

TABLE I-32
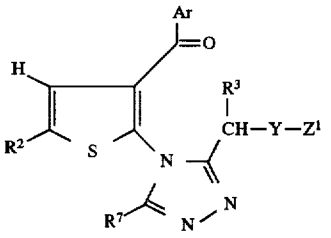
| $R^2$ | $R^3$ | $R^7$ | Ar | Y | $Z^1$ |
|---|---|---|---|---|---|
| $C_2H_5$ | H | $CH_2=CH-$ | 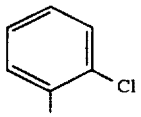 | $-NHCO-$ | 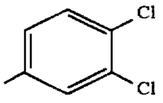 |
| $C_2H_5$ | H | $CH_3CO-$ | 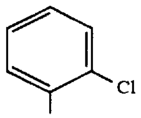 | $-NHCO-$ | 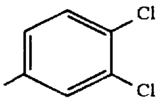 |
| $C_2H_5$ | H | $HC\equiv C-$ | 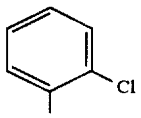 | $-NHCO-$ | 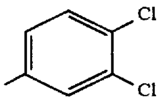 |
| $C_2H_5$ | H | $CH_3CH(OH)-$ | 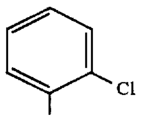 | $-NHCONH-$ | 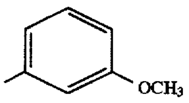 |
| $C_2H_5$ | H | 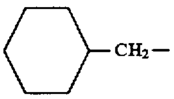 | 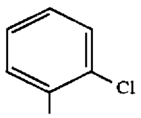 | $-NHCONH-$ | 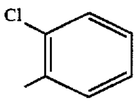 |
| $C_2H_5$ | H | 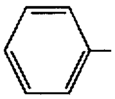 | 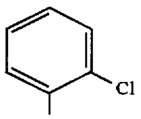 | $-NHCONH-$ | 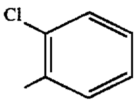 |
| $C_2H_5$ | H | 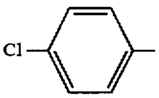 | 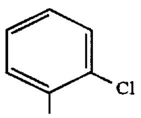 | $-NHCO-$ | 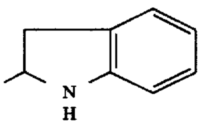 |
| $C_2H_5$ | H | 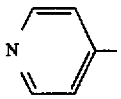 | 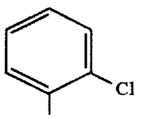 | $-NHCONH-$ | 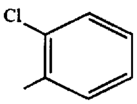 |
| $C_2H_5$ | H | 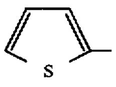 | 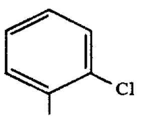 | $-NHCO-$ | 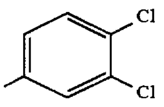 |
| $C_2H_5$ | H | 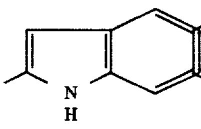 | 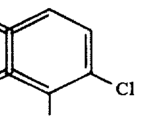 | $-NHCONH-$ | 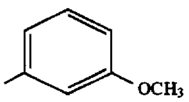 |

TABLE I-33
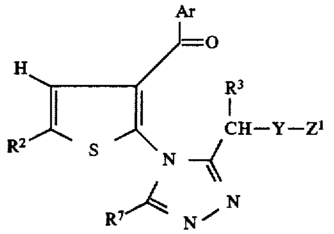
| $R^2$ | $R^3$ | $R^7$ | Ar | Y | $Z^1$ |
|---|---|---|---|---|---|
| $C_2H_5$ | H | $-CONH_2$ | 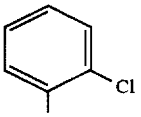 | $-NHCO-$ | 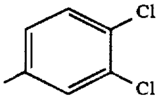 |
| $C_2H_5$ | H | $-CONMe_2$ | 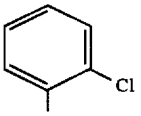 | $-NHCO-$ | 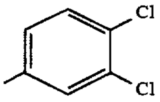 |
| $C_2H_5$ | H | $-CH_2CH_2CONH_2$ | 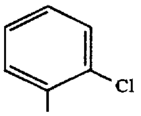 | $-NHCO-$ | 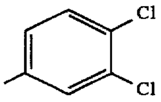 |
| $C_2H_5$ | H | $-CH_2CH_2CON$ 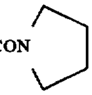 | 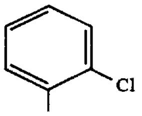 | $-NHCONH-$ | 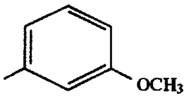 |
| $C_2H_5$ | H | 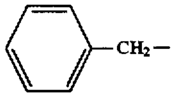 | 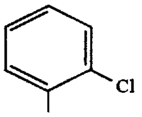 | $-NHCONH-$ | 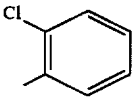 |
| $C_2H_5$ | H | 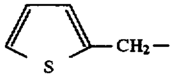 | 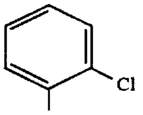 | $-NHCONH-$ | 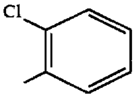 |
| $C_2H_5$ | H | 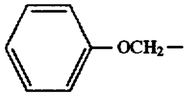 | 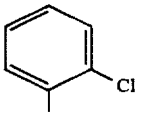 | $-NHCO-$ | 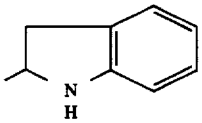 |
| $C_2H_5$ | H | 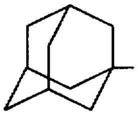 | 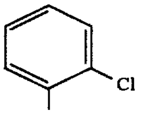 | $-NHCONH-$ | 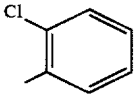 |
| $C_2H_5$ | H | 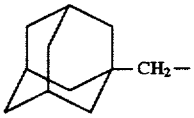 | 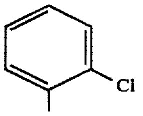 | $-NHCO-$ | 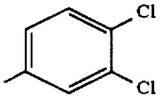 |
| $C_2H_5$ | H | 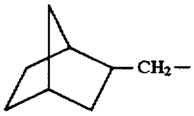 | 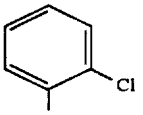 | $-NHCONH-$ | 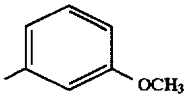 |

TABLE I-34
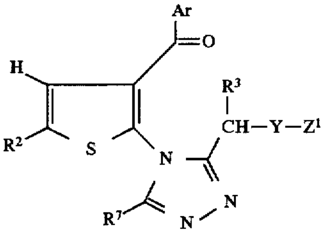
| $R^2$ | $R^3$ | $R^7$ | Ar | Y | $Z^1$ |
|---|---|---|---|---|---|
| $C_2H_5$ | H | $CH_3$ | 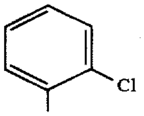 | —NHCONHCO— | 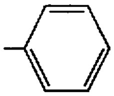 |
| $C_2H_5$ | H | $CH_3$ | 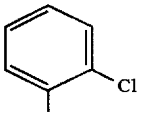 | —NHCSNHCO— | 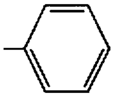 |
| $C_2H_5$ | H | $CH_3$ | 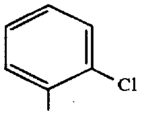 | —NHCONHSO$_2$— | 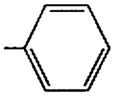 |
| $C_2H_5$ | H | $CH_3$ | 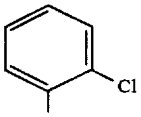 | —NHCOCONH— | 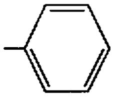 |
| $C_2H_5$ | H | $CH_3$ | 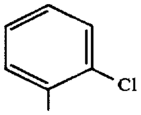 | —NHCOO— | 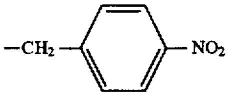 |
| $CH_3$ | $CH_3$ | $CH_3$ | 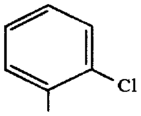 | —NHCONHCO— | 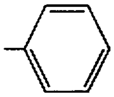 |
| $C_2H_5$ | H | $CH_3$ | 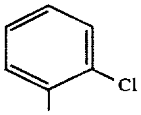 | —NHCSNHCO— | 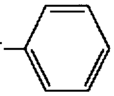 |
| $CH_3$ | H | $CH_3$ | 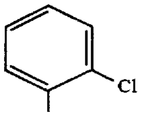 | —NHCONHSO$_2$— | 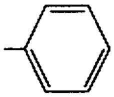 |
| $CH_3$ | H | $CH_3$ | 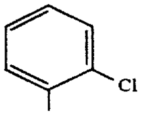 | —NHCOCONH— | 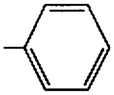 |
| $CH_3$ | H | $CH_3$ | 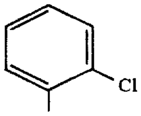 | —NHCOO— | 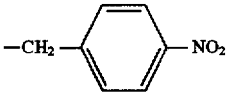 |

TABLE I-35
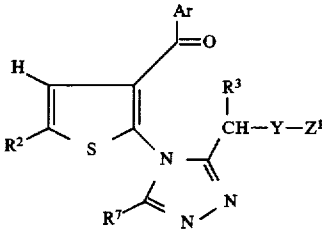
| $R^2$ | $R^3$ | $R^7$ | Ar | Y | $Z^1$ |
|---|---|---|---|---|---|
| $C_2H_5$ | H | $CH_3$ | 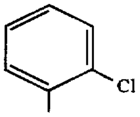 | −NHCO− | $CH_3$ |
| $C_2H_5$ | H | $CH_3$ | 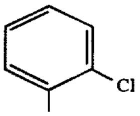 | −NHCONH− | $CH_3$ |
| $C_2H_5$ | H | $CH_3$ | 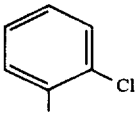 | −NHCO− | $-C_4H_9$ |
| $C_2H_5$ | H | $CH_3$ | 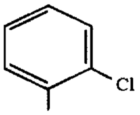 | −NHCO− | $-CH{=}CH_2$ |
| $C_2H_5$ | H | $CH_3$ | 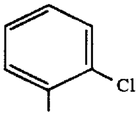 | −NHCO− | $-C{\equiv}CH$ |
| $C_2H_5$ | H | $CH_3$ | 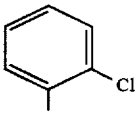 | −NHCO− | $-CH_2CH_22OH$ |
| $C_2H_5$ | H | $CH_3$ | 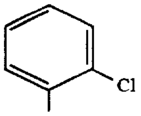 | −NHCO− | $CH_2COCH_3$ |
| $C_2H_5$ | H | $CH_3$ | 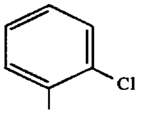 | −NHCO− | 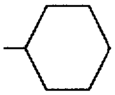 |
| $C_2H_5$ | H | $CH_3$ | 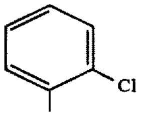 | −NHCONH− | 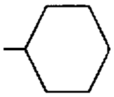 |
| $C_2H_5$ | H | $CH_3$ | 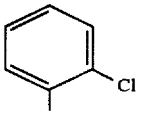 | −NHCO− | $-CH_2$ 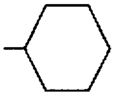 |

TABLE I-36
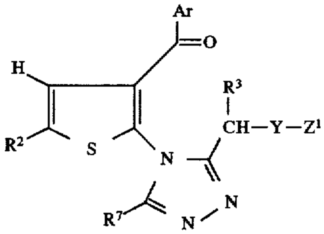
| $R^2$ | $R^3$ | $R^7$ | Ar | Y | $Z^1$ |
|---|---|---|---|---|---|
| $C_2H_5$ | H | $CH_3$ | 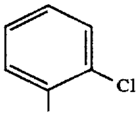 | $-NHCO-$ | 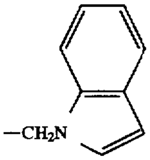 |
| $C_2H_5$ | H | $CH_3$ | 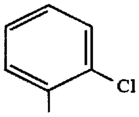 | $-NHCO-$ | 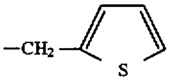 |
| $C_2H_5$ | H | $CH_3$ | 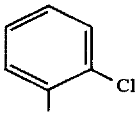 | $-NHCO-$ | 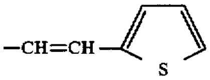 |
| $C_2H_5$ | H | $CH_3$ | 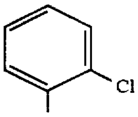 | $-NHCO-$ | 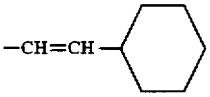 |
| $C_2H_5$ | H | $CH_3$ | 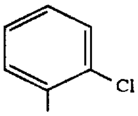 | $-NHCONH-$ | 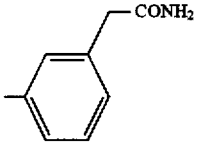 |
| $C_2H_5$ | H | $CH_3$ | 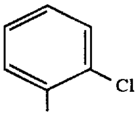 | $-NHCO-$ | 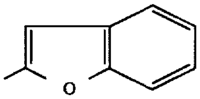 |
| $C_2H_5$ | H | $CH_3$ | 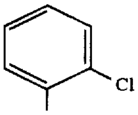 | $-NHCO-$ | 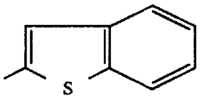 |
| $C_2H_5$ | $CH_3$ | H | 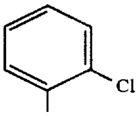 | $-NHCO-$ | 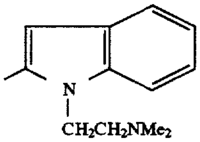 |
| $C_2H_5$ | $CH_3$ | H | 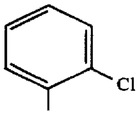 | $-NHCO-$ | 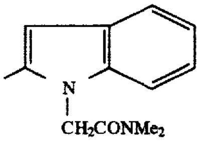 |

TABLE I-36-continued
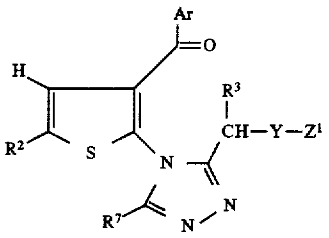
| $R^2$ | $R^3$ | $R^7$ | Ar | Y | $Z^1$ |
|---|---|---|---|---|---|
| $C_2H_5$ | $CH_3$ | H | 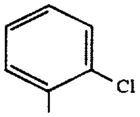 | $-NHCO-$ | 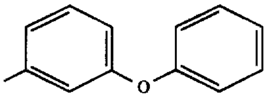 |
TABLE I-37
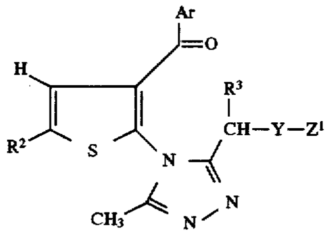
| $R^2$ | $R^3$ | Ar | Y | $Z^1$ |
|---|---|---|---|---|
| $C_2H_5$ | H | 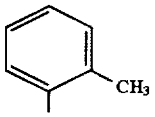 | $-NHCO-$ | 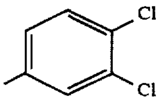 |
| $C_2H_5$ | H | 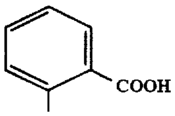 | $-NHCO-$ | 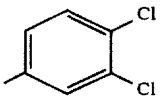 |
| $C_2H_5$ | H | 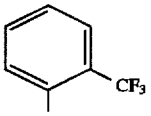 | $-NHCO-$ | 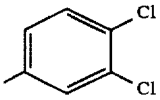 |
| $C_2H_5$ | H | 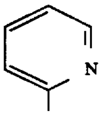 | $-NHCO-$ | 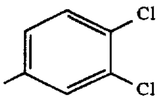 |
| $C_2H_5$ | H | 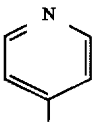 | $-NHCO-$ | 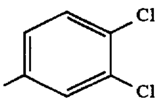 |
| $C_2H_5$ | H | 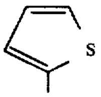 | $-NHCO-$ | 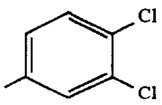 |

TABLE I-37-continued
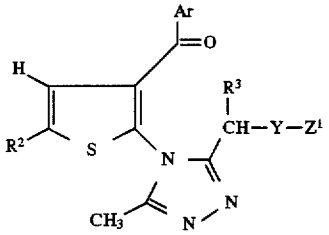
| $R^2$ | $R^3$ | Ar | Y | $Z^1$ |
|---|---|---|---|---|
| $C_2H_5$ | $-CH_2CH_2NH_2$ | 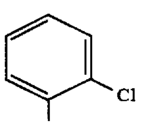 | −NHCONH− | 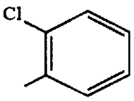 |
| $C_2H_5$ | $-CH_2CH_2NMe_2$ | 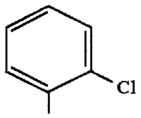 | −NHCO− | 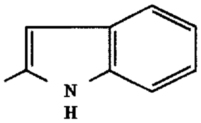 |
| $C_2H_5$ | $-CH(CH_3)_2$ | 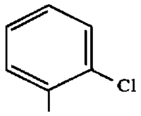 | −NHCONH− | 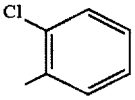 |
| $C_2H_5$ | $-CH_2CH(CH_3)_2$ | 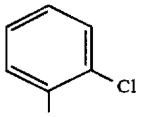 | −NHCO− | 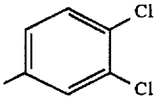 |
TABLE I-38
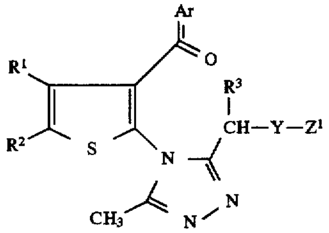
| $R^1$ | $R^2$ | $R^3$ | Ar | Y | $Z^1$ |
|---|---|---|---|---|---|
| H | COOH | H | 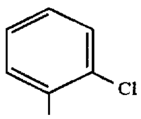 | −NHCO− | 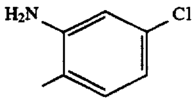 |
| H | COOH | H | 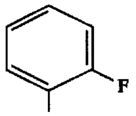 | −NHCO− | 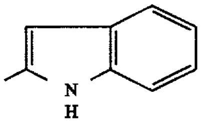 |
| H | COOH | H | 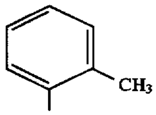 | −NHCO− | 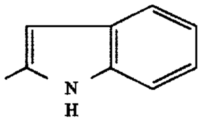 |

TABLE I-38-continued
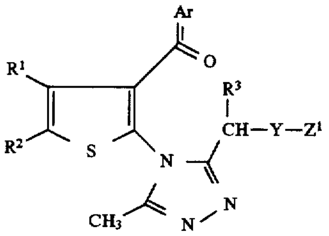
| $R^1$ | $R^2$ | $R^3$ | Ar | Y | $Z^1$ |
| --- | --- | --- | --- | --- | --- |
| H | COOH | $CH_3$ | 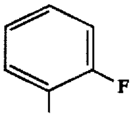 | $-NHCO-$ | 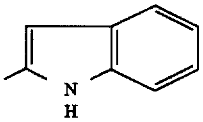 |
| H | COOH | $CH_3$ | 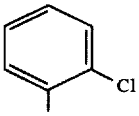 | $-NHCO-$ | 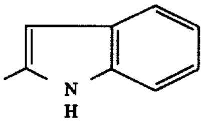 |
| H | COOH | H | 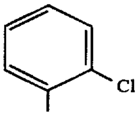 | $-NHCO-$ | 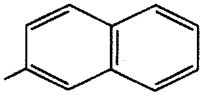 |
| H | CN | H | 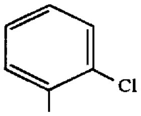 | $-NHCO-$ | 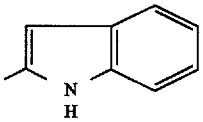 |
| H | 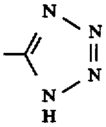 | H | 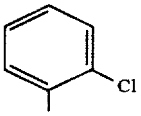 | $-NHCO-$ | 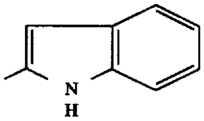 |
| H | COOH | H | 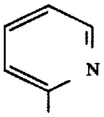 | $-NHCO-$ | 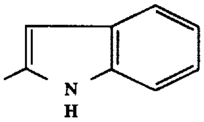 |
| H | $-CH_2COOH$ | H | 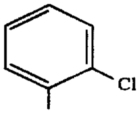 | $-NHCO-$ | 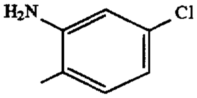 |

TABLE I-39
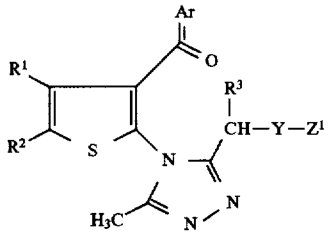
| $R^1$ | $R^2$ | $R^3$ | Ar | Y | $Z^1$ |
|---|---|---|---|---|---|
| H | $CH_2NH_2$ | H | 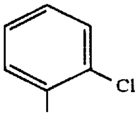 | —NHCO— | 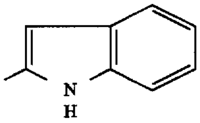 |
| H | $CH_2NH_2$ | H | 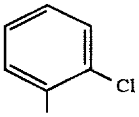 | —NHCO— | 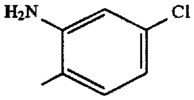 |
| H | $CH_2NH_2$ | H | 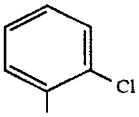 | —NHCO— | 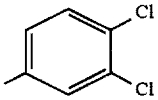 |
| H | $CH_2NH_2$ | H | 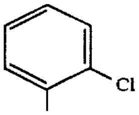 | —NHCONH— | 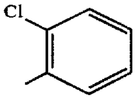 |
| H | $CH_2NH_2$ | H | 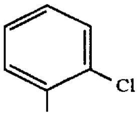 | —NHCONH— | 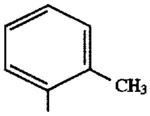 |
| H | $CH_2NH_2$ | H | 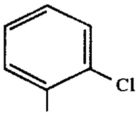 | —NHCONH— | 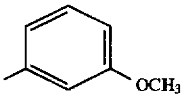 |
| H | $CH_2CH_2NH_2$ | H | 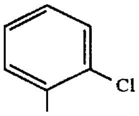 | —NHCO— | 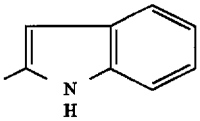 |
| H | $CH_2CH_2NH_2$ | H | 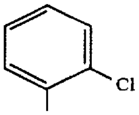 | —NHCO— | 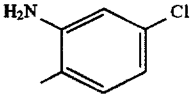 |
| H | $CH_2CH_2NH_2$ | H | 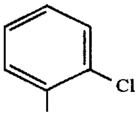 | —NHCO— | 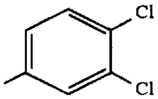 |
| H | $CH_2CH_2NH_2$ | H | 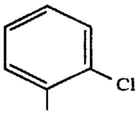 | —NHCONH— | 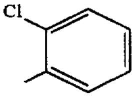 |

TABLE I-40
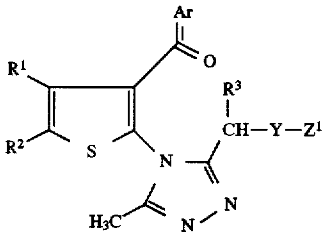
| $R^1$ | $R^2$ | $R^3$ | Ar | Y | $Z^1$ |
|---|---|---|---|---|---|
| H | $CH_2CH_2NH_2$ | H | 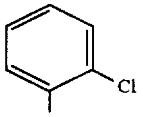 | $-NHCONH-$ | 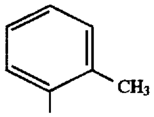 |
| H | $CH_2CH_2NH_2$ | H | 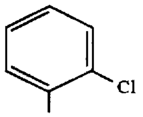 | $-NHCONH-$ | 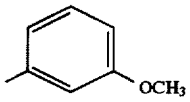 |
| H | $CH_2OH$ | H | 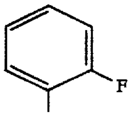 | $-NHCO-$ | 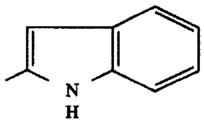 |
| H | $CH_2OH$ | H | 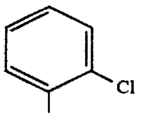 | $-NHCO-$ | 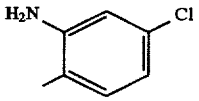 |
| H | $CH_2OH$ | H | 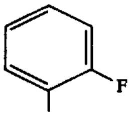 | $-NHCO-$ | 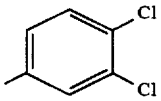 |
| H | $CH_2OH$ | H | 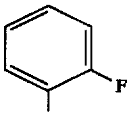 | $-NHCONH-$ | 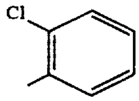 |
| H | $CH_2OH$ | H | 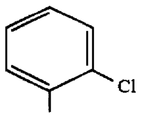 | $-NHCONH-$ | 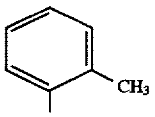 |
| H | $CH_2OH$ | H | 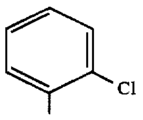 | $-NHCONH-$ | 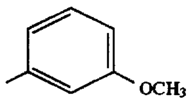 |
| H | $CH_2CH_2OH$ | H | 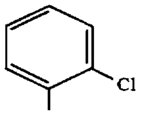 | $-NHCO-$ | 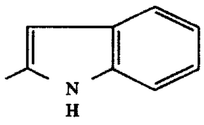 |
| H | $CH_2CH_2OH$ | H | 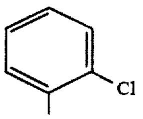 | $-NHCO-$ | 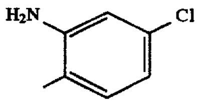 |

TABLE I-41
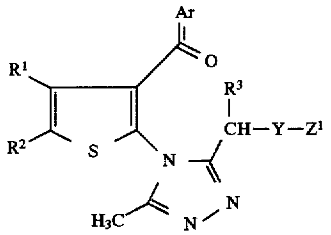
| $R^1$ | $R^2$ | $R^3$ | Ar | Y | $Z^1$ |
|---|---|---|---|---|---|
| H | $CH_2CH_2OH$ | H | 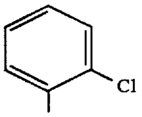 | $-NHCO-$ | 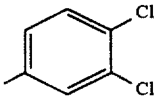 |
| H | $CH_2CH_2OH$ | H | 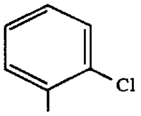 | $-NHCONH-$ | 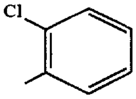 |
| H | $CH_2CH_2OH$ | H | 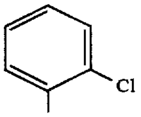 | $-NHCONH-$ | 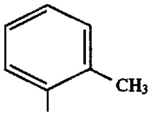 |
| H | $CH_2CH_2OH$ | H | 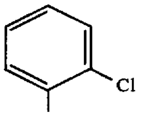 | $-NHCONH-$ | 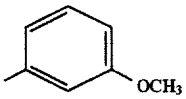 |
| H | $C_2H_5$ | H | 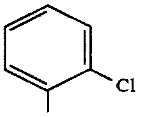 | $-NHCO-$ | 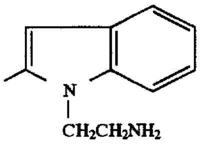 |
| H | $C_2H_5$ | H | 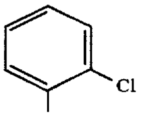 | $-NHCO-$ | 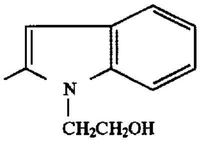 |
TABLE I-42
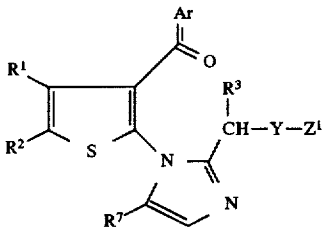
| $R^1$ | $R^2$ | $R^3$ | $R^7$ | Ar | Y | $Z^1$ |
|---|---|---|---|---|---|---|
| H | $C_2H_5$ | H | H | 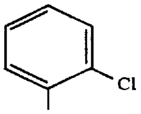 | $-OCONH-$ | 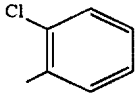 |

TABLE I-42-continued
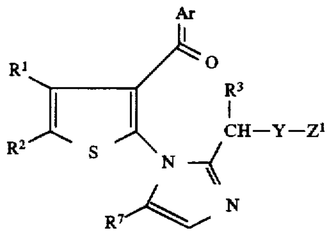
| $R^1$ | $R^2$ | $R^3$ | $R^7$ | Ar | Y | $Z^1$ |
|---|---|---|---|---|---|---|
| H | $C_2H_5$ | H | H | 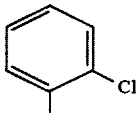 | $-OCONH-$ | 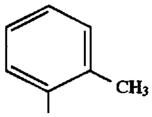 |
| H | $C_2H_5$ | H | H | 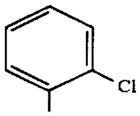 | $-OCONH-$ | 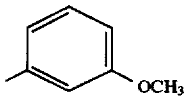 |
| H | $C_2H_5$ | H | $CH_3$ | 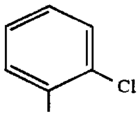 | $-OCONH-$ | 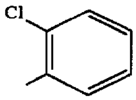 |
| H | $C_2H_5$ | H | $CH_3$ | 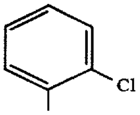 | $-OCONH-$ | 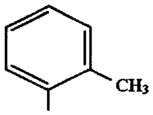 |
| H | $C_2H_5$ | H | $CH_3$ | 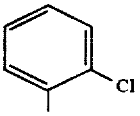 | $-OCONH-$ | 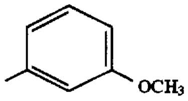 |
| H | COOH | H | H | 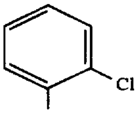 | $-OCONH-$ | 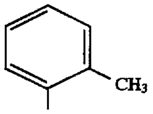 |
| H | COOH | H | H | 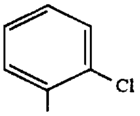 | $-OCONH-$ | 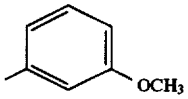 |
| H | COOH | H | $CH_3$ | 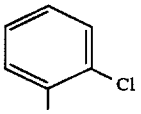 | $-OCONH-$ | 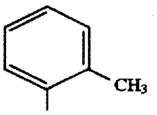 |
| H | COOH | H | $CH_3$ | 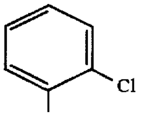 | $-OCONH-$ | 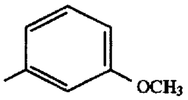 |

TABLE I-43
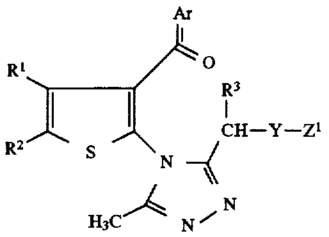
| $R^1$ | $R^2$ | $R^3$ | Ar | Y | $Z^1$ |
|---|---|---|---|---|---|
| H | $C_3H_7$ | H | 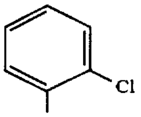 | —NHCO— | 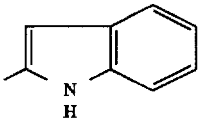 |
| H | $CH(CH_3)_2$ | H | 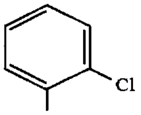 | —NHCO— | 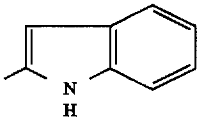 |
| H | 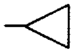 | H | 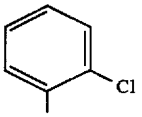 | —NHCO— | 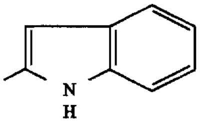 |
| H | $C_3H_7$ | H | 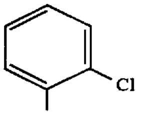 | —NHCONH— | 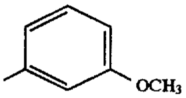 |
| H | $CH(CH_3)_2$ | H | 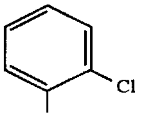 | —NHCONH— | 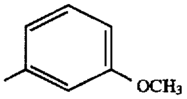 |
| H | 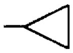 | H | 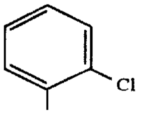 | —NHCONH— | 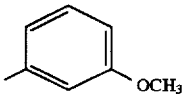 |
| H | $CH(CH_3)_2$ | H | 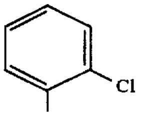 | —NHCONH— | 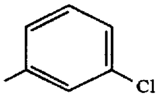 |
| H | $CH(CH_3)_2$ | H | 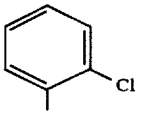 | —NHCONH— | 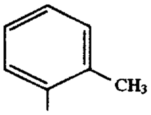 |
| H | $CH(CH_3)_2$ | H | 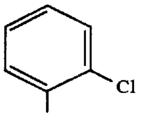 | —NHCO— | 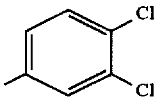 |
| H | COOH | H | 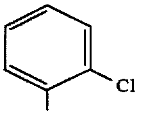 | —NHCONH— | 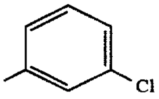 |

TABLE II-17
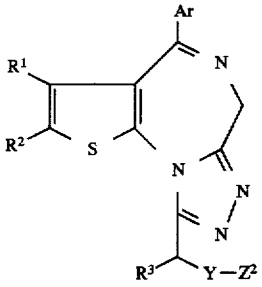
| $R^1$ | $R^2$ | $R^3$ | Ar | Y | $Z^2$ |
|---|---|---|---|---|---|
| Cl | $C_2H_5$ | H | 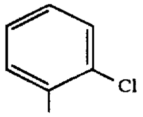 | $-NHCO-$ | 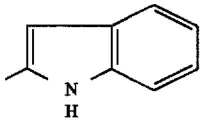 |
| Cl | $C_2H_5$ | H | 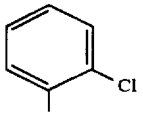 | $-NHCO-$ | 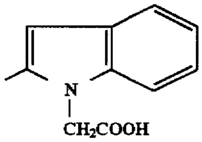 |
| Cl | $C_2H_5$ | H | 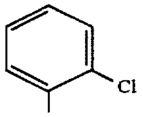 | $-NHCO-$ | 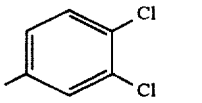 |
| Br | $C_2H_5$ | H | 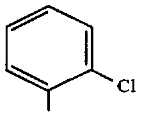 | $-NHCO-$ | 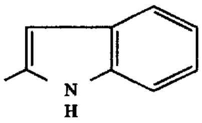 |
| Br | $C_2H_5$ | H | 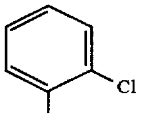 | $-NHCO-$ | 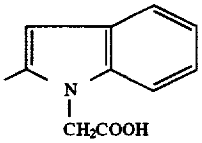 |
| Br | $C_2H_5$ | H | 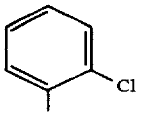 | $-NHCO-$ | 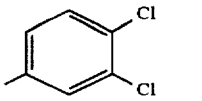 |
| Br | H | H | 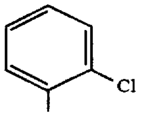 | $-NHCO-$ | 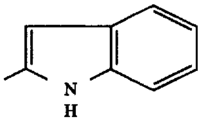 |
| Br | H | H | 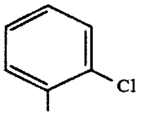 | $-NHCO-$ | 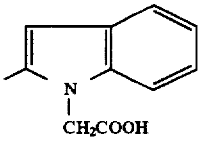 |
| Br | H | H | 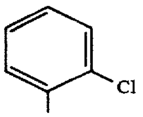 | $-NHCO-$ | 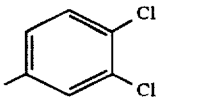 |

TABLE II-17-continued
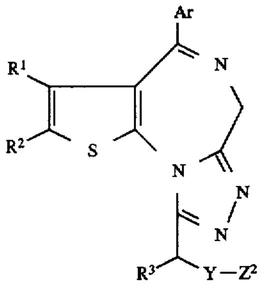
| R¹ | R² | R³ | Ar | Y | Z² |
|---|---|---|---|---|---|
| Cl | $CH_3$ | H | 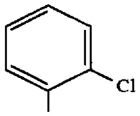 | —NHCONH— | 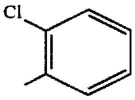 |
| Cl | $CH_3$ | H | 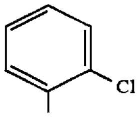 | —NHCONH— | 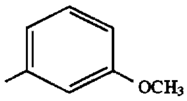 |
TABLE II-18
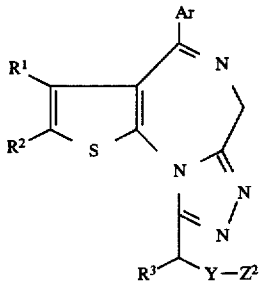
| R¹ | R² | R³ | Ar | Y | Z² |
|---|---|---|---|---|---|
| H | H | H | 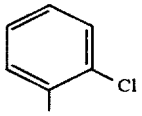 | —NHCO— | 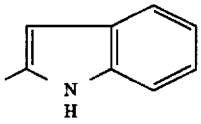 |
| H | H | H | 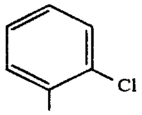 | —NHCO— | 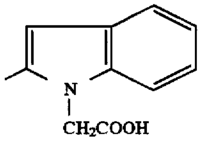 |
| H | H | H | 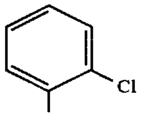 | —NHCO— | 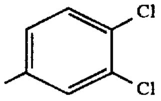 |
| H | H | H | 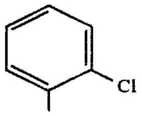 | —NHCONH— | 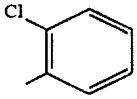 |

TABLE II-18-continued
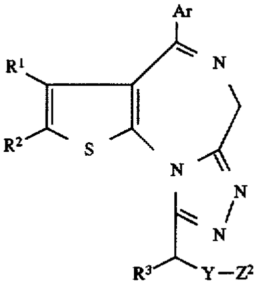
| R¹ | R² | R³ | Ar | Y | Z² |
|---|---|---|---|---|---|
| H | H | H | 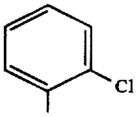 | —NHCONH— | 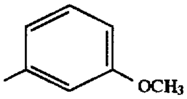 |
| H | Br | H | 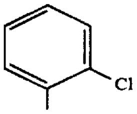 | —NHCO— | 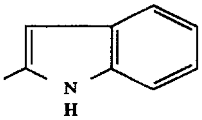 |
| H | Br | H | 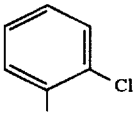 | —NHCO— | 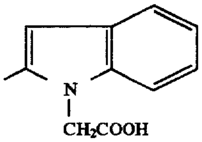 |
| H | Br | H | 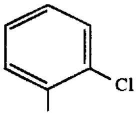 | —NHCO— | 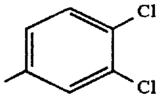 |
| H | Br | H | 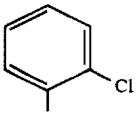 | —NHCONH— | 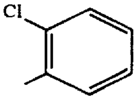 |
| H | Br | H | 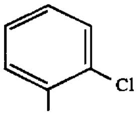 | —NHCONH— | 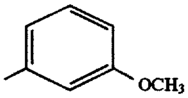 |

TABLE II-19
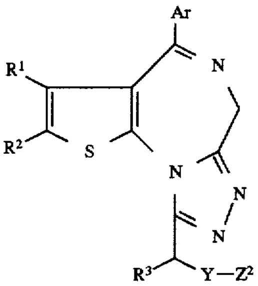
| $R^1$ | $R^2$ | $R^3$ | Ar | Y | $Z^2$ |
|---|---|---|---|---|---|
| H | $-CH_2CONMe_2$ | H | 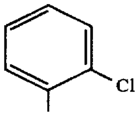 | −NHCO− | 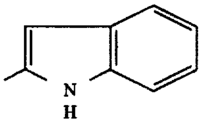 |
| H | $-CH_2CONMe_2$ | H | 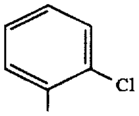 | −NHCO− | 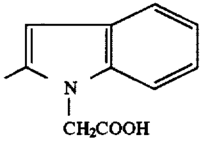 |
| H | $-CH_2CONMe_2$ | H | 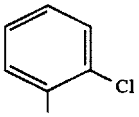 | −NHCO− | 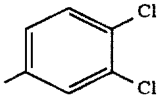 |
| H | $-CH_2CONMe_2$ | H | 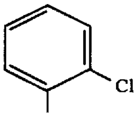 | −NHCONH− | 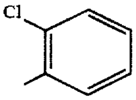 |
| H | $-CONMe_2$ | H | 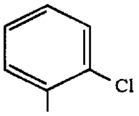 | −NHCO− | 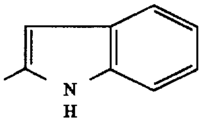 |
| H | $-CH_2CH_2CONMe_2$ | H | 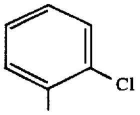 | −NHCO− | 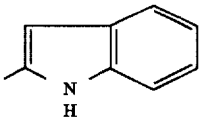 |
| H | $-CH_2CONEt_2$ | H | 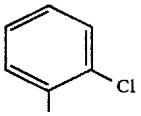 | −NHCO− | 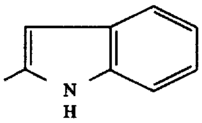 |
| H | $-CH_2CON$ 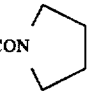 | H | 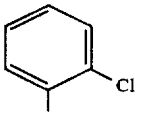 | −NHCO− | 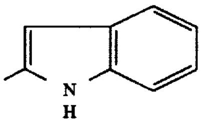 |
| H | $-CH_2CON$ 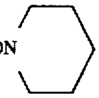 | H | 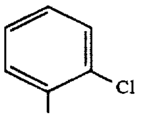 | −NHCO− | 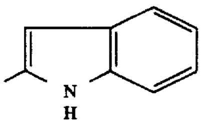 |

TABLE II-19-continued
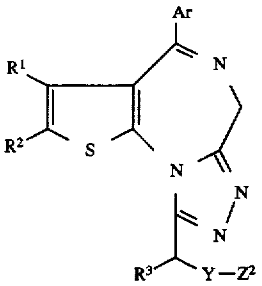
| $R^1$ | $R^2$ | $R^3$ | Ar | Y | $Z^2$ |
|---|---|---|---|---|---|
| H | $-CH_2CH_2CON$ 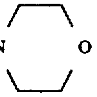 | H | 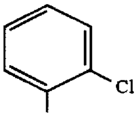 | —NHCO— | 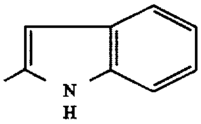 |
TABLE II-20
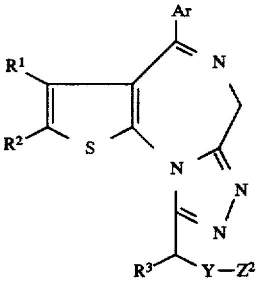
| $R^1$ | $R^2$ | $R^3$ | Ar | Y | $Z^2$ |
|---|---|---|---|---|---|
| H | $-CH_2OH$ | H | 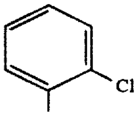 | —NHCO— | 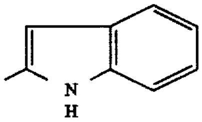 |
| H | $-CH_2OH$ | H | 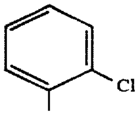 | —NHCO— | 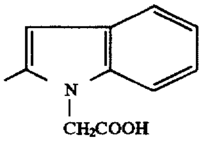 |
| H | $-CH_2OH$ | H | 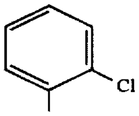 | —NHCO— | 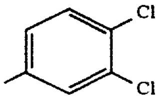 |
| H | $-CH_2OH$ | H | 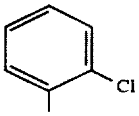 | —NHCONH— | 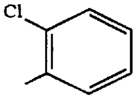 |
| H | $CH_3CO-$ | H | 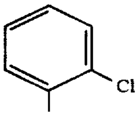 | —NHCO— | 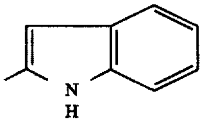 |

TABLE II-20-continued
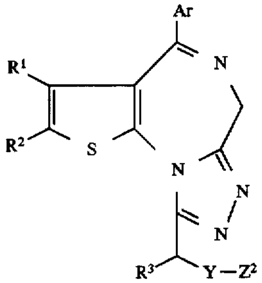
| $R^1$ | $R^2$ | $R^3$ | Ar | Y | $Z^2$ |
|---|---|---|---|---|---|
| H | $CH_3CO-$ | H | 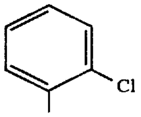 | $-NHCO-$ | 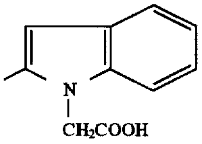 |
| H | $CH_3CO-$ | H | 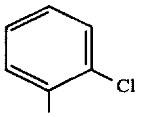 | $-NHCO-$ | 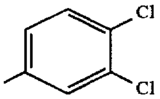 |
| H | $CH_3CO-$ | H | 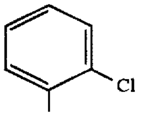 | $-NHCONH-$ | 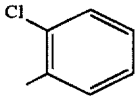 |
| H | $CH_3CH(OH)-$ | H | 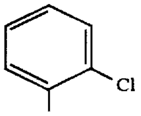 | $-NHCO-$ | 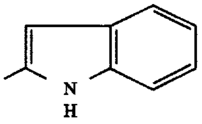 |
| H | $CH_3CH_2CO-$ | H | 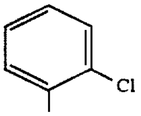 | $-NHCO-$ | 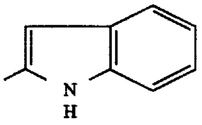 |
TABLE II-21
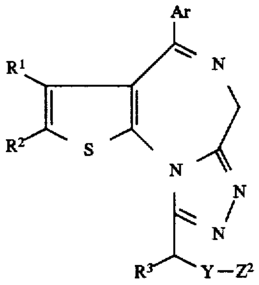
| $R^1$ | $R^2$ | $R^3$ | Ar | Y | $Z^2$ |
|---|---|---|---|---|---|
| H | 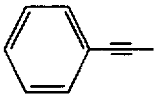 | H | 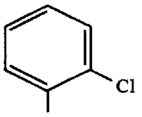 | $-NHCO-$ | 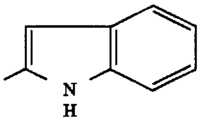 |

TABLE II-21-continued
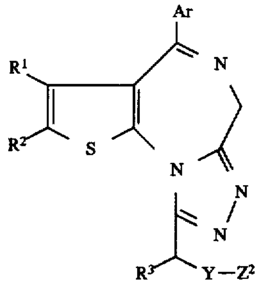
| $R^1$ | $R^2$ | $R^3$ | Ar | Y | $Z^2$ |
|---|---|---|---|---|---|
| H | 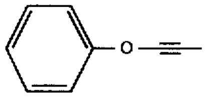 | H | 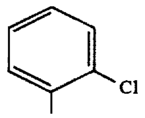 | −NHCO− | 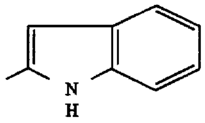 |
| | 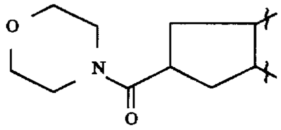 | H | 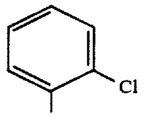 | −NHCO− | 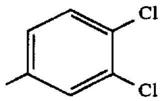 |
| | 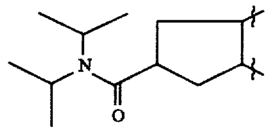 | H | 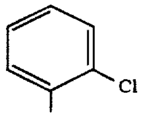 | −NHCONH− | 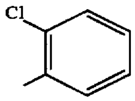 |
| | 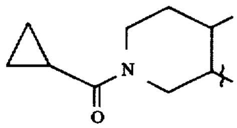 | H | 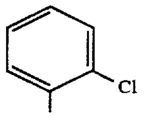 | −NHCO− | 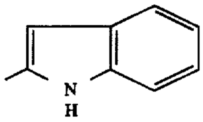 |
TABLE II-22
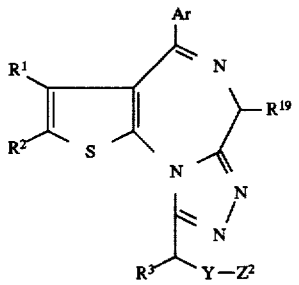
$R^1 = H$
| $R^2$ | $R^3$ | $R^{19}$ | Ar | Y | $Z^2$ |
|---|---|---|---|---|---|
| $C_2H_5$ | $CH_3$ | H | 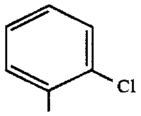 | −NHCO− | 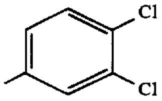 |
| $C_2H_5$ | $-CH(CH_3)_2$ | $CH_3$ | 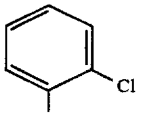 | −NHCO− | 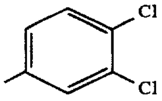 |

TABLE II-22-continued
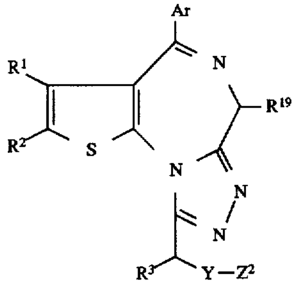
$R^1 = H$
| $R^2$ | $R^3$ | $R^{19}$ | Ar | Y | $Z^2$ |
|---|---|---|---|---|---|
| $C_2H_5$ | $-CH_2CH_2NH_2$ | $CH_3$ | 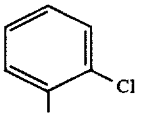 | $-NHCO-$ | 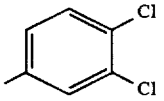 |
| $C_2H_5$ | $-CH_2CH_2N$ 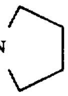 | $CH_3$ | 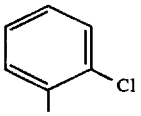 | $-NHCONH-$ | 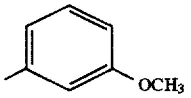 |
| $C_2H_5$ | $-CH_2CH_2COOH$ | $CH_3$ | 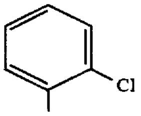 | $-NHCONH-$ | 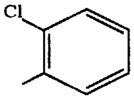 |
| $C_2H_5$ | H | $CH_3$ | 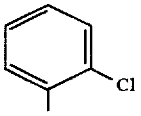 | $-NHCONH-$ | 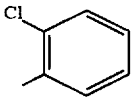 |
| $C_2H_5$ | $CH_3$ | $-CH(CH_3)_2$ | 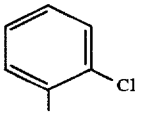 | $-NHCO-$ | 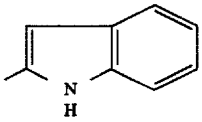 |
| $C_2H_5$ | $CH_3$ | $-CH_2CH_2NH_2$ | 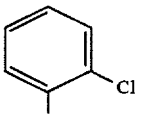 | $-NHCONH-$ | 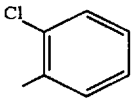 |
| $C_2H_5$ | $CH_3$ | $-CH_2CH_2N$ 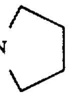 | 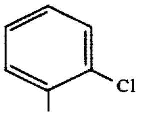 | $-NHCO-$ | 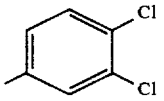 |
| $C_2H_5$ | $CH_3$ | $-CH_2CH_2COOH$ | 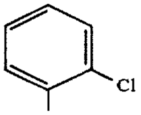 | $-NHCONH-$ | 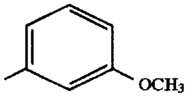 |

TABLE II-23
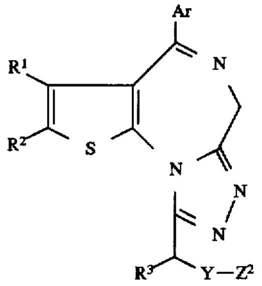
| $R^1$ | $R^2$ | $R^3$ | $R^{19}$ | Ar | Y | $Z^2$ |
|---|---|---|---|---|---|---|
| H | $C_2H_5$ | H | H | 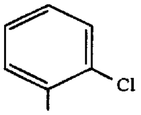 | $-NHCONHCO-$ | 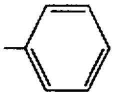 |
| H | $C_2H_5$ | H | H | 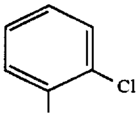 | $-NHCSNHCO-$ | 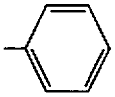 |
| H | $C_2H_5$ | H | H | 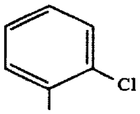 | $-NHCONHSO_2-$ | 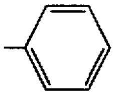 |
| H | $C_2H_5$ | H | H | 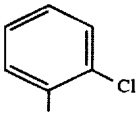 | $-NHCOCONH-$ | 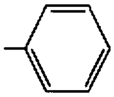 |
| H | $C_2H_5$ | H | H | 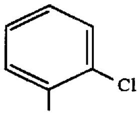 | $-NHCOO-$ | 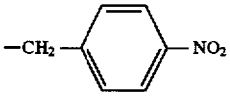 |
| H | $C_2H_5$ | $CH_3$ | H | 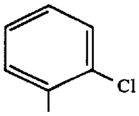 | $-OCO-$ | 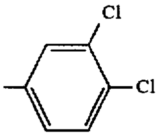 |
| H | $C_2H_5$ | H | H | 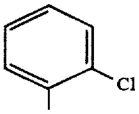 | $-OCO-$ | 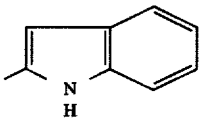 |
| H | $C_2H_5$ | H | H | 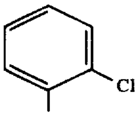 | $-OCONH-$ | 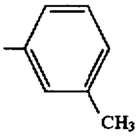 |
| H | $C_2H_5$ | H | H | 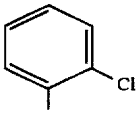 | $-NHSO_2-$ | 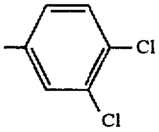 |

TABLE II-23-continued
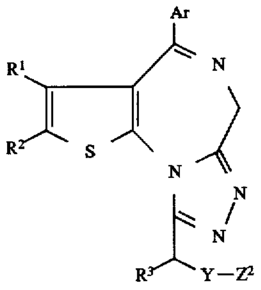
| $R^1$ | $R^2$ | $R^3$ | $R^{19}$ | Ar | Y | $Z^2$ |
|---|---|---|---|---|---|---|
| H | $C_2H_5$ | H | H | 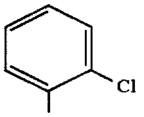 | $-NHCSNH-$ | 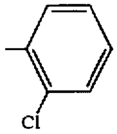 |
TABLE II-24
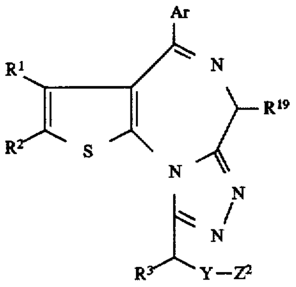
| $R^1$ | $R^2$ | $R^3$ | $R^{19}$ | Ar | Y | $Z^2$ |
|---|---|---|---|---|---|---|
| H | $C_2H_5$ | H | $CH_3$ | 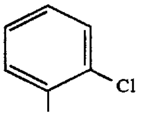 | $-NHCO-$ | $CH_3$ |
| H | $C_2H_5$ | H | $CH_3$ | 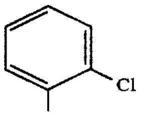 | $-NHCONH-$ | $CH_3$ |
| H | $C_2H_5$ | H | $CH_3$ | 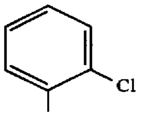 | $-NHCO-$ | $-C_4H_9$ |
| H | $C_2H_5$ | H | $CH_3$ | 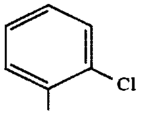 | $-NHCO-$ | $-CH=CH_2$ |
| H | $C_2H_5$ | H | $CH_3$ | 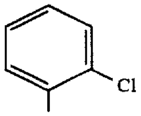 | $-NHCO-$ | $-C\equiv CH$ |

TABLE II-24-continued
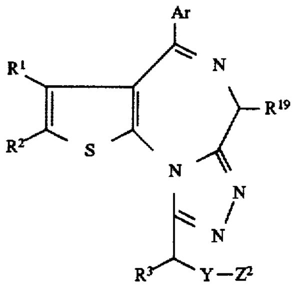
| $R^1$ | $R^2$ | $R^3$ | $R^{19}$ | Ar | Y | $Z^2$ |
| --- | --- | --- | --- | --- | --- | --- |
| H | $C_2H_5$ | H | $CH_3$ | 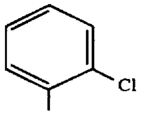 | $-NHCO-$ | $-CH_2CH_2OH$ |
| H | $C_2H_5$ | H | $CH_3$ | 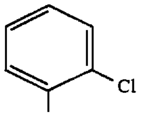 | $-NHCO-$ | $CH_2COCH_3$ |
| H | $C_2H_5$ | H | $CH_3$ | 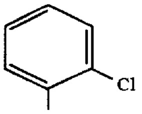 | $-NHCO-$ | 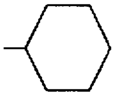 |
| H | $C_2H_5$ | H | $CH_3$ | 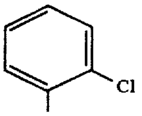 | $-NHCONH-$ | 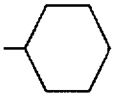 |
| H | $C_2H_5$ | H | $CH_3$ | 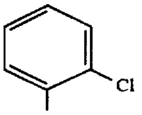 | $-NHCO-$ | $-CH_2-$ 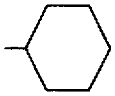 |
TABLE II-25
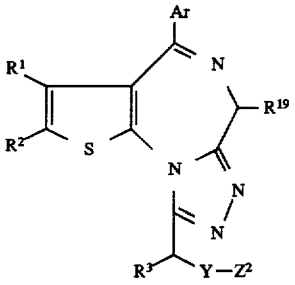
| $R^1$ | $R^2$ | $R^3$ | $R^{19}$ | Ar | Y | $Z^2$ |
| --- | --- | --- | --- | --- | --- | --- |
| H | $C_2H_5$ | H | $CH_3$ | 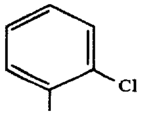 | $-NHCO-$ | 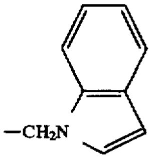 |

TABLE II-25-continued
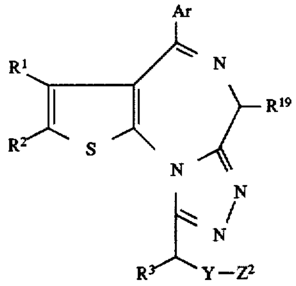
| R¹ | R² | R³ | R¹⁹ | Ar | Y | Z² |
|---|---|---|---|---|---|---|
| H | $C_2H_5$ | H | $CH_3$ | 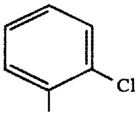 | —NHCO— | 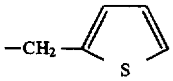 |
| H | $C_2H_5$ | H | $CH_3$ | 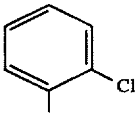 | —NHCO— | 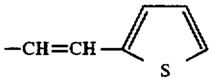 |
| H | $C_2H_5$ | H | $CH_3$ | 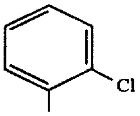 | —NHCO— | 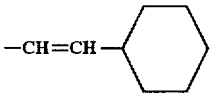 |
| H | $C_2H_5$ | H | $CH_3$ | 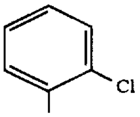 | —NHCONH— | 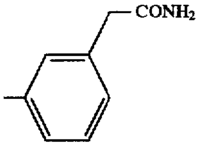 |
| H | $C_2H_5$ | H | $CH_3$ | 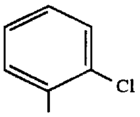 | —NHCO— | 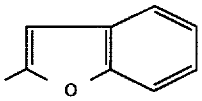 |
| H | $C_2H_5$ | H | $CH_3$ | 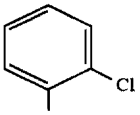 | —NHCO— | 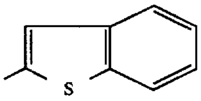 |
| H | $C_2H_5$ | $CH_3$ | H | 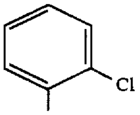 | —NHCO— | 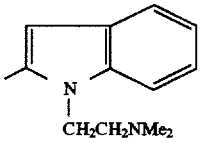 |
| H | $C_2H_5$ | $CH_3$ | H | 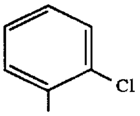 | —NHCO— | 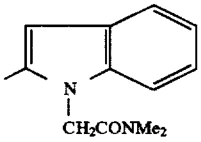 |
| H | $C_2H_5$ | $CH_3$ | H | 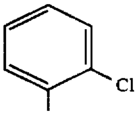 | —NHCO— | 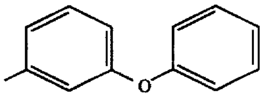 |

TABLE II-26
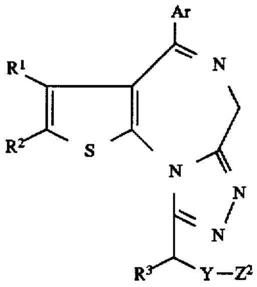
| $R^1$ | $R^2$ | $R^3$ | Ar | Y | $Z^2$ |
|---|---|---|---|---|---|
| H | $C_2H_5$ | H | 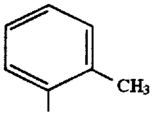 | —NHCO— | 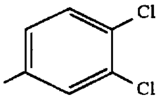 |
| H | $C_2H_5$ | H | 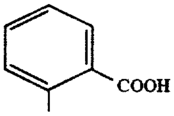 | —NHCO— | 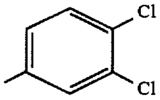 |
| H | $C_2H_5$ | H | 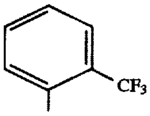 | —NHCO— | 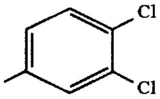 |
| H | $C_2H_5$ | H | 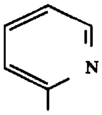 | —NHCO— | 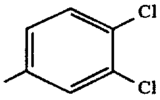 |
| H | $C_2H_5$ | H | 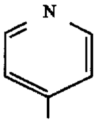 | —NHCO— | 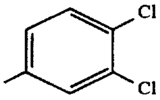 |
| H | $C_2H_5$ | H | 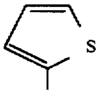 | —NHCO— | 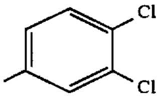 |
TABLE II-27
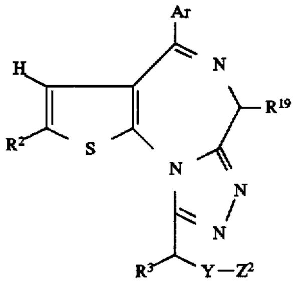
| $R^2$ | $R^3$ | $R^{19}$ | Ar | Y | $Z^2$ |
|---|---|---|---|---|---|
| $C_2H_5$ | H | H | 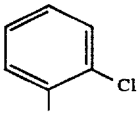 | —NHCO— | 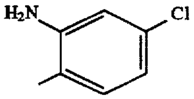 |

TABLE II-27-continued
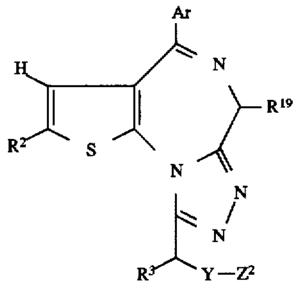
| $R^2$ | $R^3$ | $R^{19}$ | Ar | Y | $Z^2$ |
|---|---|---|---|---|---|
| $C_2H_5$ | H | H | 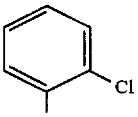 | $-NHCO-$ | 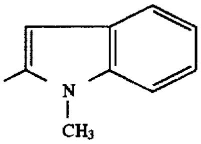 |
| $C_2H_5$ | H | H | 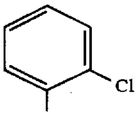 | $-NHCO-$ | 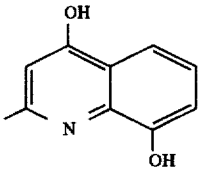 |
| $C_2H_5$ | H | H | 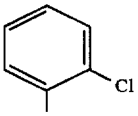 | $-NHSO_2-$ | 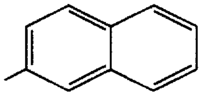 |
| $C_2H_5$ | H | H | 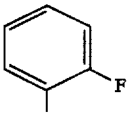 | $-NHCO-$ | 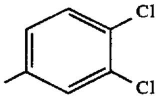 |
| $C_2H_5$ | H | H | 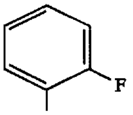 | $-NHCONH-$ | 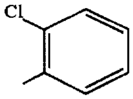 |
| $C_2H_5$ | H | H | 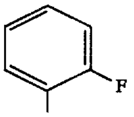 | $-NHCO-$ | 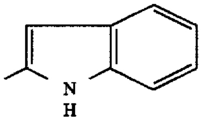 |
| $C_2H_5$ | H | H | 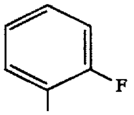 | $-NHCO-$ | 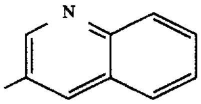 |
| $C_2H_5$ | H | H | 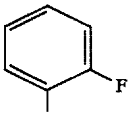 | $-NHCO-$ | 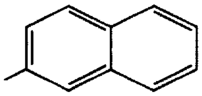 |

TABLE II-27-continued
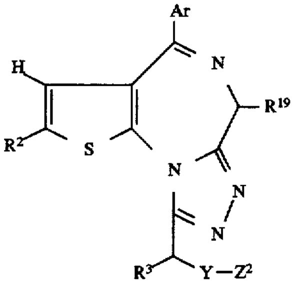
| $R^2$ | $R^3$ | $R^{19}$ | Ar | Y | $Z^2$ |
|---|---|---|---|---|---|
| $C_2H_5$ | H | H | 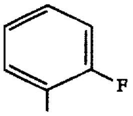 | —NHCO— | 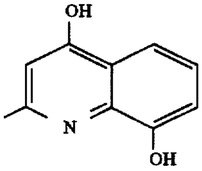 |
TABLE II-28
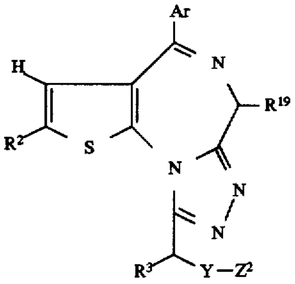
| $R^2$ | $R^3$ | $R^{19}$ | Ar | Y | $Z^2$ |
|---|---|---|---|---|---|
| $C_2H_5$ | $CH_3$ | H | 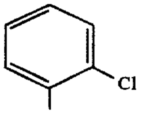 | —NHCO— | 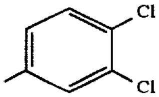 |
| $C_2H_5$ | $CH_3$ | H | 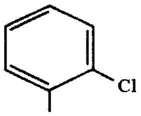 | —NHCO— | 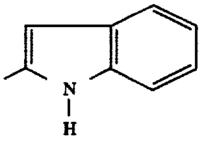 |
| $C_2H_5$ | $CH_3$ | H | 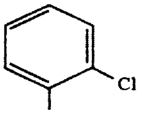 | —NHCO— | 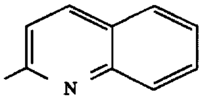 |
| $C_2H_5$ | $CH_3$ | H | 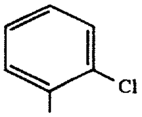 | —NHCO— | 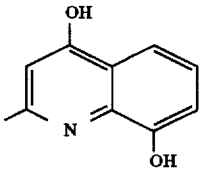 |

TABLE II-28-continued
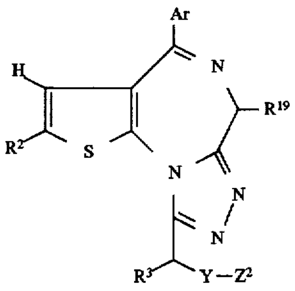
| $R^2$ | $R^3$ | $R^{19}$ | Ar | Y | $Z^2$ |
|---|---|---|---|---|---|
| $C_2H_5$ | $CH_3$ | H | 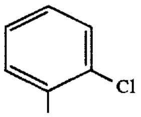 | —NHCONH— | 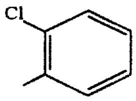 |
| $C_2H_5$ | H | $CH_3$ | 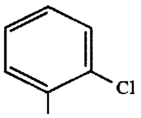 | —NHCO— | 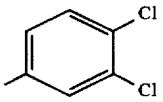 |
| $C_2H_5$ | H | $CH_3$ | 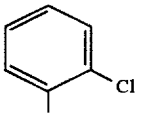 | —NHCO— | 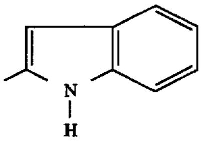 |
| $C_2H_5$ | H | $CH_3$ | 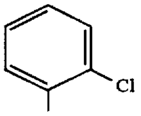 | —NHCO— | 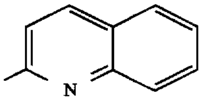 |
| $C_2H_5$ | H | $CH_3$ | 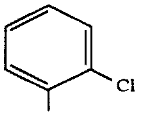 | —NHCO— | 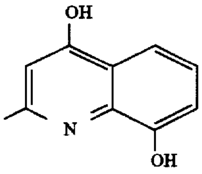 |
| $C_2H_5$ | H | $CH_3$ | 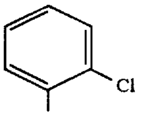 | —NHCONH— | 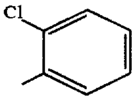 |

TABLE II-29
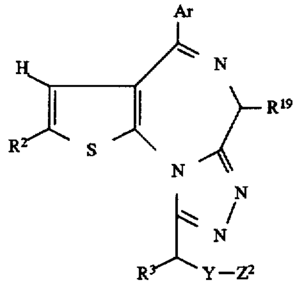
| $R^2$ | $R^3$ | $R^{19}$ | Ar | Y | $Z^2$ |
|---|---|---|---|---|---|
| $C_2H_5$ | 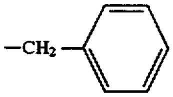 | H | 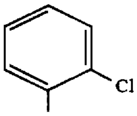 | $-NHCO-$ | 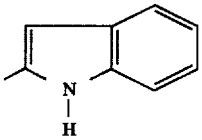 |
| $C_2H_5$ | 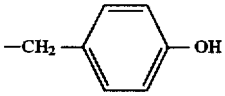 | H | 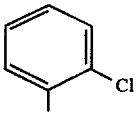 | $-NHCO-$ | 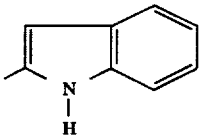 |
| $C_2H_5$ | $-(CH_2)_4NH_2$ | H | 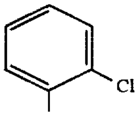 | $-NHCO-$ | 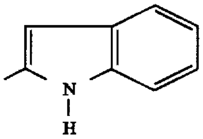 |
| $C_2H_5$ | 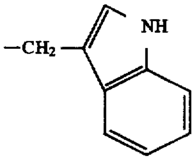 | H | 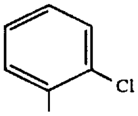 | $-NHCO-$ | 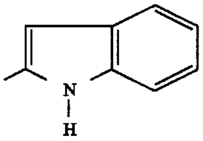 |
| $C_2H_5$ | 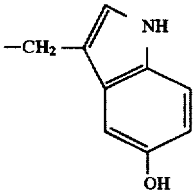 | H | 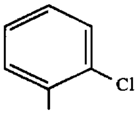 | $-NHCO-$ | 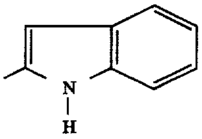 |
| $C_2H_5$ | 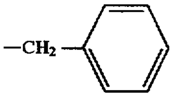 | H | 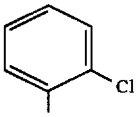 | $-NHCO-$ | 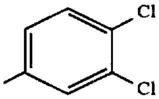 |
| $C_2H_5$ | 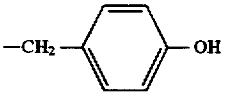 | H | 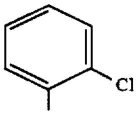 | $-NHCO-$ | 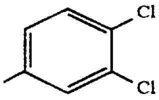 |
| $C_2H_5$ | $-(CH_2)_4NH_2$ | H | 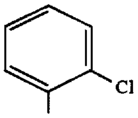 | $-NHCO-$ | 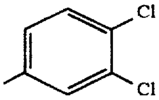 |

TABLE II-29-continued
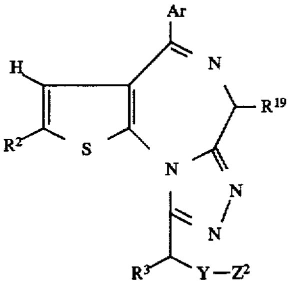
| $R^2$ | $R^3$ | $R^{19}$ | Ar | Y | $Z^2$ |
|---|---|---|---|---|---|
| $C_2H_5$ | 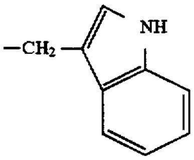 | H | 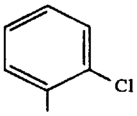 | $-NHCO-$ | 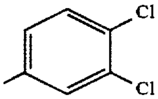 |
| $C_2H_5$ | 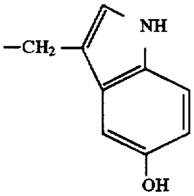 | H | 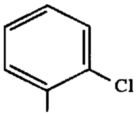 | $-NHCO-$ | 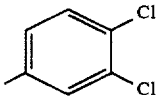 |
TABLE II-30
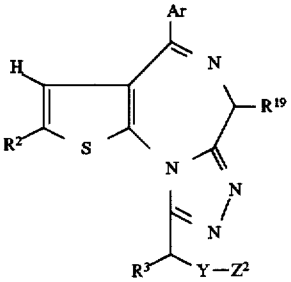
| $R^2$ | $R^3$ | $R^{19}$ | Ar | Y | $Z^2$ |
|---|---|---|---|---|---|
| $C_2H_5$ | $-CH_2CH_2COOH$ | H | 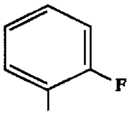 | $-NHCO-$ | 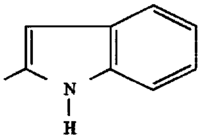 |
| Br | $-CH_2CH_2COOH$ | H | 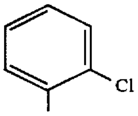 | $-NHCO-$ | 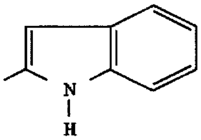 |
| $C_3H_7$ | $-CH_2CH_2COOH$ | H | 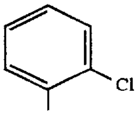 | $-NHCO-$ | 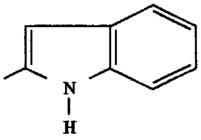 |

TABLE II-30-continued
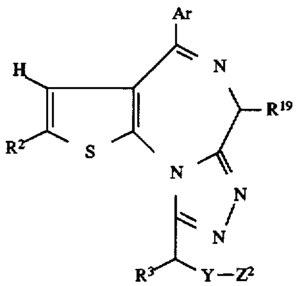
| $R^2$ | $R^3$ | $R^{19}$ | Ar | Y | $Z^2$ |
|---|---|---|---|---|---|
| $C_2H_5$ | $-CH_2CH_2COOH$ | $CH_3$ | 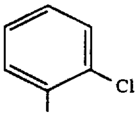 | $-NHCO-$ | 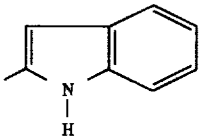 |
| $C_2H_5$ | $-CH_2CH_2COOH$ | H | 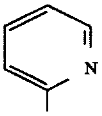 | $-NHCO-$ | 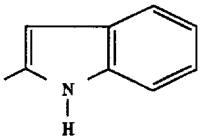 |
| $C_2H_5$ | $-CH_2CH_2COOH$ | H | 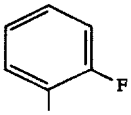 | $-NHCO-$ | 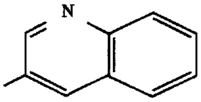 |
| Br | $-CH_2CH_2COOH$ | H | 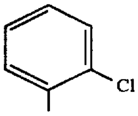 | $-NHCO-$ | 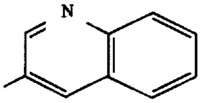 |
| $C_3H_7$ | $-CH_2CH_2COOH$ | H | 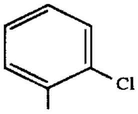 | $-NHCO-$ | 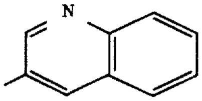 |
| $C_2H_5$ | $-CH_2CH_2COOH$ | $CH_3$ | 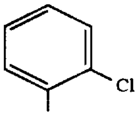 | $-NHCO-$ | 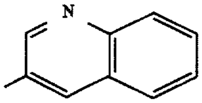 |
| $C_2H_5$ | $-CH_2CH_2COOH$ | H | 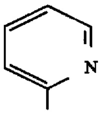 | $-NHCO-$ | 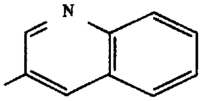 |

TABLE II-31
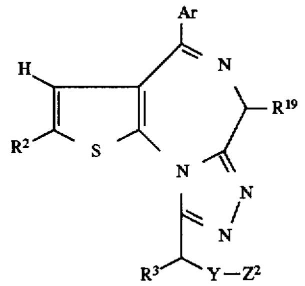
| $R^2$ | $R^3$ | $R^{19}$ | Ar | Y | $Z^2$ |
|---|---|---|---|---|---|
| $CH(CH_3)_2$ | $-(CH_2)_2COOH$ | H | 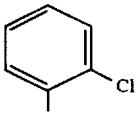 | $-NHCO-$ | 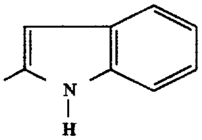 |
| $CH(CH_3)_2$ | $-(CH_2)_2COOH$ | H | 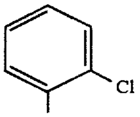 | $-NHCO-$ | 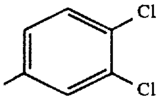 |
| $CH(CH_3)_2$ | $-(CH_2)_2COOH$ | H | 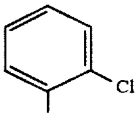 | $-NHCONH-$ | 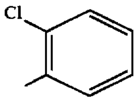 |
| $CH(CH_3)_2$ | $-(CH_2)_2COOH$ | H | 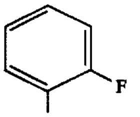 | $-NHCO-$ | 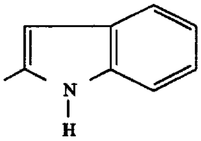 |
| $CH(CH_3)_2$ | $-(CH_2)_3COOH$ | H | 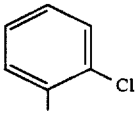 | $-NHCO-$ | 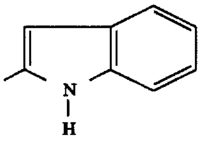 |
| 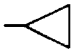 | $-(CH_2)_2COOH$ | H | 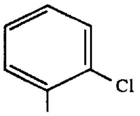 | $-NHCO-$ | 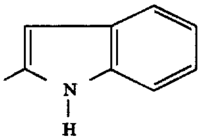 |
| 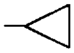 | $-(CH_2)_2COOH$ | H | 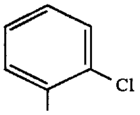 | $-NHCO-$ | 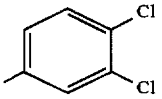 |
| 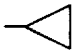 | $-(CH_2)_2COOH$ | H | 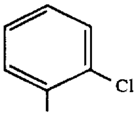 | $-NHCONH-$ | 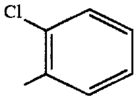 |
| 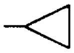 | $-(CH_2)_2COOH$ | H | 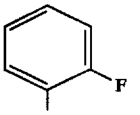 | $-NHCO-$ | 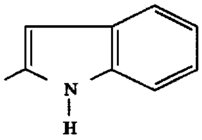 |

TABLE II-31-continued
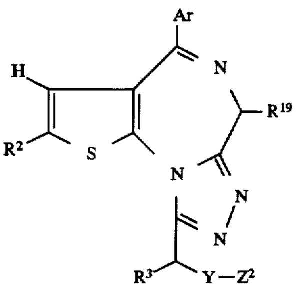
| $R^2$ | $R^3$ | $R^{19}$ | Ar | Y | $Z^2$ |
|---|---|---|---|---|---|
| 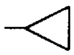 | $-(CH_2)_3COOH$ | H | 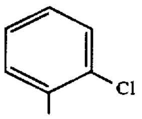 | $-NHCO-$ | 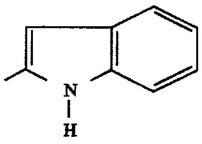 |
TABLE II-32
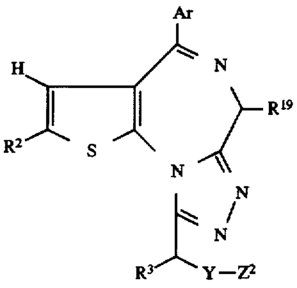
| $R^2$ | $R^3$ | $R^{19}$ | Ar | Y | $Z^2$ |
|---|---|---|---|---|---|
| $C_2H_5$ | $-(CH_2)_2COOH$ | H | 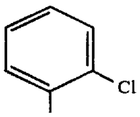 | $-NHCO-$ | 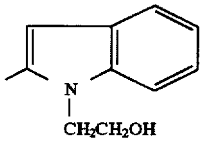 |
| $C_3H_7$ | $-(CH_2)_2COOH$ | H | 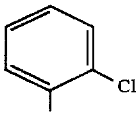 | $-NHCO-$ | 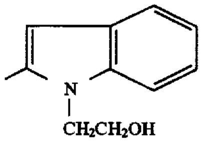 |
| Br | $-(CH_2)_2COOH$ | H | 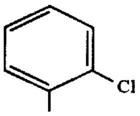 | $-NHCO-$ | 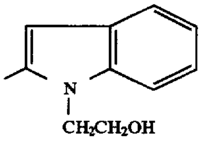 |
| $C_2H_5$ | $-(CH_2)_2COOH$ | H | 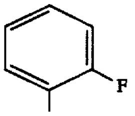 | $-NHCO-$ | 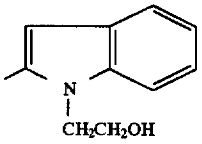 |

TABLE II-32-continued
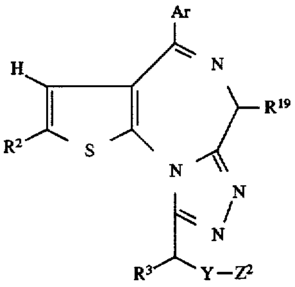
| $R^2$ | $R^3$ | $R^{19}$ | Ar | Y | $Z^2$ |
|---|---|---|---|---|---|
| $C_2H_5$ | $-(CH_2)_3COOH$ | H | 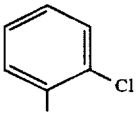 | $-NHCO-$ | 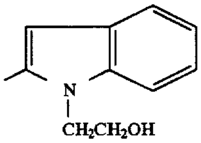 |
| $C_2H_5$ | $-(CH_2)_2COOH$ | H | 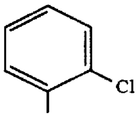 | $-NHCO-$ | 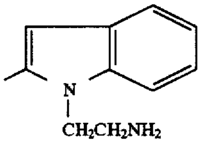 |
| $C_3H_7$ | $-(CH_2)_2COOH$ | H | 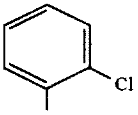 | $-NHCO-$ | 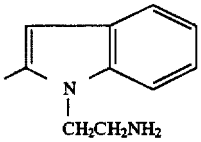 |
| Br | $-(CH_2)_2COOH$ | H | 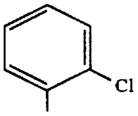 | $-NHCO-$ | 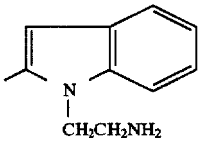 |
| $C_2H_5$ | $-(CH_2)_2COOH$ | H | 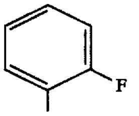 | $-NHCO-$ | 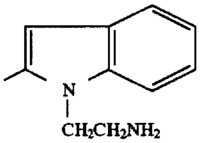 |
| $C_2H_5$ | $-(CH_2)_3COOH$ | H | 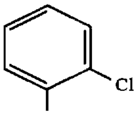 | $-NHCO-$ | 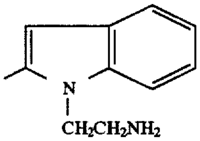 |

TABLE II-33
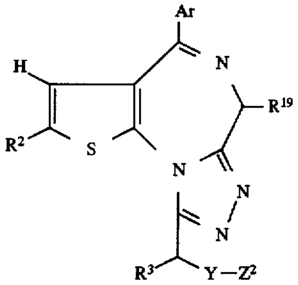
| $R^2$ | $R^3$ | $R^{19}$ | Ar | Y | $Z^2$ |
|---|---|---|---|---|---|
| $C_2H_5$ | $-CH_2CH_2OH$ | H | 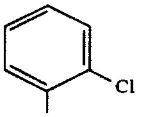 | $-NHCO-$ | 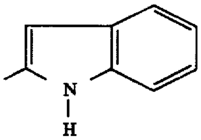 |
| $C_2H_5$ | $-CH_2CH_2OH$ | H | 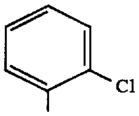 | $-NHCO-$ | 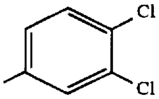 |
| $C_2H_5$ | $-CH_2CH_2OH$ | H | 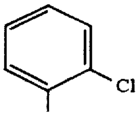 | $-NHCONH-$ | 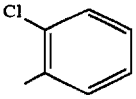 |
| $C_2H_5$ | $-CH_2CH_2OH$ | H | 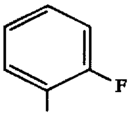 | $-NHCO-$ | 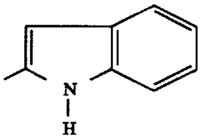 |
| $C_3H_7$ | $-CH_2CH_2OH$ | H | 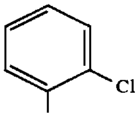 | $-NHCO-$ | 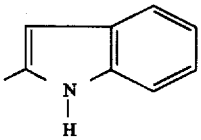 |
| $C_2H_5$ | $-CH_2CH_2CH_2OH$ | H | 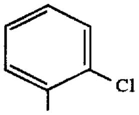 | $-NHCO-$ | 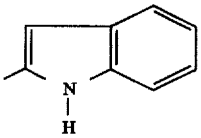 |
| $C_2H_5$ | $-CH_2CH_2CH_2OH$ | H | 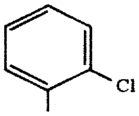 | $-NHCO-$ | 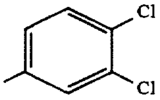 |
| $C_2H_5$ | $-CH_2CH_2CH_2OH$ | H | 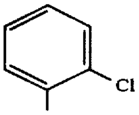 | $-NHCONH-$ | 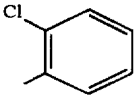 |
| $C_2H_5$ | $-CH_2CH_2CH_2OH$ | H | 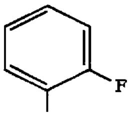 | $-NHCO-$ | 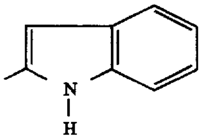 |

TABLE II-33-continued
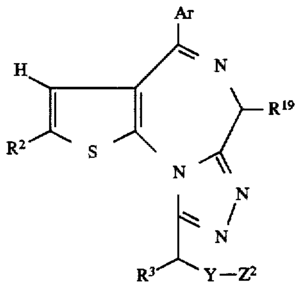
| $R^2$ | $R^3$ | $R^{19}$ | Ar | Y | $Z^2$ |
|---|---|---|---|---|---|
| $C_3H_7$ | $-CH_2CH_2CH_2OH$ | H | 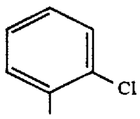 | $-NHCO-$ | 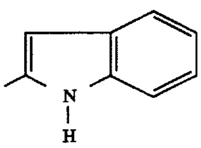 |
TABLE II-34
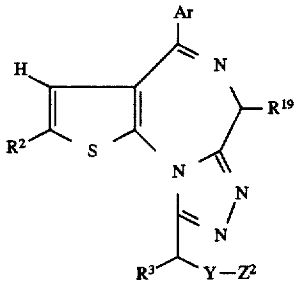
| $R^2$ | $R^3$ | $R^{19}$ | Ar | Y | $Z^2$ |
|---|---|---|---|---|---|
| $C_2H_5$ | $-CH_2CH_2NH_2$ | H | 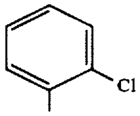 | $-NHCO-$ | 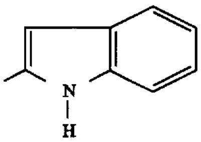 |
| $C_2H_5$ | $-CH_2CH_2NH_2$ | H | 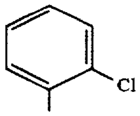 | $-NHCO-$ | 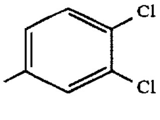 |
| $C_2H_5$ | $-CH_2CH_2NH_2$ | H | 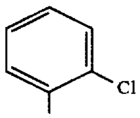 | $-NHCONH-$ | 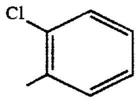 |
| $C_2H_5$ | $-CH_2CH_2NH_2$ | H | 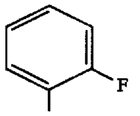 | $-NHCO-$ | 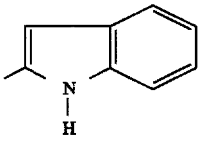 |
| $C_3H_7$ | $-CH_2CH_2NH_2$ | H | 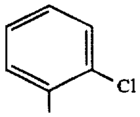 | $-NHCO-$ | 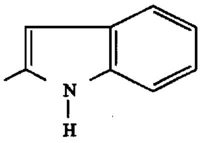 |

TABLE II-34-continued
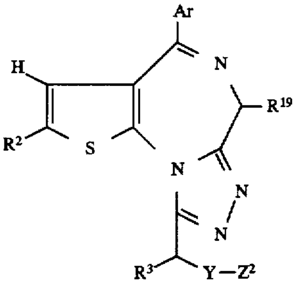
| $R^2$ | $R^3$ | $R^{19}$ | Ar | Y | $Z^2$ |
|---|---|---|---|---|---|
| $C_2H_5$ | $-CH_2CH_2CH_2NH_2$ | H | 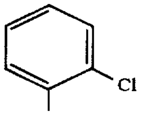 | $-NHCO-$ | 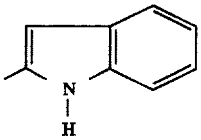 |
| $C_2H_5$ | $-CH_2CH_2CH_2NH_2$ | H | 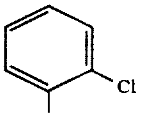 | $-NHCO-$ | 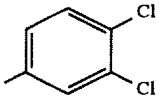 |
| $C_2H_5$ | $-CH_2CH_2CH_2NH_2$ | H | 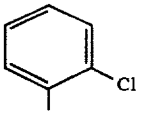 | $-NHCONH-$ | 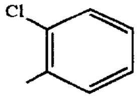 |
| $C_2H_5$ | $-CH_2CH_2CH_2NH_2$ | H | 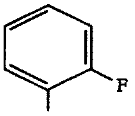 | $-NHCO-$ | 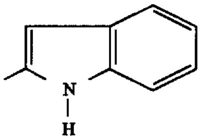 |
| $C_3H_7$ | $-CH_2CH_2CH_2NH_2$ | H | 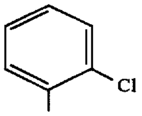 | $-NHCO-$ | 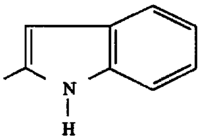 |
TABLE II-35
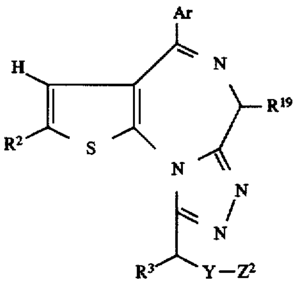
| $R^2$ | $R^3$ | $R^{19}$ | Ar | Y | $Z^2$ |
|---|---|---|---|---|---|
| $C_2H_5$ | $-(CH_2)_4NH_2$ | H | 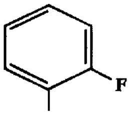 | $-NHCO-$ | 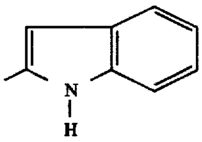 |

TABLE II-35-continued
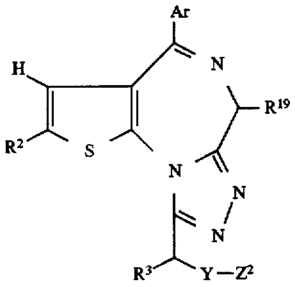
| $R^2$ | $R^3$ | $R^{19}$ | Ar | Y | $Z^2$ |
|---|---|---|---|---|---|
| $C_3H_7$ | $-(CH_2)_4NH_2$ | H | 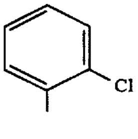 | $-NHCO-$ | 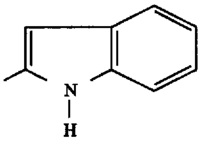 |
| Br | $-(CH_2)_4NH_2$ | H | 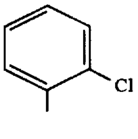 | $-NHCO-$ | 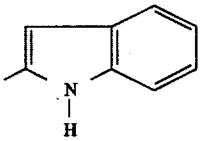 |
| $C_2H_5$ | $-(CH_2)_4NH_2$ | H | 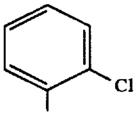 | $-NHCONH-$ | 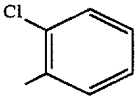 |
| $CH(CH_3)_2$ | $-(CH_2)_4NH_2$ | H | 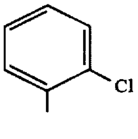 | $-NHCO-$ | 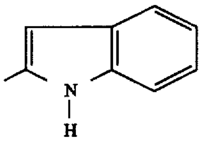 |
| $C_2H_5$ | 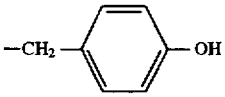 | H | 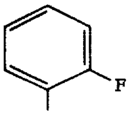 | $-NHCO-$ | 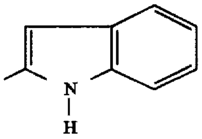 |
| $C_3H_7$ | 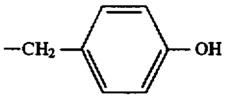 | H | 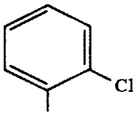 | $-NHCO-$ | 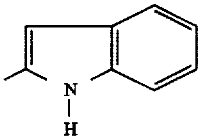 |
| Br | 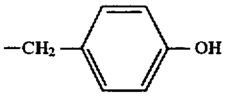 | H | 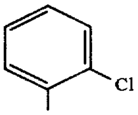 | $-NHCO-$ | 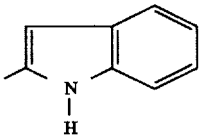 |
| $C_2H_5$ | 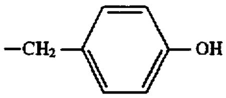 | H | 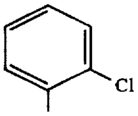 | $-NHCONH-$ | 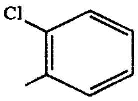 |

TABLE II-35-continued
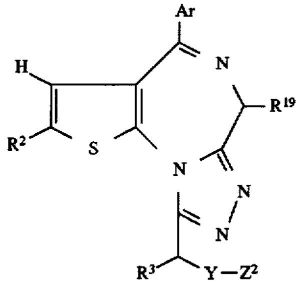
| $R^2$ | $R^3$ | $R^{19}$ | Ar | Y | $Z^2$ |
|---|---|---|---|---|---|
| $CH(CH_3)_2$ | 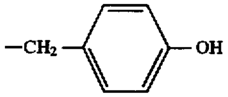 | H | 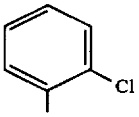 | —NHCO— | 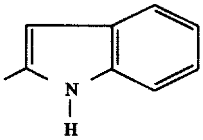 |
TABLE II-36
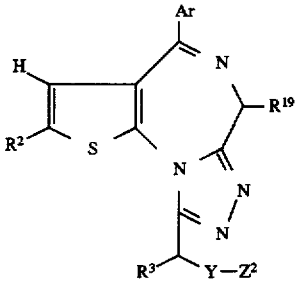
| $R^2$ | $R^3$ | $R^{19}$ | Ar | Y | $Z^2$ |
|---|---|---|---|---|---|
| $C_2H_5$ | H | H | 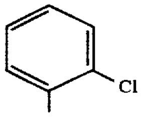 | —NHCO— | 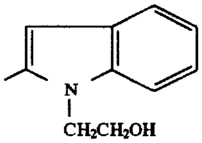 |
| $C_3H_7$ | H | H | 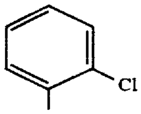 | —NHCO— | 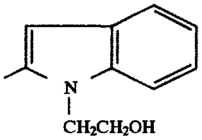 |
| Br | H | H | 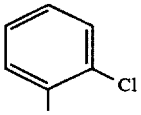 | —NHCO— | 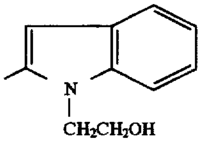 |
| $C_2H_5$ | H | H | 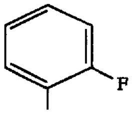 | —NHCO— | 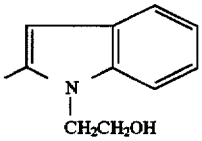 |

TABLE II-36-continued
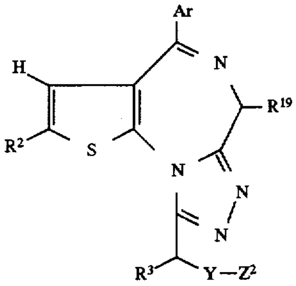
| $R^2$ | $R^3$ | $R^{19}$ | Ar | Y | $Z^2$ |
|---|---|---|---|---|---|
| $C_2H_5$ | H | H | 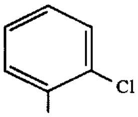 | −NHCO− | 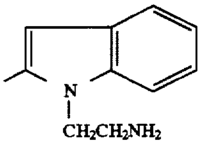 |
| $C_3H_7$ | H | H | 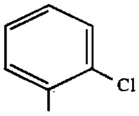 | −NHCO− | 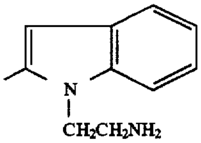 |
| Br | H | H | 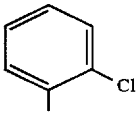 | −NHCONH− | 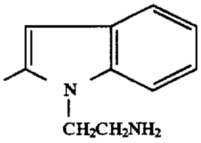 |
| $C_2H_5$ | H | H | 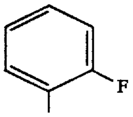 | −NHCO− | 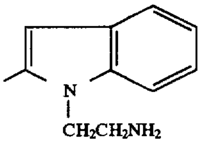 |
| $CH(CH_3)_2$ | H | H | 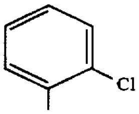 | −NHCO− | 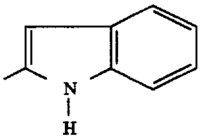 |
| 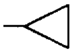 | H | H | 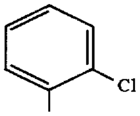 | −NHCO− | 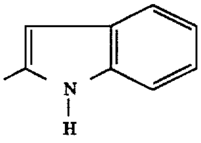 |

TABLE II-37

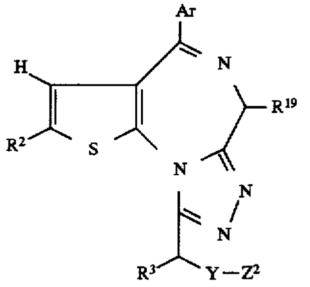

| $R^2$ | $R^3$ | $R^{19}$ | Ar | Y | $Z^2$ |
|---|---|---|---|---|---|
| $C_3H_7$ | H | H | 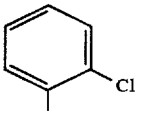 | $-NHCO-$ | 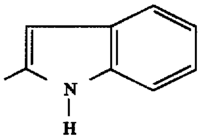 |
| $C_3H_7$ | H | H | 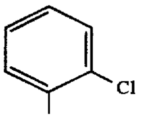 | $-NHCONH-$ | 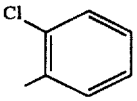 |
| $CH(CH_3)_2$ | H | H | 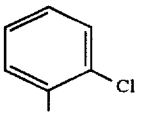 | $-NHCONH-$ | 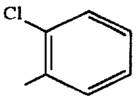 |
| 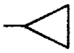 | H | H | 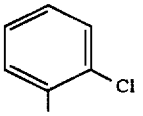 | $-NHCONH-$ | 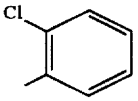 |
| $C_3H_7$ | $-CH_2CH_2COOH$ | H | 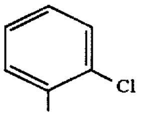 | $-NHCONH-$ | 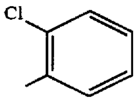 |
| $C_2H_5$ | $-CH_2CH_2COOH$ | H | 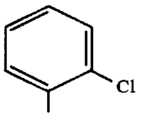 | $-NHCO-$ | 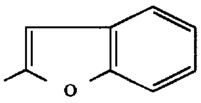 |

What is claimed is:

1. A thienotriazolodiazepine compound of the formula

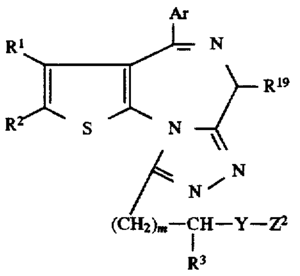

(II)

wherein $R^1$ is a hydrogen or an alkyl having 1 or 2 carbon atom(s);

$R^2$ is a hydrogen, an alkyl having 1 to 3 carbon atom(s), a cycloalkyl having 3 to 7 carbon atoms, $-(CH_2)nCOOR^4$ wherein n is 0 or 1 and $R^4$ is hydrogen or alkyl having 1 to 4 carbon atom(s), or 5-tetrazolyl;

$R^3$ is a hydrogen, an alkyl having 1 to 3 carbon atom(s), $-(CH_2)nCOOR^{14}$ wherein n is an integer of 1–3 and $R^{14}$ is hydrogen, cyclohexyl or benzyl, or $-(CH_2)nN(R^{17})(R^{18})$ wherein n is 0 or an integer of 1–5 and $R^{17}$ and $R^{18}$ are the same or different and each is hydrogen or alkyl having 1 to 5 carbon atom(s);

$R^{19}$ is a hydrogen or an alkyl having 1 to 3 carbon atoms (s);

m is 0;

Y is $-NHCO-$, $-NHCONH-$, $-NHCSNH-$ or $-NHSO_2-$;

$Z^2$ is a phenyl, a naphthyl, a heteroaryl selected from the group consisting of pyridyl, thienyl, furyl, pyrrolyl, imidazolyl, oxazolyl, isoxazolyl, thiazolyl, pyridazinyl, pyrimidinyl, pyrazinyl, indolyl, indolinyl, benzofuranyl, 2,3-dihydrobenzofuranyl, benzothienyl, benzoxazolyl, benzimidazolyl, benzothiazolyl, quinolyl, isoquinolyl, quinoxalinyl and quinazolinyl or a group of the formula: —CH═CH—$R^{13}$ wherein $R^{13}$ is phenyl, each of which may be optionally substituted with 1 or 2 substituent(s) selected from the group consisting of halogen, amino, nitro, methyl, methoxy, —$(CH_2)nCOOR^{14C}$ wherein n is 1 or 2 and $R^{14C}$ is hydrogen or alkyl having 1 to 4 carbon atom(s), and 1H-tetrazol-5-ylmethyl; and Ar is a phenyl or a phenyl having halogen on the ring, or a pharmaceutically acceptable salt thereof.

2. The compound of claim 1, wherein, in the formula (II), each symbol is as defined in the following:

$R^1$ is a hydrogen;

$R^2$ is an alkyl having 1 to 3 carbon atom(s) or a cycloalkyl having 3 to 6 carbon atoms;

$R^3$ is a hydrogen or —$(CH_2)nCOOR^{14}$ wherein n is an integer of 1–3 and $R^{14}$ is hydrogen or cyclohexyl;

$R^{19}$ is a hydrogen;

m is 0;

Y is —NHCO— or —NHCONH—;

$Z^2$ is a phenyl or a heteroaryl selected from the group consisting of pyridyl, thienyl, furyl, pyrrolyl, imidazolyl, oxazolyl, isoxazolyl, thiazolyl, pyridazinyl, pyrimidinyl, pyrazinyl, indolyl, indolinyl, benzofuranyl, 2,3-dihydrobenzofuranyl, benzothienyl, benzoxazolyl, benzimidazolyl, benzothiazolyl, quinolyl, isoquinolyl, quinoxalinyl and quinazolinyl, each of which may be optionally substituted with 1 or 2 substituent(s) selected from the group consisting of halogen, amino and methyl; and Ar is a phenyl having halogen on the ring, or a pharmaceutically acceptable salt thereof.

3. The compound of claim 1, wherein the compound of the formula (II) is a member selected from the group consisting of:

N-(4-(2-chlorophenyl)-2-ethyl-6H-thieno[3,2-f] [1,2,4] triazolo[4,3-a] [1,4]diazepin-9-ylmethyl)-3,4-dichlorobenzamide, N-(4-(2-chlorophenyl)-2-ethyl-6H-thieno[3,2-f] [1,2,4] triazolo[4,3-a] [1,4]diazepin-9-ylmethyl)indole-2-carboxamide, N-(2-chlorophenyl)-N'-(4-(2-chlorophenyl)-2-ethyl-6H-thieno[3,2-f] [1,2,4]triazolo[4,3-a] [1,4]diazepin-9-ylmethyl)urea, (R)-(−)-4-(3,4-dichlorobenzoylamino)-4-(4-(2-chlorophenyl)-2-ethyl-6H-thieno[3,2-f] [1,2,4]triazolo [4,3-a] [1,4]diazepin-9-yl)butanoic acid, cyclohexyl (R)-(−)-4-(4-(2-chlorophenyl)-2-ethyl-6H-thieno[3,2-f] [1,2,4]triazolo[4,3-a] [1,4]diazepin-9-yl)-4-(1H-indole-2-carboxamide)butanoate, (R)-(−)-4-(4-(2-chlorophenyl)-2-ethyl-6H-thieno[3,2-f] [1,2,4]triazolo[4,3-a] [1,4]diazepin-9-yl)-4-(1H-indole-2-carboxamide)butanoic acid, N-(4-(2-chlorophenyl)-2-propyl-6H-thieno[3,2-f] [1,2,4] triazolo[4,3-a] [1,4]diazepin-9-ylmethyl)-3,4-dichlorobenzamide, (R)-(−)-4-(4-(2-chlorophenyl)-2-ethyl-6H-thieno[3,2-f] [1,2,4]triazolo[4,3-a] [1,4]diazepin-9-yl)-4-(3-(2-chlorophenyl)ureido)butanoic acid, (R)-(−)-5-(3,4-dichlorobenzoylamino)-5-(4-(2-chlorophenyl)-2-ethyl-6H-thieno[3,2-f] [1,2,4]triazolo [4,3-a] [1,4]diazepin-9-yl)pentanoic acid, N-(4-(2-chlorophenyl)-2-propyl-6H-thieno[3,2-f] [1,2,4] triazolo[4,3-a] [1,4]diazepin-9-ylmethyl)indole-2-carboxamide, N-(4-(2-chlorophenyl)-2-isopropyl-6H-thieno[3,2-f] [1,2,4]triazolo[4,3-a] [1,4]diazepin-9-ylmethyl)indole-2-carboxamide, N-(4-(2-chlorophenyl)-2-cyclopropyl-6H-thieno[3,2-f] [1,2,4]triazolo[4,3-a] [1,4]diazepin-9-ylmethyl)indole-2-carboxamide, N-(2-chlorophenyl)-N'-(4-(2-chlorophenyl)-2-propyl-6H-thieno[3,2-f] [1,2,4]triazolo[4,3-a] [1,4]diazepin-9-ylmethyl)urea, N-(2-chlorophenyl)-N'-(4-(2-chlorophenyl)-2-isopropyl-6H-thieno[3,2-f] [1,2,4]triazolo[4,3-a] [1,4]diazepin-9-ylmethyl)urea, N-(2-chlorophenyl)-N'-(4-(2-chlorophenyl)-2-cyclopropyl-6H-thieno[3,2-f] [1,2,4]triazolo[4,3-a] [1,4]diazepin-9-ylmethyl)urea, (R)-4-(4-(2-chlorophenyl)-2-propyl-6H-thieno[3,2-f] [1,2,4]triazolo[4,3-a] [1,4]diazepin-9-yl)-4-(indole-2-carboxamide)butanoic acid, (R)-4-(4-(2-chlorophenyl)-2-isopropyl-6H-thieno[3,2-f] [1,2,4]triazolo[4,3-a] [1,4]diazepin-9-yl)-4-(indole-2-carboxamide)butanoic acid, (R)-4-(4-(2-chlorophenyl)-2-cyclopropyl-6H-thieno[3,2-f] [1,2,4]triazolo[4,3-a] [1,4]diazepin-9-yl)-4-(indole-2-carboxamide)butanoic acid, (R)-4-(4-(2-chlorophenyl)-2-propyl-6H-thieno[3,2-f] [1,2,4]triazolo[4,3-a] [1,4]diazepin-9-yl)-4-(3-(2-chlorophenyl)ureido)butanoic acid, (R)-4-(4-(2-chlorophenyl)-2-isopropyl-6H-thieno[3,2-f] [1,2,4]triazolo[4,3-a] [1,4]diazepin-9-yl)-4-(3-(2-chlorophenyl)ureido)butanoic acid, and (R)-4-(4-(2-chlorophenyl)-2-cyclopropyl-6H-thieno[3,2-f] [1,2,4]triazolo[4,3-a] [1,4]diazepin-9-yl)-4-(3-(2-chlorophenyl)ureido)butanoic acid, or a pharmaceutically acceptable salt thereof.

4. A pharmaceutical composition comprising the compound of claim 1 or a pharmaceutically acceptable salt thereof in an amount effective for treatment, and a pharmaceutically acceptable additive.

5. A method for treatment of a digestive disease, which comprises administering to a patient in need thereof a compound of claim 1 or a pharmaceutically acceptable salt thereof.

* * * * *